US008729078B2

(12) United States Patent
Billedeau et al.

(10) Patent No.: US 8,729,078 B2
(45) Date of Patent: May 20, 2014

(54) INHIBITORS OF BRUTON'S TYROSINE KINASE

(75) Inventors: Roland Joseph Billedeau, Santa Clara, CA (US); Rama K. Kondru, Morris Plains, NJ (US); Francisco Javier Lopez-Tapia, Honolulu, HI (US); Yan Lou, Fremont, CA (US); Timothy D. Owens, San Carlos, CA (US); Yimin Qian, Wayne, NJ (US); Sung-Sau So, Verona, NJ (US); Kshitij C. Thakkar, Clifton, NJ (US); Jutta Wanner, Montclair, NJ (US); Omar Jose Morales, New Milford, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/472,541

(22) Filed: May 16, 2012

(65) Prior Publication Data

US 2012/0295885 A1    Nov. 22, 2012

Related U.S. Application Data

(60) Provisional application No. 61/635,470, filed on Apr. 19, 2012, provisional application No. 61/486,809, filed on May 17, 2011.

(51) Int. Cl.
*A01N 43/58* (2006.01)
*A61K 31/50* (2006.01)
*C07D 237/00* (2006.01)

(52) U.S. Cl.
USPC ......................... 514/248; 544/237

(58) Field of Classification Search
USPC ......................... 514/248; 544/237
See application file for complete search history.

(56) References Cited

U.S. PATENT DOCUMENTS

| 2010/0160303 A1 | 6/2010 | Liu et al. |
| 2010/0222325 A1 | 9/2010 | Berthel et al. |

FOREIGN PATENT DOCUMENTS

| WO | 2005/005414 | 1/2005 |
| WO | 2009/098144 | 8/2009 |
| WO | 2010/006970 | 1/2010 |

OTHER PUBLICATIONS

Skinner et al., *J. Exp. Med.* 201:1837-1852 ( 2005).
Islam and Smith, *Immunol. Rev.* 178:49-63 ( 2000).
International Search Report for PCT/EP2012/058845 dated Jul. 16, 2012.
Lindvall et al., *Immunol. Rev.* 203:200-215 ( 2005).
Singh et al., *Tetrahedron Letters* 50:15-18 ( 2009).
Jansson and Holmdahl, *Clin. Exp. Immunol.* 94:459-465 ( 1993).
Horwood et al., *J. Exp. Med.* 197:1603-1611 ( 2003).
Rosen et al., *New End. J. Med.* 333:431 ( 1995).
Khan et al., *Immunity* 3:283-299 ( 1995).
Jiang et al., *J. Org. Chem.* 69:2327-2331 ( 2004).
Vassilev et al., *J. Biol. Chem.* 274:1646-1656 ( 1998).
Yuen et al., *Tetrahedron Letters* 46:7899-7903 ( 2005).
Rastetter et al., *Annu Rev Med* 55:477-503 ( 2004).
Ellmeier et al., *J. Exp. Med.* 192:1611-1623 ( 2000).
Hunter, *Cell* 50:823-829 ( 1987).
Iida et al., *J. Org. Chem.* 70:9222-9229 ( 2005).
Pan et al., *Chem. Med. Chem.* 2:58-61 ( 2007).
Feldhahn et al., *J. Exp. Med.* 201:1837-1852 ( 2005).
Iwaki et al., *J. Biol. Chem.* 280:40261-40270 ( 2005).

*Primary Examiner* — Paul V. Ward

(57) ABSTRACT

This application discloses compounds according to generic Formula I:

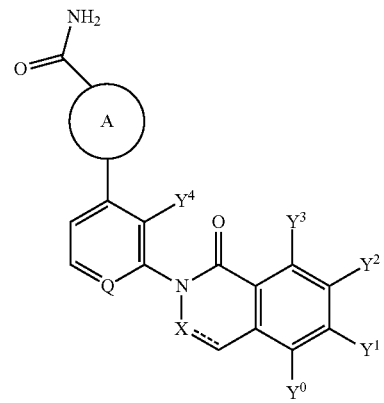

wherein all variables are defined as described herein, which inhibit Btk. The compounds disclosed herein are useful to modulate the activity of Btk and treat diseases associated with excessive Btk activity. The compounds are further useful to treat inflammatory and auto immune diseases associated with aberrant B-cell proliferation such as rheumatoid arthritis. Also disclosed are compositions containing compounds of Formula I and at least one carrier, diluent or excipient.

18 Claims, No Drawings

INHIBITORS OF BRUTON'S TYROSINE KINASE

PRIORITY TO RELATED APPLICATIONS

This application is entitled to the benefit of U.S. provisional patent application Ser. No. 61/635,470 filed on Apr. 19, 2012, and U.S. Provisional patent application Ser. No. 61/486,809 filed on May 17, 2011.

FIELD OF THE INVENTION

The present invention relates to the use of novel compounds which inhibit Btk and are useful for the treatment of auto-immune and inflammatory diseases caused by aberrant B-cell activation.

BACKGROUND OF THE INVENTION

Protein kinases constitute one of the largest families of human enzymes and regulate many different signaling processes by adding phosphate groups to proteins (T. Hunter, *Cell* 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a target to modulate cellular function with small molecular kinase inhibitors and thus make good drug design targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. *Annu Rev Med* 2004 55:477). Therefore inhibitors of the protein kinases that play a role in B-cell activation should be useful therapeutics for B-cell mediated disease pathology such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (Btk) is a non-BCR associated kinase that is membrane proximal and immediately downstream from BCR. Lack of Btk has been shown to block BCR signaling and therefore inhibition of Btk could be a useful therapeutic approach to block B-cell mediated disease processes.

Btk is a member of the Tec family of tyrosine kinases, and has been shown to be a critical regulator of early B-cell development and mature B-cell activation and survival (Khan et al. *Immunity* 1995 3:283; Ellmeier et al. *J. Exp. Med.* 2000 192:1611). Mutation of Btk in humans leads to the condition X-linked agammaglobulinemia (XLA) (reviewed in Rosen et al. *New Eng. J. Med.* 1995 333:431 and Lindvall et al. *Immunol. Rev.* 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for Btk in autoimmune and inflammatory diseases has also been provided by Btk-deficient mouse models. In preclinical murine models of systemic lupus erythematosus (SLE), Btk-deficient mice show marked amelioration of disease progression. In addition, Btk-deficient mice are resistant to collagen-induced arthritis (Jansson and Holmdahl *Clin. Exp. Immunol.* 1993 94:459). A selective Btk inhibitor has been demonstrated dose-dependent efficacy in a mouse arthritis model (Z. Pan et al., *Chem. Med Chem.* 2007 2:58-61).

Btk is also expressed by cells other than B-cells that may be involved in disease processes. For example, Btk is expressed by mast cells and Btk-deficient bone marrow derived mast cells demonstrate impaired antigen induced degranulation (Iwaki et al. *J. Biol. Chem.* 2005 280:40261). This shows Btk could be useful to treat pathological mast cells responses such as allergy and asthma. Also monocytes from XLA patients, in which Btk activity is absent, show decreased TNF alpha production following stimulation (Horwood et al. *J Exp Med* 197:1603, 2003). Therefore TNF alpha mediated inflammation could be modulated by small molecular Btk inhibitors. Also, Btk has been reported to play a role in apoptosis (Islam and Smith *Immunol. Rev.* 2000 178:49,) and thus Btk inhibitors would be useful for the treatment of certain B-cell lymphomas and leukemias (Feldhahn et al. *J. Exp. Med.* 2005 201:1837,).

SUMMARY OF THE INVENTION

The present application provides the Btk inhibitor compounds of Formula I, methods of use thereof, as described herein below:

The application provides a compound of Formula I,

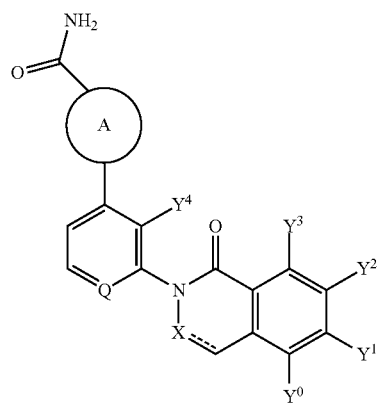

I wherein:
---- is either a single or double bond;
A is 5-membered heteroaryl or a 5,6-membered bicyclic heteroaryl, wherein the $CONH_2$ is attached to the 5-membered heteroaryl, each optionally substituted with one or more A';
A' is —NHR or $R^4$;
R is H, —$R^1$, —$R^1$-$R^2$-$R^3$, —$R^1$-$R^3$, or —$R^2$-$R^3$;
  $R^1$ is aryl, heteroaryl, cycloalkyl, heterocycloalkyl, or heteroaryl fused with a heterocycloalkyl, each of which is optionally substituted with one or more $R^{1'}$ or $R^{1''}$;
  each $R^{1'}$ is independently halo, nitro, cyano, lower alkyl sulfonamido, —$S(O)_2$, or oxo;

each $R^{1'''}$ is independently lower alkyl, cycloalkyl, heterocycloalkyl, lower alkoxy, amino, or amido, each optionally substituted with one or more $R^{1''''}$;

each $R^{1''''}$ is independently hydroxy, halo, amino, alkyl amino, dialkyl amino, or heterocycloalkyl;

$R^2$ is —C(=O), —C(=O)O, —C(=O)$NR^{2'}$, —NHC(=O)O, —C($R^{2'}$)$_2$, —O, —C(=NH)$NR^{2'}$, or —S(=O)$_2$;

each $R^{2'}$ is independently H or lower alkyl;

$R^3$ is H or $R^4$;

$R^4$ is lower alkyl, lower haloalkyl, lower alkoxy, amino, lower alkyl amino, lower dialkyl amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, heterocycloalkyl alkyl, bicyclic cycloalkyl, bicyclic heterocycloalkyl, spirocycloalkyl, or spiroheterocycloalkyl, each of which is optionally substituted with one or more lower alkyl, halo, lower alkyl amino, lower dialkyl amino, hydroxy, hydroxy lower alkyl, lower alkoxy, halo, nitro, amino, amido, acyl, cyano, oxo, guanidino, hydroxyl amino, carboxy, carbamoyl, carbamate, halo lower alkoxy, or halo lower alkyl, wherein two lower alkyl groups may together form a ring;

Q is CH or N;

X is CH, N, or N(X');

X' is lower alkyl;

$Y^0$ is H, halogen or lower alkyl;

$Y^1$ is $Y^{1a}$, $Y^{1b}$, $Y^{1c}$, or $Y^{1d}$;

$Y^{1a}$ is H or halogen;

$Y^{1b}$ is lower alkyl, optionally substituted with one or more substituents selected from the group consisting of lower haloalkyl, halogen, hydroxy, amino, cyano, and lower alkoxy;

$Y^{1c}$ is lower cycloalkyl, optionally substituted with one or more substituents selected from the group consisting of lower alkyl, lower haloalkyl, halogen, hydroxy, amino, cyano, and lower alkoxy;

$Y^{1d}$ is amino, optionally substituted with one or more lower alkyl, alkoxy lower alkyl, or hydroxy lower alkyl;

$Y^2$ is H, halogen or lower alkyl;

$Y^3$ is H, halogen, lower alkyl, lower haloalkyl, lower alkoxy, or lower hydroxy alkyl; and $Y^4$ is H, lower alkyl, or lower hydroxyalkyl;

or a pharmaceutically acceptable salt thereof.

The application provides a method for treating an inflammatory and/or autoimmune condition comprising administering to a patient in need thereof a therapeutically effective amount of the compound of Formula I.

The application provides a pharmaceutical composition comprising the compound of Formula I, admixed with at least one pharmaceutically acceptable carrier, excipient or diluent.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "-----" drawn through a bond each refer to the point of attachment of a functional group or other chemical moiety to the rest of the molecule of which it is a part. Thus, for example:

MeC(=O)$OR^4$ wherein

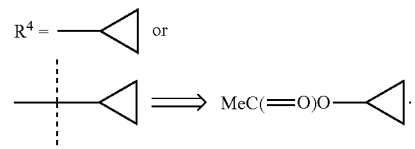

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of Formulae I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro[3.3]heptane. The term spiroheterocycloalkyl, as used herein, means a spirocyclic heterocycloalkyl, such as, for example, 2,6-diazaspiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "PCy$_3$" refers to a phosphine trisubstituted with three cyclic moieties.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" or "lower cycloalkyl" as used herein refers to a cycloalkyl composed of 3 to 7 carbons in the carbocyclic ring.

The term carboxy-alkyl as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —$CO_2H$ moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N, O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of Btk

The application provides a compound of Formula I,

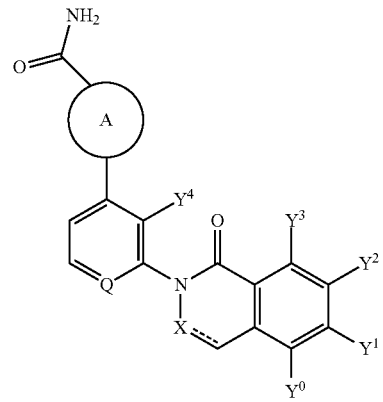

wherein:
--- is either a single or double bond;
A is 5-membered heteroaryl or a 5,6-membered bicyclic heteroaryl, wherein the $CONH_2$ is attached to the 5-membered heteroaryl, each optionally substituted with one or more A';
   A' is —NHR or $R^4$;
   R is H, —$R^1$, —$R^1$-$R^2$-$R^3$, —$R^1$-$R^3$, or —$R^2$-$R^3$;
     $R^1$ is aryl, heteroaryl, cycloalkyl, heterocycloalkyl, or heteroaryl fused with a heterocycloalkyl, each of which is optionally substituted with one or more $R^{1'}$ or $R^{1''}$;
     each $R^{1'}$ is independently halo, nitro, cyano, lower alkyl sulfonamido, —$S(O)_2$, or oxo;
     each $R^{1''}$ is independently lower alkyl, cycloalkyl, heterocycloalkyl, lower alkoxy, amino, or amido, each optionally substituted with one or more $R^{1'''}$;
     each $R^{1'''}$ is independently hydroxy, halo, amino, alkyl amino, dialkyl amino, or heterocycloalkyl;
   $R^2$ is —C(=O), —C(=O)O, —C(=O)$NR^{2'}$, —NHC(=O)O, —C($R^{2'}$)$_2$, —O, —C(=NH)$NR^{2'}$, or —$S(=O)_2$;
   each $R^{2'}$ is independently H or lower alkyl;
   $R^3$ is H or $R^4$;
   $R^4$ is lower alkyl, lower haloalkyl, lower alkoxy, amino, lower alkyl amino, lower dialkyl amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, heterocycloalkyl alkyl, bicyclic cycloalkyl, bicyclic heterocycloalkyl, spirocycloalkyl, or spiroheterocycloalkyl, each of which is optionally substituted with one or more lower alkyl, halo, lower alkyl amino, lower dialkyl amino, hydroxy, hydroxy lower alkyl, lower alkoxy, halo, nitro, amino, amido, acyl, cyano, oxo, guanidino, hydroxyl amino, carboxy, carbamoyl, carbamate, halo lower alkoxy, or halo lower alkyl, wherein two lower alkyl groups may together form a ring;
Q is CH or N;
X is CH, N, or N(X');
   X' is lower alkyl;
$Y^0$ is H, halogen or lower alkyl;
$Y^1$ is $Y^{1a}$, $Y^{1b}$, $Y^{1c}$, or $Y^{1d}$;

$Y^{1a}$ is H or halogen;

$Y^{1b}$ is lower alkyl, optionally substituted with one or more substituents selected from the group consisting of lower haloalkyl, halogen, hydroxy, amino, cyano, and lower alkoxy;

$Y^{1c}$ is lower cycloalkyl, optionally substituted with one or more substituents selected from the group consisting of lower alkyl, lower haloalkyl, halogen, hydroxy, amino, cyano, and lower alkoxy;

$Y^{1d}$ is amino, optionally substituted with one or more lower alkyl, alkoxy lower alkyl, or hydroxy lower alkyl;

$Y^2$ is H, halogen or lower alkyl;

$Y^3$ is H, halogen, lower alkyl, lower haloalkyl, lower alkoxy, or lower hydroxy alkyl; and $Y^4$ is H, lower alkyl, or lower hydroxyalkyl;

or a pharmaceutically acceptable salt thereof.

The application provides a compound of Formula I, wherein X is N.

The application provides a compound of Formula I, where Q is CH.

The application provides a compound of Formula I, where $Y^1$ is $Y^{1a}$.

The application provides a compound of Formula I, where $Y^{1a}$ is H.

The application provides a compound of Formula I, wherein $Y^1$ is lower alkyl or lower cycloalkyl.

The application provides a compound of Formula I, wherein $Y^1$ is tert-butyl, or iso-propyl, cyclopropyl, or iso-propylnitrile.

The application provides a compound of Formula I, wherein $Y^1$ is tert-butyl.

The application provides a compound of Formula I, wherein X is N and $Y^1$ is tert-butyl or cyclopropyl.

The application provides a compound of Formula I, wherein $Y^2$ is H.

The application provides a compound of Formula I, wherein $Y^3$ is H or halogen.

The application provides a compound of Formula I, wherein $Y^3$ is H or F.

The application provides a compound of Formula I, wherein $Y^0$ is H, $Y^2$ is H, $Y^3$ is F or H, and $Y^4$ is hydroxymethyl.

The application provides a compound of Formula I, wherein Q is CH, X is N, and ---- is a double bond.

The application provides a compound of Formula I, wherein A is furanyl, imidazolyl, thiazolyl, pyrrolyl, pyrazolyl, phenyl, indolyl, pyrrolo[2,3-b]pyridinyl, or oxazolyl.

The application provides a compound of Formula I, wherein $Y^1$ is tert-butyl or cyclopropyl.

The application provides a compound of Formula I, wherein $Y^3$ is F.

The application provides a compound of Formula I, wherein $Y^3$ is H or F and X is N.

The application provides a compound of Formula I, wherein $Y^3$ is H or F and $Y^1$ is tert-butyl or cyclopropyl.

The application provides a compound of Formula I, wherein $Y^3$ is H or F, X is N, and $Y^1$ is tert-butyl or cyclopropyl.

The application provides a compound of Formula I, wherein $Y^4$ is lower hydroxyalkyl.

The application provides a compound of Formula I, wherein $Y^4$ is hydroxymethyl.

The application provides a compound of Formula I, wherein A is furanyl optionally substituted with one or more A'.

The application provides a compound of Formula I, wherein $Y^3$ is H or F, X is N, and $Y^1$ is tert-butyl or cyclopropyl and A is furanyl optionally substituted with one or more A'.

The application provides a compound of Formula I, wherein A is imidazolyl optionally substituted with one or more A'.

The application provides a compound of Formula I, wherein $Y^3$ is H or F, X is N, and $Y^1$ is tert-butyl or cyclopropyl and A is imidazolyl optionally substituted with one or more A'.

The application provides a compound of Formula I, wherein A is thiazolyl optionally substituted with one or more A'.

The application provides a compound of Formula I, wherein $Y^3$ is H or F, X is N, and $Y^1$ is tert-butyl or iso-propyl and A is thiazolyl optionally substituted with one or more A'.

The application provides a compound of Formula I, wherein A is pyrrolyl optionally substituted with one or more A'.

The application provides a compound of Formula I, wherein $Y^3$ is H or F, X is N, and $Y^1$ is tert-butyl or iso-propyl and A is pyrrolyl optionally substituted with one or more A'.

The application provides a compound of Formula I, wherein A is pyrazolyl optionally substituted with one or more A'.

The application provides a compound of Formula I, wherein $Y^3$ is H or F, X is N, and $Y^1$ is tert-butyl or iso-propyl and A is pyrazolyl optionally substituted with one or more A'.

The application provides a compound of Formula I, wherein A is optionally substituted with one or more A'.

The application provides a compound of Formula I, wherein $Y^3$ is H or F, X is N, and $Y^1$ is tert-butyl or iso-propyl and A phenyl optionally substituted with one or more A'.

The application provides a compound of Formula I, wherein A is indolyl optionally substituted with one or more A'.

The application provides a compound of Formula I, wherein $Y^3$ is H or F, X is N, and $Y^1$ is tert-butyl or iso-propyl and A is indolyl optionally substituted with one or more A'.

The application provides a compound of Formula I, wherein A is pyrrolo[2,3-b]pyridinyl optionally substituted with one or more A'.

The application provides a compound of Formula I, wherein $Y^3$ is H or F, X is N, and $Y^1$ is tert-butyl or iso-propyl and A is pyrrolo[2,3-b]pyridinyl optionally substituted with one or more A'.

The application provides a compound of Formula I, wherein A is oxazolyl optionally substituted with one or more A'.

The application provides a compound of Formula I, wherein $Y^3$ is H or F, X is N, and $Y^1$ is tert-butyl or iso-propyl and A is oxazolyl optionally substituted with one or more A'.

The application provides a compound of Formula I, wherein $Y^3$ is hydroxymethyl.

The application provides a compound of Formula I, wherein $Y^3$ is hydroxymethyl, X is N, and $Y^1$ is tert-butyl or iso-propyl.

The application provides a compound of Formula I selected from the group consisting of:

4-[3-(6-tert-Butyl-1-oxo-1H-phthalazin-2-yl)-2-hydroxymethyl-phenyl]-1-methyl-1H-imidazole-2-carboxylic acid amide;

2-[3-(6-tert-Butyl-1-oxo-1H-phthalazin-2-yl)-2-hydroxymethyl-phenyl]-thiazole-4-carboxylic acid amide;

4-[3-(6-tert-Butyl-1-oxo-1H-phthalazin-2-yl)-2-hydroxymethyl-phenyl]-1H-pyrrole-2-carboxylic acid amide;

4-[3-(6-tert-Butyl-1-oxo-1H-phthalazin-2-yl)-2-hydroxymethyl-phenyl]-1-methyl-1H-pyrrole-2-carboxylic acid amide;

5-[3-(6-tert-Butyl-1-oxo-1H-phthalazin-2-yl)-2-hydroxymethyl-phenyl]-1-methyl-1H-pyrrole-2-carboxylic acid amide;

2-[3-(6-tert-Butyl-1-oxo-1H-phthalazin-2-yl)-2-hydroxymethyl-phenyl]-4-methyl-oxazole-5-carboxylic acid amide;

2-[3-(6-tert-Butyl-8-fluoro-1-oxo-1H-phthalazin-2-yl)-2-hydroxymethyl-phenyl]-thiazole-4-carboxylic acid amide;

4-[3-(6-tert-Butyl-8-fluoro-1-oxo-1H-phthalazin-2-yl)-2-hydroxymethyl-phenyl]-1-methyl-1H-imidazole-2-carboxylic acid amide;

4-[3-(6-tert-Butyl-8-fluoro-1-oxo-1H-phthalazin-2-yl)-2-hydroxymethyl-phenyl]-1-methyl-1H-pyrrole-2-carboxylic acid amide;

5-[3-(6-tert-Butyl-8-fluoro-1-oxo-1H-phthalazin-2-yl)-2-hydroxymethyl-phenyl]-furan-2-carboxylic acid amide;

4-[3-(6-tert-Butyl-8-fluoro-1-oxo-1H-phthalazin-2-yl)-2-hydroxymethyl-phenyl]-furan-2-carboxylic acid amide;

4-[3-(6-tert-Butyl-8-hydroxymethyl-1-oxo-1H-phthalazin-2-yl)-2-hydroxymethyl-phenyl]-1-methyl-1H-pyrrole-2-carboxylic acid amide;

4-[3-(6-Cyclopropyl-8-fluoro-1-oxo-1H-isoquinolin-2-yl)-2-hydroxymethyl-phenyl]-1-methyl-1H-pyrrole-2-carboxylic acid amide;

4-[3-(6-tert-Butyl-3-methyl-1-oxo-3,4-dihydro-1H-phthalazin-2-yl)-2-hydroxymethyl-phenyl]-1-methyl-1H-pyrrole-2-carboxylic acid amide;

1-[3-(6-tert-Butyl-8-fluoro-1-oxo-1H-phthalazin-2-yl)-2-hydroxymethyl-phenyl]-1H-pyrrolo[2,3-b]pyridine-3-carboxylic acid amide;

4-[2-(6-tert-Butyl-8-fluoro-1-oxo-1H-phthalazin-2-yl)-3-hydroxymethyl-pyridin-4-yl]-1-methyl-1H-pyrrole-2-carboxylic acid amide;

1-[3-(6-tert-Butyl-8-fluoro-1-oxo-1H-phthalazin-2-yl)-2-hydroxymethyl-phenyl]-1H-indole-3-carboxylic acid amide;

1-[3-(6-tert-Butyl-1-oxo-1H-phthalazin-2-yl)-2-hydroxymethyl-phenyl]-1H-indole-3-carboxylic acid amide;

1-[3-(6-tert-Butyl-1-oxo-1H-phthalazin-2-yl)-2-hydroxymethyl-phenyl]-3-[4-(morpholine-4-carbonyl)-phenylamino]-1H-pyrazole-4-carboxylic acid amide;

1-[3-(6-tert-Butyl-8-fluoro-1-oxo-1H-phthalazin-2-yl)-2-hydroxymethyl-phenyl]-3-[4-(morpholine-4-carbonyl)-phenylamino]-1H-pyrazole-4-carboxylic acid amide;

1-[3-(6-tert-Butyl-8-fluoro-1-oxo-1H-phthalazin-2-yl)-phenyl]-3-[4-(morpholine-4-carbonyl)-phenylamino]-1H-pyrazole-4-carboxylic acid amide;

1-[3-(6-tert-Butyl-8-fluoro-1-oxo-1H-phthalazin-2-yl)-2-hydroxymethyl-phenyl]-3-[4-(1-hydroxy-1-methyl-ethyl)-phenylamino]-1H-pyrazole-4-carboxylic acid amide;

1-[3-(6-tert-Butyl-8-fluoro-1-oxo-1H-phthalazin-2-yl)-2-hydroxymethyl-phenyl]-3-(5-chloro-pyridin-2-ylamino)-1H-pyrazole-4-carboxylic acid amide;

3-[5-(2-Azetidin-1-yl-1,1-dimethyl-ethoxy)-pyridin-2-ylamino]-1-[3-(6-tert-butyl-8-fluoro-1-oxo-1H-phthalazin-2-yl)-2-hydroxymethyl-phenyl]-1H-pyrazole-4-carboxylic acid amide;

1-[3-(6-tert-Butyl-8-fluoro-1-oxo-1H-phthalazin-2-yl)-2-hydroxymethyl-phenyl]-3-(5-methyl-4,5,6,7-tetrahydro-pyrazolo[1,5-c]pyrazin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(pyridin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(4-methanesulfonyl-phenylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(1-methyl-1H-pyrazol-3-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(pyrazin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(5-fluoro-pyridin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(1,5-dimethyl-1H-pyrazol-3-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(5-trifluoromethyl-pyridin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(5-methyl-pyridin-2-ylamino)-1H-pyrazole-4-carboxylic acid amide;

1-[3-(6-tert-Butyl-1-oxo-1H-phthalazin-2-yl)-2-hydroxymethyl-phenyl]-3-(1,5-dimethyl-1H-pyrazol-3-ylamino)-1H-pyrazole-4-carboxylic acid amide;

1-[3-(6-tert-Butyl-1-oxo-1H-phthalazin-2-yl)-2-hydroxymethyl-phenyl]-3-(5-fluoro-pyridin-2-ylamino)-1H-pyrazole-4-carboxylic acid amide;

1-[3-(6-tert-Butyl-1-oxo-1H-phthalazin-2-yl)-2-hydroxymethyl-phenyl]-3-(pyrazin-2-ylamino)-1H-pyrazole-4-carboxylic acid amide;

1-[3-(6-tert-Butyl-1-oxo-1H-phthalazin-2-yl)-2-hydroxymethyl-phenyl]-3-(5-methyl-pyridin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(5-methanesulfonyl-pyridin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(5-cyano-pyridin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-1H-pyrazole-3-carboxylic acid amide;

1-[3-(6-tert-Butyl-8-fluoro-1-oxo-1H-phthalazin-2-yl)-2-hydroxymethyl-phenyl]-1H-pyrazole-4-carboxylic acid amide;

7-[3-(6-tert-Butyl-8-fluoro-1-oxo-1H-phthalazin-2-yl)-2-hydroxymethyl-phenyl]-7H-pyrrolo[2,3-d]pyrimidine-5-carboxylic acid amide;

1-[3-(6-tert-Butyl-8-fluoro-1-oxo-1H-phthalazin-2-yl)-2-hydroxymethyl-phenyl]-6-(4-methyl-piperazin-1-yl)-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-morpholin-4-yl-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-(6-ethoxy-pyridin-3-yl)-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-(2-fluoro-phenyl)-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-(2-chloro-phenyl)-1H-pyrrolo[2,3-b]pyridine-3-carboxylic acid amide;

6-Bromo-1-[3-(6-tert-butyl-8-fluoro-1-oxo-1H-phthalazin-2-yl)-2-hydroxymethyl-phenyl]-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-(1,2-dihydroxy-ethyl)-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-(1,1-dioxo-1$\lambda^6$-thiomorpholin-4-yl)-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-(2-dimethylamino-ethylamino)-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-dimethylaminomethyl-1H-pyrrolo[2,3-b]pyridine-3-carboxylic acid amide;

3-(4-Acetyl-phenylamino)-1-[3-(6-tert-butyl-1-oxo-1H-phthalazin-2-yl)-2-hydroxymethyl-phenyl]-1H-pyrazole-4-carboxylic acid amide;

1-[3-(6-tert-Butyl-1-oxo-1H-phthalazin-2-yl)-2-hydroxymethyl-phenyl]-3-(pyridin-2-ylamino)-1H-pyrazole-4-carboxylic acid amide;

1-[3-(6-tert-Butyl-1-oxo-1H-phthalazin-2-yl)-2-hydroxymethyl-phenyl]-3-(5-dimethylaminomethyl-pyridin-2-ylamino)-1H-pyrazole-4-carboxylic acid amide; and 1-[3-(6-tert-Butyl-8-fluoro-1-oxo-1H-phthalazin-2-yl)-phenyl]-1H-pyrazole-4-carboxylic acid amide.

The application provides the use of the compound of Formula I as therapeutically active substance.

The application provides the use of the compound of Formula I for treating an inflammatory and/or autoimmune condition.

The application provides the use of the compound of Formula I for treating an inflammatory condition.

The application provides the use of the compound of Formula I for treating rheumatoid arthritis or asthma.

The application provides the compound of Formula I for use in the treatment of an inflammatory and/or autoimmune condition.

The application provides the compound of Formula I for use in the treatment of an inflammatory condition.

The application provides the compound of Formula I for use in the treatment of rheumatoid arthritis or asthma.

The application provides a method for treating an inflammatory and/or autoimmune condition comprising administering to a patient in need thereof a therapeutically effective amount of the compound of Formula I.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of Formula I.

The application provides a pharmaceutical composition comprising the compound of Formula I, admixed with at least one pharmaceutically acceptable carrier, excipient or diluent.

The application provides a use of the compound of Formula I in the manufacture of a medicament for the treatment of an inflammatory disorder.

The application provides a use of the compound of Formula I in the manufacture of a medicament for the treatment of an autoimmune disorder.

The application provides a use of the compound of Formula I in the manufacture of a medicament for the treatment of an inflammatory and/or autoimmune disorder.

The application provides a use of the compound of Formula I in the manufacture of a medicament for the treatment of rheumatoid arthritis or asthma.

The application provides a compound, method, or composition as described herein.

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of pyridazinone compounds according to generic Formula I:

TABLE I

| Compound | Nomenclature | Structure |
|---|---|---|
| I-1 | 4-[3-(6-tert-Butyl-1-oxo-1H-phthalazin-2-yl)-2-hydroxymethyl-phenyl]-1-methyl-1H-imidazole-2-carboxylic acid amide | 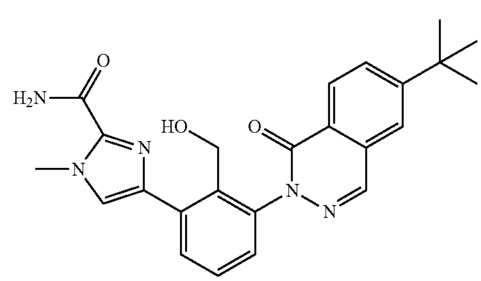 [SMILES: Cn1cc(-c2cccc(-n3ncc4cc(C(C)(C)C)ccc4c3=O)c2CO)nc1C(N)=O] |

TABLE I-continued

| Compound | Nomenclature | Structure |
|---|---|---|
| I-2 | 2-[3-(6-tert-Butyl-1-oxo-1H-phthalazin-2-yl)-2-hydroxymethyl-phenyl]-thiazole-4-carboxylic acid amide | 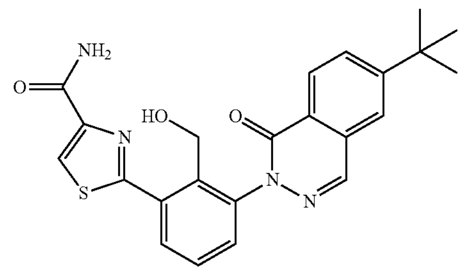 [SMILES: CC(C)(C)c1ccc2c(=O)n(-c3cccc(-c4nc(C(N)=O)cs4)c3CO)ncc2c1] |
| I-3 | 4-[3-(6-tert-Butyl-1-oxo-1H-phthalazin-2-yl)-2-hydroxymethyl-phenyl]-1H-pyrrole-2-carboxylic acid amide | 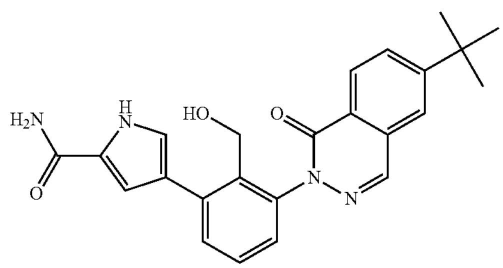 [SMILES: CC(C)(C)c1ccc2c(=O)n(-c3cccc(-c4c[nH]c(C(N)=O)c4)c3CO)ncc2c1] |
| I-4 | 4-[3-(6-tert-Butyl-1-oxo-1H-phthalazin-2-yl)-2-hydroxymethyl-phenyl]-1-methyl-1H-pyrrole-2-carboxylic acid amide | 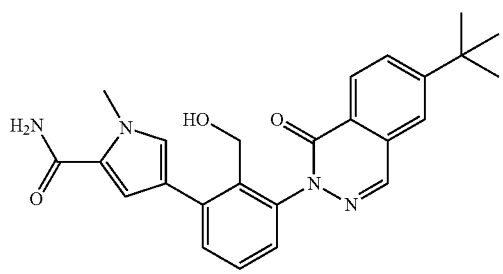 [SMILES: Cn1cc(-c2cccc(-n3ncc4cc(C(C)(C)C)ccc4c3=O)c2CO)cc1C(N)=O] |
| I-5 | 5-[3-(6-tert-Butyl-1-oxo-1H-phthalazin-2-yl)-2-hydroxymethyl-phenyl]-1-methyl-1H-pyrrole-2-carboxylic acid amide | 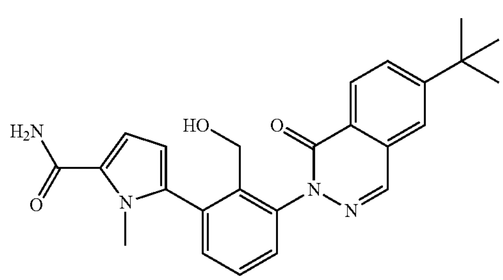 [SMILES: Cn1c(C(N)=O)ccc1-c1cccc(-n2ncc3cc(C(C)(C)C)ccc3c2=O)c1CO] |
| I-6 | 2-[3-(6-tert-Butyl-1-oxo-1H-phthalazin-2-yl)-2-hydroxymethyl-phenyl]-4-methyl-oxazole-5-carboxylic acid amide | 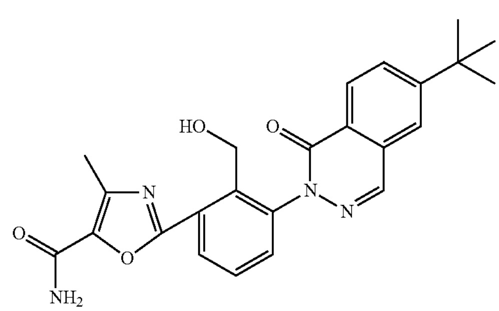 [SMILES: Cc1nc(-c2cccc(-n3ncc4cc(C(C)(C)C)ccc4c3=O)c2CO)oc1C(N)=O] |

TABLE I-continued

| Compound | Nomenclature | Structure |
|---|---|---|
| I-7 | 2-[3-(6-tert-Butyl-8-fluoro-1-oxo-1H-phthalazin-2-yl)-2-hydroxymethyl-phenyl]-thiazole-4-carboxylic acid amide | 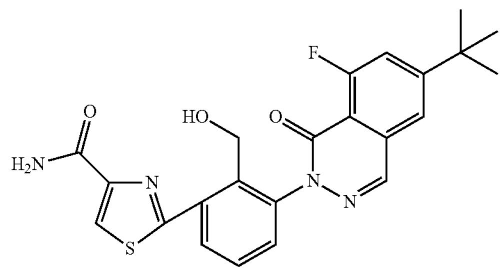 [SMILES: CC(C)(C)c1cc(F)c2c(=O)n(-c3cccc(-c4nc(C(N)=O)cs4)c3CO)ncc2c1] |
| I-8 | 4-[3-(6-tert-Butyl-8-fluoro-1-oxo-1H-phthalazin-2-yl)-2-hydroxymethyl-phenyl]-1-methyl-1H-imidazole-2-carboxylic acid amide | 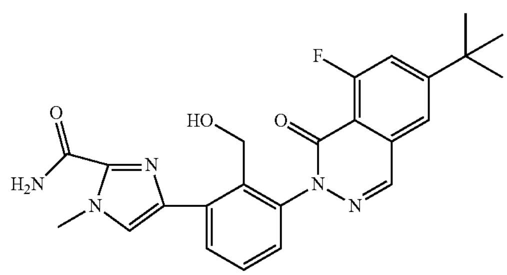 [SMILES: Cn1cc(-c2cccc(-n3ncc4cc(C(C)(C)C)cc(F)c4c3=O)c2CO)nc1C(N)=O] |
| I-9 | 4-[3-(6-tert-Butyl-8-fluoro-1-oxo-1H-phthalazin-2-yl)-2-hydroxymethyl-phenyl]-1-methyl-1H-pyrrole-2-carboxylic acid amide | 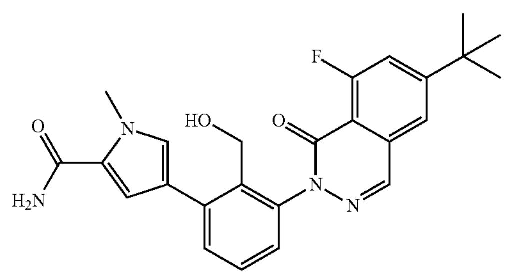 [SMILES: Cn1cc(-c2cccc(-n3ncc4cc(C(C)(C)C)cc(F)c4c3=O)c2CO)cc1C(N)=O] |
| I-10 | 5-[3-(6-tert-Butyl-8-fluoro-1-oxo-1H-phthalazin-2-yl)-2-hydroxymethyl-phenyl]-furan-2-carboxylic acid amide | 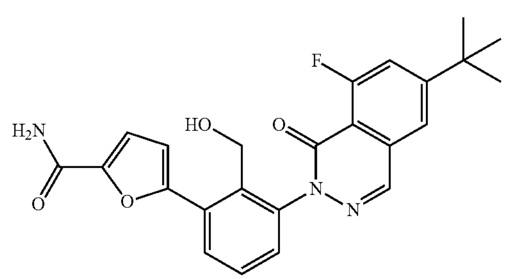 [SMILES: CC(C)(C)c1cc(F)c2c(=O)n(-c3cccc(-c4ccc(C(N)=O)o4)c3CO)ncc2c1] |
| I-11 | 4-[3-(6-tert-Butyl-8-fluoro-1-oxo-1H-phthalazin-2-yl)-2-hydroxymethyl-phenyl]-furan-2-carboxylic acid amide | 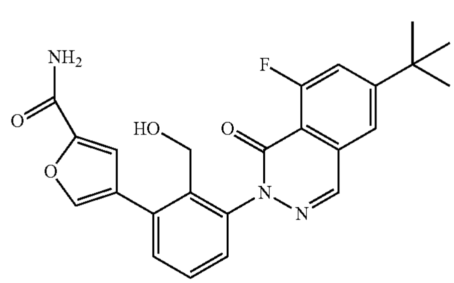 [SMILES: CC(C)(C)c1cc(F)c2c(=O)n(-c3cccc(-c4coc(C(N)=O)c4)c3CO)ncc2c1] |

TABLE I-continued

| Compound | Nomenclature | Structure |
| --- | --- | --- |
| I-12 | 4-[3-(6-tert-Butyl-8-hydroxymethyl-1-oxo-1H-phthalazin-2-yl)-2-hydroxymethyl-phenyl]-1-methyl-1H-pyrrole-2-carboxylic acid amide | 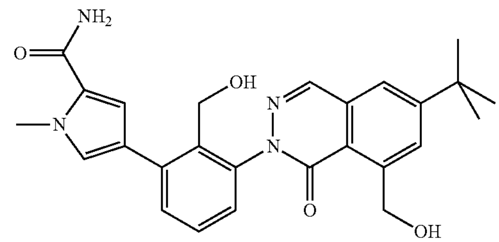 [SMILES: Cn1cc(-c2cccc(-n3ncc4cc(C(C)(C)C)cc(CO)c4c3=O)c2CO)cc1C(N)=O] |
| I-13 | 4-[3-(6-Cyclopropyl-8-fluoro-1-oxo-1H-isoquinolin-2-yl)-2-hydroxymethyl-phenyl]-1-methyl-1H-pyrrole-2-carboxylic acid amide | 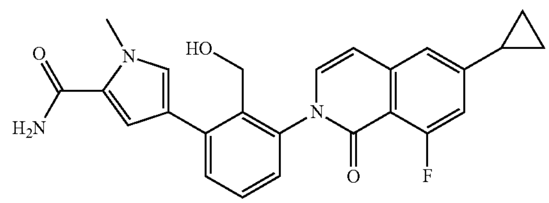 [SMILES: Cn1cc(-c2cccc(-n3ccc4cc(C5CC5)cc(F)c4c3=O)c2CO)cc1C(N)=O] |
| I-14 | 4-[3-(6-tert-Butyl-3-methyl-1-oxo-3,4-dihydro-1H-phthalazin-2-yl)-2-hydroxymethyl-phenyl]-1-methyl-1H-pyrrole-2-carboxylic acid amide | 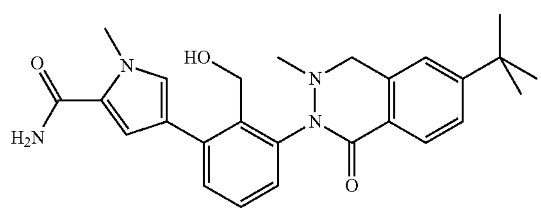 [SMILES: CN1Cc2cc(C(C)(C)C)ccc2C(=O)N1c1cccc(-c2cc(C(N)=O)n(C)c2)c1CO] |
| I-15 | 1-[3-(6-tert-Butyl-8-fluoro-1-oxo-1H-phthalazin-2-yl)-2-hydroxymethyl-phenyl]-1H-pyrrolo[2,3-b]pyridine-3-carboxylic acid amide | 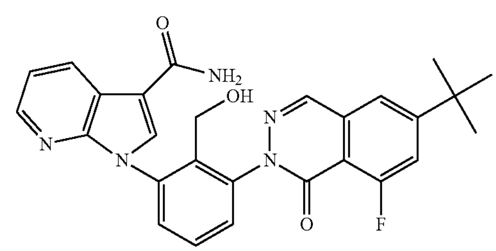 [SMILES: CC(C)(C)c1cc(F)c2c(=O)n(-c3cccc(-n4cc(C(N)=O)c5cccnc54)c3CO)ncc2c1] |
| I-16 | 4-[2-(6-tert-Butyl-8-fluoro-1-oxo-1H-phthalazin-2-yl)-3-hydroxymethyl-pyridin-4-yl]-1-methyl-1H-pyrrole-2-carboxylic acid amide | 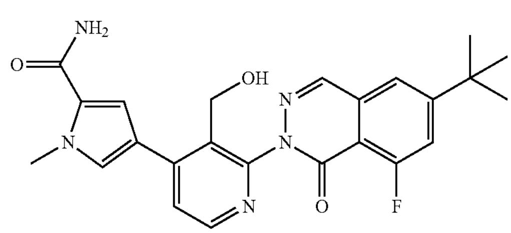 [SMILES: Cn1cc(-c2ccnc(-n3ncc4cc(C(C)(C)C)cc(F)c4c3=O)c2CO)cc1C(N)=O] |
| I-17 | 1-[3-(6-tert-Butyl-8-fluoro-1-oxo-1H-phthalazin-2-yl)-2-hydroxymethyl-phenyl]-1H-indole-3-carboxylic acid amide | 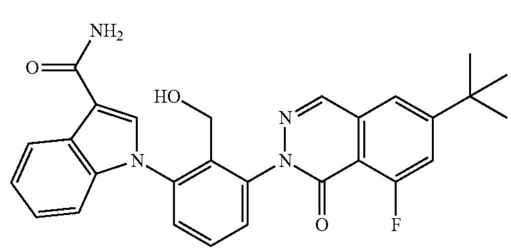 [SMILES: CC(C)(C)c1cc(F)c2c(=O)n(-c3cccc(-n4cc(C(N)=O)c5ccccc54)c3CO)ncc2c1] |

TABLE I-continued

| Compound | Nomenclature | Structure |
|---|---|---|
| I-18 | 1-[3-(6-tert-Butyl-1-oxo-1H-phthalazin-2-yl)-2-hydroxymethyl-phenyl]-1H-indole-3-carboxylic acid amide | 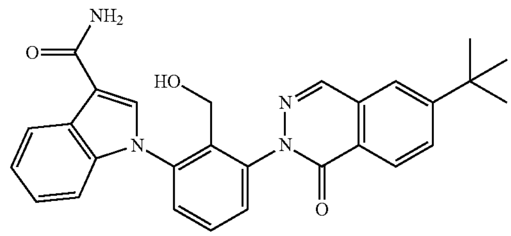 [SMILES: CC(C)(C)c1ccc2c(=O)n(-c3cccc(-n4cc(C(N)=O)c5ccccc54)c3CO)ncc2c1] |
| I-19 | 1-[3-(6-tert-Butyl-1-oxo-1H-phthalazin-2-yl)-2-hydroxymethyl-phenyl]-3-[4-(morpholine-4-carbonyl)-phenylamino]-1H-pyrazole-4-carboxylic acid amide | 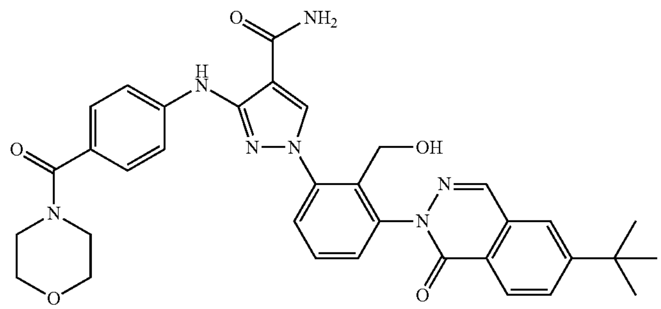 [SMILES: CC(C)(C)c1ccc2c(=O)n(-c3cccc(-n4cc(C(N)=O)c(Nc5ccc(C(=O)N6CCOCC6)cc5)n4)c3CO)ncc2c1] |
| I-20 | 1-[3-(6-tert-Butyl-8-fluoro-1-oxo-1H-phthalazin-2-yl)-2-hydroxymethyl-phenyl]-3-[4-(morpholine-4-carbonyl)-phenylamino]-1H-pyrazole-4-carboxylic acid amide | 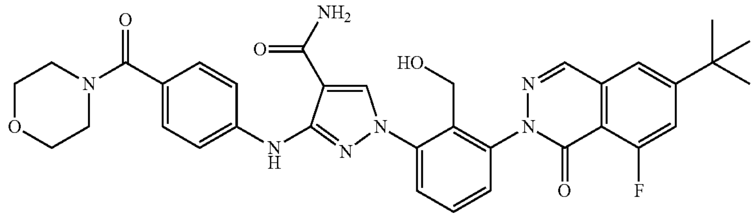 [SMILES: CC(C)(C)c1cc(F)c2c(=O)n(-c3cccc(-n4cc(C(N)=O)c(Nc5ccc(C(=O)N6CCOCC6)cc5)n4)c3CO)ncc2c1] |
| I-21 | 1-[3-(6-tert-Butyl-8-fluoro-1-oxo-1H-phthalazin-2-yl)-phenyl]-3-[4-(morpholine-4-carbonyl)-phenylamino]-1H-pyrazole-4-carboxylic acid amide | 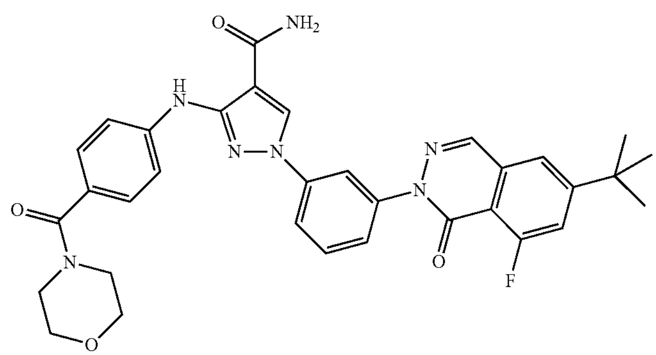 [SMILES: CC(C)(C)c1cc(F)c2c(=O)n(-c3cccc(-n4cc(C(N)=O)c(Nc5ccc(C(=O)N6CCOCC6)cc5)n4)c3)ncc2c1] |
| I-22 | 1-[3-(6-tert-Butyl-8-fluoro-1-oxo-1H-phthalazin-2-yl)-2-hydroxymethyl-phenyl]-3-[4-(1-hydroxy-1-methyl-ethyl)-phenylamino]-1H-pyrazole-4-carboxylic acid amide | 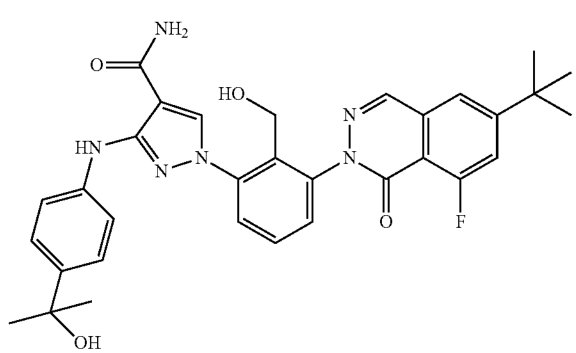 [SMILES: CC(C)(C)c1cc(F)c2c(=O)n(-c3cccc(-n4cc(C(N)=O)c(Nc5ccc(C(C)(C)O)cc5)n4)c3CO)ncc2c1] |

TABLE I-continued

| Compound | Nomenclature | Structure |
|---|---|---|
| I-23 | 1-[3-(6-tert-Butyl-8-fluoro-1-oxo-1H-phthalazin-2-yl)-2-hydroxymethyl-phenyl]-3-(5-chloro-pyridin-2-ylamino)-1H-pyrazole-4-carboxylic acid amide | 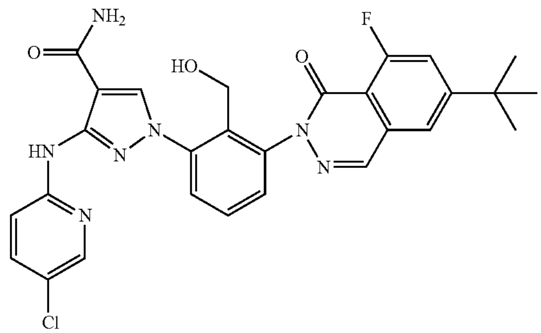 [SMILES: CC(C)(C)c1cc(F)c2c(=O)n(-c3cccc(-n4cc(C(N)=O)c(Nc5ccc(Cl)cn5)n4)c3CO)ncc2c1] |
| I-24 | 3-[5-(2-Azetidin-1-yl-1,1-dimethyl-ethoxy)-pyridin-2-ylamino]-1-[3-(6-tert-butyl-8-fluoro-1-oxo-1H-phthalazin-2-yl)-2-hydroxymethyl-phenyl]-1H-pyrazole-4-carboxylic acid amide | 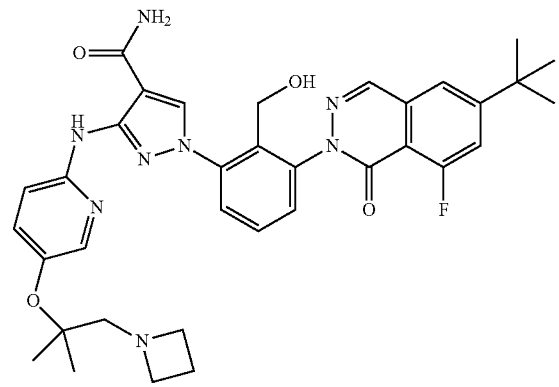 [SMILES: CC(C)(CN1CCC1)Oc1ccc(Nc2nn(-c3cccc(-n4ncc5cc(C(C)(C)C)cc(F)c5c4=O)c3CO)cc2C(N)=O)nc1] |
| I-25 | 1-[3-(6-tert-Butyl-8-fluoro-1-oxo-1H-phthalazin-2-yl)-2-hydroxymethyl-phenyl]-3-(5-methyl-4,5,6,7-tetrahydro-pyrazolo[1,5-a]pyrazin-2-ylamino)-1H-pyrazole-4-carboxylic acid amide | 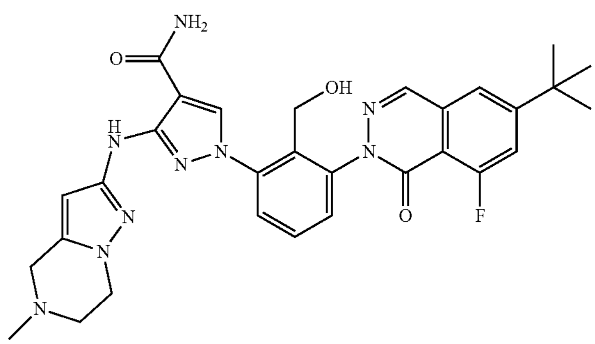 [SMILES: CN1CCn2nc(Nc3nn(-c4cccc(-n5ncc6cc(C(C)(C)C)cc(F)c6c5=O)c4CO)cc3C(N)=O)cc2C1] |
| I-26 | 1-[3-(6-tert-Butyl-8-fluoro-1-oxo-1H-phthalazin-2-yl)-2-hydroxymethyl-phenyl]-3-(pyridin-2-ylamino)-1H-pyrazole-4-carboxylic acid amide | 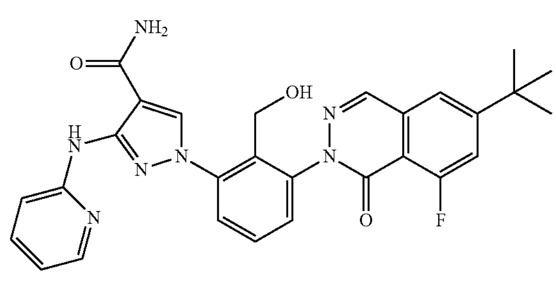 [SMILES: CC(C)(C)c1cc(F)c2c(=O)n(-c3cccc(-n4cc(C(N)=O)c(Nc5ccccn5)n4)c3CO)ncc2c1] |

TABLE I-continued

| Compound | Nomenclature | Structure |
|---|---|---|
| I-27 | 1-[3-(6-tert-Butyl-8-fluoro-1-oxo-1H-phthalazin-2-yl)-2-hydroxymethyl-phenyl]-3-(4-methanesulfonyl-phenylamino)-1H-pyrazole-4-carboxylic acid amide | 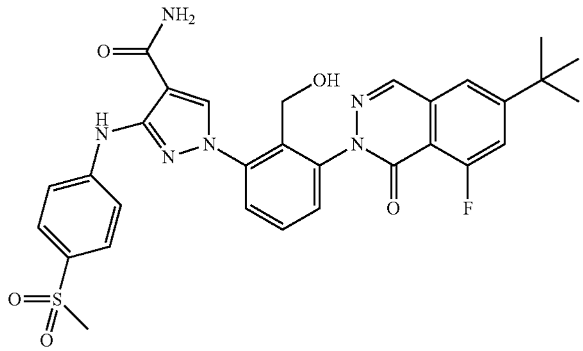 [SMILES: CC(C)(C)c1cc(F)c2c(=O)n(-c3cccc(-n4cc(C(N)=O)c(Nc5ccc(S(C)(=O)=O)cc5)n4)c3CO)ncc2c1] |
| I-28 | 1-[3-(6-tert-Butyl-8-fluoro-1-oxo-1H-phthalazin-2-yl)-2-hydroxymethyl-phenyl]-3-(1-methyl-1H-pyrazol-3-ylamino)-1H-pyrazole-4-carboxylic acid amide | 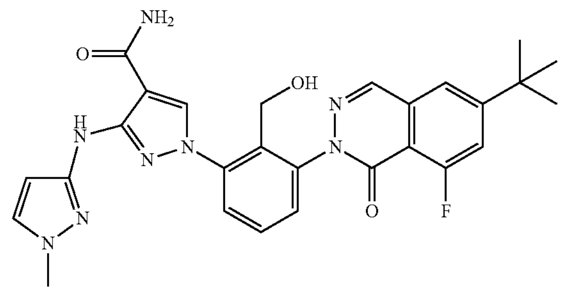 [SMILES: Cn1ccc(Nc2nn(-c3cccc(-n4ncc5cc(C(C)(C)C)cc(F)c5c4=O)c3CO)cc2C(N)=O)n1] |
| I-29 | 1-[3-(6-tert-Butyl-8-fluoro-1-oxo-1H-phthalazin-2-yl)-2-hydroxymethyl-phenyl]-3-(pyrazin-2-ylamino)-1H-pyrazole-4-carboxylic acid amide | 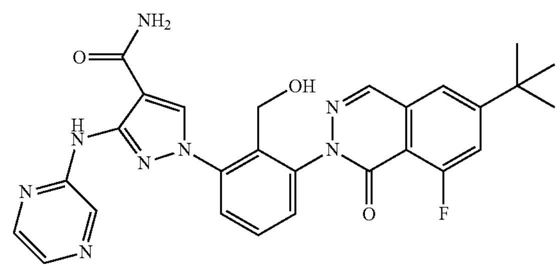 [SMILES: CC(C)(C)c1cc(F)c2c(=O)n(-c3cccc(-n4cc(C(N)=O)c(Nc5cnccn5)n4)c3CO)ncc2c1] |
| I-30 | 1-[3-(6-tert-Butyl-8-fluoro-1-oxo-1H-phthalazin-2-yl)-2-hydroxymethyl-phenyl]-3-(5-fluoro-pyridin-2-ylamino)-1H-pyrazole-4-carboxylic acid amide | 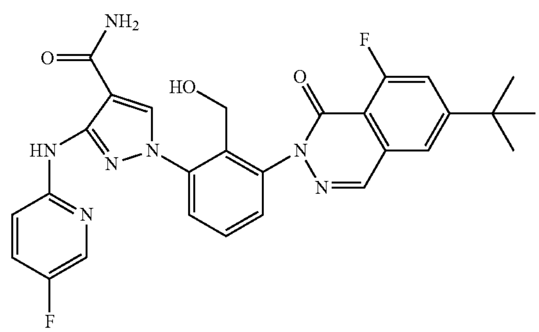 [SMILES: CC(C)(C)c1cc(F)c2c(=O)n(-c3cccc(-n4cc(C(N)=O)c(Nc5ccc(F)cn5)n4)c3CO)ncc2c1] |
| I-31 | 1-[3-(6-tert-Butyl-8-fluoro-1-oxo-1H-phthalazin-2-yl)-2-hydroxymethyl-phenyl]-3-(1,5-dimethyl-1H-pyrazol-3-ylamino)-1H-pyrazole-4-carboxylic acid amide | 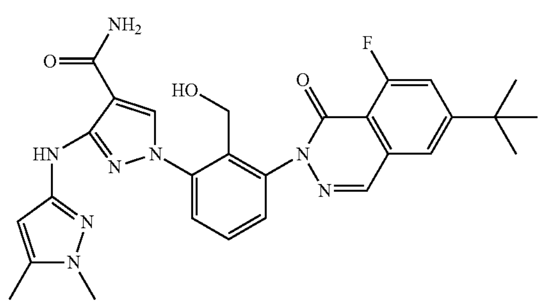 [SMILES: Cc1cc(Nc2nn(-c3cccc(-n4ncc5cc(C(C)(C)C)cc(F)c5c4=O)c3CO)cc2C(N)=O)nn1C] |

TABLE I-continued

| Compound | Nomenclature | Structure |
|---|---|---|
| I-32 | 1-[3-(6-tert-Butyl-8-fluoro-1-oxo-1H-phthalazin-2-yl)-2-hydroxymethyl-phenyl]-3-(5-trifluoromethyl-pyridin-2-ylamino)-1H-pyrazole-4-carboxylic acid amide | 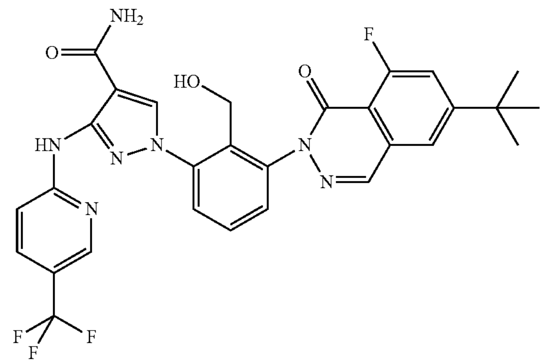 [SMILES: CC(C)(C)c1cc(F)c2c(=O)n(-c3cccc(-n4cc(C(N)=O)c(Nc5ccc(C(F)(F)F)cn5)n4)c3CO)ncc2c1] |
| I-33 | 1-[3-(6-tert-Butyl-8-fluoro-1-oxo-1H-phthalazin-2-yl)-2-hydroxymethyl-phenyl]-3-(5-methyl-pyridin-2-ylamino)-1H-pyrazole-4-carboxylic acid amide | 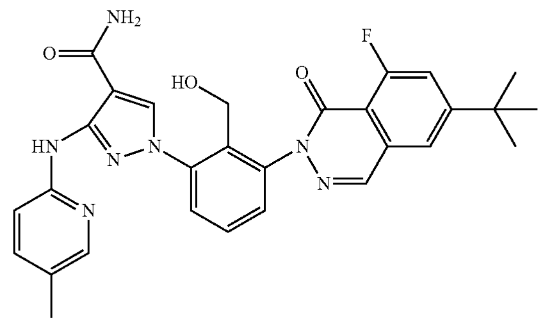 [SMILES: Cc1ccc(Nc2nn(-c3cccc(-n4ncc5cc(C(C)(C)C)cc(F)c5c4=O)c3CO)cc2C(N)=O)nc1] |
| I-34 | 1-[3-(6-tert-Butyl-1-oxo-1H-phthalazin-2-yl)-2-hydroxymethyl-phenyl]-3-(1,5-dimethyl-1H-pyrazol-3-ylamino)-1H-pyrazole-4-carboxylic acid amide | 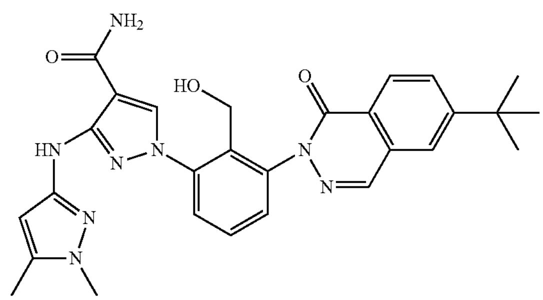 [SMILES: Cc1cc(Nc2nn(-c3cccc(-n4ncc5cc(C(C)(C)C)ccc5c4=O)c3CO)cc2C(N)=O)nn1C] |
| I-35 | 1-[3-(6-tert-Butyl-1-oxo-1H-phthalazin-2-yl)-2-hydroxymethyl-phenyl]-3-(5-fluoro-pyridin-2-ylamino)-1H-pyrazole-4-carboxylic acid amide | 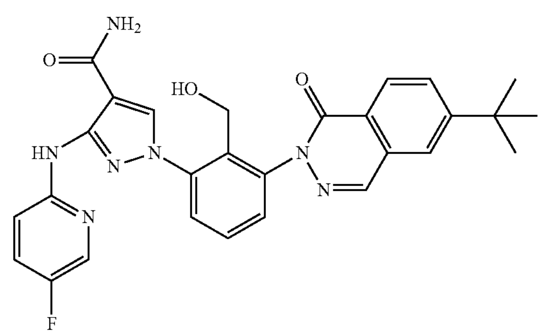 [SMILES: CC(C)(C)c1ccc2c(=O)n(-c3cccc(-n4cc(C(N)=O)c(Nc5ccc(F)cn5)n4)c3CO)ncc2c1] |
| I-36 | 1-[3-(6-tert-Butyl-1-oxo-1H-phthalazin-2-yl)-2-hydroxymethyl-phenyl]-3-(pyrazin-2-ylamino)-1H-pyrazole-4-carboxylic acid amide | 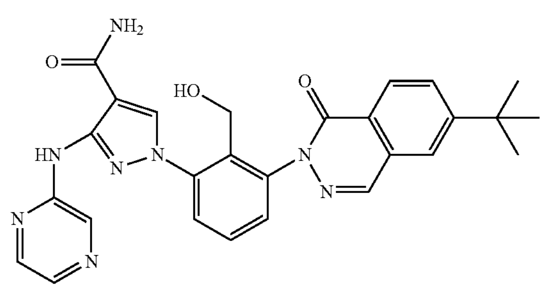 [SMILES: CC(C)(C)c1ccc2c(=O)n(-c3cccc(-n4cc(C(N)=O)c(Nc5cnccn5)n4)c3CO)ncc2c1] |

TABLE I-continued

| Compound | Nomenclature | Structure |
|---|---|---|
| I-37 | 1-[3-(6-tert-Butyl-1-oxo-1H-phthalazin-2-yl)-2-hydroxymethyl-phenyl]-3-(5-methyl-pyridin-2-ylamino)-1H-pyrazole-4-carboxylic acid amide | 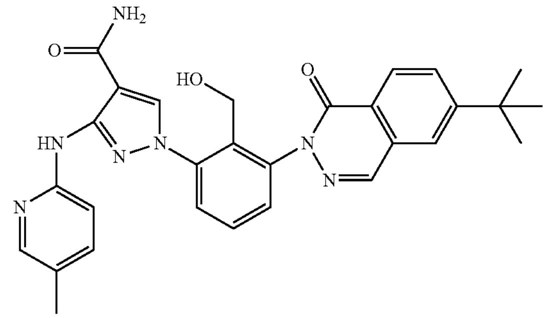 [SMILES: Cc1ccc(Nc2nn(-c3cccc(-n4ncc5cc(C(C)(C)C)ccc5c4=O)c3CO)cc2C(N)=O)nc1] |
| I-38 | 1-[3-(6-tert-Butyl-8-fluoro-1-oxo-1H-phthalazin-2-yl)-2-hydroxymethyl-phenyl]-3-(5-methanesulfonyl-pyridin-2-ylamino)-1H-pyrazole-4-carboxylic acid amide | 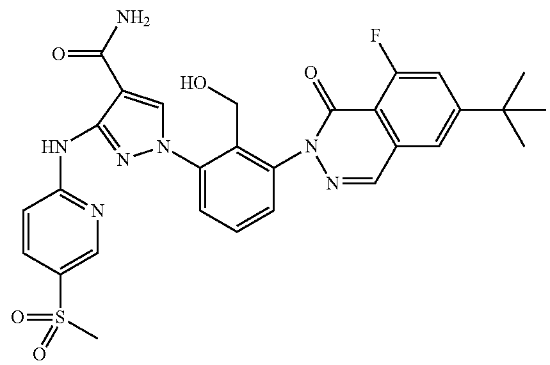 [SMILES: CC(C)(C)c1cc(F)c2c(=O)n(-c3cccc(-n4cc(C(N)=O)c(Nc5ccc(S(C)(=O)=O)cn5)n4)c3CO)ncc2c1] |
| I-39 | 1-[3-(6-tert-Butyl-8-fluoro-1-oxo-1H-phthalazin-2-yl)-2-hydroxymethyl-phenyl]-3-(5-cyano-pyridin-2-ylamino)-1H-pyrazole-4-carboxylic acid amide | 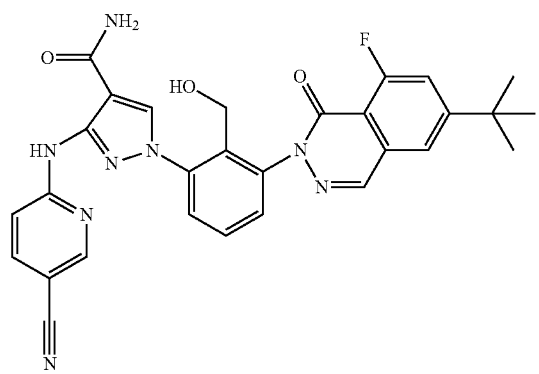 [SMILES: CC(C)(C)c1cc(F)c2c(=O)n(-c3cccc(-n4cc(C(N)=O)c(Nc5ccc(C#N)cn5)n4)c3CO)ncc2c1] |
| I-40 | 1-[3-(6-tert-Butyl-8-fluoro-1-oxo-1H-phthalazin-2-yl)-2-hydroxymethyl-phenyl]-1H-pyrazole-3-carboxylic acid amide | 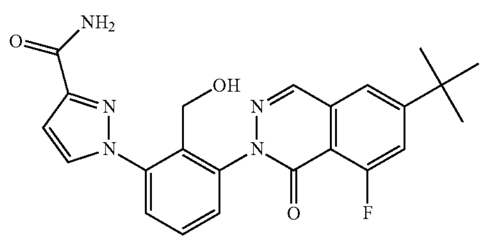 [SMILES: CC(C)(C)c1cc(F)c2c(=O)n(-c3cccc(-n4ccc(C(N)=O)n4)c3CO)ncc2c1] |
| I-41 | 1-[3-(6-tert-Butyl-8-fluoro-1-oxo-1H-phthalazin-2-yl)-2-hydroxymethyl-phenyl]-1H-pyrazole-4-carboxylic acid amide | 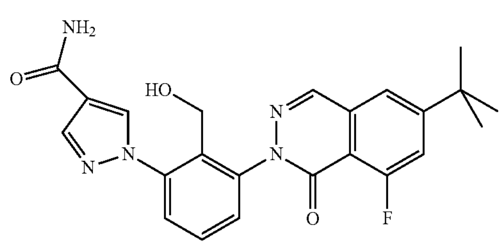 [SMILES: CC(C)(C)c1cc(F)c2c(=O)n(-c3cccc(-n4cc(C(N)=O)cn4)c3CO)ncc2c1] |

TABLE I-continued

| Compound | Nomenclature | Structure |
|---|---|---|
| I-42 | 7-[3-(6-tert-Butyl-8-fluoro-1-oxo-1H-phthalazin-2-yl)-2-hydroxymethyl-phenyl]-7H-pyrrolo[2,3-d]pyrimidine-5-carboxylic acid amide | 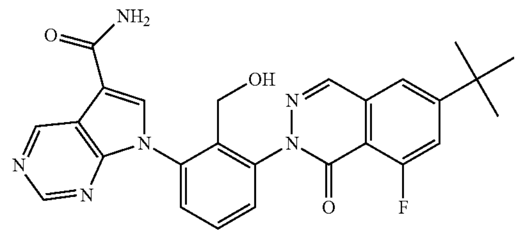 [SMILES: CC(C)(C)c1cc(F)c2c(=O)n(-c3cccc(-n4cc(C(N)=O)c5cncnc54)c3CO)ncc2c1] |
| I-43 | 1-[3-(6-tert-Butyl-8-fluoro-1-oxo-1H-phthalazin-2-yl)-2-hydroxymethyl-phenyl]-6-(4-methyl-piperazin-1-yl)-1H-pyrrolo[2,3-b]pyridine-3-carboxylic acid amide | 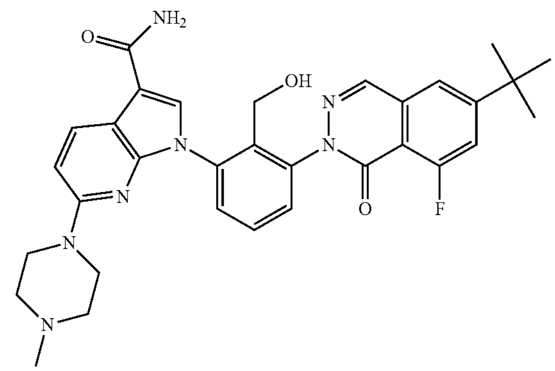 [SMILES: CN1CCN(c2ccc3c(C(N)=O)cn(-c4cccc(-n5ncc6cc(C(C)(C)C)cc(F)c6c5=O)c4CO)c3n2)CC1] |
| I-44 | 1-[3-(6-tert-Butyl-8-fluoro-1-oxo-1H-phthalazin-2-yl)-2-hydroxymethyl-phenyl]-6-morpholin-4-yl-1H-pyrrolo[2,3-b]pyridine-3-carboxylic acid amide | 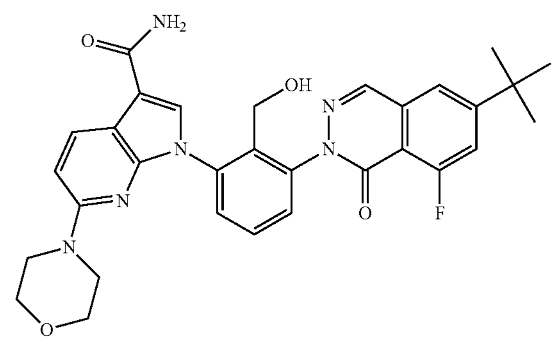 [SMILES: CC(C)(C)c1cc(F)c2c(=O)n(-c3cccc(-n4cc(C(N)=O)c5ccc(N6CCOCC6)nc54)c3CO)ncc2c1] |
| I-45 | 1-[3-(6-tert-Butyl-8-fluoro-1-oxo-1H-phthalazin-2-yl)-2-hydroxymethyl-phenyl]-6-(6-ethoxy-pyridin-3-yl)-1H-pyrrolo[2,3-b]pyridine-3-carboxylic acid amide | 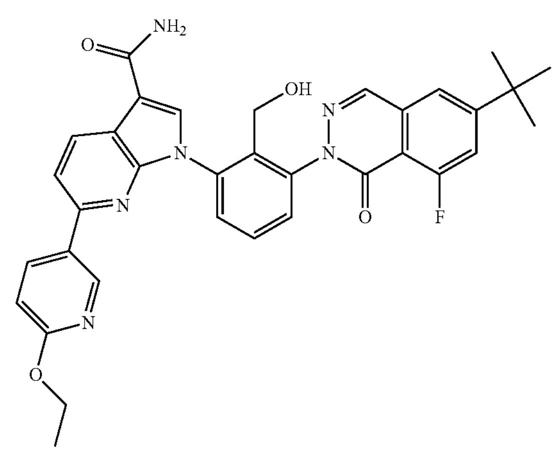 [SMILES: CCOc1ccc(-c2ccc3c(C(N)=O)cn(-c4cccc(-n5ncc6cc(C(C)(C)C)cc(F)c6c5=O)c4CO)c3n2)cn1] |

TABLE I-continued

| Compound | Nomenclature | Structure |
|---|---|---|
| I-46 | 1-[3-(6-tert-Butyl-8-fluoro-1-oxo-1H-phthalazin-2-yl)-2-hydroxymethyl-phenyl]-6-(2-fluoro-phenyl)-1H-pyrrolo[2,3-b]pyridine-3-carboxylic acid amide | 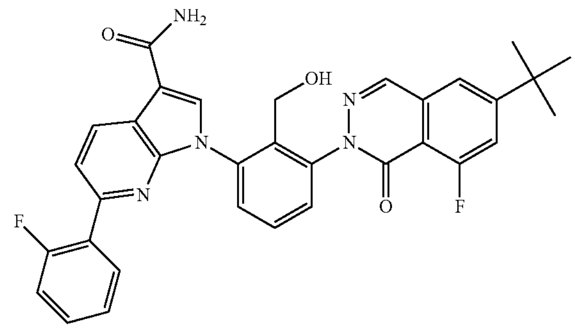 [SMILES: CC(C)(C)c1cc(F)c2c(=O)n(-c3cccc(-n4cc(C(N)=O)c5ccc(-c6ccccc6F)nc54)c3CO)ncc2c1] |
| I-47 | 1-[3-(6-tert-Butyl-8-fluoro-1-oxo-1H-phthalazin-2-yl)-2-hydroxymethyl-phenyl]-6-(2-chloro-phenyl)-1H-pyrrolo[2,3-b]pyridine-3-carboxylic acid amide | 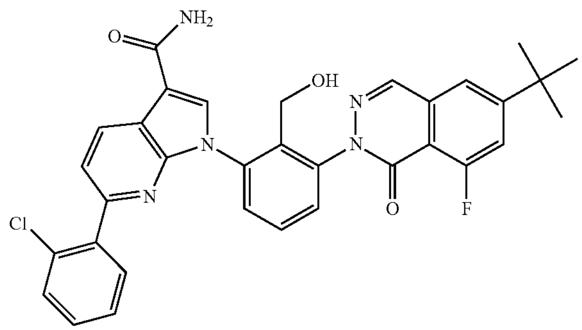 [SMILES: CC(C)(C)c1cc(F)c2c(=O)n(-c3cccc(-n4cc(C(N)=O)c5ccc(-c6ccccc6Cl)nc54)c3CO)ncc2c1] |
| I-48 | 6-Bromo-1-[3-(6-tert-butyl-8-fluoro-1-oxo-1H-phthalazin-2-yl)-2-hydroxymethyl-phenyl]-1H-pyrrolo[2,3-b]pyridine-3-carboxylic acid amide | 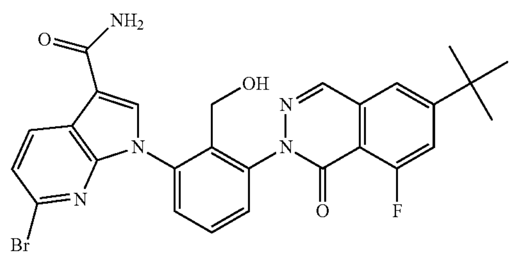 [SMILES: CC(C)(C)c1cc(F)c2c(=O)n(-c3cccc(-n4cc(C(N)=O)c5ccc(Br)nc54)c3CO)ncc2c1] |
| I-49 | 1-[3-(6-tert-Butyl-8-fluoro-1-oxo-1H-phthalazin-2-yl)-2-hydroxymethyl-phenyl]-6-(1,2-dihydroxy-ethyl)-1H-pyrrolo[2,3-b]pyridine-3-carboxylic acid amide | 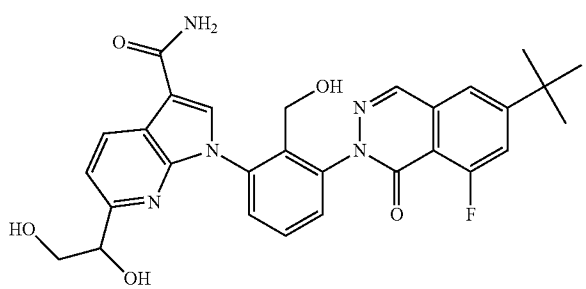 [SMILES: CC(C)(C)c1cc(F)c2c(=O)n(-c3cccc(-n4cc(C(N)=O)c5ccc(C(O)CO)nc54)c3CO)ncc2c1] |
| I-50 | 1-[3-(6-tert-Butyl-8-fluoro-1-oxo-1H-phthalazin-2-yl)-2-hydroxymethyl-phenyl]-6-(1,1-dioxo-1$\lambda^6$-thiomorpholin-4-yl)-1H-pyrrolo[2,3-b]pyridine-3-carboxylic acid amide | 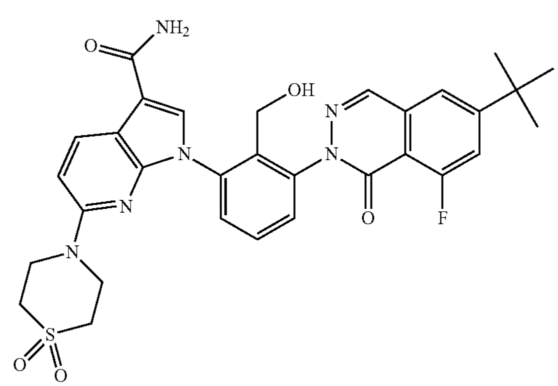 [SMILES: CC(C)(C)c1cc(F)c2c(=O)n(-c3cccc(-n4cc(C(N)=O)c5ccc(N6CCS(=O)(=O)CC6)nc54)c3CO)ncc2c1] |

TABLE I-continued

| Compound | Nomenclature | Structure |
|---|---|---|
| I-51 | 1-[3-(6-tert-Butyl-8-fluoro-1-oxo-1H-phthalazin-2-yl)-2-hydroxymethyl-phenyl]-6-(2-dimethylamino-ethylamino)-1H-pyrrolo[2,3-b]pyridine-3-carboxylic acid amide | 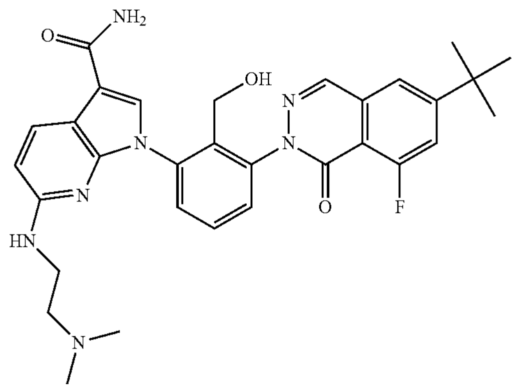 [SMILES: CN(C)CCNc1ccc2c(C(N)=O)cn(-c3cccc(-n4ncc5cc(C(C)(C)C)cc(F)c5c4=O)c3CO)c2n1] |
| I-52 | 1-[3-(6-tert-Butyl-8-fluoro-1-oxo-1H-phthalazin-2-yl)-2-hydroxymethyl-phenyl]-6-dimethylaminomethyl-1H-pyrrolo[2,3-b]pyridine-3-carboxylic acid amide | 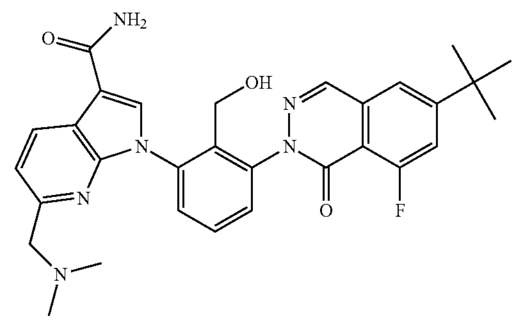 [SMILES: CN(C)Cc1ccc2c(C(N)=O)cn(-c3cccc(-n4ncc5cc(C(C)(C)C)cc(F)c5c4=O)c3CO)c2n1] |
| I-53 | 3-(4-Acetyl-phenylamino)-1-[3-(6-tert-butyl-1-oxo-1H-phthalazin-2-yl)-2-hydroxymethyl-phenyl]-1H-pyrazole-4-carboxylic acid amide | 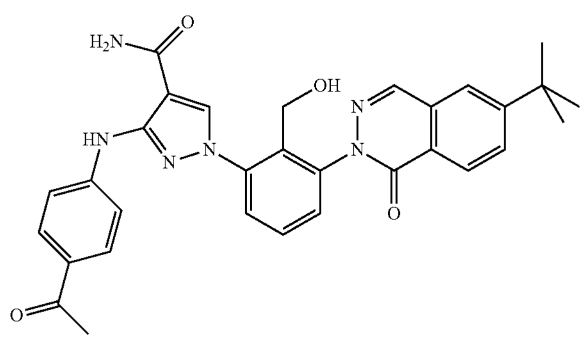 [SMILES: CC(=O)c1ccc(Nc2nn(-c3cccc(-n4ncc5cc(C(C)(C)C)ccc5c4=O)c3CO)cc2C(N)=O)cc1] |
| I-54 | 1-[3-(6-tert-Butyl-1-oxo-1H-phthalazin-2-yl)-2-hydroxymethyl-phenyl]-3-(pyridin-2-ylamino)-1H-pyrazole-4-carboxylic acid amide | 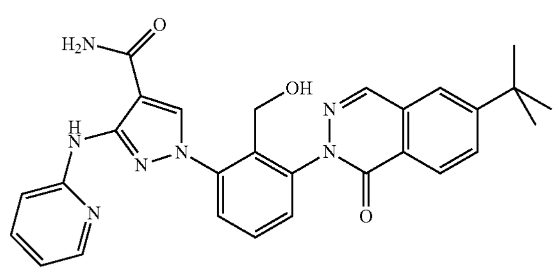 [SMILES: CC(C)(C)c1ccc2c(=O)n(-c3cccc(-n4cc(C(N)=O)c(Nc5ccccn5)n4)c3CO)ncc2c1] |

TABLE I-continued

| Compound | Nomenclature | Structure |
|---|---|---|
| I-55 | 1-[3-(6-tert-Butyl-1-oxo-1H-phthalazin-2-yl)-2-hydroxymethyl-phenyl]-3-(5-dimethylaminomethyl-pyridin-2-ylamino)-1H-pyrazole-4-carboxylic acid amide | 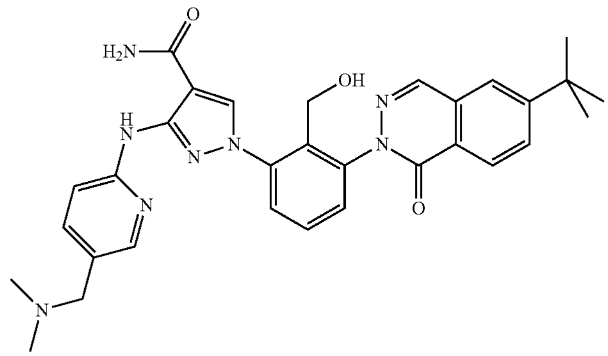 [SMILES: CN(C)Cc1ccc(Nc2nn(-c3cccc(-n4ncc5cc(C(C)(C)C)ccc5c4=O)c3CO)cc2C(N)=O)nc1] |
| I-56 | 1-[3-(6-tert-Butyl-8-fluoro-1-oxo-1H-phthalazin-2-yl)-phenyl]-1H-pyrazole-4-carboxylic acid amide | 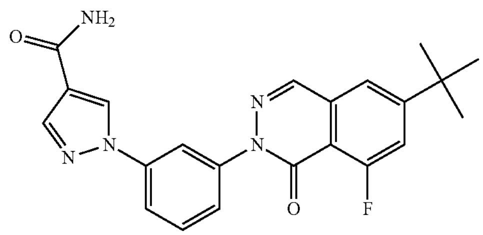 [SMILES: CC(C)(C)c1cc(F)c2c(=O)n(-c3cccc(-n4cc(C(N)=O)cn4)c3)ncc2c1] |

Synthesis: General Synthetic Schemes

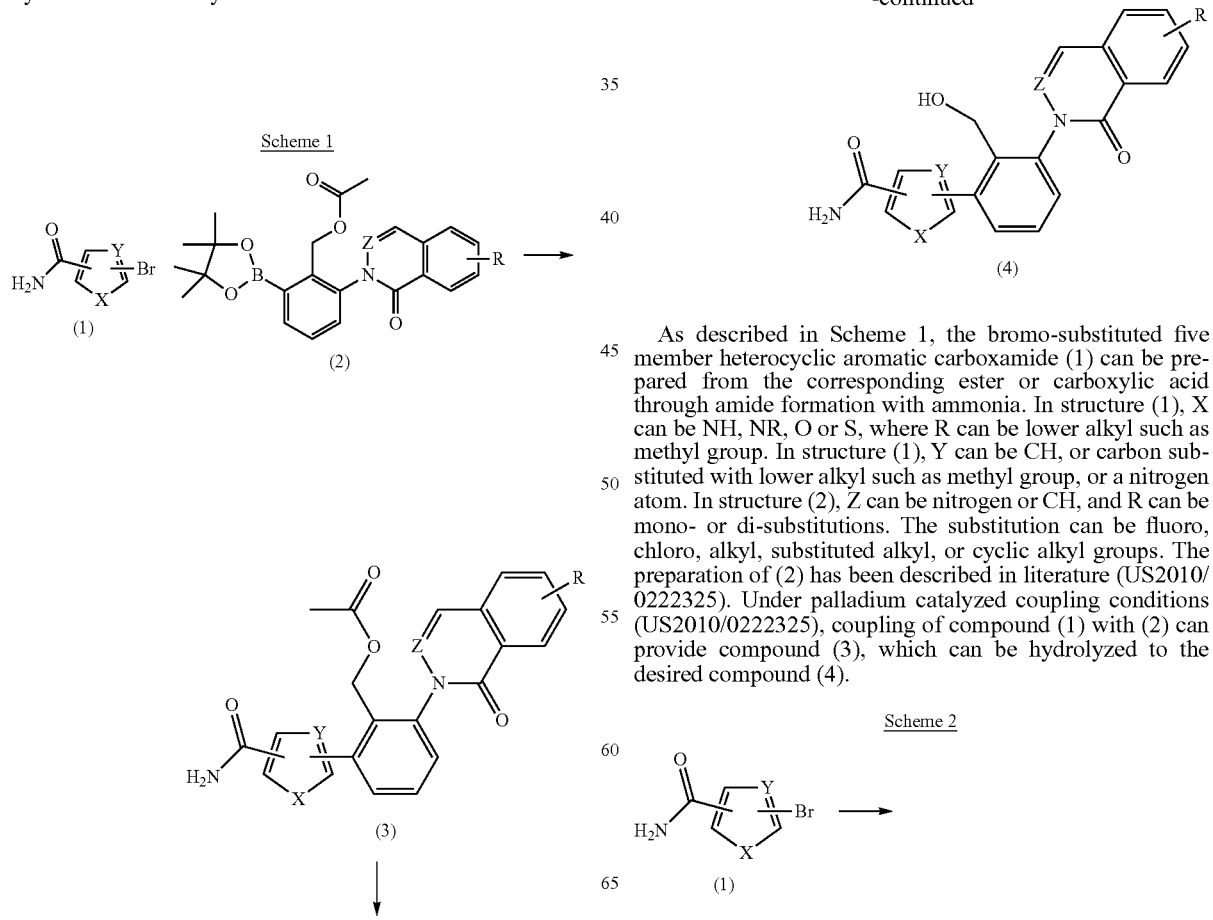

As described in Scheme 1, the bromo-substituted five member heterocyclic aromatic carboxamide (1) can be prepared from the corresponding ester or carboxylic acid through amide formation with ammonia. In structure (1), X can be NH, NR, O or S, where R can be lower alkyl such as methyl group. In structure (1), Y can be CH, or carbon substituted with lower alkyl such as methyl group, or a nitrogen atom. In structure (2), Z can be nitrogen or CH, and R can be mono- or di-substitutions. The substitution can be fluoro, chloro, alkyl, substituted alkyl, or cyclic alkyl groups. The preparation of (2) has been described in literature (US2010/0222325). Under palladium catalyzed coupling conditions (US2010/0222325), coupling of compound (1) with (2) can provide compound (3), which can be hydrolyzed to the desired compound (4).

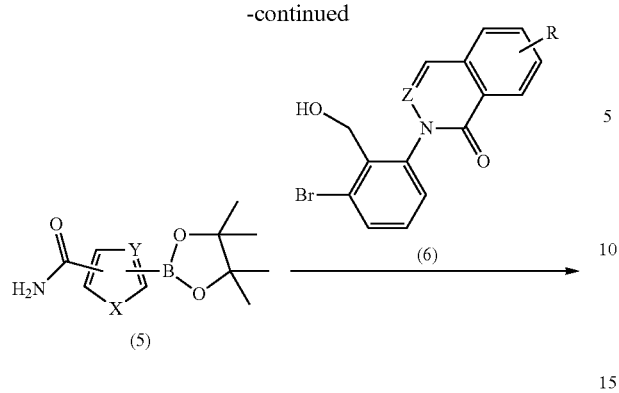

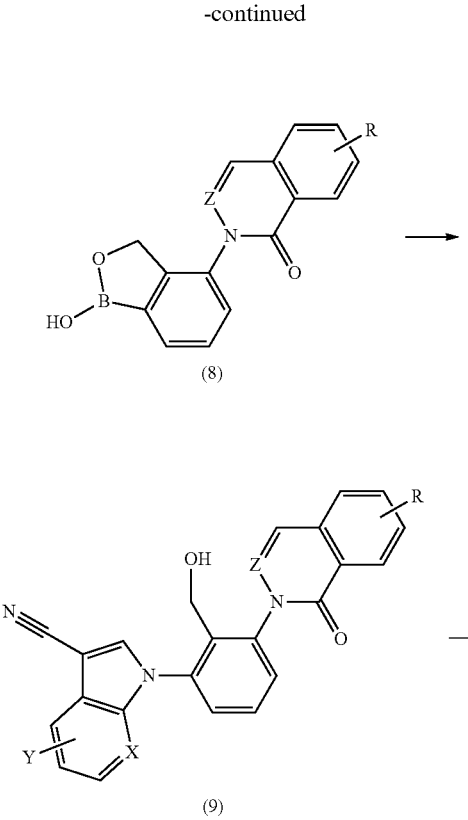

Alternatively, the 5-membered carboxamide (4) can be prepared according to Scheme (2). The bromo-substituted five member heterocyclic aromatic carboxamide (1) can be prepared from the corresponding ester or carboxylic acid through amide formation with ammonia. In structure (1), X can be NH, NR, O or S, where R can be lower alkyl such as methyl group. In structure (1), Y can be CH, or carbon substituted with lower alkyl such as methyl group, or a nitrogen atom. The bromo-substituted five member heterocyclic aromatic carboxamide (1) can be converted to the corresponding pinacolatoborate (5) by reacting with bis-pinacolatoborane under palladium catalyzed aryl borate formation conditions (US2010/0222325). In structure (6), Z can be nitrogen or CH, and R can be mono- or di-substitutions. The substitution can be fluoro, chloro, alkyl, substituted alkyl, or cyclic alkyl groups. The preparation of compound (6) is described in Scheme 9. Aryl bromide (6) can be coupled with 5-membered heteroaromatic borate (5) under palladium catalyzed coupling conditions (US2010/0222325) to provide the desired compound (4).

The 5-membered heterocyclic carboxamide can be fused to an aromatic ring to give a bicyclic heteroaromatic carboxamide as shown in Scheme 3. The indole or aza-indole derivatives (7) can be coupled with aryl boronic acid (8) under palladium catalyzed coupling conditions to provide aryl-substituted indole or aza-indole (9) according to similar conditions in literature (*Tetrahedron Letters* 2009, 50, 15-18). The preparation of aryl boronic acid (8) is described in Scheme 9. In structure (7), X can be CH or nitrogen, and Y can be alkyl, alkyl substituted with hetero atoms, or heterocycles. In structure (8), R can be mono- or di-substitutions. The substitution can be fluoro, chloro, alkyl, substituted alkyl, or cyclic alkyl groups. In structure (8), Z can be nitrogen or CH. The hydrolysis of the cyano group in compound (9) can be achieved under neutral conditions in the presence of platinum catalysis (*Journal of Organic Chemistry* 2004, 69, 2327-2331) to provide the corresponding carboxamide (10).

Scheme 3

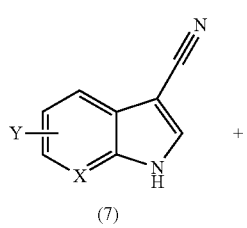

Scheme 4

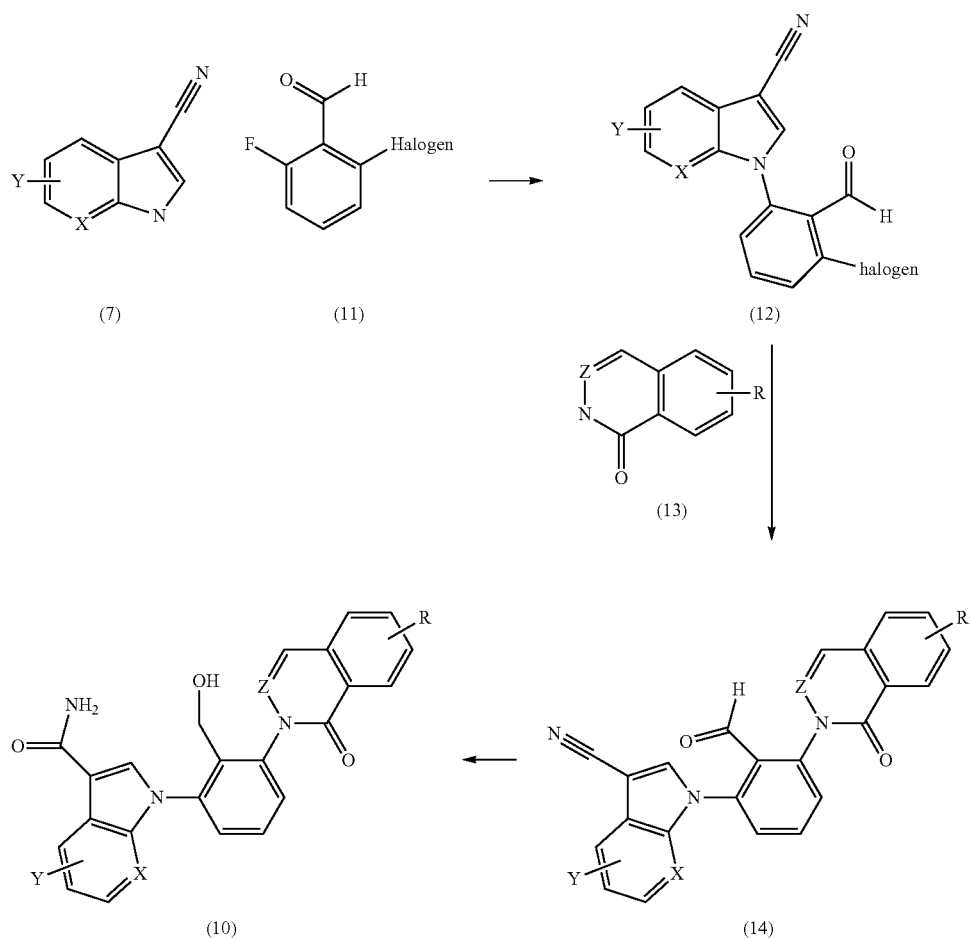

Alternatively, carboxamide (10) can be prepared according to Scheme 4. In structure (7), X can be CH or nitrogen, and Y can be alkyl, alkyl substituted with hetero atoms, or heterocycles. Under basic conditions, such as potassium tert-butoxide, compound (7) can react with aryl fluoride (11) through a nucleophilic aromatic substitution reaction to give compound (12), where halogen in compound (II) can be bromo or iodo atom. Treatment of compound (12) with (13) in the presence of cuprous iodide (US2010/0222325) can give compound (14). The preparation of compound (13) has been described in literature (US2010/0222325), where R can be mono- or di-substitutions. The substitution can be fluoro, chloro, alkyl, substituted alkyl, or cyclic alkyl groups. In structure (13), Z can be nitrogen or CH. The aldehyde group in compound (14) can be reduced to an alcohol by using reducing reagent, such as sodium borohydride. The hydrolysis of the cyano group in compound (14) can be achieved under neutral conditions in the presence of platinum catalysis (*Journal of Organic Chemistry* 2004, 69, 2327-2331) to provide the corresponding carboxamide (10).

Scheme 5

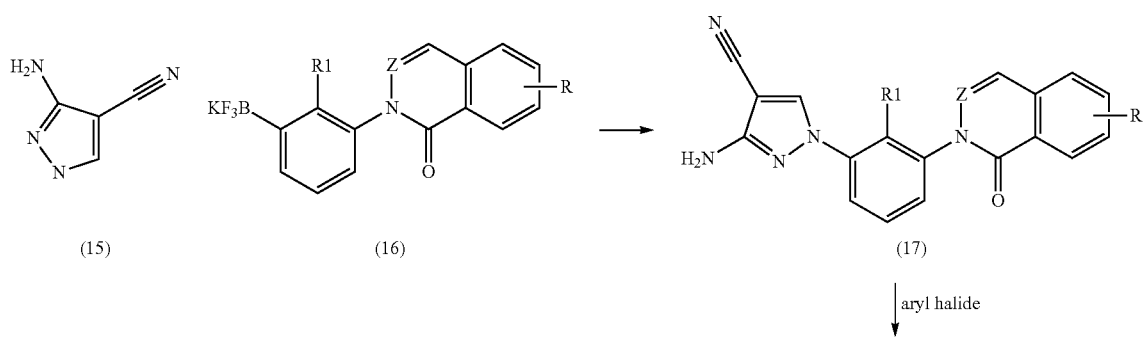

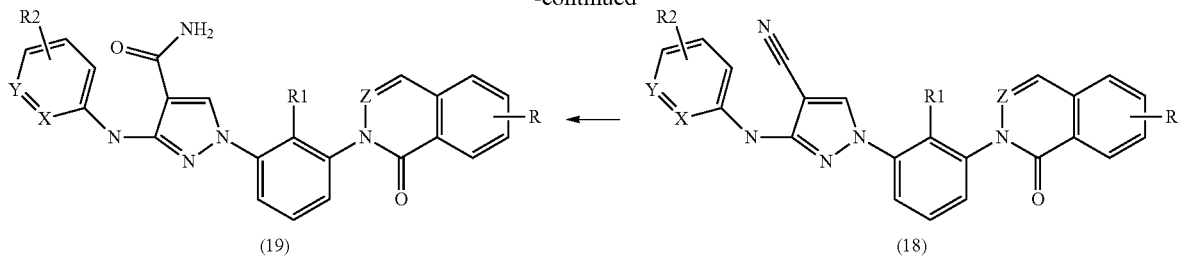

For compounds where the 5-membered heteroaromatic carboxamide is aminopyrazole carboxamide, the preparation is described in Scheme 5. The commercially available aminopyrazole nitrile (15) can be reacted with potassium trifluoroborate salt (16) in the presence of copper acetate to provide compound (17). For the mixed regio-isomers of N-arylation during the conversion of (15) to (17), the desired compound (17) can be separated under super critical fluid chromatography (SFC) conditions. In structure (16), R1 can be hydrogen, alkyl, and acetoxy groups. In structure (16), R can be mono- or di-substitutions. The substitution can be fluoro, chloro, alkyl, substituted alkyl, or cyclic alkyl groups, and Z can be nitrogen or carbon. The preparation of compound (16) is described in Scheme 10. The N-arylation reaction of compound (17) with aryl halide, such as aryl bromide, under palladium catalysis conditions, can provide compound (18), where, X and Y can be CH, or one of the X and Y can be nitrogen. The R2 group in aryl halide can be dialkylaminocarbonyl, aminoalkyl, heterocyclic alkyl, methylsulfonyl, mono- or di-hydroxy substituted alkyl groups. The aryl halide reactant in the conversion of (17) to (18) is not limited to 6-membered aromatic halide, and it can be 5-membered aromatic halide or 5-membered aromatic halide fused with a heterocycle. The hydrolysis of cyano group in (18) can give the desired carboxamide (19).

Scheme 6

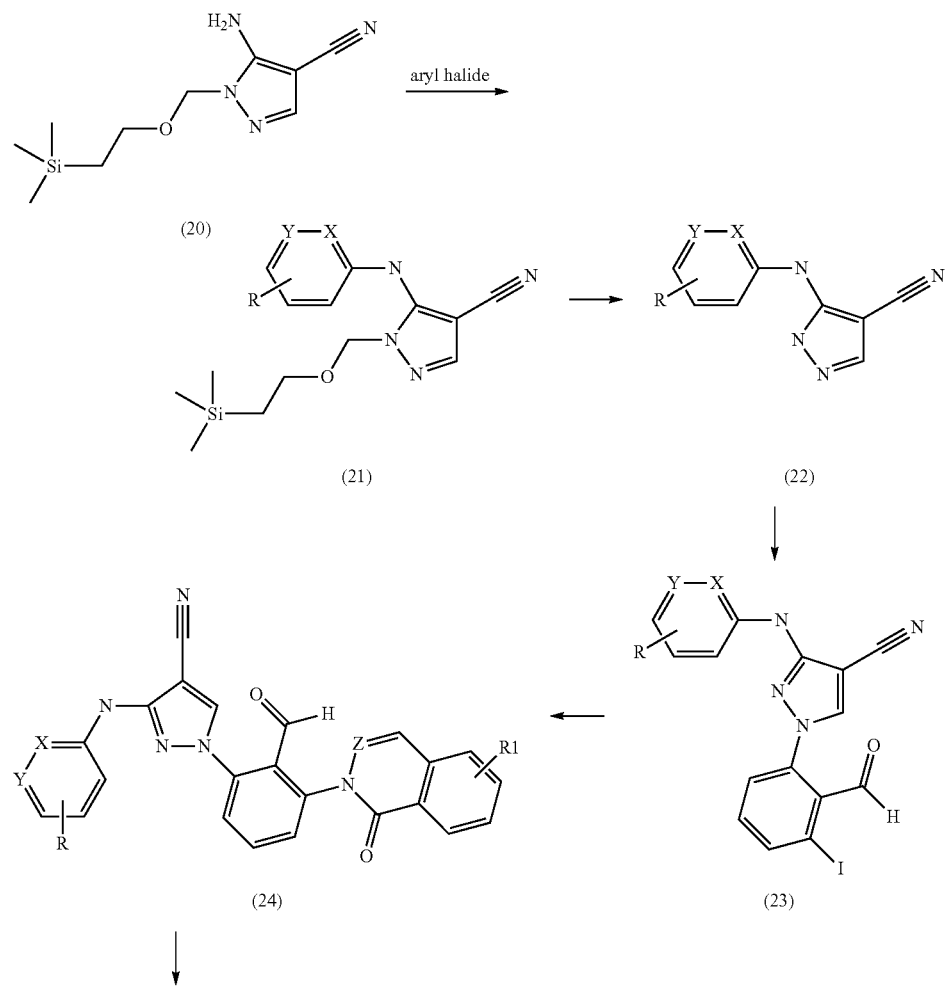

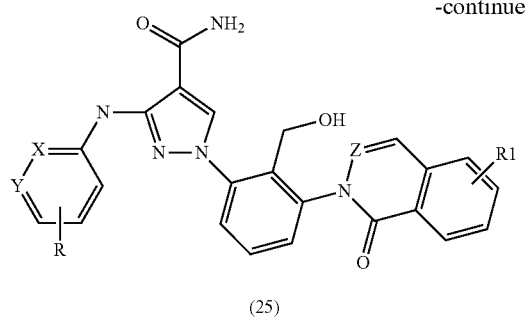

(25)

The alternative route of preparing 5-membered aromatic carboxamide containing aminopyrazole moieties is described in Scheme 6. Protection of the NH group in compound (15) with trimethylsilylethoxymethylene chloride (SEM-Cl) in the presence of base, such as sodium hydride, can give two region-isomers. The two region-isomers can be separated to give (20). N-arylation of (20) with aryl halide in the presence of palladium catalysis can give compound (21), where, X and Y can be CH, or one of the X and Y can be nitrogen. The R group in aryl halide can be dialkylaminocarbonyl, aminoalkyl, heterocyclic alkyl, methylsulfonyl, mono- or di-hydroxy substituted alkyl groups. The aryl halide reactant in the conversion of (20) to (21) is not limited to 6-membered aromatic halide, and it can be 5-membered aromatic halide or 5-membered aromatic halide fused with a heterocycle. The deprotection of the SEM group in (21) can be achieved under acid conditions, such as dilute hydrochloric acid, or basic conditions, such as tetrabutylammonium fluoride, to give compound (22). Treatment of compound (22) with 2-fluoro-6-iodobenzaldehyde in the presence of base, such as potassium tert-butoxide, can provide compound (23). Under Cu(I) catalysis conditions, such as cuprous iodide, compound (23) can be N-arylated by compound (13) to give compound (24), where Z and R1 in compound (24) are defined the same as Z and R in compound (13). Reduction of the aldehyde in compound (24) followed by the nitrile hydrolysis can give the desired carboxamide (25).

Scheme 7

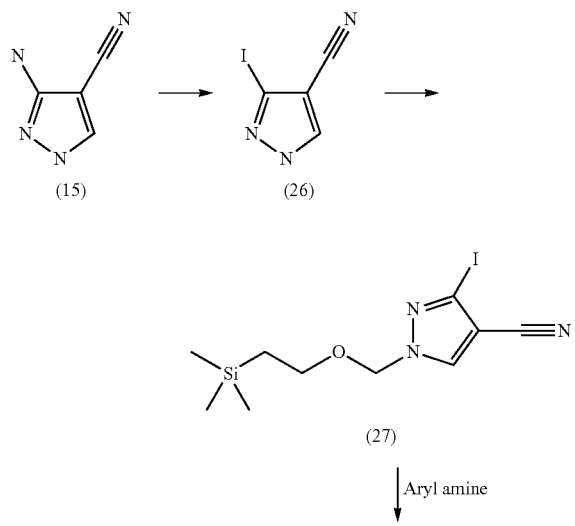

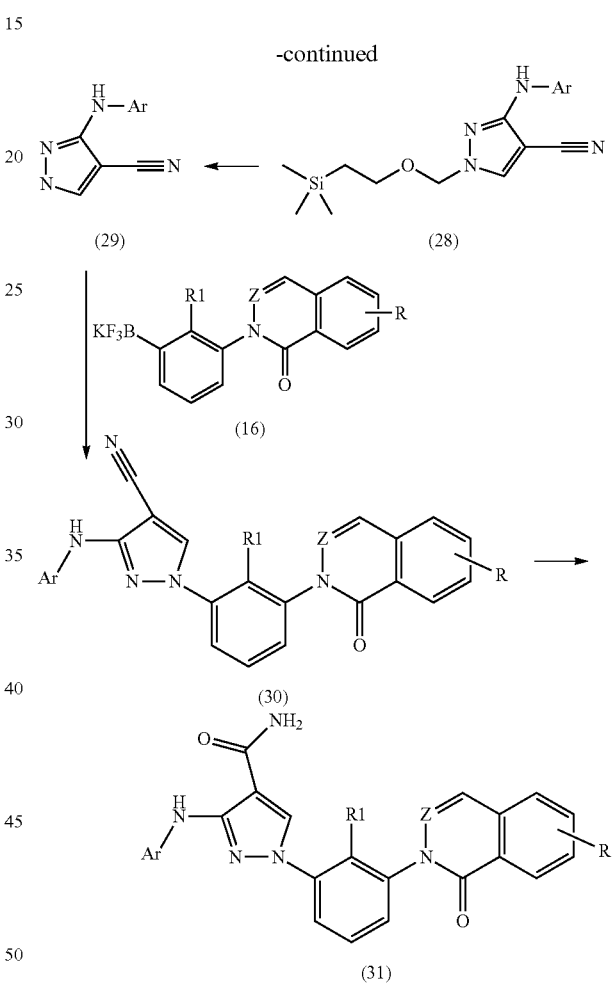

The alternative route of preparing 5-membered aromatic carboxamide containing aminopyrazole moieties is described in Scheme 7. The commercial available compound (15) can be converted to the corresponding iodide (26) according to literature procedure (WO2005/005414). Protection of the NH group in (26) with SEM-Cl can give compound (27) according literature procedure (WO2005/005414). Compound (27) can react with aryl amine in the presence of palladium catalyst, such as bis(tri-tert-butylphosphine) palladium (0), to give the N-arylated product (28), where aryl group can be heteroaromatic moieties, and aryl group can be substituted with dialkylaminocarbonyl, aminoalkyl, heterocyclic alkyl, methylsulfonyl, mono- or di-hydroxy substituted alkyl groups. The deprotection of the SEM group in (28) can be achieved under acid conditions, such as dilute hydrochloric acid, or basic conditions, such as tetrabutylammonium fluoride, to give compound (29). Treatment of compound (29) with potassium trifluoroborate salt (16) in the presence of Cu(II) catalysis, such as copper acetate, can provide compound (30), where R and R1 groups in compound (16) are defined as described in Scheme 5. Hydrolysis of the cyano group in compound (30) can give the desired carboxamide (31).

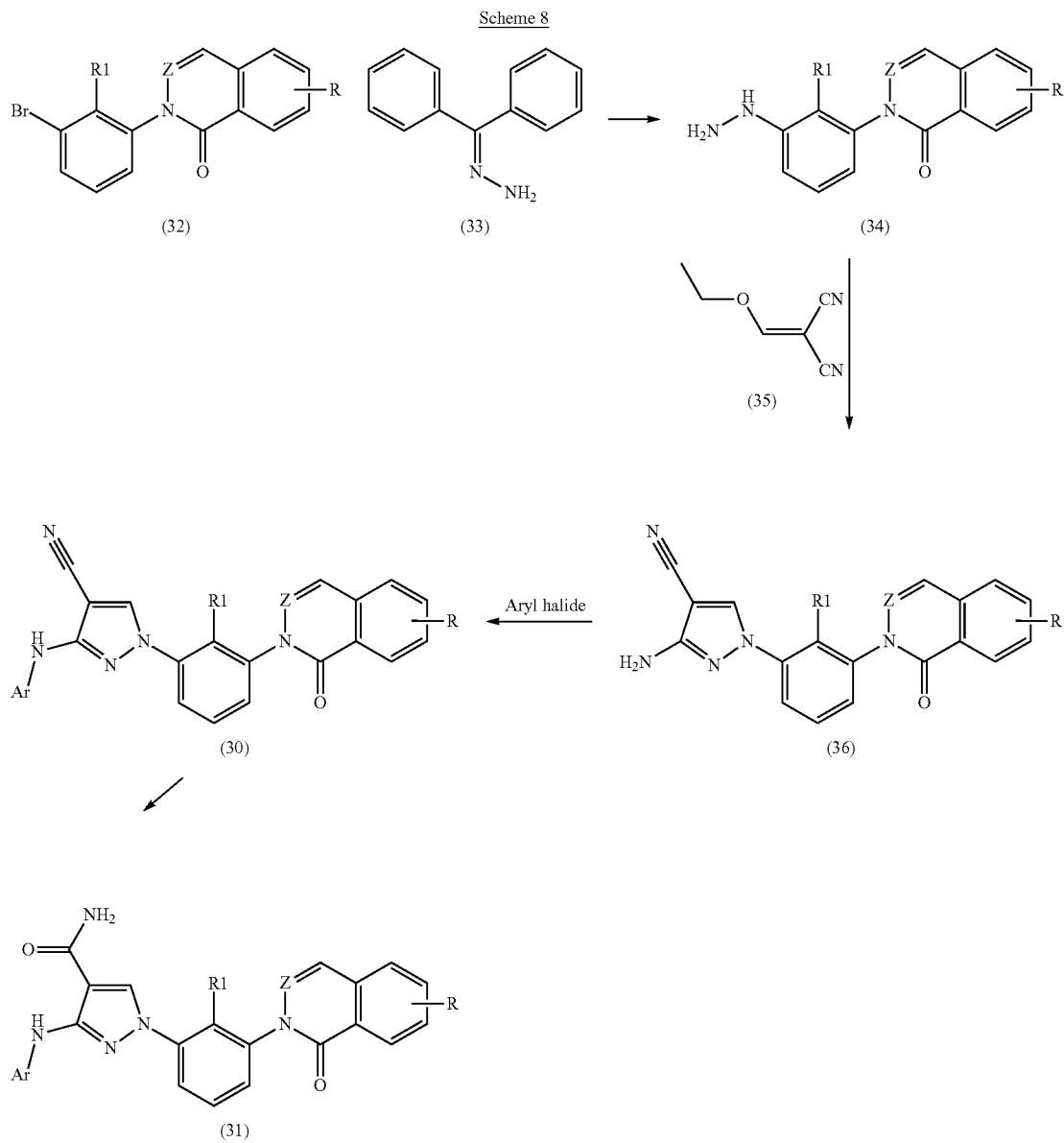

In the conversion of (29) to (30) in Scheme 7, the desired regioisomer of N-arylation product can be obtained through the purification of the mixed regioisomers.

Alternatively, the desired aminopyrazole derivative can be prepared according to Scheme 8. Compound (32) can be obtained by treating R1-substituted 2,6-dibromobenzene with compound (13) in the presence of cuprous iodide. N-arylation of the commercial available hydrazone (33) with compound (32) under palladium catalysis conditions followed by hydrolysis under acidic conditions can give the desired hydrazine (34). Treating compound (34) with the commercial available compound (35) can be achieved by using similar literature procedure (*Journal of Organic Chemistry* 2005, 70, 9222) to give the desired aminopyrazole (36). Compound (36) can be N-arylated with aryl halide as described in the preparation of compound (18) in Scheme 5. Nitrile hydrolysis in compound (30) can give the desired carboxamide (31).

Scheme 9

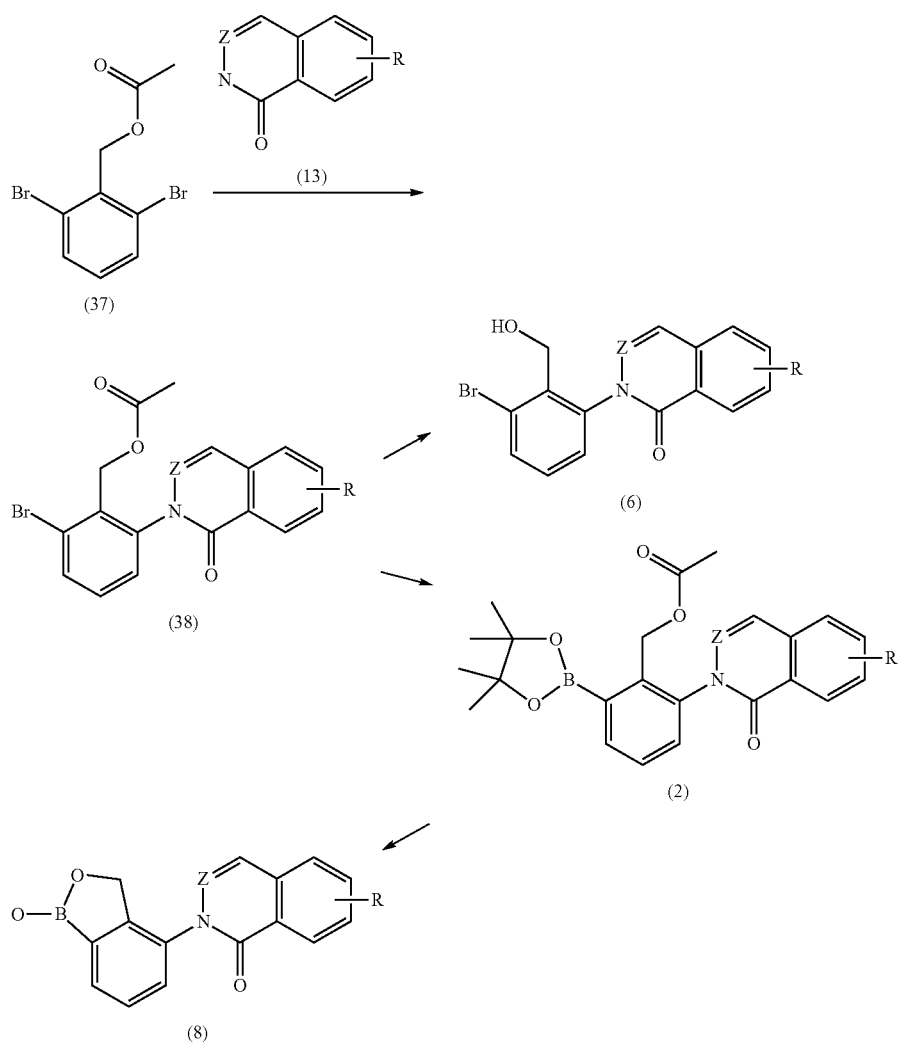

The preparation of the required aryl borate (2), aryl boronic acid (8) and the intermediate (6) is described in Scheme 9. Compound (37) can be substituted with compound (13) in the presence of cuprous iodide to give the N-arylation product (38). Hydrolysis of (38) under mild basic condition can give the desired hydroxyl derivative (6). The transformation of (38) to (2) can be accomplished by using bis(pinacolato) borane under palladium catalysis conditions. Hydrolysis of borate (2) can lead to boronic acid (8).

Scheme 10

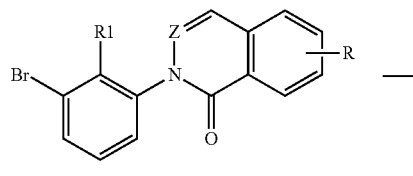

-continued

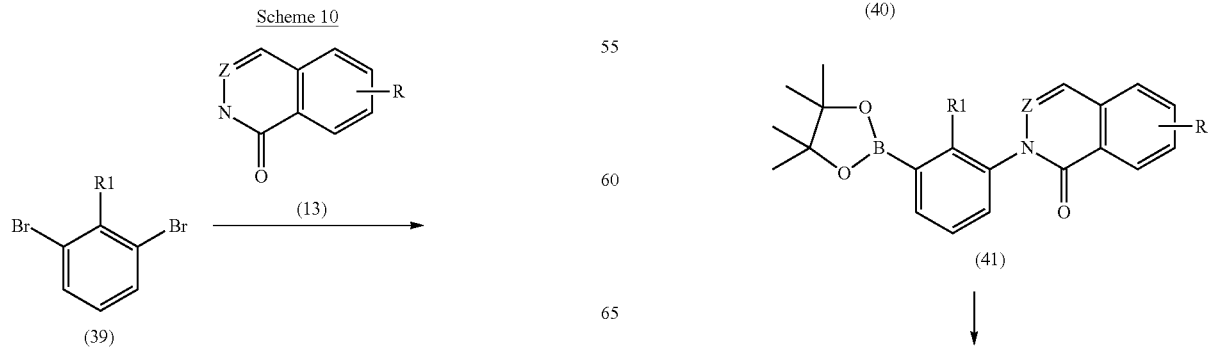

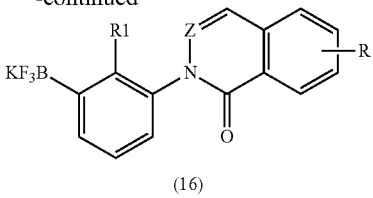

(16)

Finally, the preparation of the required potassium trifluoroborate salt (16) is described in Scheme 10. N-arylation of compound (13) with aryl bromide (39) in the presence of cuprous iodide can give compound (40), where R can be mono- or di-substitutions. Conversion of (40) to (41) can be achieved by using bis(pinacolato)borane in the presence of palladium catalysis. The pinacolyl borate ester (41) can be transformed to the corresponding salt of trifluoroborate (16) according to literature procedure (*Tetrahedron Letters* 2005, 46, 7899).

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multidose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Methods of Treatment

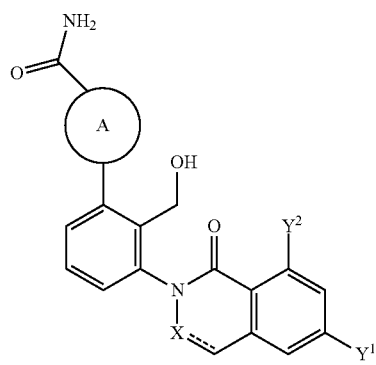

I

The compounds of generic Formula I inhibit Bruton's tyrosine kinase (Btk). Activation of Btk by upstream kinases results in activation of phospholipase-Cγ which, in turn, stimulates release of pro-inflammatory mediators. The compounds of generic Formula I, incorporating 1-oxo-1H-phthalazin-2-yl side chains exhibit unexpectedly enhanced inhibitory activity compared to analogues with other side chains. Notably, fluorine substitution on the unsaturated side chains produces an unexpected approximately 5-10-fold increase in potency in human whole blood. The hydroxymethyl substitution on the phenyl ring further provides unexpectedly increased potency and compared to analogues with alternative substitution at that position. Compounds of Formula I are useful in the treatment of arthritis and other anti-inflammatory and auto-immune diseases. Compounds according to Formula I are, accordingly, useful for the treatment of arthritis. Compounds of Formula I are useful for inhibiting Btk in cells and for modulating B-cell development. The present invention further comprises pharmaceutical compositions containing compounds of Formula I admixed with pharmaceutically acceptable carrier, excipients or diluents.

The primary carboxamide derivatives described herein are kinase inhibitors, in particular Btk inhibitors. These inhibitors can be useful for treating one or more diseases responsive to kinase inhibition, including diseases responsive to Btk inhibition and/or inhibition of B-cell proliferation, in mammals. Without wishing to be bound to any particular theory, it is believed that the interaction of the compounds of the invention with Btk results in the inhibition of Btk activity and thus in the pharmaceutical utility of these compounds. Accordingly, the invention includes a method of treating a mammal, for instance a human, having a disease responsive to inhibition of Btk activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to Btk include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

An embodiment includes a method of treating a patient having an autoimmune and/or inflammatory disease, or an acute inflammatory reaction responsive to inhibition of Btk activity and/or B-cell proliferation.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-05 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., *J. Biol. Chem.* 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. *J. Exp. Med.* 2005 201(11):1837-1852).

Methods of Treatment

The application provides a method for treating an inflammatory and/or autoimmune condition comprising administering to a patient in need thereof a therapeutically effective amount of the compound of Formula I.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of Formula I.

The application provides a method for treating an inflammatory and/or autoimmune condition comprising administering to a patient in need thereof a therapeutically effective amount of the Btk inhibitor compound of Formula I.

The application provides a method for treating an inflammatory condition comprising administering to a patient in need thereof a therapeutically effective amount of the compound of Formula I.

The application provides a method for treating arthritis comprising administering to a patient in need thereof a therapeutically effective amount of the Btk inhibitor compound of Formula I.

The application provides a method for treating asthma comprising administering to a patient in need thereof a therapeutically effective amount of the Btk inhibitor compound of Formula I.

The application provides a method of inhibiting B-cell proliferation comprising administering to a patient in need thereof a therapeutically effective amount of the Btk inhibitor compound of Formula I.

The application provides a method for inhibiting Btk activity comprising administering the Btk inhibitor compound of any one of Formula I, wherein the Btk inhibitor compound exhibits an $IC_{50}$ of 50 micromolar or less in an in vitro biochemical assay of Btk activity.

In one variation of the above method, the Btk inhibitor compound exhibits an $IC_{50}$ of 100 nanomolar or less in an in vitro biochemical assay of Btk activity.

In another variation of the above method, the compound exhibits an $IC_{50}$ of 10 nanomolar or less in an in vitro biochemical assay of Btk activity.

The application provides a method for treating an inflammatory condition comprising co-administering to a patient in need thereof a therapeutically effective amount of an anti-inflammatory compound in combination with the Btk inhibitor compound of Formula I.

The application provides a method for treating arthritis comprising co-administering to a patient in need thereof a therapeutically effective amount of an anti-inflammatory compound in combination with the Btk inhibitor compound of Formula I.

The application provides a method for treating a lymphoma or a BCR-ABL1$^+$ leukemia cells by administering to a patient in need thereof a therapeutically effective amount of the Btk inhibitor compound of Formula I.

EXAMPLES

Abbreviations

Commonly used abbreviations include: acetyl (Ac), azo-bis-isobutylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether (Et$_2$O), ethyl isopropyl ether (EtOiPr), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl)palladium(II) (Pd(dppf)Cl$_2$), palladium(II) acetate (Pd(OAc)$_2$), tris(dibenzylideneacetone)dipalladium(0) (Pd$_2$(dba)$_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-BuMe$_2$Si (TBDMS), tetra-n-butylammonium fluoride (TBAF), triethylamine (TEA or Et$_3$N), 2,2,6,6-tetramethylpiperidine 1-oxyl (TEMPO), trimethylsilylethoxymethyl (SEM), triflate or CF$_3$SO$_2$-(Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

General Conditions

Compounds of the present invention can be prepared beginning with the commercially available starting materials by utilizing general synthetic techniques and procedures known to those skilled in the art. Outlines below are reaction schemes suitable for preparing such compounds. Further exemplification can be found in the specific examples.

Preparative Examples

4-Bromo-1-methyl-1H-imidazole-2-carboxylic acid amide (Intermediate-1)

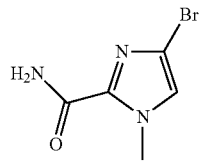

To the solution of 1-methyl-1H-imidazole (2 g, 24.4 mmol) in 16 mL of DCM was added dropwise 4.4 g of trichloroacetyl chloride and the resulting mixture was stirred at 25° C. for 6 h. The mixture was cooled to 0° C. and 3.4 mL of triethylamine was added dropwise with stirring. The solvent was evaporated and the residue was purified by flash column chromatography (petroleum ether/DCM=4/1) to give 2,2,2-trichloro-1-(1-methyl-1H-imidazol-2-yl)ethanone (3.1 g, yield 56%). $^1$H NMR (300 MHz, CDCl$_3$) δ 7.35 (s, 1H), 7.16 (s, 1H), 4.06 (s, 3H).

To the solution of 2,2,2-trichloro-1-(1-methyl-1H-imidazol-2-yl)ethanone (1.5 g, 6.6 mmol) in 26 mL of anhydrous THF was added 2.35 g of NBS at −10° C. The resulting mixture was stirred at −10° C. for 2 h, then 25° C. for 16 h. The solution was evaporated and the residue was purified by silica gel column (DCM as eluent) to give 1-(-4-bromo-1-methyl-1H-imidazol-2-yl)-2,2,2-trichloroethanone (1.18 g, yield 58%). $^1$H NMR (300 MHz, CDCl$_3$) δ 7.15 (s, 1H), 4.05 (s, 3H).

To the solution of 1.18 g of 1-(-4-bromo-1-methyl-1H-imidazol-2-yl)-2,2,2-trichloroethanone in 10 mL of methanol was added 42 mg of sodium methoxide and the resulting mixture was stirred at 25° C. for 20 min. TLC showed completion of the reaction. The solution was evaporated, redissolved in 30 mL of DCM, washed with water (15 mL×2) and brine (15 mL). The solution was dried over anhydrous sodium sulfate and filtered. The residue was purified by silica gel column (DCM/MeOH=60/1) to give 4-bromo-1-methyl-1H-imidazole-2-carboxylic acid methyl ester (0.575 g, yield 68%). $^1$H NMR (300 MHz, CDCl$_3$) δ 7.02 (s, 1H), 4.00 (s, 3H). 3.93 (s, 3H). LC-MS calcd for C$_6$H$_7$BrN$_2$O$_2$ (m/e) 217.97, obsd 219 and 221 [M+1]$^+$ To the saturated solution of ammonia in MeOH was added 165 mg of 4-bromo-1-methyl-1H-imidazole-2-carboxylic acid methyl ester and the resulting mixture was stirred at 20° C. for 16 h. The solution was evaporated to give 4-bromo-1-methyl-1H-imidazole-2-carboxylic acid amide (154 mg, yield 100%). LC-MS calcd for C$_5$H$_6$BrN$_3$O (m/e) 202.97, obsd 204 and 206 [M+1]$^+$.

2-Bromothiazole-4-carboxylic acid amide (Intermediate-2)

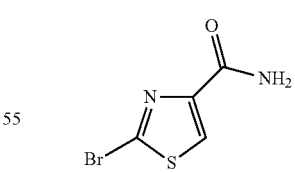

2-Bromothiazole-4-carboxylic acid methyl ester (50 mg) was dissolved in a solution of saturated ammonia in methanol (4 ml). The reaction solution was stirred overnight at room temperature. The solvent was removed under reduced pressure to give 2-bromothiazole-4-carboxylic acid amide (46 mg, yield 100%) as a yellow solid. $^1$H NMR (300 MHz, CDCl$_3$): δ 8.11 (s, 1H). LC-MS calcd for C$_4$H$_3$BrN$_2$OS (m/e) 205.91, obsd 207 and 209 [M+1]$^+$.

4-Bromo-1-methyl-1H-pyrrole-2-carboxylic acid amide (Intermediate-3)

4-Bromo-1-methyl-1H-pyrrole-2-carboxylic acid (122 mg, 0.60 mmol), HATU (274 mg, 0.72 mmol) and DIEA (194 mg, 1.50 mmol) were dissolved in DMF (5 mL). The reaction mixture was stirred at room temperature with ammonia gas bubbled through continuously overnight. The reaction mixture was diluted with 100 mL of DCM, and then washed with water (50 mL). The aqueous layer was extracted with DCM (20 mL×2). All organic layers were combined, dried over sodium sulfate, filtered and concentrated. The residue was purified by silica gel chromatography (petroleum ether/ethyl acetate 6/1) to give 4-bromo-1-methyl-1H-pyrrole-2-carboxylic acid amide (56 mg, yield 46%). $^1$H NMR (300 MHz, CDCl$_3$): δ 6.74 (d, J=1.8 Hz, 1H), 6.59 (d, J=1.8 Hz, 1H), 3.92 (s, 3H). LC-MS calcd for C$_6$H$_7$BrN$_2$O (m/e) 201.97, obsd 203 and 205 [M+1]$^+$.

Acetic acid 2-(6-tert-butyl-1-oxo-1H-phthalazin-2-yl)-6-(4,4,5,5-tetramethyl-[1,3,2]dioxaborolan-2-yl)-benzyl ester (Intermediate-4)

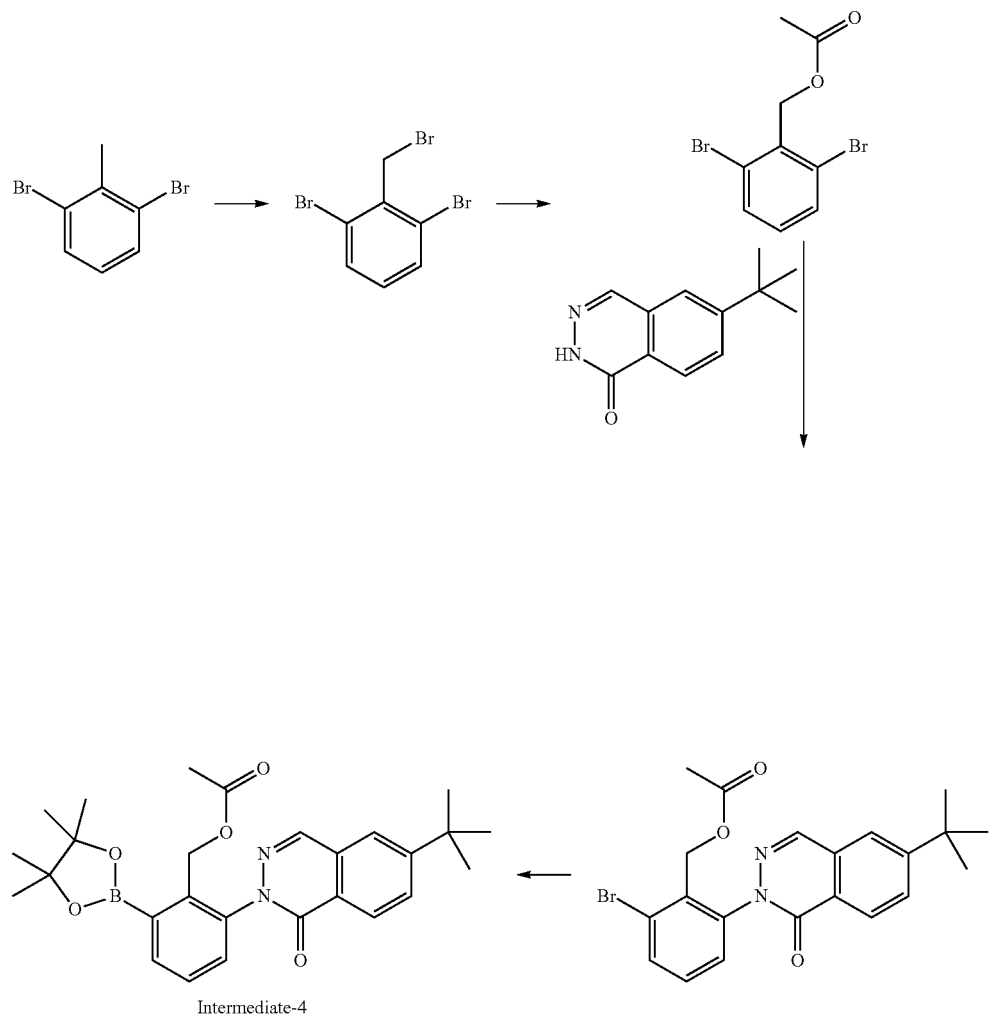

Intermediate-4

To the solution of 2,6-dibromotoluene (55.5 g, 222.1 mmol) and NBS (43.5 g, 244.3 mmol) in carbon tetrachloride (300 mL) was added benzoyl peroxide (5.37 g, 22.2 mmol). The reaction mixture was refluxed for 20 h, cooled to room temperature, washed with water (300 mL×3) and brine (300 mL) and dried over anhydrous sodium sulfate. The solution was filtered and evaporated to give 1,3-dibromo-2-bromomethylbenzene as a yellow power (71 g). This material was used for next step without further purification.

To the solution of 1,3-dibromo-2-bromomethylbenzene (71.3 g) in DMF (300 mL) was added sodium acetate (91.7 g) and the resulting mixture was stirred at 105° C. for 6 h. The mixture was cooled and quenched with water (1500 mL) and extracted with ethyl acetate (1000 mL×2). The combined organic layers were washed with water (1000 mL) and brine (1000 mL), dried over anhydrous sodium sulfate and filtered. The residue was purified by silica gel column (200-300 mesh, eluting with petroleum ether/ethyl acetate 30/1) to give acetic acid 2,6-dibromobenzyl ester as a yellow oil (59.42 g, yield 89%). $^1$H NMR (300 MHz, d6-DMSO) δ 7.57 (d, J=8.0 Hz, 2H), 7.07 (t, J=7.8 Hz, 1H), 5.41 (s, 2H), 2.11 (s, 3H).

Under $N_2$, acetic acid 2,6-dibromobenzyl ester (34.88 g, 113 mmol), 6-tert-butyl-2H-phthazin-1-one (4.56 g, 22.5 mmol), $Cs_2CO_3$ (14.72 g, 45 mmol), CuI (6.44 g, 33.8 mmol) and N,N-dimethylethane-1,2-diamine (2 g, 22.7 mmol) were dissolved in DMF (92 mL). The reaction mixture was stirred at 150° C. for 4 h, then cooled to room temperature, diluted with ethyl acetate (500 mL), and washed with 500 mL of water. The aqueous layer was separated and extracted with ethyl acetate (200 mL×2). The combined organic layers were washed with water (300 mL×2) and brine (300 mL), dried over anhydrous sodium sulfate. The solution was filtered and evaporated. The residue was purified by silica gel chromatography (petroleum ether/ethyl acetate 4/1) to give acetic acid 2-bromo-6-(6-tert-butyl-1-oxo-1H-phthalazin-2-yl)-benzyl ester (6.2 g, 64% yield). $^1$H NMR (300 MHz, $CDCl_3$) δ 8.39 (d, J=8.3 Hz, 1H), 8.25 (s, 1H), 7.91-7.87 (m, 1H), 7.72 (s, 2H), 7.41-7.35 (m, 2H), 5.17 (s, 2H), 1.91 (s, 3H), 1.44 (s, 9H). LC-MS calcd for $C_{21}H_{21}BrN_2O_3$ (m/e) 428.07, obsd 429 and 431 $[M+1]^+$.

Under $N_2$, acetic acid 2-bromo-6-(6-tert-butyl-1-oxo-1H-phthalazin-2-yl)-benzyl ester (1.43 g, 10.7 mmol), bis(pinacolato)diboron (1.03 g, 4.05 mmol), KOAc (0.99 g, 10.1 mmol) and $Pd(dppf)Cl_2$ (0.3 g, 0.36 mmol) in 16.7 mL of DMSO were stirred at 80° C. for 16 h. The mixture was cooled to room temperature, diluted with ethyl acetate (100 mL), and washed with 100 mL of water. The aqueous layer was extracted with ethyl acetate (50 mL×2). The combined organic layers were washed with water (100 mL×2) and brine (100 mL), dried over anhydrous sodium sulfate. The solution was filtered and evaporated. The residue was purified by silica gel chromatography (petroleum ether/ethyl acetate 2/1) to give acetic acid 2-(6-tert-butyl-1-oxo-1H-phthalazin-2-O-6-(4,4,5,5-tetramethyl-[1,3,2]dioxaborolan-2-yl)-benzyl ester as a greenish solid (1.45 g, 91% yield). $^1$H NMR (300 MHz, $CDCl_3$) δ 8.39 (d, J=8.5 Hz, 1H), 8.23 (s, 1H), 7.96 (dd, J=6.4, 2.5 Hz, 1H), 7.86 (dd, J=8.5, 1.8 Hz, 1H), 7.71 (d, J=1.7 Hz, 2H), 7.52-7.45 (m, 2H), 5.30 (s, 2H), 1.86 (s, 3H), 1.43 (s, 9H), 1.33 (s, 12H). LC-MS calcd for $C_{27}H_{33}BN_2O_5$ (m/e) 476.25, obsd 477 $[M+1]^+$.

Acetic acid 2-(6-tert-butyl-8-fluoro-1-oxo-1H-phthalazin-2-yl)-6-(4,4,5,5-tetramethyl-[1,3,2]dioxaborolan-2-yl)-benzyl ester (Intermediate-5)

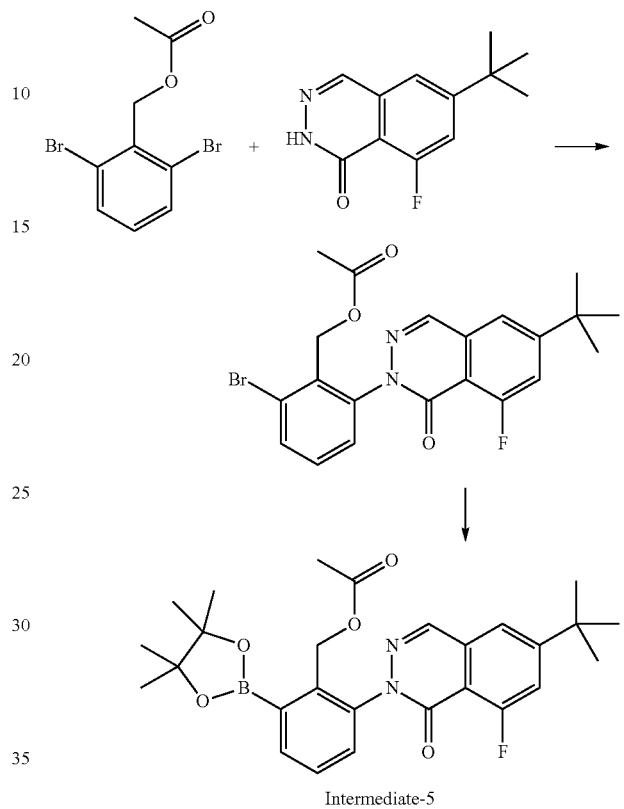

Intermediate-5

Under $N_2$, acetic acid 2,6-dibromobenzyl ester (24.74 g, 80.3 mmol), 6-tert-butyl-8-fluoro-2H-phthazin-1-one (3.54 g, 16.1 mmol), $Cs_2CO_3$ (10.46 g, 32.1 mmol), CuI (4.61 g, 24.2 mmol) and N,N-dimethylethane-1,2-diamine (1.42 g, 16.1 mmol) were dissolved in DMF (70 mL). The reaction mixture was stirred at 150° C. for 4 h. The resulting mixture was cooled to room temperature and diluted with ethyl acetate (200 mL), and then 200 mL of water was added. The mixture was separated and the aqueous layer was extracted with ethyl acetate (200 mL×2). The organic layers were combined and washed with water (200 mL) and brine (200 mL). The solution was dried over anhydrous sodium sulfate, filtered and concentrated. The resulting crude product was purified by silica gel chromatography (petroleum ether/ethyl acetate 4/1) to give 2-bromo-6-(6-tert-butyl-8-fluoro-1-oxo-1H-phthalazin-2-yl)-benzyl ester (3.21 g, 45%). $^1$H NMR (300 MHz, $CDCl_3$): δ 8.17 (d, J=2.7 Hz, 1H), 7.71 (t, J=4.8 Hz, 1H), 7.50-7.45 (m, 2H), 7.36 (s, 1H), 7.34 (d, J=0.9 Hz, 1H), 5.17 (s, 2H), 1.94 (s, 3H), 1.42 (s, 9H). LC-MS calcd for $C_{21}H_{20}BrFN_2O_3$ (m/e) 446.06, obsd 447 and 449 $[M+1]^+$.

Under $N_2$, 2-bromo-6-(6-tert-butyl-8-fluoro-1-oxo-1H-phthalazin-2-yl)-benzyl ester (1.51 g, 3.39 mmol), bispinacolato diboron (1.03 g, 4.06 mmol), KOAc (0.998 g, 10.7 mmol) and $Pd(dppf)Cl_2$ (0.277 g, 0.339 mmol) were dissolved in dry DMSO (80 mL). The reaction mixture was stirred at 80° C. for 24 h. The reaction mixture was diluted with ethyl acetate (100 mL) and washed with water (200 mL×2). The aqueous layer was extracted with ethyl acetate (100 mL×2). The combined organic layers were washed with water (200 mL×2) and brine (200 mL) and dried over anhydrous sodium sulfate. The solution was filtered and concentrated. The residue was purified by chromatography (petroleum ether/ethyl acetate 2/1) to give acetic acid 2-(6-tert-butyl-8-fluoro-1-oxo-1H-phthalazin-2-yl)-6-(4,4,5,5-tetramethyl-[1,3,2]dioxaborolan-2-yl)-benzyl ester (1.26 g, 75%). $^1$H NMR (300 MHz, CDCl$_3$): δ 8.17 (d, J=2.6, 2.4 Hz, 1H), 7.95 (dd, J=6.9, 2.2 Hz, 1H), 7.49-7.44 (m, 4H), 6.31 (br s, 2H), 1.90 (s, 3H), 1.42 (s, 9H), 1.34 (s, 12H). LC-MS calcd for C$_{27}$H$_{32}$BFN$_2$O$_5$ (m/e) 494.24, obsd 495 [M+1]$^+$.

6-tert-Butyl-2-(3-chloro-2-hydroxymethyl-phenyl)-8-hydroxymethyl-2H-phthalazin-1-one (Intermediate-6)

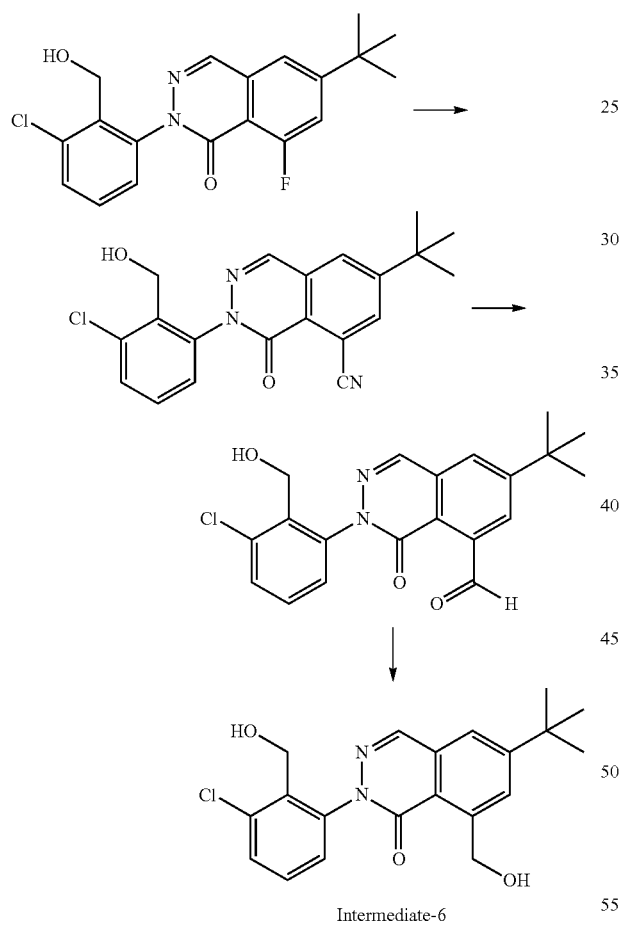

Intermediate-6

To a 100 mL round-bottomed flask were added 6-tert-butyl-2-[3-chloro-2-(hydroxymethyl)phenyl]-8-fluorophthalazin-1(2H)-one (671 mg, 1.86 mmol, prepared according to US2010/0222325), sodium cyanide (365 mg, 7.44 mmol) and DMSO (10 mL) to give a light yellow suspension. The mixture was stirred at 80° C. for 16 hrs. Additional sodium cyanide (182 mg, 3.72 mmol) was added and the mixture was further stirred at 80° C. for 60 hrs. The mixture was cooled to room temperature and extracted with ethyl acetate and water. The organic layer was washed with water and brine, dried over sodium sulfate and filtered. Solvents were evaporated and the residue was purified through flash column chromatography (220 g silica gel, 0% to 40% acetone in heptane) to give 7-tert-butyl-3-[3-chloro-2-(hydroxymethyl)phenyl]-4-oxo-3,4-dihydrophthalazine-5-carbonitrile as a yellow solid (390 mg, 57% yield).

In a 250 mL round bottom flask was added 7-tert-butyl-3-[3-chloro-2-(hydroxymethyl)phenyl]-4-oxo-3,4-dihydrophthalazine-5-carbonitrile (390 mg, 1.06 mmol) and toluene*8 mL). The solution was cooled under ice bath and DIBAH in toluene (2.33 mL, 2.33 mmol) was added. The mixture was stirred under ice bath for 1 hr and then diluted with dichloromethane and quenched with 1M hydrochloric acid. The mixture was stirred for 10 minutes and extracted with dichloromethane. The organic layer was washed with water and brine, dried over sodium sulfate and filtered. Solvents were evaporated and the crude material was purified by flash column chromatography (silica gel, 120 g, 0% to 35% ethyl acetate in heptane) to give 7-tert-butyl-3-[3-chloro-2-(hydroxymethyl)phenyl]-4-oxo-3,4-dihydrophthalazine-5-carbaldehyde (147 mg, 37.4%) as a light yellow powder.

The above 7-tert-butyl-3-[3-chloro-2-(hydroxymethyl)phenyl]-4-oxo-3,4-dihydrophthalazine-5-carbaldehyde (147 mg, 0.396 mmol) was combined with dichloroethane (5 mL) and methanol (5 mL) to give a yellow solution. Sodium borohydride (27 mg, 0.714 mmol) was added and the mixture was stirred at room temperature for 4 hrs. The mixture was treated with 1N hydrochloric acid and extracted with dichloromethane. The organic layer was washed with brined and dried over sodium sulfate. After the evaporation of solvents, the residue was purified by flash column chromatography (silica gel 40 g, 0% to 40% ethyl acetate in heptane) to give 6-tert-butyl-2-[3-chloro-2-(hydroxymethyl)phenyl]-8-(hydroxymethyl)phthalazin-1(2H)-one as a light yellow solid (39 mg, 26.4%). LC/MS calcd for C$_{20}$H$_{21}$ClN$_2$O$_3$ (m/e) 372.12, obsd 371.1 (M−H, ES−).

Example 1

5-[3-(6-tert-Butyl-8-fluoro-1-oxo-1H-phthalazin-2-yl)-2-hydroxymethyl-phenyl]furan-2-carboxylic acid amide

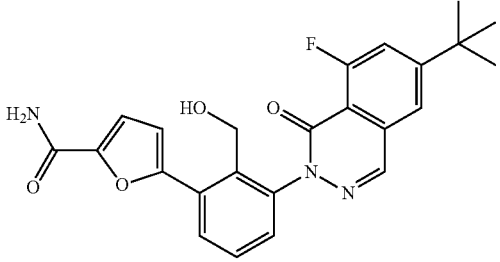 [SMILES: CC(C)(C)c1cc(F)c2c(=O)n(-c3cccc(-c4ccc(C(N)=O)o4)c3CO)ncc2c1]

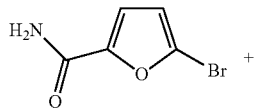

Hz, 1H) 7.81-8.03 (m, 3H) 8.52 (d, J=2.64 Hz, 1H); LC/MS calcd for $C_{24}H_{22}FN_3O_4$ (m/e) 435.16, obsd 458 [M+Na]$^+$.

Example 2

4-[3-(6-tert-Butyl-8-fluoro-1-oxo-1H-phthalazin-2-yl)-2-hydroxymethyl-phenyl]furan-2-carboxylic acid amide

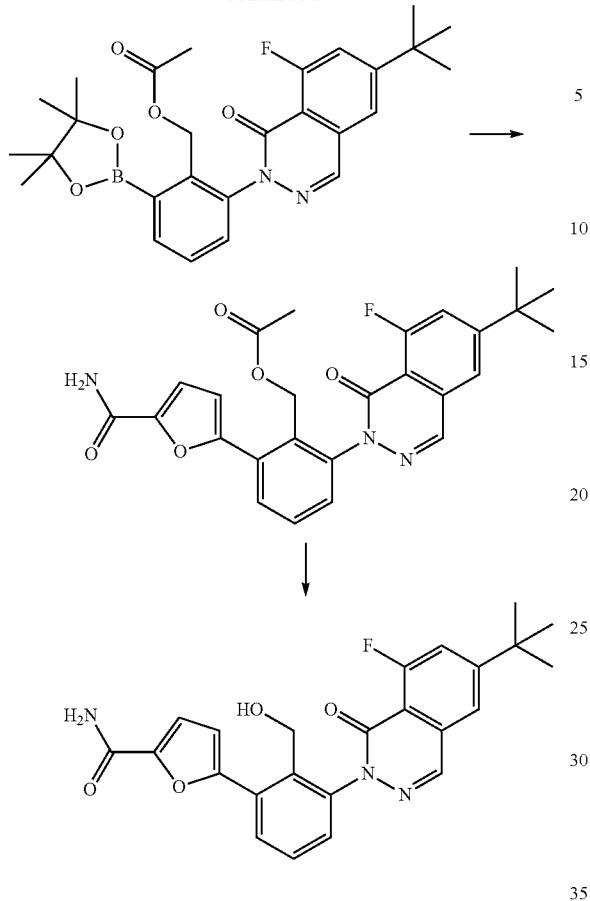

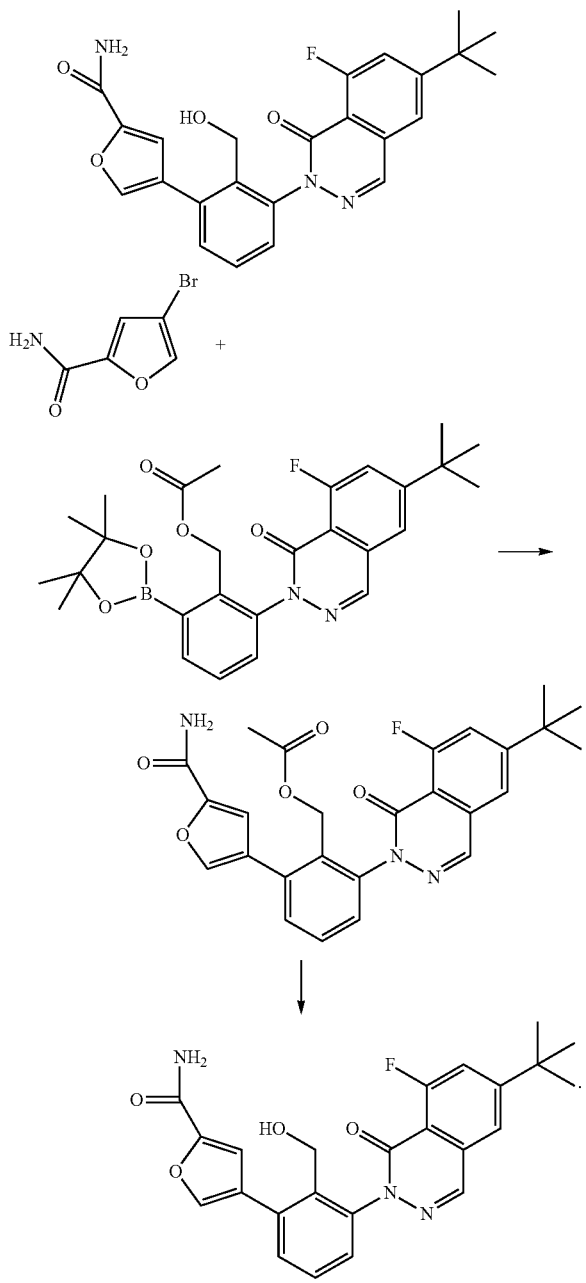

In a microwave flask, a suspension of 5-bromofuran-2-carboxamide (200 mg, 1.05 mmol), acetic acid 2-(6-tert-butyl-8-fluoro-1-oxo-1H-phthalazin-2-yl)-6-(4,4,5,5-tetramethyl-[1,3,2]dioxaborolan-2-yl)-benzyl ester (Intermediate-5, 1.04 g, 2.11 mmol), X-PHOS (50.2 mg, 0.105 mmol), Pd$_2$(dba)$_3$ (48.2 mg, 0.052 mmol) and potassium phosphate (894 mg, 4.21 mmol) in dioxane (7 ml) and water (0.7 ml) was degassed with argon for 3-5 min. The mixture was set in a microwave at 125° C. for 30 min. Water was added and the mixture was extracted with ethyl acetate twice. The organic layer was washed with brine, dried over sodium sulfate and evaporated to dryness. The crude material was purified by flash column chromatography (ethyl acetate in hexanes, gradient to 100% ethyl acetate) to obtain acetic acid 2-(6-tert-butyl-8-fluoro-1-oxo-1H-phthalazin-2-yl)-6-(5-carbamoyl-furan-2-yl)-benzyl ester (78.5 mg, 16%).

To a solution of the above acetate (78.5 mg, 0.164 mmol) in methanol (2 mL) was added potassium carbonate (4.5 mg, 0.033 mmol). The mixture was stirred under N$_2$ for 5 h. Dichloromethane was added and the mixture was washed with water. The aqueous phase was extracted once with dichloromethane. The combined organics were dried over sodium sulfate and evaporated to dryness. Ethyl acetate was added, and the suspension was stirred for 5 min and solid was filtered off and dried to obtain 5-[3-(6-tert-butyl-8-fluoro-1-oxo-1H-phthalazin-2-yl)-2-hydroxymethyl-phenyl]-furan-2-carboxylic acid amide (42 mg, 59%). $^1$H NMR (300 MHz, DMSO-d$_6$) δ ppm 1.38 (s, 9H) 4.33-4.53 (m, 2H) 4.66-4.92 (m, 1H) 7.05 (d, J=3.78 Hz, 1H) 7.20 (d, J=3.40 Hz, 1H) 7.29-7.47 (m, 2H) 7.50-7.63 (m, 1H) 7.75 (dd, J=13.41, 1.70

In a microwave flask a suspension of 4-bromofuran-2-carboxamide (150 mg, 0.79 mmol) 2-(6-tert-butyl-8-fluoro-1-oxophthalazin-2(1H)-yl)-6-(4,4,5,5-tetramethyl-1,3,2-dioxaborolan-2-yl)benzyl acetate (intermediate 5, 468 mg, 0.95 mmol), X-PHOS (37.6 mg, 0.079 mmol), Pd$_2$(dba)$_3$ (36.1 mg, 0.040 mmol) and potassium phosphate (670 mg, 3.16 mmol) in dioxane (5 mL) and water (0.5 mL) was degassed with argon by bubbling for 5 min. The mixture was set in a microwave at 125° C. for 30 min. Water was added and the mixture was extracted with ethyl acetate twice. The organic layer was washed with brine, dried over sodium sulfate and evaporated to dryness. The crude material was purified by flash column chromatography (ethyl acetate in hexanes, linear gradient to 100% EtOAc) to obtain 2-(6-tert-butyl-8-fluoro-1-oxophthalazin-2(1H)-yl)-6-(5-carbamoylfuran-3-yl)benzyl acetate (273 mg, 0.572 mmol, 72.4% yield).

To a solution of the above acetate (262.6 mg, 0.55 mmol) in methanol (5 mL) was added potassium carbonate (15.2 mg, 0.11 mmol). The mixture was stirred under $N_2$ for 3.5 h. Dichloromethane (50 mL) was added and the mixture was washed with water, dried over sodium sulfate and concentrated to dryness. The crude material was purified by flash column chromatography (ethyl acetate in hexanes, linear gradient to 100% EtOAc) to give 4-[3-(6-tert-butyl-8-fluoro-1-oxo-1H-phthalazin-2-yl)-2-hydroxymethyl-phenyl]-furan-2-carboxylic acid amide (192 mg, 80%). $^1$H NMR (300 MHz, CHLOROFORM-d) δ ppm 1.36-1.62 (m, 9H) 4.40 (br. s., 2H) 7.35 (dd, J=6.80, 2.64 Hz, 1H) 7.44-7.64 (m, 5H) 8.14 (d, J=1.13 Hz, 4H) 8.29 (d, J=2.64 Hz, 1H); LC/MS calcd for $C_{24}H_{22}FN_3O_4$ (m/e) 435.16, obsd 436 $[M+H]^+$.

Example 3

4-[3-(6-tert-Butyl-1-oxo-1H-phthalazin-2-yl)-2-hydroxymethyl-phenyl]-1-methyl-1H-imidazole-2-carboxylic acid amide

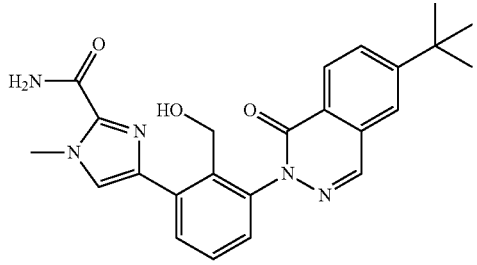 [SMILES: Cn1cc(-c2cccc(-n3ncc4cc(C(C)(C)C)ccc4c3=O)c2CO)nc1C(N)=O]

This compound was prepared with the same method as described in Example 1 by using 4-bromo-1-methyl-1H-imidazole-2-carboxylic acid amide (intermediate-1) and acetic acid 2-(6-tert-butyl-1-oxo-1H-phthalazin-2-yl)-6-(4,4,5,5-tetramethyl-[1,3,2]dioxaborolan-2-yl)-benzyl ester (intermediate 4). The desired compound was prepared in two steps (33% yield). $^1$H NMR (300 MHz, CDCl$_3$) δ 8.46 (d, J=8.5 Hz, 1H), 8.36 (s, 1H), 7.95-7.91 (m, 2H), 7.77 (d, J=1.6 Hz, 1H), 7.70 (s, 1H), 7.54 (t, J=7.9 Hz, 1H), 7.36 (dd, J=7.9, 1.3 Hz, 1H), 4.42 (br s, 2H), 4.14 (s, 3H), 1.46 (s, 9H). LC-MS calcd for $C_{24}H_{25}N_5O_3$ (m/e) 431.20, obsd 432 $[M+1]^+$.

Example 4

2-[3-(6-tert-Butyl-1-oxo-1H-phthalazin-2-yl)-2-hydroxymethyl-phenyl]-thiazole-4-carboxylic acid amide

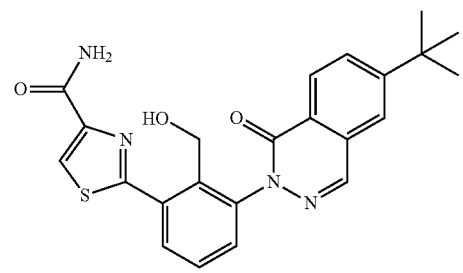 [SMILES: CC(C)(C)c1ccc2c(=O)n(-c3cccc(-c4nc(C(N)=O)cs4)c3CO)ncc2c1]

This compound was prepared with the same method as described in Example 1 by using 2-bromothiazole-4-carboxylic acid amide (intermediate-2) and acetic acid 2-(6-tert-butyl-1-oxo-1H-phthalazin-2-yl)-6-(4,4,5,5-tetramethyl-[1,3,2]dioxaborolan-2-yl)-benzyl ester (intermediate 4). The desired compound was prepared in two steps (25% yield). $^1$H NMR (300 MHz, DMSO-d$_6$): δ 8.56 (s, 1H), 8.41 (s, 1H), 8.24 (d, J=8.4 Hz, 1H), 8.05-8.00 (m, 2H), 7.82 (dd, J=1.8, 7.2 Hz, 1H), 7.61-7.58 (m, 2H), 4.54-4.45 (m, 2H), 1.41 (s, 9H). LC-MS calcd for $C_{23}H_{22}N_4O_3S$ (m/e) 434.14, obsd 435 $[M+1]^+$.

Example 5

4-[3-(6-tert-Butyl-1-oxo-1H-phthalazin-2-yl)-2-hydroxymethyl-phenyl]-1-methyl-1H-pyrrole-2-carboxylic acid amide

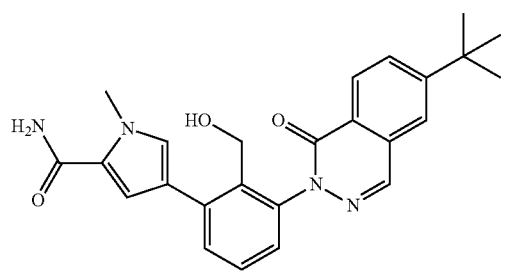 [SMILES: Cn1cc(-c2cccc(-n3ncc4cc(C(C)(C)C)ccc4c3=O)c2CO)cc1C(N)=O]

This compound was prepared with the same method as described in Example 1 by using 4-bromo-1-methyl-1H-pyrrole-2-carboxylic acid amide (intermediate-3) and acetic acid 2-(6-tert-butyl-1-oxo-1H-phthalazin-2-yl)-6-(4,4,5,5-tetramethyl-[1,3,2]dioxaborolan-2-yl)-benzyl ester (intermediate 4). The desired compound was prepared in two steps (20% yield). $^1$H NMR (300 MHz, DMSO-d$_6$) δ 8.54 (s, 1H), 8.25 (d, J=8.4 Hz, 1H), 8.04 (d, J=1.5 Hz, 1H), 8.01 (dd, J=1.8, 8.4 Hz, 1H), 7.48-7.45 (m, 2H), 7.28-7.23 (m, 2H), 7.08 (d, J=1.8

Hz, 1H), 4.35 (s, 2H), 3.89 (s, 3H), 1.41 (s, 9H). LC-MS calcd for $C_{25}H_{26}N_4O_3$ (m/e) 430.20, obsd 431 [M+1]$^+$.

Example 6

2-[3-(6-tert-Butyl-8-fluoro-1-oxo-1H-phthalazin-2-yl)-2-hydroxymethyl-phenyl]thiazole-4-carboxylic acid amide

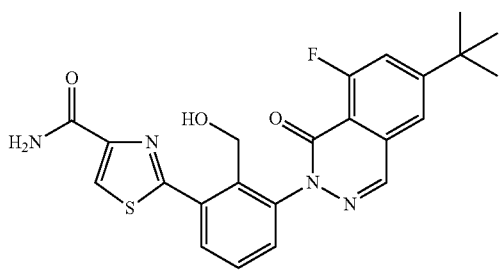 [SMILES: CC(C)(C)c1cc(F)c2c(=O)n(-c3cccc(-c4nc(C(N)=O)cs4)c3CO)ncc2c1]

This compound was prepared with the same method as described in Example 1 by using 2-bromothiazole-4-carboxylic acid amide (intermediate-2) and acetic acid 2-(6-tert-butyl-8-fluoro-1-oxo-1H-phthalazin-2-yl)-6-(4,4,5,5-tetramethyl-[1,3,2]dioxaborolan-2-yl)-benzyl ester (intermediate 5). The desired compound was prepared in two steps (10% yield). $^1$H NMR (300 MHz, DMSO-d$_6$) δ 8.59 (d, J=2.4 Hz, 1H), 8.46 (s, 1H), 7.94 (d, J=1.8 Hz, 1H), 7.88-7.79 (m, 2H), 7.66-7.63 (m, 2H), 4.61-4.52 (m, 2H), 1.46 (s, 9H). LC-MS calcd for $C_{23}H_{21}FN_4O_3S$ 452.13, obsd 453 [M+1]$^+$.

Example 7

4-[3-(6-tert-Butyl-8-fluoro-1-oxo-1H-phthalazin-2-yl)-2-hydroxymethylphenyl]-1-methyl-1H-imidazole-2-carboxylic acid amide

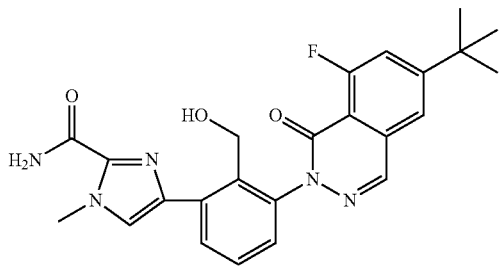 [SMILES: Cn1cc(-c2cccc(-n3ncc4cc(C(C)(C)C)cc(F)c4c3=O)c2CO)nc1C(N)=O]

This compound was prepared with the same method as described in Example 1 by using 4-bromo-1-methyl-1H-imidazole-2-carboxylic acid amide (intermediate-1) and acetic acid 2-(6-tert-butyl-8-fluoro-1-oxo-1H-phthalazin-2-yl)-6-(4,4,5,5-tetramethyl-[1,3,2]dioxaborolan-2-yl)-benzyl ester (intermediate 5). The desired compound was prepared in two steps (12% yield). $^1$H NMR (300 MHz, DMSO-d$_6$) δ 8.50 (d, J=2.7 Hz, 1H), 7.87-7.71 (m, 5H), 7.50-7.44 (m, 2H), 7.30 (dd, J=1.2, 7.8 Hz, 1H), 4.38-4.33 (m, 2H), 4.00 (s, 3H), 1.39 (s, 9H). LC-MS calcd for $C_{24}H_{24}FN_5O_3$ (m/e) 449.19, obsd 450 [M+1]$^+$.

Example 8

4-[3-(6-tert-Butyl-8-fluoro-1-oxo-1H-phthalazin-2-yl)-2-hydroxymethyl-phenyl]-1-methyl-1H-pyrrole-2-carboxylic acid amide

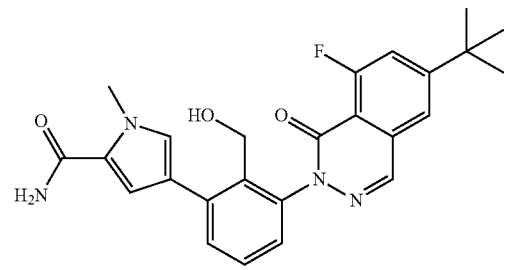 [SMILES: Cn1cc(-c2cccc(-n3ncc4cc(C(C)(C)C)cc(F)c4c3=O)c2CO)cc1C(N)=O]

This compound was prepared with the same method as described in Example 1 by using 4-bromo-1-methyl-1H-pyrrole-2-carboxylic acid amide (intermediate-3) and acetic acid 2-(6-tert-butyl-8-fluoro-1-oxo-1H-phthalazin-2-yl)-6-(4,4,5,5-tetramethyl-[1,3,2]dioxaborolan-2-yl)-benzyl ester (intermediate 5). The desired compound was prepared in two steps (60% yield). $^1$H NMR (300 MHz, d$_6$-DMSO) δ 8.49-8.48 (m, 1H), 7.86 (s, 1H), 7.73 (d, J=13.2 Hz, 1H), 7.44-7.42 (m, 3H), 7.25-7.23 (m, 2H), 7.06 (br s, 2H), 4.56 (s, 1H), 4.36 (s, 2H), 3.88 (s, 3H), 1.37 (s, 9H). LC-MS calcd for $C_{25}H_{25}FN_4O_3$ (m/e) 448.19, obsd 449.1 [M+H]$^+$.

Example 9

4-[3-(6-tert-Butyl-1-oxo-1H-phthalazin-2-yl)-2-hydroxymethyl-phenyl]-1H-pyrrole-2-carboxylic acid amide

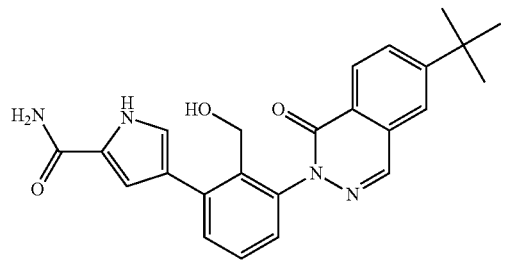

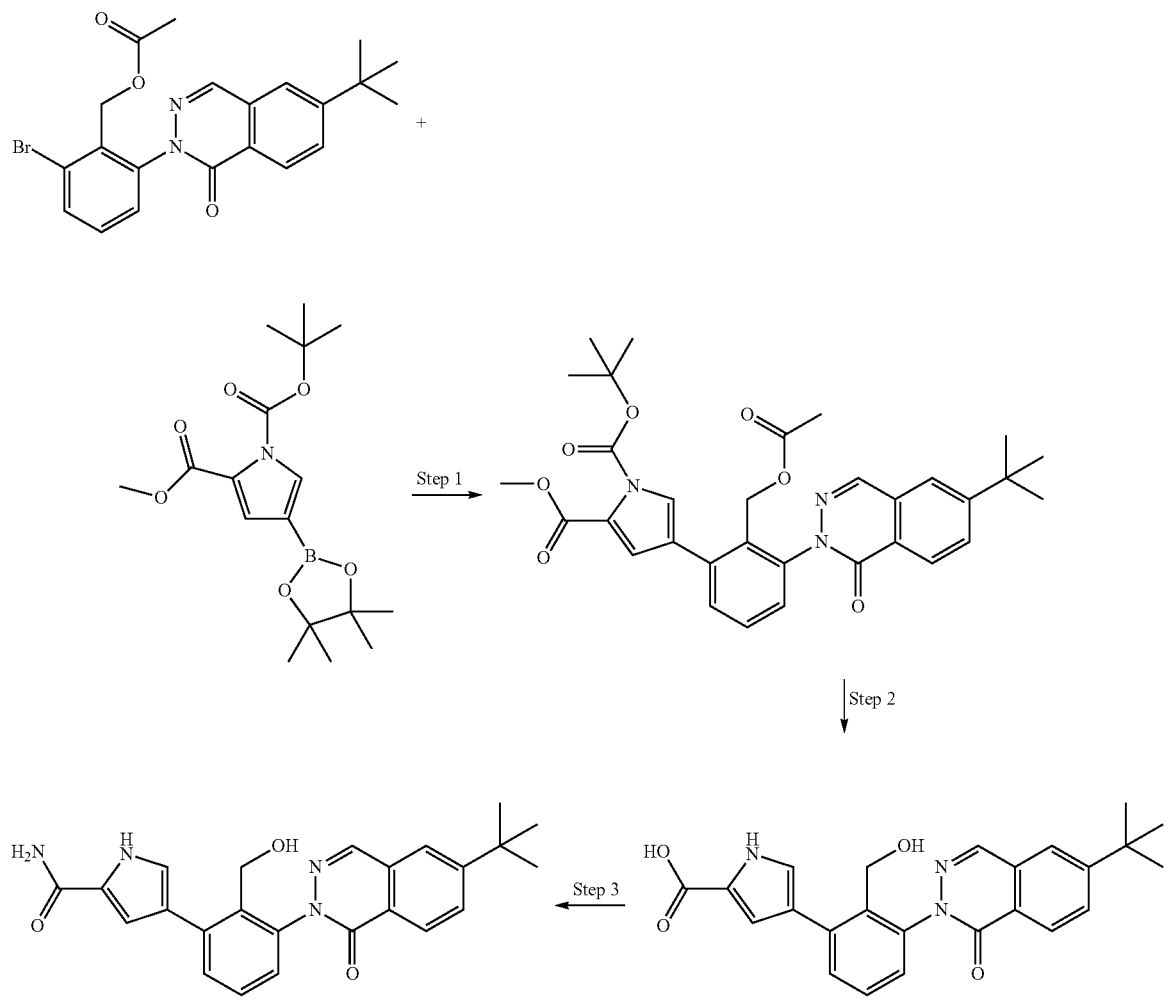

Step 1: Under $N_2$, a mixture of acetic acid 2-bromo-6-(6-tert-butyl-1-oxo-1H-phthalazin-2-yl)-benzyl ester (preparation described in intermediate-4, 300 mg, 0.699 mmol), 4-(4,4,5,5-tetramethyl-[1,3,2]dioxaborolan-2-yl)-pyrrole-1,2-dicarboxylic acid 1-tert-butyl ester 2-methyl ester (270 mg, 0.769 mmol), Pd(dppf)Cl$_2$ (171 mg, 0.21 mmol) and K$_2$CO$_3$ (289 mg, 2.19 mmol) in dioxane (15 mL) and water (3 mL) was heated at 100° C. for 4 h. The mixture was concentrated to dryness. The residue was purified by silica gel column chromatography (eluted with petroleum ether/ethyl acetate with a ratio of 2/1) to give 4-[2-acetoxymethyl-3-(6-tert-butyl-1-oxo-1H-phthalazin-2-yl)-phenyl]-pyrrole-1,2-dicarboxylic acid 1-tert-butyl ester 2-methyl ester (160 mg, yield 40%). LC-MS calcd for $C_{32}H_{35}N_3O_7$ (m/e) 573.25, obsd 473 [M-Boc+1]$^+$.

Step 2: To a solution of 4-[2-acetoxymethyl-3-(6-tert-butyl-1-oxo-1H-phthalazin-2-yl)-phenyl]-pyrrole-1,2-dicarboxylic acid 1-tert-butyl ester 2-methyl ester (136 mg, 0.24 mmol) in 5 mL of dioxane and 5 mL of water was added NaOH (40 mg) and the reaction mixture was stirred at room temperature for 20 h. The mixture was concentrated under reduced pressure. The residue was dissolved in 8 mL of water, and acidified with 1 N HCl to pH 3-4. The mixture was extracted with ethyl acetate (5 mL×3). The combined organic layers were dried over Na$_2$SO$_4$ and concentrated under reduced pressure to give 4-[3-(6-tert-butyl-1-oxo-1H-phthalazin-2-yl)-2-hydroxymethyl-phenyl]-1H-pyrrole-2-carboxylic acid (99 mg, yield 100%). LC-MS calcd for $C_{24}H_{23}N_3O_4$ (m/e) 417.17, obsd 418 [M+1]$^+$.

Step 3: HATU (104 mg, 0.27 mmol) and triethyl amine (1 mL) were added to a solution of 4-[3-(6-tert-butyl-1-oxo-1H-phthalazin-2-yl)-2-hydroxymethyl-phenyl]-1H-pyrrole-2-carboxylic acid (95 mg, 0.23 mmol) in dry THF (15 mL). Ammonia gas was bubbled through the solution for 5 h. The mixture was concentrated under reduced pressure. The residue was purified by preparative TLC (petroleum ether/ethyl acetate=2:1) to give 4-[3-(6-tert-butyl-1-oxo-1H-phthalazin-2-yl)-2-hydroxymethyl-phenyl]-1H-pyrrole-2-carboxylic acid amide (25 mg, yield 26%) as a white solid. $^1$H NMR (300 MHz, CD$_3$OD) δ 8.43 (s, 1H), 8.28 (d, J=8.5 Hz, 1H), 7.98-7.92 (m, 2H), 7.52-7.39 (m, 2H), 7.26-7.19 (m, 2H), 7.03 (d, J=1.6 Hz, 1H), 4.38 (s, 2H), 1.38 (s, 9H). LC-MS calcd for $C_{24}H_{24}N_4O_3$ (m/e) 416.18, obsd 417 [M+1]$^+$.

Example 10

5-[3-(6-tert-Butyl-1-oxo-1H-phthalazin-2-yl)-2-hydroxymethyl-phenyl]-1-methyl-1H-pyrrole-2-carboxylic acid amide

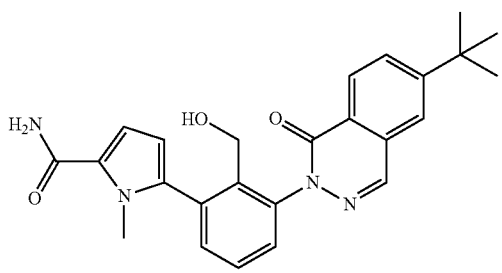 [SMILES: Cn1c(C(N)=O)ccc1-c1cccc(-n2ncc3cc(C(C)(C)C)ccc3c2=O)c1CO]

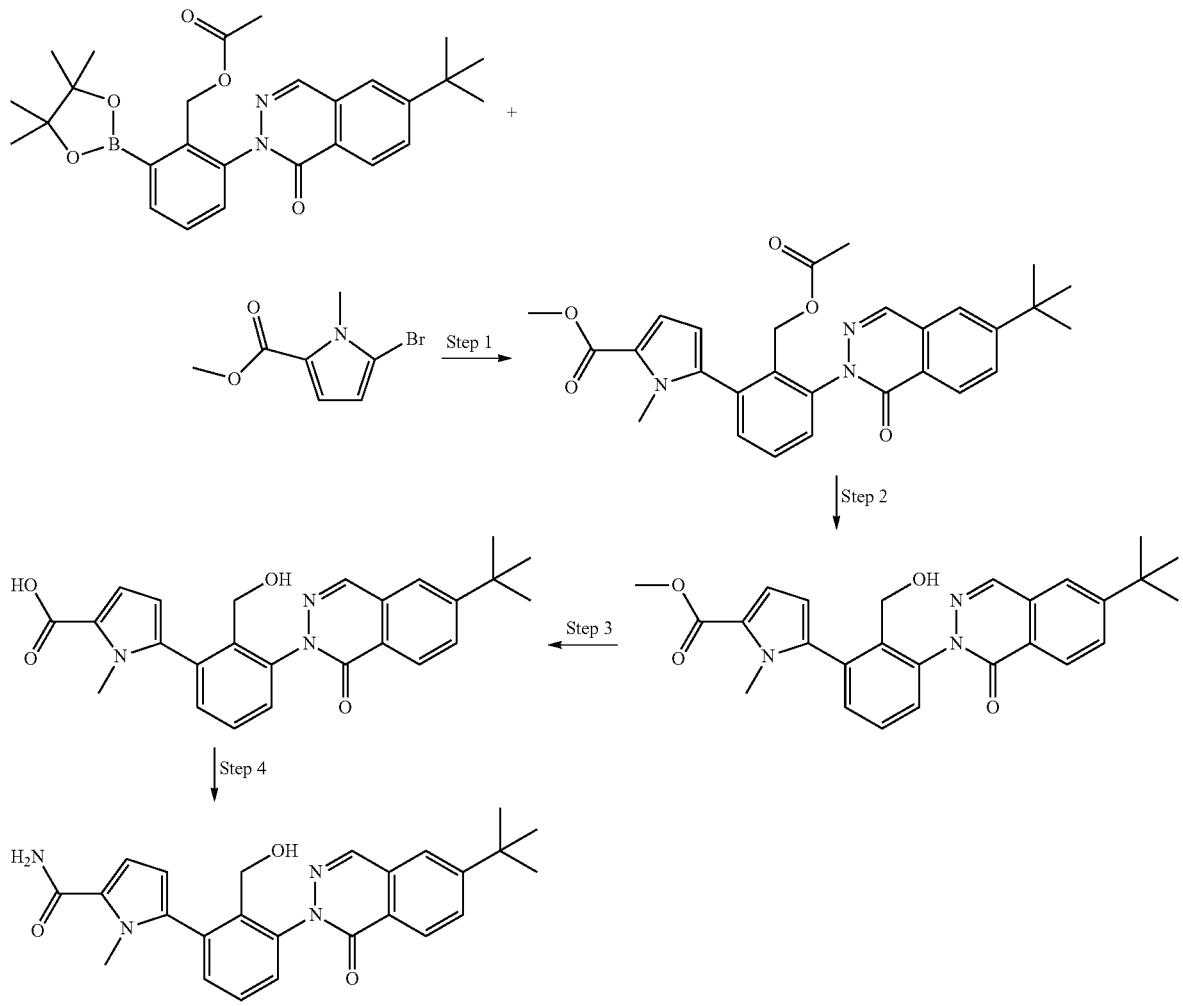

Step 1: Under $N_2$, a mixture of acetic acid 2-(6-tert-butyl-1-oxo-1H-phthalazin-2-yl)-6-(4,4,5,5-tetramethyl-[1,3,2]dioxaborolan-2-yl)-benzyl ester (described in the preparation of intermediate 4, 300 mg, 0.63 mmol), 5-bromo-1-methyl-1H-pyrrole-2-carboxylic acid methyl ester (150 mg, 0.69 mmol), Pd(dppf)Cl$_2$ (150 mg, 0.19 mmol) and $K_2CO_3$ (261 mg, 1.9 mmol) in dioxane (15 mL) and water (3 mL) were heated at 100° C. for 3 h. The mixture was concentrated to dryness. The residue was purified by silica gel column chromatography (eluted with petroleum ether/ethyl acetate from the ratio of 8:1 to 5:1) to give 5-[2-acetoxymethyl-3-(6-tert-butyl-1-oxo-1H-phthalazin-2-yl)-phenyl]-1-methyl-1H-pyrrole-2-carboxylic acid methyl ester (237 mg, yield 77%) as a yellow liquid. LC-MS calcd for $C_{28}H_{29}N_3O_5$ (m/e) 487.21, obsd 997 [2M+Na]$^+$.

Step 2: A mixture of 5-[2-acetoxymethyl-3-(6-tert-butyl-1-oxo-1H-phthalazin-2-yl)-phenyl]-1-methyl-1H-pyrrole-2-carboxylic acid methyl ester (237 mg, 0.486 mmol) in saturated NH$_3$/MeOH (20 mL) was stirred at room temperature for 48 h. The mixture was evaporated to dryness to give 5-[3-(6-tert-butyl-1-oxo-1H-phthalazin-2-yl)-2-hydroxymethyl-phenyl]-1-methyl-1H-pyrrole-2-carboxylic acid methyl ester (150 mg, yield 68%) as a yellow solid. LC-MS calcd for $C_{26}H_{27}N_3O_4$ (m/e) 445.20, obsd 913 [2M+Na]$^+$.

Step 3: Water (5 mL) was added to a solution of 5-[3-(6-tert-butyl-1-oxo-1H-phthalazin-2-yl)-2-hydroxymethyl-phenyl]-1-methyl-1H-pyrrole-2-carboxylic acid methyl ester (150 mg, 0.337 mmol) in dioxane (5 mL). The mixture was stirred for 5 min and NaOH (40 mg) was added. The reaction mixture was stirred at room temperature for 16 h. The mixture was concentrated under reduced pressure. The residue was extracted with diethyl ether (5 mL×3). The combined organic layers were washed with brine, dried over Na$_2$SO$_4$ and concentrated under reduced pressure to give 5-[3-(6-tert-butyl-1-oxo-1H-phthalazin-2-yl)-2-hydroxymethyl-phenyl]-1-methyl-1H-pyrrole-2-carboxylic acid (113 mg, yield 78%) as a yellow solid. LC-MS calcd for C$_{25}$H$_{25}$N$_3$O$_4$ (m/e) 431.18, obsd 885 [2M+23]$^+$.

Step 4: HATU (110 mg, 0.288 mmol) was added to a solution of 5-[3-(6-tert-butyl-1-oxo-1H-phthalazin-2-yl)-2-hydroxymethyl-phenyl]-1-methyl-1H-pyrrole-2-carboxylic acid (113 mg, 0.262 mmol) in dry THF (15 mL). Ammonia gas was bubbled through the solution. The mixture was stirred at room temperature under NH$_3$ (g) for 16 h. The mixture was concentrated under reduced pressure. The residue was purified by preparative HPLC to give 5-[3-(6-tert-butyl-1-oxo-1H-phthalazin-2-yl)-2-hydroxymethyl-phenyl]-1-methyl-1H-pyrrole-2-carboxylic acid amide (25 mg, yield 22%) as a white solid. $^1$H NMR (300 MHz, CD$_3$OD) δ 8.42 (s, 1H), 8.27 (d, J=8.5 Hz, 1H), 8.02-7.90 (m, 2H), 7.54-7.35 (m, 2H), 7.24-7.13 (m, 2H), 7.02 (d, J=1.9 Hz, 1H), 4.37 (s, 2H), 3.87 (s, 3H), 1.37 (s, 9H). LC-MS calcd for C$_{25}$H$_{26}$N$_4$O$_3$ (m/e) 430.20, obsd 883 [2M+Na]$^+$.

Example 11

2-[3-(6-tert-Butyl-1-oxo-1H-phthalazin-2-yl)-2-hydroxymethyl-phenyl]-4-methyl-oxazole-5-carboxylic acid amide

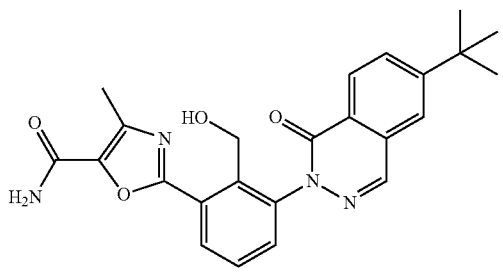 [SMILES: Cc1nc(-c2cccc(-n3ncc4cc(C(C)(C)C)ccc4c3=O)c2CO)oc1C(N)=O]

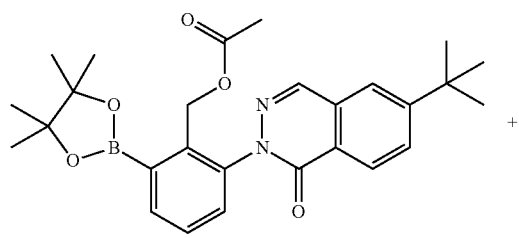

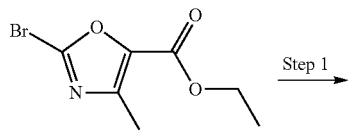

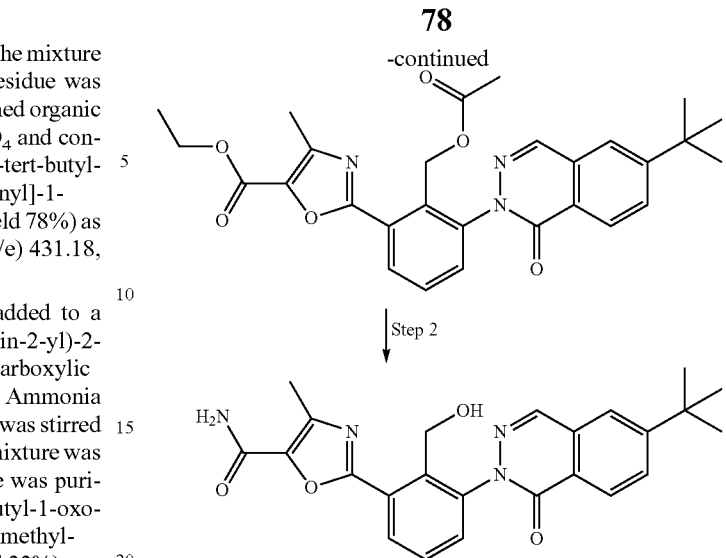

Step 1: Under N$_2$, acetic acid 2-(6-tert-butyl-1-oxo-1H-phthalazin-2-yl)-6-(4,4,5,5-tetramethyl-[1,3,2]dioxaborolan-2-yl)-benzyl ester (preparation described in intermediate-4, 72 mg, 0.153 mmol), 2-bromo-4-methyl-oxazole-5-carboxylic acid ethyl ester (34 mg, 0.146 mmol), Pd(dppf)Cl$_2$ (36 mg, 0.0438 mmol) and K$_2$CO$_3$ (61 mg, 0.438 mmol) were dissolved in dioxane/H$_2$O (5:1, 6 mL). The reaction mixture was stirred at 100° C. for about 1.5 h. The solvent was removed under reduced pressure, and the residue was purified by silica gel chromatography (petroleum ether/ethyl acetate=2:1) to give 2-[2-acetoxymethyl-3-(6-tert-butyl-1-oxo-1H-phthalazin-2-yl)-phenyl]-4-methyl-oxazole-5-carboxylic acid ethyl ester.

Step 2: The above 2-[2-acetoxymethyl-3-(6-tert-butyl-1-oxo-1H-phthalazin-2-yl)-phenyl]-4-methyl-oxazole-5-carboxylic acid ethyl ester was dissolved in 10 mL of NH$_3$/MeOH. The reaction was stirred at room temperature for two days. The solvent was removed under reduced pressure and the residue was purified by silica gel chromatography (petroleum ether/ethyl acetate=1:1) to give 2-[3-(6-tert-butyl-1-oxo-1H-phthalazin-2-yl)-2-hydroxymethyl-phenyl]-4-methyl-oxazole-5-carboxylic acid amide (47 mg, yield 68% for two steps) as a white solid. $^1$H NMR (300 MHz, DMSO-d$_6$): δ 8.57 (s, 1H), 8.24 (d, J=8.1 Hz, 1H), 8.20 (dd, J=2.1, 8.4 Hz, 1H), 8.06-8.00 (m, 2H), 7.66-7.58 (m, 2H), 4.73-4.57 (m, 2H), 2.46 (s, 3H), 1.41 (s, 9H). LC-MS calcd for C$_{24}$H$_{24}$N$_4$O$_4$ (m/e) 432.18, obsd 433 [M+H]$^+$.

Example 12

4-[3-(6-Cyclopropyl-8-fluoro-1-oxo-1H-isoquinolin-2-yl)-2-hydroxylmethyl-phenyl]-1-methyl-1H-pyrrole-2-carboxylic acid amide

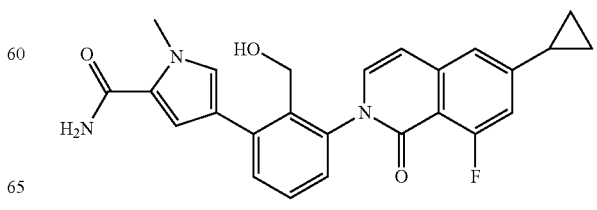

Step 1: 1-(4-bromo-1-methyl-1H-pyrrol-2-yl)-2,2,2-trifluoroethanone (5.0 g, 19.5 mmol) was dissolved in ammonium hydroxide (72.5 ml, 29.4% aqueous solution) and stirred at room temperature for 45 min. The solution was brought to pH=7 with 2N HCl. The solid precipitate was collected by filtration. The solid was washed with water and dried overnight under reduced pressure at 50° C. The aqueous layer was extracted twice with dichloromethane. The organic phase was concentrated in vacuo to afford more solid. Solid from the filtration and extraction were combined to afford 4-bromo-1-methyl-1H-pyrrole-2-carboxylic acid amide (3.2 g, 81%) as a white solid: LC/MS-ESI observed [M+H]+ 203 and 205.

Step 2: To a 25 mL microwave tube, bis(pinacolato)diboron (2.5 g, 9.85 mmol), 4-bromo-1-methyl-1H-pyrrole-2-carboxamide (1.0 g, 4.93 mmol) and potassium acetate (1.45 g, 14.8 mmol) were added. Bis(dibenzylideneacetone)palladium (142 mg, 246 µmol) was added followed by X-phos (235 mg, 493 µmol). 1,4-Dioxane (10.0 mL) was added to give a black solution. The tube was sealed and the mixture was purged with argon for 10 min. The reaction mixture was heated to 65° C. and stirred for 18 h. The crude reaction mixture was poured into 100 mL of H₂O and extracted with ethyl acetate (4×100 mL). The organic phase was with brine, dried over Na₂SO₄ and concentrated in vacuo. The crude material was purified by flash chromatography (silica gel, 150 g, 5%-50% ethyl acetate/hexanes gradient). Concentrated in vacuo to give 1-methyl-4-(4,4,5,5-tetramethyl-[1,3,2]dioxaborolan-2-yl)-1H-pyrrole-2-carboxylic acid amide (973 mg, 79%) as a light yellow foam. LC/MS-ESI observed [M+H]+ 251.

Step 3: To a 10 mL microwave vial, 1-methyl-4-(4,4,5,5-tetramethyl-1,3,2-dioxaborolan-2-yl)-1H-pyrrole-2-carboxamide (100 mg, 400 µmol, Eq: 1.00), 2-(3-chloro-2-(hydroxymethyl)phenyl)-6-cyclopropyl-8-fluoroisoquinolin-1(2H)-one (137 mg, 400 µmol, Eq: 1.00), X-phos (19.1 mg, 40.0 µmol, Eq: 0.1), Pd₂(dba)₃ (18.3 mg, 20.0 µmol, Eq: 0.05), and potassium phosphate tribasic (212 mg, 1.00 mmol, Eq: 2.50) were added, followed by 1,4-dioxane (5 ml) and water (0.5 ml) to give a dark brown suspension. The reaction mixture was stirred while purging with argon for 10 min. The solution was heated at 125° C. in a microwave for 30 min. The reaction mixture was cooled to room temperature. The reaction mixture was diluted with 50 mL of dichloromethane and extracted with water. The aqueous was concentrated in vacuo. The crude material was purified by flash chromatography (silica gel, 25%-50% [60:10:1 dichloromethane:methanol:aqueous ammonium hydroxide]/dichloromethane gradient) to give 4-[3-(6-cyclopropyl-8-fluoro-1-oxo-1H-isoquinolin-2-yl)-2-hydroxylmethyl-phenyl]-1-methyl-1H-pyrrole-2-carboxylic acid amide (25.9 mg, 15%) as a white solid: LC/MS-ESI observed [M+H]+ 432.

Example 13

4-[3-(6-tert-Butyl-3-methyl-1-oxo-3,4-dihydro-1H-phthalazin-2-yl)-2-hydroxymethyl-phenyl]-1-methyl-1H-pyrrole-2-carboxylic acid amide

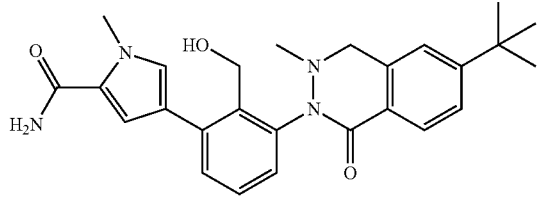 [SMILES: CN1Cc2cc(C(C)(C)C)ccc2C(=O)N1c1cccc(-c2cc(C(N)=O)n(C)c2)c1CO]

Step 1: In a 100 mL round-bottomed flask, 6-tert-butyl-2-(3-chloro-2-(hydroxymethyl)phenyl)-3-methyl-3,4-dihydrophthalazin-1(2H)-one (500 mg, 1.39 mmol, Eq: 1.00), acetic anhydride (711 mg, 657 µl, 6.97 mmol, Eq: 5) and pyridine (331 mg, 338 µl, 4.18 mmol, Eq: 3) were combined with dichloromethane (10.0 ml) to give a colorless solution. The reaction mixture was heated to 45° C. and stirred for 8 h. Cooled to room temperature and stirred for 48 h. The crude reaction mixture was concentrated in vacuo to a tan oil. The crude material was purified by flash chromatography (silica gel, 20%-30% ethyl acetate/hexanes gradient) to give 2-(6-tert-butyl-3-methyl-1-oxo-3,4-dihydrophthalazin-2(1H)-yl)-6-chlorobenzyl acetate (489 mg, 88%): ¹H NMR (300 MHz, CHLOROFORM-d) δ ppm 1.37 (s, 9H) 2.03 (s, 3H) 2.62 (s, 3H) 4.45 (s, 2H) 5.33 (s, 2H) 7.23 (d, J=1.51 Hz, 1H) 7.35-7.39 (m, 2H) 7.43-7.52 (m, 2H) 8.03 (d, J=8.31 Hz, 1H).

Step 2: In a 50 mL 2-necked flask fitted with a condenser with an argon balloon and a thermometer, 2-(6-tert-butyl-3-methyl-1-oxo-3,4-dihydrophthalazin-2(1H)-yl)-6-chlorobenzyl acetate (489 mg, 1.22 mmol, Eq: 1.00) and bis(pinacolato)diboron (619 mg, 2.44 mmol, Eq: 2) were combined with 1,4-dioxane (20.0 ml) to give a colorless solution. Stirred until all dissolved. The mixture was evacuated and back-filled with argon three times then potassium acetate (359 mg, 3.66 mmol, Eq: 3) was added. Bis(dibenzylideneacetone)palladium (35.1 mg, 61.0 µmol, Eq: 0.05) was added. X-phos (58.1 mg, 122 µmol, Eq: 0.1) was added. The mixture was evacuated and back-filled with argon three times. The reaction mixture was heated to 65° C. and stirred for 18 h. The reaction mixture was cooled to room temperature and poured into 50 mL H₂O then extracted with ethyl acetate (4×50 mL). The organics phases were combined and washed with brine. Decolorizing charcoal added to the organic layer. The solution stirred for 5 min. The solution was filtered through Celite and then concentrated in vacuo. The crude material was purified by flash chromatography (silica, 25% ethyl acetate/hexanes) to give 2-(6-tert-butyl-3-methyl-1-oxo-3,4-dihydrophthalazin-2(1H)-yl)-6-(4,4,5,5-tetramethyl-1,3,2-dioxaborolan-2-yl)benzyl acetate (518 mg, 82%): ¹H NMR (300 MHz, CHLOROFORM-d) δ ppm 1.35 (d, J=9.44 Hz, 21H) 1.99 (s, 3H) 2.62 (s, 3H) 4.44 (br. s., 2H) 5.44 (s, 2H) 7.22 (d, J=1.51 Hz, 1H) 7.36-7.58 (m, 3H) 7.87 (dd, J=7.18, 1.89 Hz, 1H) 8.04 (d, J=8.31 Hz, 1H).

Step 3: In a 10 ml microwave vial, 4-bromo-1-methyl-1H-pyrrole-2-carboxamide (82.5 mg, 406 µmol, Eq: 1.00), [prepared in Example 12, Step 1], 2-(6-tert-butyl-3-methyl-1-oxo-3,4-dihydrophthalazin-2(1H)-yl)-6-(4,4,5,5-tetramethyl-1,3,2-dioxaborolan-2-yl)benzyl acetate (200 mg, 406 µmol, Eq: 1.00), X-phos (19.4 mg, 40.6 µmol, Eq: 0.10), and potassium phosphate tribasic (259 mg, 1.22 mmol, Eq: 3.00) were combined with 1,4-dioxane (5 ml) and water (0.5 ml) to give a dark brown suspension. The reaction mixture was stirred while purging with argon for 10 min. The reaction mixture was heated at 125° C. in the microwave for 30 min. The reaction mixture was diluted with 50 mL of dichloromethane and dried (MgSO₄). Concentrated in vacuo. The crude material was purified by flash chromatography (silica, 20%-100% ethyl acetate/hexanes gradient) to give 2-(6-tert-butyl-3-methyl-1-oxo-3,4-dihydrophthalazin-2(1H)-yl)-6-(5-carbamoyl-1-methyl-1H-pyrrol-3-yl)benzyl acetate (31 mg, 16%): ¹H NMR (300 MHz, CHLOROFORM-d) δ ppm 1.37 (s, 9H) 1.98 (s, 3H) 2.68 (s, 3H) 3.99 (s, 2H) 5.28 (s, 2H) 6.72 (d, J=1.89 Hz, 1H) 6.84-6.94 (m, 1H) 7.23 (d, J=1.51 Hz, 1H) 7.27-7.52 (m, 5H) 7.61 (s, 1H) 8.04 (d, J=7.93 Hz, 1H).

Step 4: To 2-(6-tert-butyl-3-methyl-1-oxo-3,4-dihydrophthalazin-2(1H)-yl)-6-(5-carbamoyl-1-methyl-1H-pyrrol-3-yl)benzyl acetate (31 mg, 63.4 µmol, Eq: 1.00) in tetrahydrofuran was added NaOH (1.0 M (aqueous) 1.0 mL, 1.00 mmol, Eq: 15.8). The reaction mixture heated at 60° C. for 4 h. The mixture was cooled to room temperature. The solution was diluted with sat NaHCO₃ (aqueous) and dichloromethane. The layers were separated. The aqueous layer was extracted once with dichloromethane. The organic extracts were combined and dried over MgSO₄. The solution was filtered. Concentrated in vacuo to give 4-[3-(6-tert-Butyl-3-methyl-1-oxo-3,4-dihydro-1H-phthalazin-2-yl)-2-hydroxymethyl-phenyl]-1-methyl-1H-pyrrole-2-carboxylic acid amide (28 mg, 99%): ¹H NMR (300 MHz, CHLOROFORM-d) δ ppm 1.26-1.40 (m, 9H) 2.56 (s, 3H) 3.95 (s, 3H) 4.53 (br. s., 2H) 5.23 (s, 2H) 6.93 (d, J=1.89 Hz, 1H) 7.14 (d, J=1.89 Hz, 1H) 7.24-7.38 (m, 3H) 7.39-7.53 (m, 1H) 7.64 (dd, J=5.67, 3.40 Hz, 1H) 8.01 (d, J=8.31 Hz, 1H). LC/MS-ESI observed [M+H]⁺ 447.

Example 14

4-[3-(6-tert-Butyl-8-hydroxymethyl-1-oxo-1H-phthalazin-2-yl)-2-hydroxymethyl-phenyl]-1-methyl-1H-pyrrole-2-carboxylic acid amide

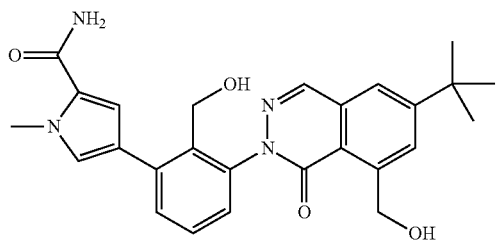 [SMILES: Cn1cc(-c2cccc(-n3ncc4cc(C(C)(C)C)cc(CO)c4c3=O)c2CO)cc1C(N)=O]

To a 15 mL tube were added 6-tert-butyl-2-[3-chloro-2-(hydroxymethyl)phenyl]-8-(hydroxymethyl)phthalazin-1(2H)-one (39 mg, 0.105 mmol), 1-methyl-4-(4,4,5,5-tetramethyl-1,3,2-dioxaborolan-2-yl)-1H-pyrrole-2-carboxamide (26.2 mg, 0.105 mmol, prepared from Intermediate-3 and bis(pinacolato)diboron under the same condition of borate formation described in the preparation of Intermediate-4), X-Phos (4.99 mg, 0.0105 mmol) and tris-potassium phosphate (55.5 mg, 0.262 mmol). Dioxane (5 mL) and water (0.5 mL) were added followed by the addition of Pd₂(dba)₃ (4.79 mg, 0.00523 mmol). The mixture was purged with argon and then heated to 125° C. with stirring for 30 minutes. Additional Pd₂(dba)₃ (6.0 mg, 0.00655 mmol) was added and the mixture was further stirred at 125° C. for 30 minutes. The mixture was extracted with dichloromethane and water. The organic layer was washed with brine and dried over sodium sulfate. Solvents were evaporated and the residue was purified by flash column chromatography (12 g silica gel, 0% to 10% methanol in dichloromethane). The desired fraction was further purified by preparative TLC (silica gel, dichloromethane/methanol/ammonium hydroxide 90/10/1) to give 4-[3-(6-tert-butyl-8-hydroxymethyl-1-oxo-1H-phthalazin-2-yl)-2-hydroxymethyl-phenyl]-1-methyl-1H-pyrrole-2-carboxylic acid amide as a light yellow powder (7.6 mg, 15.8% yield). LC/MS clacd for C₂₆H₂₈N₄O₄ (m/e) 460.21, obsd 459.0 (M−H, ES−). 1H-NMR (300 MHz, CDCl₃)

Example 15

1-[3-(6-tert-Butyl-1-oxo-1H-phthalazin-2-yl)-2-hydroxymethyl-phenyl]-3-[4-(morpholine-4-carbonyl)-phenylamino]-1H-pyrazole-4-carboxylic acid amide

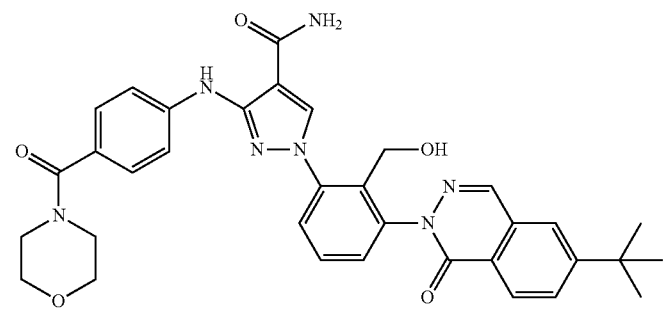

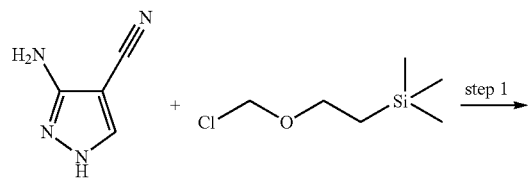

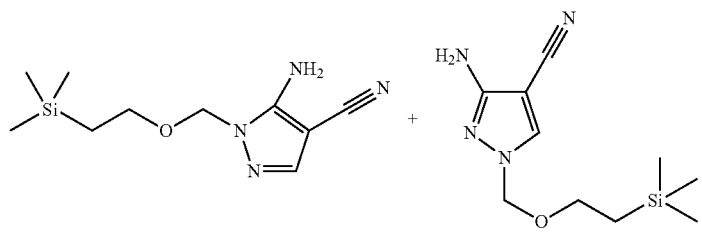

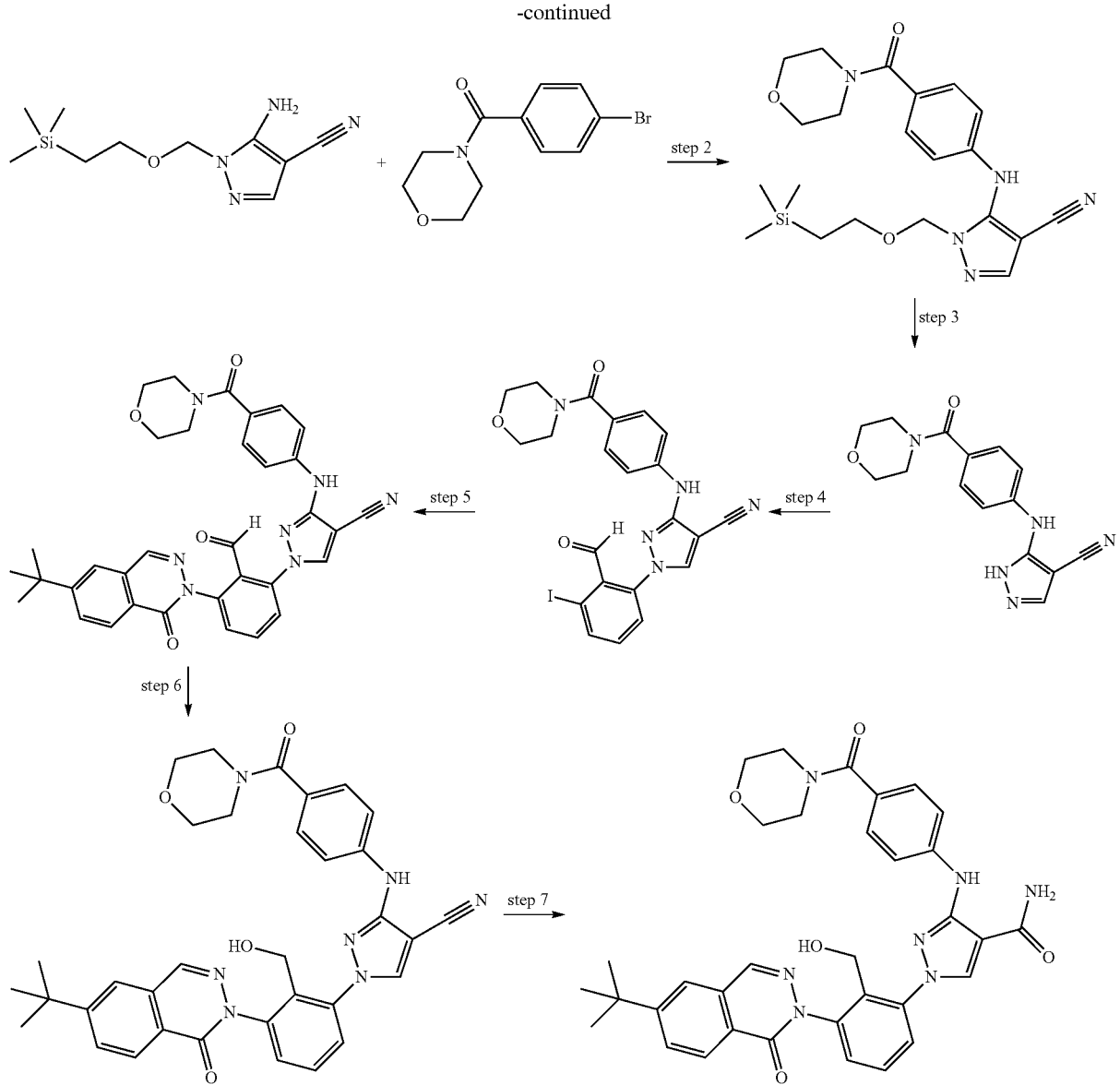

Step 1: 3-Amino-1H-pyrazole-4-carbonitrile (10 g, 92.5 mmol) was dissolved in 100 mL of DMF and the solution was stirred at 0° C. Sodium hydride (60% in mineral oil, 7.4 g, 185 mmol) was added in small portions. The mixture was stirred for 30 minutes and (2-(chloromethoxy)ethyl)trimethylsilane (90% purity, 17.1 g, 92.5 mmol) was added. The mixture was stirred at room temperature for 1 hr and then extracted with chloroform and aqueous ammonium chloride solution. The organic layer was washed with brine and dried over sodium sulfate, filtered and concentrated. The residue was purified through ISCO flash column chromatography (220 g silica gel, ethyl acetate in hexanes 5% to 40% in 25 minutes). The fractions with a slightly larger $R_f$ as the major component were evaporated and then crystallized from 7% ethyl acetate in hexanes to give a white crystalline pure compound as 1N-trimethylsilylethoxymethyl-5-amino-4-cyanopyrazole (3.75 g). The fractions with a slightly lower $R_f$ as the major component were evaporated and then crystallized from 4% ethyl acetate in hexanes to give a pure crystalline compound as 1N-trimethylsilylethoxymethyl-3-amino-4-cyanopyrazole (3.50 g). The mother liquor and fractions containing both components were combined and evaporated to give a mixture (7.4 g, total yield for this step 67%). For 1N-trimethylsilylethoxymethyl-5-amino-4-cyanopyrazole: LC/MS calcd for $C_{10}H_{18}N_4OSi$ (m/e) 238.12, obsd 237.2 (M−H, ES−); $^1$H NMR (400 MHz, DMSO-$d_6$) δ ppm 0.00 (s, 9H), 0.82 (t, J=8.0 Hz, 2H), 3.53 (t, J=8.0 Hz, 2H), 5.24 (s, 2H) 6.80 (s, 2H) 7.58 (s, 1H); For 1N-trimethylsilylethoxymethyl-3-amino-4-cyanopyrazole: $^1$H NMR (400 MHz, DMSO-$d_6$) δ ppm 0.00 (s, 9H), 0.83 (t, J=8.0 Hz, 2H), 3.51 (t, J=8.0 Hz, 2H), 5.15 (s, 2H), 5.65 (s, 2H), 8.28 (s, 1H).

Step 2: 5-Amino-1-(2-(trimethylsilyl)ethoxy)methyl)-1H-pyrazole-4-carbonitrile from step 1 (476 mg, 2.0 mmol) and (4-bromophenyl)(morpholino)methanone (539 mg, 2.0 mmol, prepared from 4-bromobenzoyl chloride and morpholine) were dissolved in warm toluene (10 mL) and cesium carbonate (976 mg, 3.0 mmol) was added followed by addition of toluene (4 mL). The mixture was degassed with argon and bis(tri-tert-butylphosphine)palladium (102 mg, 0.2 mmol) was added. The mixture was sealed and stirred at 120°

C. for 5 hrs. The mixture was filtered and rinsed with ethyl acetate (60 mL). The organic layer was extracted with ethyl acetate and water. The organic layer was dried over sodium sulfate, filtered and concentrated. The residue was purified through ISCO flash column chromatography using ethyl acetate (containing 8% methanol) in hexanes (5% to 50% in 15 minutes, 50 g silica gel) to give a desired fraction which was crystallized from ether and hexanes to provide white crystalline material as 5-[4-(morpholine-4-carbonyl)-phenylamino]-1-(2-trimethylsilanyl-ethoxymethyl)-1H-pyrazole-4-carbonitrile (631 mg, 74.1% yield). LC/MS clacd for $C_{21}H_{29}N_5O_3Si$ (m/e) 427.20, obsd 428.0 (M+H, ES+); $^1H$ NMR (400 MHz, CDCl$_3$) δ ppm 0.02 (s, 9H), 0.95 (t, J=8.0 Hz, 2H), 3.61 (t, J=8.0 Hz, 2H), 3.50-3.80 (m, 8H), 5.44 (s, 2H), 6.57 (br. s., 1H), 7.02 (d, J=8.5 Hz, 2H), 7.42 (d, J=8.5 Hz, 2H), 7.68 (s, 1H).

Step 3: 5-(4-(Morpholine-4-carbonyl)phenylamino)-1-((2-(trimethylsilyl)ethoxy)methyl)-1H-pyrazole-4-carbonitrile (880 mg, 2.06 mmol) was dissolved in 40 mL of ethanol. Hydrochloric acid (2N) was added and the mixture was stirred at room temperature overnight. After 16 hrs at room temperature, LC/MS indicated 60% desired material and 40% un-reacted starting material. The mixture was heated to 65° C. and stirred for 2 hrs. LC/MS indicated complete consumption of the starting material and the formation of the desired product. The mixture was treated with sodium hydroxide solution (4 g NaOH in 40 mL of water) under ice bath. The resulting mixture was extracted with ethyl acetate twice (350 mL). The organic layer was washed with brine and dried over sodium sulfate. TLC indicated a clean spot. Solvents were evaporated and the residue was triturated with dry ether to give 5-[4-(morpholine-4-carbonyl)-phenylamino]-1H-pyrazole-4-carbonitrile as a white solid (530 mg, 86.6% yield). H-NMR is consistent with the desired structure. LC/MS is clean and consistent with the desired molecular weight. LC/MS clacd for $C_{15}H_{15}N_5O_2$ (m/e) 297.12, obsd 298.0 (M+H, ES+).

Step 4: Potassium tert-butoxide (68 mg, 0.60 mmol) was dissolved in 3 mL of DMSO and stirred at room temperature for 5 minutes. 5-(4-(Morpholine-4-carbonyl)phenylamino)-1H-pyrazole-4-carbonitrile (150 mg, 0.505 mmol) was added and the mixture was stirred for 5 minutes. 2-Fluoro-6-iodo-benzaldehyde (378 mg, 1.51 mmol) was added and the mixture was stirred at room temperature for 24 hrs. The mixture was extracted with ethyl acetate and water. The organic layer was washed with brine and dried. Solvents were evaporated. The residue was triturated with ethyl acetate. The solid was filtered to give an off white solid 71 mg. Analysis of the white solid by TLC and LC/MS indicated a clean material. The filtrate was concentrated and dissolved in dichloromethane and purified through ISCO flash column chromatography using methanol in dichloromethane (0 to 5% in 15 minutes, 24 g silica gel) to give a pale pink solid 58 mg. Both isolated solids showed the same from TLC and LC/MS as the desired 1-(2-formyl-3-iodo-phenyl)-3-[4-(morpholine-4-carbonyl)-phenylamino]-1H-pyrazole-4-carbonitrile (48.5% yield). LC/MS clacd for $C_{22}H_{18}N_5O_3I$ (m/e) 527.05, obsd 526.0 (M−H, ES−); $^1H$ NMR (400 MHz, CDCl$_3$) δ ppm 3.52-3.85 (m, 8H), 6.60 (br. s, 1H), 7.33 (t, J=8.0 Hz, 1H), 7.38-7.49 (m, 4H), 7.52 (d, J=8.1 Hz, 1H), 8.04 (s, 1H), 8.08 (d, J=8.0 Hz, 1H), 9.93 (br. s, 1H).

Step 5: 1-(2-Formyl-3-iodophenyl)-3-(4-(morpholine-4-carbonyl)phenylamino)-1H-pyrazole-4-carbonitrile (71 mg, 0.135 mmol), 6-tert-butylphthalazin-1(2H)-one (27.2 mg, 0.135 mmol), cuprous iodide (25.6 mg, 0.135 mmol) and sodium bicarbonate (22.6 mg, 0.269 mmol) were combined in 2 mL of DMSO. The mixture was thoroughly degassed with argon and then stirred in an oil bath preheated to 100° C. After 1 hr, the mixture was extracted with dichloromethane and water. The organic layer was dried over sodium sulfate and filtered. Solvents were evaporated and the residue was purified by flash column chromatography (12 g silica gel, 0% to 5% methanol in dichloromethane) to give 1-(3-(6-tert-butyl-1-oxophthalazin-2(1H)-yl)-2-formylphenyl)-3-[4-(morpholine-4-carbonyl)phenylamino]-1H-pyrazole-4-carbonitrile as a pale pink solid (34 mg, 42% yield). LC/MS clacd for $C_{34}H_{31}N_7O_4$ (m/e) 601.24, obsd 602.1 (M+H, ES+); $^1H$ NMR (400 MHz, CDCl$_3$) δ ppm 1.45 (s, 9H), 3.68 (br. m., 8H), 6.68 (br. s., 1H), 7.39 (d, J=8.6 Hz, 2H), 7.46 (d, J=8.6 Hz, 2H), 7.57 (dd, J=8.0, 1.1 Hz, 1H), 7.65-7.74 (m, 1H), 7.74-7.81 (m, 2H), 7.93 (dd, J=8.6, 1.8 Hz, 1H), 8.17 (s, 1H), 8.40 (d, J=8.6 Hz, 1H), 8.47 (br. s., 1H), 9.90 (br. s., 1H).

Step 6: 1-(3-(6-tert-Butyl-1-oxophthalazin-2(1H)-yl)-2-formylphenyl)-3-[4-(morpholine-4-carbonyl)phenylamino]pyrazole-4-carbonitrile (53 mg, 0.0875 mmol) was dissolved in 6 mL of dichloromethane and 2 mL of methanol. Sodium borohydride solution (8.28 mg, 0.219 mmol) in water (0.5 mL) and methanol (1.0 mL) was added in drops. The mixture was stirred at room temperature for 1 hr. LC/MS showed a clean desired product. The mixture was evaporated to dryness and extracted with dichloromethane and water. The organic layer was dried over sodium sulfate and evaporated to give a pure desired 1-[3-(6-tert-butyl-1-oxophthalazin-2(1H)-yl)-2-(hydroxymethyl)phenyl]-3-[4-(morpholine-4-carbonyl)phenylamino]-1H-pyrazole-4-carbonitrile (52.8 mg, 100% yield). LC/MS clacd for $C_{34}H_{33}N_7O_4$ (m/e) 603.26, obsd 604.1 (M+H, ES+); $^1H$ NMR (400 MHz, CDCl$_3$) δ ppm 1.47 (s, 9H), 3.61-3.77 (m, 8H), 4.35 (br. s., 2H), 6.59 (br. s., 1H), 7.43 (d, J=8.6 Hz, 2H), 7.50 (d, J=8.1 Hz, 1H), 7.58 (d, J=8.6 Hz, 2H), 7.67 (t, J=8.1 Hz, 1H), 7.80 (d, J=1.7 Hz, 1H), 7.83 (dd, J=8.1, 1.3 Hz, 1H), 7.97 (dd, J=8.6, 1.7 Hz, 1H), 8.39 (d, J=0.5 Hz, 1H), 8.48 (d, J=8.6 Hz, 1H), 8.79 (s, 1H).

Step 7: 1-[3-(6-tert-Butyl-1-oxophthalazin-2(1H)-yl)-2-(hydroxymethyl)phenyl]-3-[4-(morpholine-4-carbonyl)phenylamino]-1H-pyrazole-4-carbonitrile (52 mg, 0.0861 mmol) was dissolved in 4 mL of THF and 0.4 mL of water. Then dihydrogen tris(dimethylphosphinito)hydroplatinate (CAS#173416-05-2, 3 mg, 8% eq) was added. The mixture was refluxed for 1 hr. TLC indicated complete consumption of the starting material. LC/MS indicated the clean product formed with the correct MW. The mixture was evaporated to dryness and then dissolved in dichloromethane, dried over sodium sulfate and filtered. After the evaporation of solvents, the residue was purified through flash column chromatography (24 g silica gel, methanol in dichloromethane, 0% to 5% in 16 minutes) to give 1-[3-(6-tert-butyl-1-oxo-1H-phthalazin-2-yl)-2-hydroxymethyl-phenyl]-3-[4-(morpholine-4-carbonyl)-phenylamino]-1H-pyrazole-4-carboxylic acid amide as a white solid (41 mg, 76.6% yield). LC/MS clacd for $C_{34}H_{35}N_7O_5$ (m/e) 621.27, obsd 622.1 (M+H, ES+); $^1H$ NMR (400 MHz, DMSO-d6) δ ppm 1.41 (s, 9H) 3.41-3.71 (m, 8H), 4.37 (br. s., 2H), 4.74 (br. s., 1H), 7.36 (d, J=6.3 Hz, 3H), 7.49-7.71 (m, 5H), 7.80 (br. s., 1H), 8.04 (d, J=9.1 Hz, 2H), 8.25 (d, J=6.6 Hz, 1H), 8.56 (br. s., 2H), 9.44 (br. s., 1H).

Example 16

1-[3-(6-tert-Butyl-8-fluoro-1-oxo-1H-phthalazin-2-yl)-2-hydroxymethyl-phenyl]-3-[4-(morpholine-4-carbonyl)-phenylamino]-1H-pyrazole-4-carboxylic acid amide

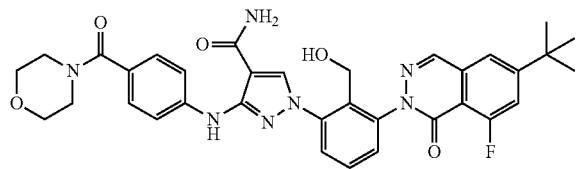 [SMILES: CC(C)(C)c1cc(F)c2c(=O)n(-c3cccc(-n4cc(C(N)=O)c(Nc5ccc(C(=O)N6CCOCC6)cc5)n4)c3CO)ncc2c1]

This compound was prepared with the same method described in Example 15 (step 5, 6 and 7 of Example 15) by using 6-tert-butyl-8-fluoro-2H-phthalazin-1-one (prepared according to US2010/0222325).

1-(2-Formyl-3-iodophenyl)-3-(4-(morpholine-4-carbonyl)phenylamino)-1H-pyrazole-4-carbonitrile (115 mg, 0.218 mmol), 6-tert-butyl-8-fluorophthalazin-1(2H)-one (48 mg, 0.218 mmol), cuprous iodide (41.5 mg, 0.218 mmol) and sodium bicarbonate (36.6 mg, 0.436 mmol) were combined in 2 mL of DMSO. The mixture was thoroughly degassed with argon and stirred in an oil bath preheated to 100° C. for 1 hr. The mixture was extracted with dichloromethane and water. The organic layer was washed with brine, dried over sodium sulfate and filtered. Solvents were evaporated and the residue was purified by flash column chromatography using methanol in dichloromethane (0% to 5% in 16 minutes, 24 g silica gel) to give 1-[3-(6-tert-butyl-8-fluoro-1-oxo-1H-phthalazin-2-yl)-2-formyl-phenyl]-3-[4-(morpholine-4-carbonyl)-phenylamino]-1H-pyrazole-4-carbonitrile as a pale pink solid (54 mg, 40% yield). LC/MS clacd for $C_{34}H_{30}FN_7O_4$ (m/e) 619.23, obsd 620.0 (M+H, ES+); $^1$H NMR (400 MHz, CDCl$_3$) δ ppm 1.43 (s, 9H), 3.56-3.76 (m, 8H), 6.61 br. s., 1H), 7.40 (d, J=8.6 Hz, 2H), 7.46 (d, J=8.6 Hz, 2H), 7.52 (dd, J=12.4, 1.8 Hz, 1H), 7.55-7.59 (m, 2H), 7.64 (d, J=7.8 Hz, 1H), 7.78 (t, J=8.1 Hz, 1H), 8.16 (s, 1H), 8.32 (s, 1H), 9.97 (s, 1H).

1-[3-(6-tert-Butyl-8-fluoro-1-oxo-1H-phthalazin-2-yl)-2-formyl-phenyl]-3-[4-(morpholine-4-carbonyl)-phenylamino]-1H-pyrazole-4-carbonitrile (52 mg, 0.0839 mmol) was dissolved in 6 mL of dichloromethane and 2 mL of methanol. Sodium borohydride solution (9.52 mg, 0.252 mmol) in water (0.5 mL) and methanol (1.0 mL) was added in drops. The mixture was stirred at room temperature for 1 hr. LC/MS showed a clean desired product. The mixture was evaporated to dryness and extracted with dichloromethane and water. The organic layer was dried over sodium sulfate and evaporated to give a pure desired 1-[3-(6-tert-butyl-8-fluoro-1-oxo-1H-phthalazin-2-yl)-2-hydroxymethyl-phenyl]-3-[4-(morpholine-4-carbonyl)-phenylamino]-1H-pyrazole-4-carbonitrile (51 mg, 98% yield). LC/MS clacd for $C_{34}H_{32}FN_7O_4$ (m/e) 621.25, obsd 622.1 (M+H, ES+); $^1$H NMR (400 MHz, CDCl$_3$) δ ppm 1.45 (s, 9H), 3.59-3.77 (m, 8H), 4.37 (br. s., 2H), 6.59 (br. s., 1H), 7.43 (d, J=8.6 Hz, 2H), 7.48 (dd, J=7.8, 1.3 Hz, 1H), 7.54-7.61 (m, 4H), 7.66 (t, J=8.1 Hz, 1H), 7.81 (dd, J=8.1, 1.3 Hz, 1H), 8.32 (d, J=2.5 Hz, 1H), 8.74 (s, 1H).

1-(3-(6-tert-Butyl-8-fluoro-1-oxophthalazin-2(1H)-yl)-2-(hydroxymethyl)phenyl)-3-(4-(morpholine-4-carbonyl)phenylamino)-1H-pyrazole-4-carbonitrile (46 mg, 0.074 mmol) was dissolved in 4 mL of THF and 0.5 mL of water. Then dihydrogen tris(dimethylphosphinito)hydroplatinate (3 mg, 0.0069 mmol) was added and the mixture was stirred under fluxing. After 1 hr, TLC indicated complete consumption of the starting material. LC/MS indicated clean desired product formed. The mixture was evaporated and the residue was dissolved in dichloromethane and dried over sodium sulfate, filtered through micron filter and evaporated. The residue was purified through flash column chromatography using methanol in methylene chloride (1.5% to 5% methanol in 10 minutes, 12 g silica gel) to give 1-[3-(6-tert-butyl-8-fluoro-1-oxo-1H-phthalazin-2-yl)-2-hydroxymethyl-phenyl]-3-[4-(morpholine-4-carbonyl)-phenylamino]-1H-pyrazole-4-carboxylic acid amide as a white solid (36 mg, 76.1% yield). LC/MS clacd for $C_{34}H_{34}FN_7O_5$ (m/e) 639.26, obsd 640.1 (M+H, ES+); $^1$H NMR (400 MHz, DMSO-d6) δ ppm 1.38 (s, 9H), 3.50 (br., 4H), 3.59 (br., 4H), 4.38 (br. s., 2H), 4.78 (t, J=5.2 Hz, 1H), 7.36 (d, J=8.6 Hz, 3H), 7.52-7.69 (m, 5H), 7.76 (d, J=13.1 Hz, 2H), 7.88 (s, 1H), 8.54 (m, 2H), 9.44 (s, 1H).

Example 17

1-[3-(6-tert-Butyl-8-fluoro-1-oxo-1H-phthalazin-2-yl)-phenyl]-3-[4-(morpholine-4-carbonyl)-phenylamino]-1H-pyrazole-4-carboxylic acid amide

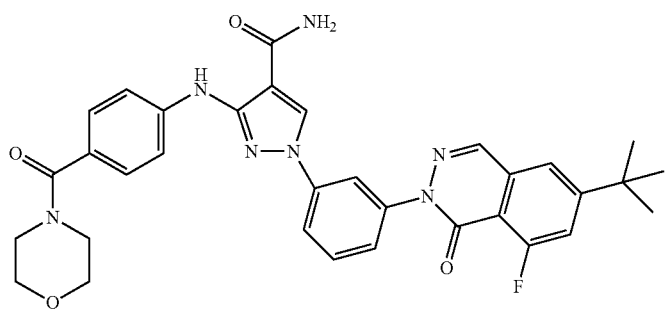

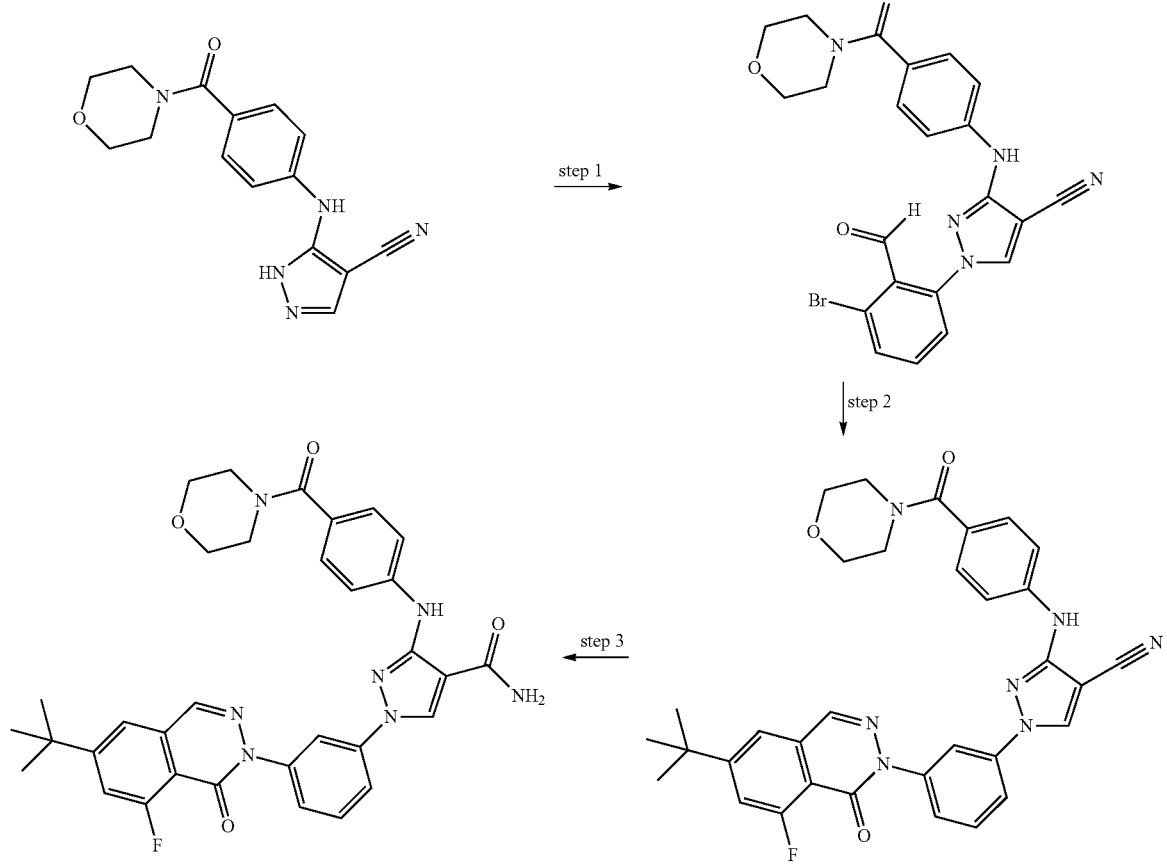

Step 1: Potassium tert-butoxide (120 mg, 1.07 mmol) was dissolved in 5 mL of DMSO and stirred at rt for 5 minutes. Then 5-(4-(morpholine-4-carbonyl)phenylamino)-1H-pyrazole-4-carbonitrile (290 mg, 0.975 mmol) was added and the mixture was stirred for 5 minutes. To this solution was added 2-bromo-6-fluorobenzaldehyde (396 mg, 1.95 mmol) and the mixture was stirred at room temperature overnight. The mixture was extracted with ethyl acetate and water. The organic layer was washed with water and brine, dried over sodium sulfate and evaporated. The residue was triturated with 20 mL of ethyl acetate and filtered to give the desired compound 70 mg. The filtrate was separated by flash column chromatography to give a second batch desired compound (110 mg) as 1-(3-bromo-2-formyl-phenyl)-3-[4-(morpholine-4-carbonyl)-phenylamino]-1H-pyrazole-4-carbonitrile (38.4% yield). LC/MS clacd for $C_{22}H_{18}BrN_5O_3$ (m/e) 479.06, obsd 477.8 (M−H, ES−); $^1$H NMR (300 MHz, DMSO-d6) δ ppm 3.50 (br. s., 4H), 3.59 (d, J=3.8 Hz, 4H), 7.34 (d, J=8.7 Hz, 2H), 7.53 (d, J=8.7 Hz, 2H), 7.65 (t, J=7.9 Hz, 1H), 7.79 (d, J=7.9 Hz, 1H), 7.85 (d, J=7.9 Hz, 1H), 9.08 (s, 1H), 9.47 (s, 1H), 10.07 (s, 1H). NOE analysis of $^1$H-NMR confirmed the desired regio-chemistry.

Step 2: 1-(3-Bromo-2-formylphenyl)-3-(4-(morpholine-4-carbonyl)phenylamino)-1H-pyrazole-4-carbonitrile (34 mg, 0.0708 mmol), 6-tert-butyl-8-fluorophthalazin-1(2H)-one (31.2 mg, 0.142 mmol), cuprous iodide (27 mg, 0.142 mmol) and sodium bicarbonate (14.9 mg, 0.177 mmol) were combined in 1 mL of DMSO. The solution was degassed with argon and then heated in a microwave at 120° C. for 1 hr. The resulting mixture was extracted with ethyl acetate and ammonium chloride solution. The organic layer was concentrated and purified by flash column chromatography using ethyl acetate (containing 5% methanol) in hexanes (5% to 80% linear gradient in 15 minutes, 12 g silica gel) to give the pure desired product. This material was triturated with ether in hexanes and filtered to give 1-[3-(6-tert-butyl-8-fluoro-1-oxo-1H-phthalazin-2-yl)-phenyl]-3-[4-(morpholine-4-carbonyl)-phenylamino]-1H-pyrazole-4-carbonitrile (18.2 mg, 41.5% yield) as a pale pink solid. LC/MS clacd for $C_{33}H_{30}FN_7O_3$ (m/e) 591.24, obsd 592.0 (M+H, ES+); $^1$H NMR (400 MHz, DMSO-d6) δ ppm 1.38 (s, 9H), 3.50 (br., 4H), 3.59 (br., 4H), 7.37 (d, J=8.6 Hz, 2H), 7.59 (d, J=8.3 Hz, 1H), 7.65-7.71 (m, 3H), 7.78 (d, J=13.1 Hz, 1H), 7.87-7.93 (m, 2H), 8.08 (s, 1H), 8.58 (d, J=2.3 Hz, 1H), 9.29 (s, 1H), 9.47 (s, 1H).

Step 3: 1-(3-(6-tert-Butyl-8-fluoro-1-oxophthalazin-2(1H)-yl)phenyl)-3-(4-(morpholine-4-carbonyl)phenylamino)-1H-pyrazole-4-carbonitrile (30 mg, 0.050 mmol) was dissolved in 4 mL of THF and 0.5 mL of water. Then dihydrogen tris(dimethylphosphinito)hydroplatinate (2.3 mg, 0.0052 mmol) was added and the mixture was stirred under fluxing. After 1 hr, TLC indicated complete consumption of the starting material. LC/MS indicated clean desired product formed. The mixture was evaporated and the residue was dissolved in dichloromethane and dried over sodium sulfate, filtered through micron filter and evaporated. The residue was purified through flash column chromatography using methanol in methylene chloride (0% to 5% methanol in 10 minutes, 12 g silica gel) to give 1-[3-(6-tert-butyl-8-fluoro-1-oxo-1H-phthalazin-2-yl)-phenyl]-3-[4-(morpholine-4-carbonyl)-phenylamino]-1H-pyrazole-4-carboxylic acid amide as a white solid (21 mg, 68% yield). LC/MS clacd for $C_{33}H_{32}FN_7O_4$ (m/e) 609.25, obsd 608.0 (M–H, ES–); $^1$H NMR (400 MHz, DMSO-d6) δ ppm 1.39 (s, 9H), 3.51 (br. s., 4H), 3.59 (br. s., 4H), 7.39 (d, J=8.3 Hz, 3H), 7.56 (d, J=7.8 Hz, 1H), 7.65-7.73 (m, 3H), 7.75-7.86 (m, 3H), 7.89 (s, 1H), 7.98 (br. s., 1H), 8.60 (d, J=2.0 Hz, 1H), 9.04 (s, 1H), 9.42 (s, 1H).

Example 18

1-(3-(6-tert-butyl-8-fluoro-1-oxophthalazin-2(1H)-yl)-2-(hydroxymethyl)phenyl)-1H-indole-3-carboxamide

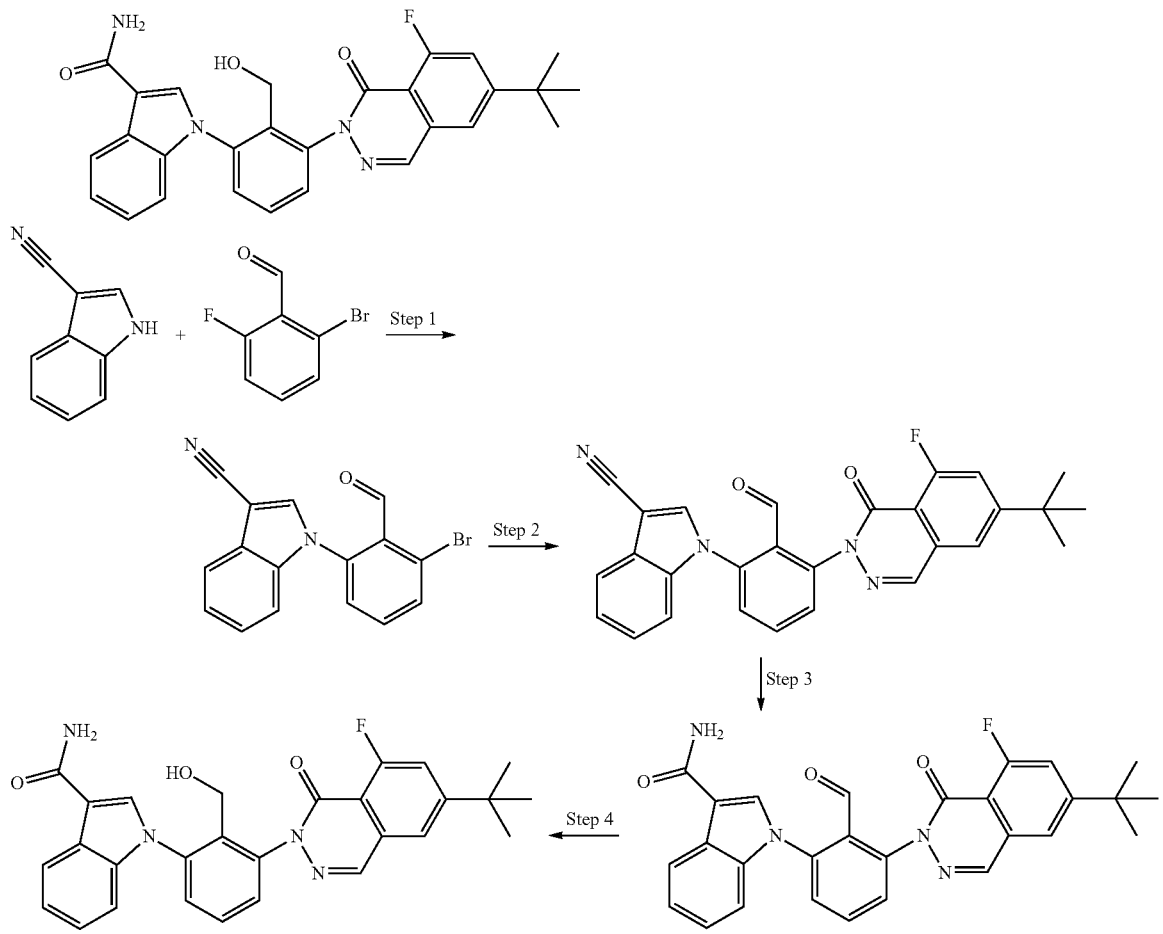

Step 1: To a cooled (ice bath) solution of 1H-indole-3-carbonitrile (1 g, 7.03 mmol) in dry dimethylformamide (10 mL) under nitrogen atmosphere was added sodium hydride (383 mg, 8.44 mmol, 60% in oil) in 2 portions over about 4 minutes. The material was stirred for 5 minutes and then the ice bath was removed and the mixture warmed to ambient. 2-Bromo-6-fluorobenzaldehyde (1.43 g, 7.03 mmol) was added as a powder in one portion. The material was stirred vigorously for 2 hours. The mixture was placed on a rotary evaporator attached to a mechanical pump and the solvent was stripped. The remainder was taken up in a 5% solution of aqueous ammonium chloride (40 ml) and ethyl acetate (40 ml) and transferred to a separatory funnel. The organic phase was collected and washed with 50% diluted brine solution (40 ml). The ethyl acetate phase was collected and the aqueous phase was back extracted with ethyl acetate (2×35 mL). The organic phases were combined, dried (magnesium sulfate), filtered and stripped. The crude product was adsorbed onto silica (10 g, from dichloromethane) and purified by HPLC (dry loading; silica gel; 40 g) eluting with 100% methylene chloride to provide semi-pure product (990 mg). This material was purified via trituration from hot dichloromethane/hexane to provide 1-(3-bromo-2-formylphenyl)-1H-indole-3-carbonitrile as an orange solid (354 mg, 16% yield). $^1$H NMR (300 MHz, CHLOROFORM-d) δ ppm 7.02-7.11 (m, 1H) 7.27-7.38 (m, 2H) 7.45 (d, J=7.93 Hz, 1H) 7.61 (t, J=8.12 Hz, 1H) 7.68 (s, 1H) 7.80-7.86 (m, 1H) 7.90 (dd, J=7.93, 1.13 Hz, 1H) 10.05 (s, 1H).

Step 2: To a solution of 6-tert-butyl-8-fluorophthlazine-1 (2H)-one (prepared according to US2010/0222325) 36 mg, 0.16 mmol) and 1-(3-bromo-2-formylphenyl)-1H-indole-3-carbonitrile (59 mg, 0.18 mmol) in dry dimethylsulfoxide (1.8 mL) was added sodium bicarbonate (31 mg, 0.36 mmol) under an argon atmosphere. Next copper iodide (35 mg, 0.18 mmol) was added and the mixture was heated to 110° C. for 2 hours. The reaction was cooled to ambient and taken up in water (40 ml) and dichloromethane (40 ml). The material was filtered through a plug of celite, rinsing well with dichloromethane. The filtrate was transferred to a reparatory funnel and the dichloromethane phase was collected. This was washed with a 50% solution of diluted brine (40 ml). The organic phase was collected and the aqueous phases back extracted with dichloromethane (2×35 ml). The dichloromethane phases were combined, dried (MgSO4), filtered and stripped. Then the identical reaction was repeated on a larger scale using 1-(3-bromo-2-formylphenyl)-1H-indole-3-carbonitrile (290 mg, 0.89 mmol) and similar scaled amounts of the reagents described above and under identical procedure and work up. The crude from the two reactions was combined and purified by HPLC (silica gel, eluting with 100% $CH_2Cl_2$ to 1% $MeOH/CH_2Cl_2$) to provide a semi-pure product. The material was further purified by preparative thin layer chromatography (3 plates, eluting with 0.5% $MeOH/CH_2Cl_2$ and then re-eluting with 0.75% and then 1% $MeOH/CH_2Cl_2$). The product band was collected to provide 1-(3-(6-tert-butyl-8-fluoro-1-oxophthalazin-2(1H)-yl)-2-formylphenyl)-1H-indole-3 carbonitrile as a yellow foamy solid. (384 mg, 77% yield). LC/MS calcd for $C_{28}H_{21}FN_4O_2$ (m/e) 464.49, obsd 465.0 (M+H, ES+): $^1$H NMR (300 MHz, CHLOROFORM-d) δ ppm 1.42 (s, 9H) 7.24-7.32 (m, 1H) 7.34-7.41 (m, 2H) 7.46-7.60 (m, 3H) 7.75 (d, J=7.55 Hz, 1H) 7.81 (s, 1H) 7.83-7.87 (m, 1H) 7.90 (t, J=7.96 Hz, 1H) 8.25 (d, J=2.64 Hz, 1H) 9.56 (s, 1H).

Step 3: A round bottom flask containing 1-(3-(6-tert-butyl-8-fluoro-1-oxophthalazin-2(1H)-yl)-2-formylphenyl)-1H-indole-3 carbonitrile (12 mg, 0.03 mmol) was taken up in 10% water/tetrahydrofuran (1.5 ml). Next hydrido(dimethylphosphinousacid-kp)[hydrogen bis-(dimethylphosphinito-kp)]platinum(II) catalyst (2 mg, 0.005 mmol) was added and the mixture was heated to reflux (oil bath). After 1 hour the mixture was cooled to ambient and the volatiles stripped (rotary evaporator) to provide a crude product. This reaction (as described above—but using 10% H2O/ethanol as solvent) was repeated on a 61 mg scale (0.24 mmol) and worked up as described. The combined crude material from the 2 reactions was purified by preparative thin layer chromatography (3 plates, eluting with 5% $MeOH/CH_2Cl_2$ and then re-developing again with 5% $MeOH/CH_2Cl_2$). The product band was collected to provide 1-(3-(6-tert-butyl-8-fluoro-1-oxophthalazin-2(1H)-yl)-2-formylphenyl)-1H-indole-3-carboxamide as a light yellow solid (51 mg). LC/MS calcd for $C_{28}H_{23}FN_4O_3$ (m/e) 482.52, obsd 483.0 (M+H, ES+): $^1$H NMR (300 MHz, CHLOROFORM-d) δ ppm 1.40 (s, 9H) 6.03 (br. s, 2H) 7.20-7.36 (m, 3H) 7.44-7.59 (m, 3H) 7.66 (d, J=7.93 Hz, 1H) 7.81 (t, J=7.60 Hz, 1H) 7.91 (s, 1H) 8.19 (m, 1H) 8.23 (d, J=2.64 Hz, 1H) 9.52 (s, 1H)

Step 4: To a cooled (ice bath) flask containing 1-(3-(6-tert-butyl-8-fluoro-1-oxophthalazin-2(1H)-yl)-2-formylphenyl)-1H-indole-3-carboxamide (51 mg, 0.11 mmol) dissolved in methanol/dichloromethane (1.35 ml, 2.9:1) was added a solution of sodium borohydride (20 mg, 0.53 mmol) in water (0.35 ml), via slow drop-wise addition. The mixture was stirred for 10 minutes and then taken up in dichloromethane (20 ml) and water (20 ml). The contents were poured into a separatory funnel and agitated. The organic phase was collected and washed with a solution of 50% diluted brine (20 ml). The dichloromethane layer was collected and the aqueous phases were back extracted with methylene chloride (2×20 mL). The organic phases were combined, dried over magnesium sulfate, filtered and stripped. The crude material was purified by filtration through a short column of silica gel, eluting with 7.5% methanol/dichloromethane. The desired fraction was collected and then the material was crystallized from a solution of hot dichloromethane/hexanes to provide white crystalline product as 1-(3-(6-tert-butyl-8-fluoro-1-oxophthalazin-2(1H)-yl)-2-(hydroxymethyl)phenyl)-1H-indole-3-carboxamide (37 mg). LC/MS calcd for $C_{28}H_{25}FN_4O_3$ (m/e) 484.54, obsd 485.0 (M+H, ES+): $^1$H NMR (300 MHz, CHLOROFORM-d) δ ppm 1.44 (s, 9H) 4.03-4.37 (m, 2H) 5.49-6.00 (br. s, 2H) 7.18-7.38 (m, 3H) 7.49-7.71 (m, 5H) 8.13-8.28 (m, 2H) 8.32 (d, J=2.64 Hz, 1H).

Example 19

1-(3-(6-tert-butyl-1-oxophthalazin-2(1H)-yl)-2-(hydroxymethyl)-phenyl)-1H-indole-3-carboxamide

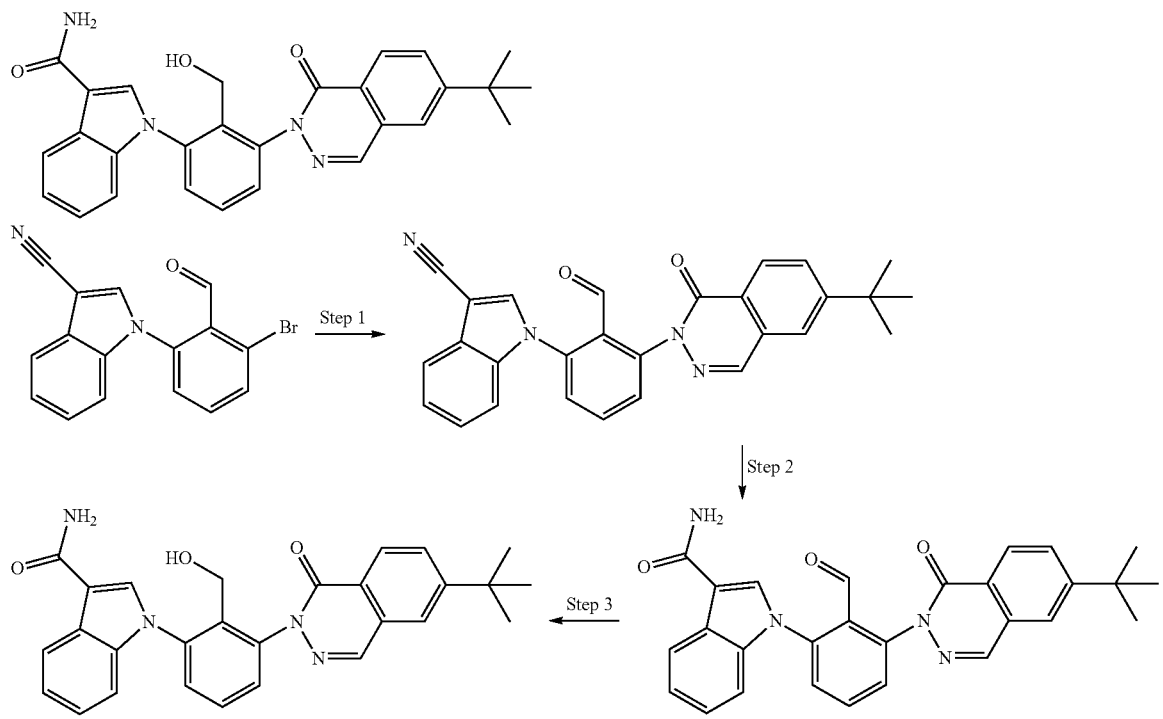

Step 1: The preparation of 1-(3-(6-tert-butyl-1-oxoph-thalazin-2(1H)-yl)-2-formylphenyl)-1H-indole-3-carbonitrile, via reaction of 1-(3-bromo-2-formylphenyl)-1H-indole-3-carbonitrile (222 mg, 40% pure, 0.27 mmol, synthesis described above in Example 18, step 1) with 6-tert-butylphthalzin-1(2H)-one (138 mg, 0.68 mmol) was carried out in a procedure analogous to that described in Example 18. Similar work up and purification provided desired product as a light yellow-white solid (82 mg, 66% yield). LC/MS calcd for $C_{28}H_{22}N_4O_2$ (m/e) 446.51, obsd 447.0 (M+H, ES+): $^1$H NMR (300 MHz, CHLOROFORM-d) δ ppm 1.44 (s, 9H) 7.23-7.40 (m, 3H) 7.55 (dd, J=7.93, 1.13 Hz, 2H) 7.72-7.94 (m, 6H) 8.32 (s, 1H) 8.39 (d, J=8.31 Hz, 1H) 9.59 (s, 1H).

Step 2: The preparation of 1-(3-(6-tert-butyl-1-oxoph-thalazin-2(1H)-yl)-2-formylphenyl)-1H-indole-3-carboxamide, via nitrile hydrolysis of 1-(3-(6-tert-butyl-1-oxoph-thalazin-2(1H)-yl)-2-formylphenyl)-1H-indole-3-carbonitrile (82 mg, 0.18 mmol) and use of catalyst hydrido (dimethylphosphinousacid-kp)[hydrogen bis-(dimethylphosphinito-kp)]platinum(II) catalyst (5 mg, 0.064 mmol) was carried out in a procedure analogous to that described in Example 18. Similar work up and purification provided desired product as a light yellow glassy solid (54 mg, 63% yield). LC/MS calcd for $C_{28}H_{24}N_4O_3$ (m/e) 464.5, obsd 465.0 (M+H, ES+): $^1$H NMR (300 MHz, CHLOROFORM-d) δ ppm 1.44 (s, 9H) 7.21-7.37 (m, 3H) 7.48-7.59 (m, 2H) 7.67-7.76 (m, 2H) 7.85 (t, J=7.93, 1.00 Hz, 1H) 7.90 (s, 1H) 8.14-8.20 (m, 1H) 8.30 (s, 1H) 8.37 (d, J=8.31 Hz, 1H) 9.56 (s, 1H)

Step 3: The preparation of 1-(3-(6-tert-butyl-1-oxoph-thalazin-2(1H)-yl)-2-(hydroxymethyl)-phenyl)-1H-indole-3-carboxamide, via reduction of 1-(3-(6-tert-butyl-1-oxoph-thalazin-2(1H)-yl)-2-formylphenyl)-1H-indole-3-carbonitrile (54 mg, 0.12 mmol) by use of sodium borohydride (22 mg, 0.58 mmol) was carried out in a procedure analogous to that described in Example 18. Similar work up and purification provided desired product as a white crystalline solid (36 mg, 64% yield). LC/MS calcd for $C_{28}H_{26}N_4O_3$ (m/e) 466.54, obsd 467.0 (M+H, ES+): $^1$H NMR (300 MHz, CHLOROFORM-d) δ ppm 1.46 (s, 9H) 4.07 (br. d, J=11.70 Hz, 1H) 4.30 (br. d, J=11.70 Hz, 1H) 5.60-5.97 (m, 2H) 7.20-7.38 (m, 3H) 7.52-7.71 (m, 3H) 7.80 (d, J=1.89 Hz, 1H) 7.96 (dd, J=8.31, 1.89 Hz, 1H) 8.17-8.29 (m, 2H) 8.39 (s, 1H) 8.46 (d, J=8.31 Hz, 1H).

Example 20

1-[3-(6-tert-Butyl-8-fluoro-1-oxo-1H-phthalazin-2-yl)-2-hydroxymethyl-phenyl]-1H-pyrrolo[2,3-b]pyridine-3-carboxylic acid amide

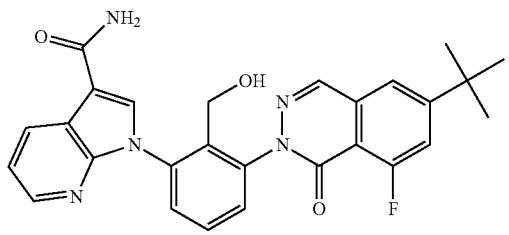

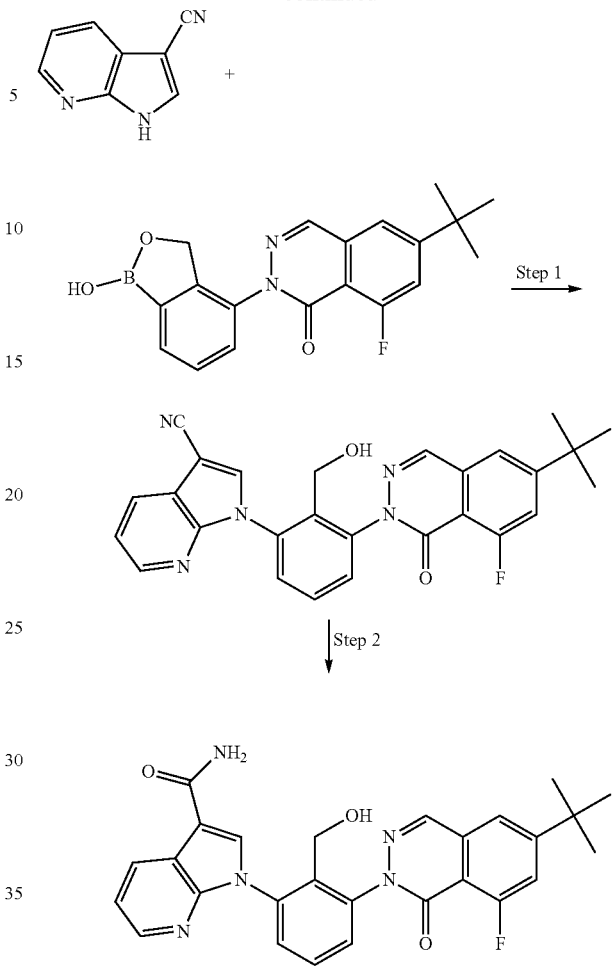

Step 1: In a 100 mL pear-shaped flask, 1H-pyrrolo[2,3-b]pyridine-3-carbonitrile (150 mg, 1.05 mmol, Eq: 1.00), copper(II) acetate (381 mg, 2.1 mmol, Eq: 2), pyridine (166 mg, 170 μl, 2.1 mmol, Eq: 2) and 6-tert-butyl-8-fluoro-2-(1-hydroxy-1,3-dihydro-benzo[c][1,2]oxaborol-4-yl)-2H-phthalazin-1-one (706 mg, 1.15 mmol, Eq: 1.1) was combined with methylene chloride (10 ml) to give a turquoise suspension. The reaction mixture was flushed with nitrogen. The reaction mixture was heated to 80° C. and stirred for 16 hr. The reaction was diluted with saturated NH$_4$Cl (50 mL) and extracted with EtOAc (3×50 mL). The mixture was separated on ISCO using 30-50% EtOAc in hexanes to give the 1-[3-(6-tert-Butyl-8-fluoro-1-oxo-1H-phthalazin-2-yl)-2-hydroxymethyl-phenyl]-1H-pyrrolo[2,3-b]pyridine-3-carbonitrile (122 mg, 25%) as an off white foam. $^1$H NMR (DMSO-d$_6$) δ: 8.64 (dd, J=7.9, 1.6 Hz, 1H), 8.60 (d, J=2.5 Hz, 1H), 8.45 (s, 1H), 8.36 (dd, J=4.8, 1.8 Hz, 1H), 7.94 (d, J=1.8 Hz, 1H), 7.82 (dd, J=13.2, 1.6 Hz, 1H), 7.66-7.78 (m, 3H), 7.63 (dd, J=7.3, 2.3 Hz, 1H), 7.36 (dd, J=8.0, 4.8 Hz, 1H), 7.18 (br. s., 1H), 4.72 (t, J=5.4 Hz, 1H), 4.11-4.34 (m, 2H), 1.44 (s, 9H). MS m/e 468.5 (M+H$^+$).

Step 2: A stirred solution of 1-(3-(6-tert-butyl-8-fluoro-1-oxophthalazin-2(1H)-yl)-2-(hydroxymethyl)phenyl)-1H-pyrrolo[2,3-b]pyridine-3-carbonitrile (610 mg, 783 μmol, Eq: 1.00), acetaldoxime (139 mg, 143 μl, 2.35 mmol, Eq: 3) and indium (III) chloride (8.66 mg, 39.1 μmol, Eq: 0.05) in toluene (25.2 ml) was heated to 110° C. and stirred for 3 h. The reaction mixture was poured into 15 mL EtOAc and extracted with sat NH$_4$Cl (1×25 mL). The organic layers were dried over MgSO$_4$ and concentrated in vacuo. After removal of solvent and residue was separated by flash chromatography (silica gel, 12 g, 80% to 100% EtOAc in hexanes) gave 66 mgs of desired product with impurity. This material was re-purified by preparative reverphase HPLC in TFA. The desired product was neutralized with NaHCO$_3$ (1×25 mL). The organic layers were dried over MgSO$_4$ and concentrated in vacuo., extracted with ethyl acetate/methanol (9:1) to give 1-[3-(6-tert-Butyl-8-fluoro-1-oxo-1H-phthalazin-2-yl)-2-hydroxymethyl-phenyl]-1H-pyrrolo[2,3-b]pyridine-3-carboxylic acid amide (43 mgs, 12%) as white solid. $^1$H NMR (DMSO-d$_6$) δ: 8.64 (dd, J=7.9, 1.6 Hz, 1H), 8.60 (d, J=2.5 Hz, 1H), 8.45 (s, 1H), 8.36 (dd, J=4.8, 1.8 Hz, 1H), 7.94 (d, J=1.8 Hz, 1H), 7.82 (dd, J=13.2, 1.6 Hz, 1H), 7.66-7.78 (m, 3H), 7.63 (dd, J=7.3, 2.3 Hz, 1H), 7.36 (dd, J=8.0, 4.8 Hz, 1H), 7.18 (br. s., 1H), 4.72 (t, J=5.4 Hz, 1H), 4.11-4.34 (m, 2H), 1.44 (s, 9H). MS m/e 486.6 (M+H$^+$).

Example 21

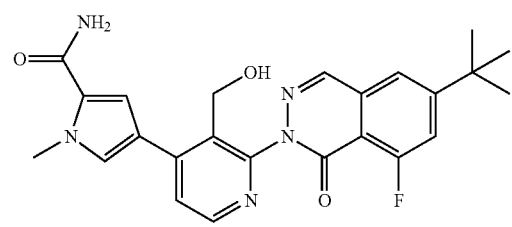

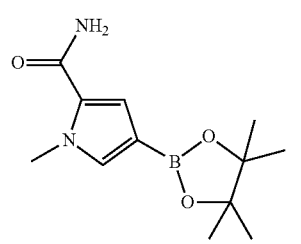

+

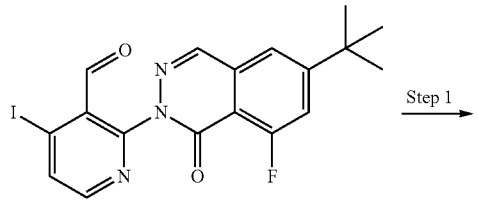

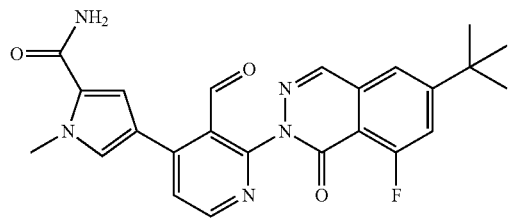

Step 2 ↓

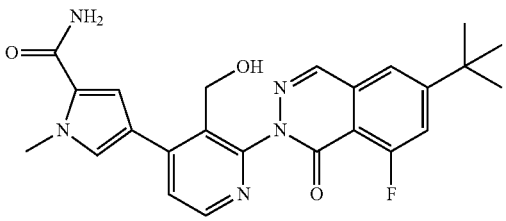

Step 1: In a 100 mL round-bottomed flask, 1-methyl-4-(4,4,5,5-tetramethyl-1,3,2-dioxaborolan-2-yl)-1H-pyrrole-2-carboxamide (61.0 mg, 244 μmol, Eq: 1.10), 2-(6-tert-butyl-8-fluoro-1-oxophthalazin-2(1H)-yl)-4-iodonicotinaldehyde (100 mg, 222 μmol, Eq: 1.00) and [1,1'-bis(Diphenylphosphino)ferrocene]dichloro palladium (II) (16.2 mg, 22.2 μmol, Eq: 0.1) were combined with dioxane (667 μl) to give a red solution. Potassium carbonate (61.3 mg, 443 μmol, Eq: 2) in water (66.7 μl) was added and the resultant suspension was heated to 70° C. and stirred for 32 h. The reaction was diluted with ethyl acetate (10 mL), washed with brine, dried over Na$_2$SO$_4$ and concentrated in vacuo. The crude material was purified by flash chromatography (silica gel, 12 g, 10% to 15% EtOAc in hexanes to give 4-[2-(6-tert-Butyl-8-fluoro-1-oxo-1H-phthalazin-2-yl)-3-formyl-pyridin-4-yl]-1-methyl-1H-pyrrole-2-carboxylic acid amide (28 mgs, 28.2%) as an off white solid. $^1$H NMR (DMSO-d$_6$) δ: 10.06 (s, 1H), 8.72 (d, J=5.3 Hz, 1H), 8.53 (d, J=2.5 Hz, 1H), 7.91 (d, J=1.8 Hz, 1H), 7.79 (dd, J=13.3, 1.8 Hz, 1H), 7.73 (d, J=5.3 Hz, 1H), 7.69-7.76 (m, 1H), 7.50 (d, J=1.8 Hz, 1H), 7.17 (d, J=2.0 Hz, 1H), 7.12 (br. s., 1H), 3.93 (s, 3H), 1.39 (s, 9H); MS m/e 448.5 (M+H$^+$).

Step 2: In a 25 mL pear-shaped flask, 4-(2-(6-tert-butyl-8-fluoro-1-oxophthalazin-2(1H)-yl)-3-formylpyridin-4-yl)-1-methyl-1H-pyrrole-2-carboxamide (28 mg, 62.6 μmol, Eq: 1.00) was combined with CH$_2$Cl$_2$ (3 ml) and MeOH (1 ml) to give a colorless solution. Sodium borohydride (4.73 mg, 125 μmol, Eq: 2.00) was added. The reaction mixture was stirred for 1 h. The reaction mixture was poured into EtOAc (25 mL) and extracted with sat NH$_4$Cl (3×10 mL). The organic layers were dried over MgSO$_4$ and concentrated in vacuo followed by lyophilization to give 4-[2-(6-tert-Butyl-8-fluoro-1-oxo-1H-phthalazin-2-yl)-3-hydroxymethyl-pyridin-4-yl]-1-methyl-1H-pyrrole-2-carboxylic acid amide (14 mg, 50%) as a white solid. $^1$H NMR (DMSO-d$_6$) δ ppm 8.52 (d, J=2.8 Hz, 1H), 8.46 (d, J=5.0 Hz, 1H), 7.90 (d, J=1.8 Hz, 1H), 7.77 (dd, J=13.3, 1.8 Hz, 1H), 7.55-7.72 (m, 1H), 7.52 (d, J=5.0 Hz, 1H), 7.49 (d, J=1.8 Hz, 1H), 7.23 (d, J=2.0 Hz, 1H), 7.04 (br. s., 1H), 4.88 (br. s., 1H), 4.29-4.57 (m, 2H), 3.91 (s, 3H), 1.39 (s, 9H); MS m/e 450.5 (M+H$^+$).

Example 22

1-[3-(6-tert-Butyl-8-fluoro-1-oxo-1H-phthalazin-2-yl)-2-hydroxymethyl-phenyl]-3-[4-(1-hydroxy-1-methyl-ethyl)-phenylamino]-1H-pyrazole-4-carboxylic acid amide

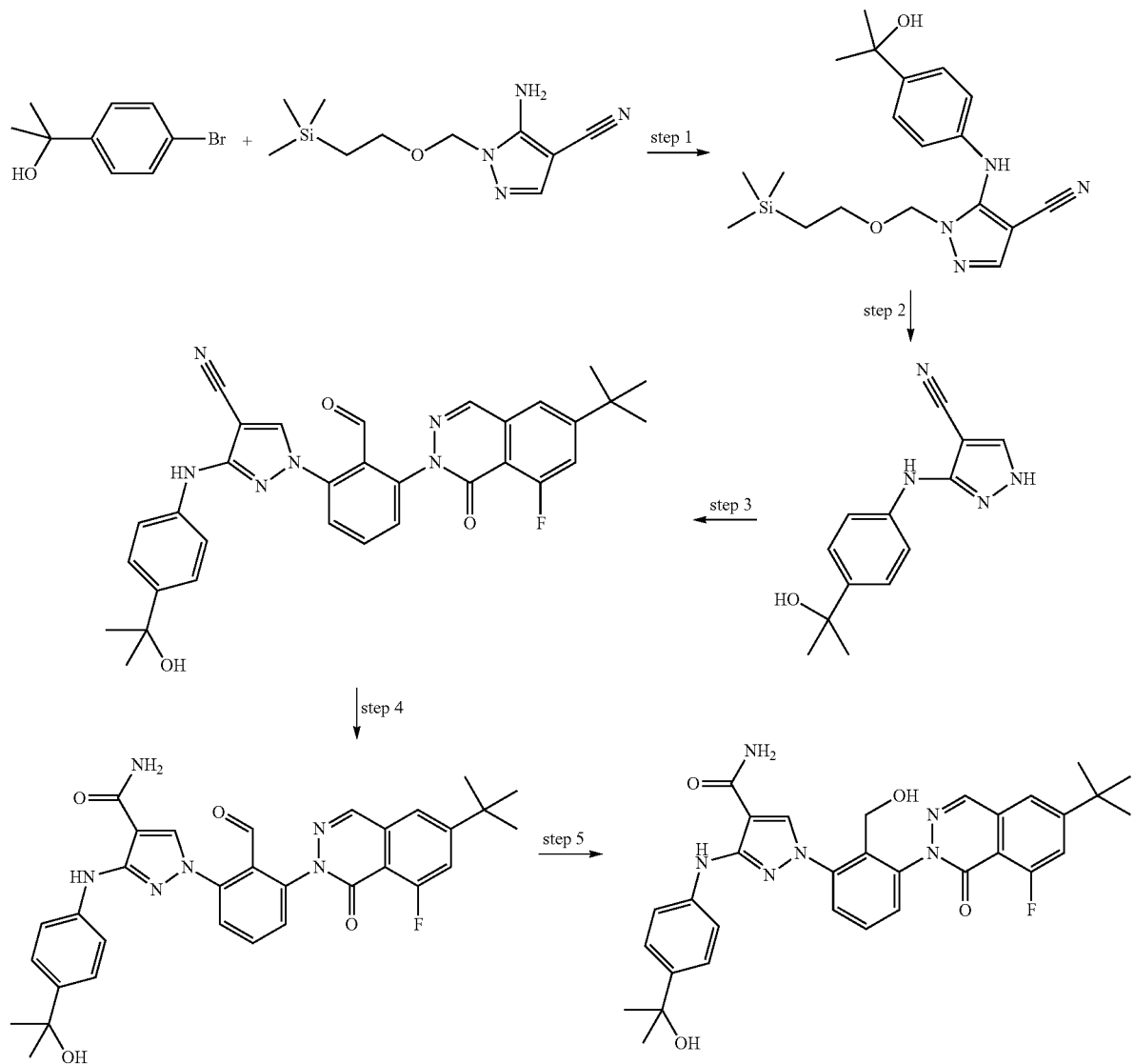

Step 1: 5-Amino-1-(2-(trimethylsilyl)ethoxy)methyl)-1H-pyrazole-4-carbonitrile from step 1, example 15 (500 mg, 2.1 mmol), 2-(4-bromophenyl)propan-2-ol (519 mg, 2.41 mmol), and cesium carbonate (1.03 g, 3.15 mmol) were taken up anhydrous toluene (14 ml). The mixture was degassed with argon and bis(tri-tert-butylphosphine)palladium (107 mg, 0.21 mmol) was added. The mixture was again degassed with argon and then stirred under argon at 120° C. for 4.5 hours. Additional 2-(4-bromophenyl)propan-2-ol (50 mg) was added and the mixture heated for 2 more hours. The material was cooled to ambient and stirred overnight. The crude was filtered through a plug of celite, rinsing well with ethyl acetate (60 ml). The organic layer was shaken with water (60 ml) in a separatory funnel and collected. The aqueous phase was back extracted with ethyl acetate (2×40 ml). The combined organic phase was dried with magnesium sulfate, filtered and stripped. The remainder was purified through Analogix flash column chromatography using ethyl acetate in hexanes (10% to 45% gradient, 23 g silica gel) to provide 5-(4-(2-hydroxypropan-2-yl)phenylamino)-1-((2-(trimethylsilyl)ethoxy)methyl)-1H-pyrazole-4-carbonitrile as a red-brown viscous oil (482 mg, 62% yield). LC/MS calc'd for $C_{19}H_{28}N_4O_2Si$ (m/e) 372.55, obs'd 371 (M–H, ES–).

Step 2: 5-(4-(2-Hydroxypropan-2-yl)phenylamino)-1-((2-(trimethylsilyl)ethoxy)methyl)-1H-pyrazole-4-carbonitrile (480 mg, 1.13 mmol) was taken up in a solution of tetrabutylammonium fluoride (1M, 16.8 ml) and the flask was sealed. The mixture was placed in an oil bath heated to 110° C. and stirred for 28 hours. The mixture was cooled to ambient. Water (60 ml) and diethyl ether (60 ml) were added and the material was shaken in a reparatory funnel and the organic phase was collected. The aqueous phase was back extracted with diethyl ether (2×50 ml). The organic phase was combined, dried from magnesium sulfate, filtered and stripped. The crude remainder was purified through Analogix flash column chromatography using ethyl acetate in hexanes (30% to 90% gradient, 40 g silica gel) to provide 3-(4-(2-hydroxypropan-2-yl)phenylamino)-1H-pyrazol-4-carbonitrile as an off-white powder (128 mg, 47% yield). LC/MS calc'd for $C_{13}H_{14}N_4O$ (m/e) 242.28, obs'd 241 (M−H, ES−).

Step 3. 3-(4-(2-hydroxypropan-2-yl)phenylamino)-1H-pyrazol-4-carbonitrile was converted to 1-[3-(6-tert-butyl-8-fluoro-1-oxo-1H-phthalazin-2-yl)-2-formyl-phenyl]-3-[4-(1-hydroxy-1-methyl-ethyl)-phenylamino]-1H-pyrazole-4-carbonitrile by following a similar protocol to that described in Example 15.

Step 4: 1-[3-(6-tert-Butyl-8-fluoro-1-oxo-1H-phthalazin-2-yl)-2-formyl-phenyl]-3-[4-(1-hydroxy-1-methyl-ethyl)-phenylamino]-1H-pyrazole-4-carbonitrile (78 mg, 0.14 mmol) and dihydrogen tris(dimethylphosphinito)hydroplatinate (7.1 mg, 0.12 eq) were taken up in tetrahydrofuran (3.1 ml) and water (0.31 ml). The material was stirred and heated to reflux (oil bath) for 1 hour. The mixture was cooled to ambient and the volatiles were stripped (rotary evaporator). The crude material was purified by preparative thin layer chromatography (2 plates, eluting first with 7% methanol in methylene chloride and then re-developing with 6% methanol in methylene chloride). The product band was collected, providing desired 1-[3-(6-tert-butyl-8-fluoro-1-oxo-1H-phthalazin-2-yl)-2-formyl-phenyl]-3-[4-(1-hydroxy-1-methyl-ethyl)-phenylamino]-1H-pyrazole-4-carboxylic acid amide as a light yellow powder (41 mg). LC/MS calcd for $C_{32}H_{31}FN_6O_4$ (m/e) 582.62, obsd 581.0 (M−H, ES−).

Step 5: 1-[3-(6-tert-Butyl-8-fluoro-1-oxo-1H-phthalazin-2-yl)-2-formyl-phenyl]-3-[4-(1-hydroxy-1-methyl-ethyl)-phenylamino]-1H-pyrazole-4-carboxylic acid amide (34 mg, 0.06 mmol) was dissolved in a solution of 1:1 methanol and dichloromethane (15 ml). To this was added a solution of sodium borohydride (11 mg, 0.29 mmol) dissolved in water (0.25 ml), via drop-wise addition. After 10 minutes stirring the volatiles were stripped (rotary evaporator) and the remainder was taken up in dichloromethane (30 ml) and water (30 ml) and shaken in a separatory funnel. The organic phase was collected and the aqueous phase was back extracted with dichloromethane (2×25 ml). The organic extracts were combined, dried from magnesium sulfate, filtered and stripped. The crude was purified by silica gel chromatography (1 g, eluting with 7.5% methanol in dichloromethane) providing the desired product 1-[3-(6-tert-butyl-8-fluoro-1-oxo-1H-phthalazin-2-yl)-2-hydroxymethyl-phenyl]-3-[4-(1-hydroxy-1-methyl-ethyl)-phenylamino]-1H-pyrazole-4-carboxylic acid amide as an off-white powder (32 mg). LC/MS calcd for $C_{32}H_{33}FN_6O_4$ (m/e) 584.66, obsd 583 (M−H, ES−).

Example 23

1-[3-(6-tert-Butyl-8-fluoro-1-oxo-1H-phthalazin-2-yl)-2-hydroxymethyl-phenyl]-3-(5-chloro-pyridin-2-ylamino)-1H-pyrazole-4-carboxylic acid amide

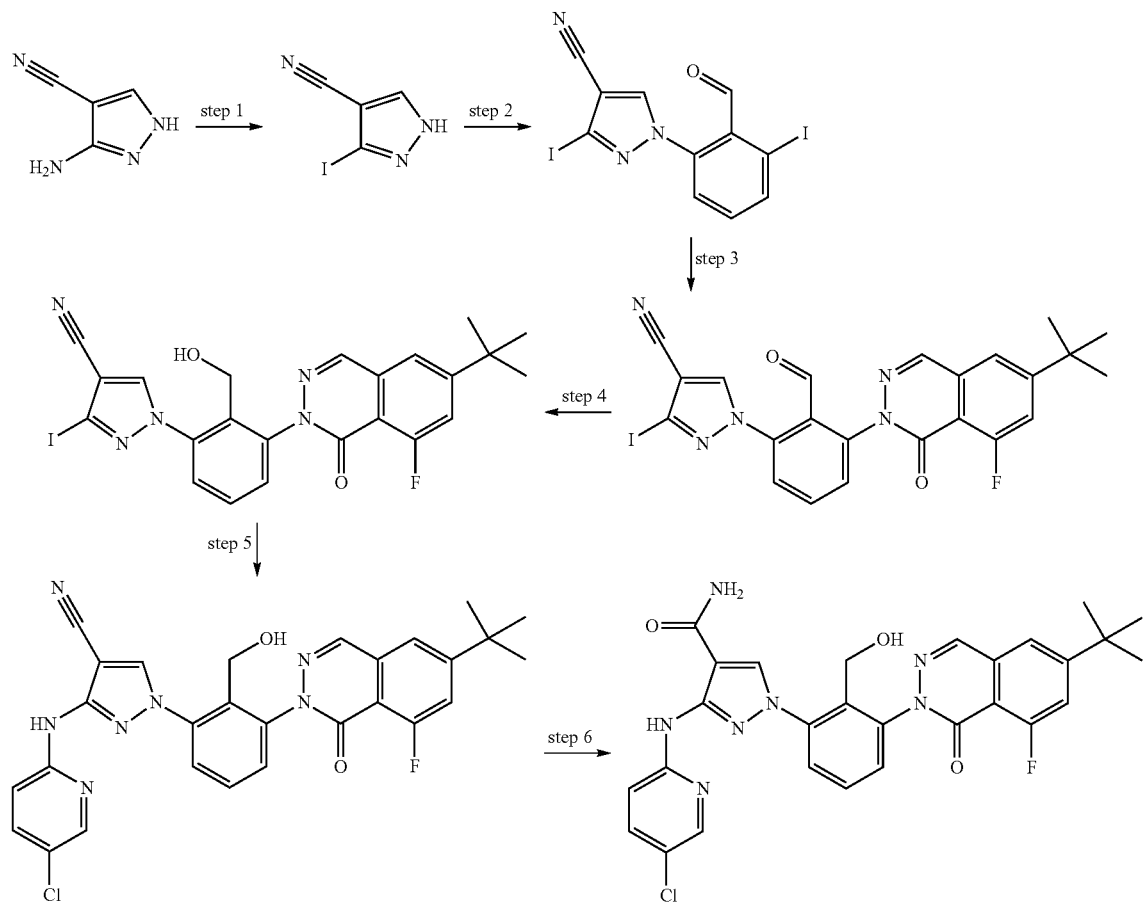

Step 1: Followed similar procedure as WO2005/5414 A2. Thus, 3-amino-4-cyanopyrazole (11 g, 102 mmol) was taken up in methylene iodide (150 ml, 1.87 mol) and the flask was cooled to −10° C. With efficient stirring isoamyl nitrite (92.4 ml, 688 mmol) was added via drop-wise addition over 40 minutes. After complete addition the mixture was stirred for 5 minutes. The addition flask was then removed and replaced with an efficient condenser and the material was heated (oil bath) at 100° C. for 2 hours. The flask was cooled to ambient and the solvent was removed (rotary evaporator and finally mechanical pump). The remainder was taken up in ethyl acetate (120 ml) and transferred to a separatory funnel. A 5% aqueous solution of sodium metabisulfite (120 ml) was added and the biphasic mixture was shaken. The organic phase was collected and shaken with a solution of 1 N hydrochloric acid (aqueous, 120 ml) followed by water (120 ml). The organic phase was collected and the aqueous phases were back extracted with ethyl acetate (2×100 ml). The organic extracts were combined, dried from magnesium sulfate, filtered and stripped. The crude product was adsorbed onto silica (about 25 g, from dichloromethane) and purified (dry loading) by Analogix flash column chromatography using ethyl acetate in hexanes (23% to 50% gradient, 80 g silica gel) to provide a light yellow powder (20 g). This material was further purified by crystallization from hot ethyl acetate/hexanes to provide 3-iodo-1H-pyrazole-4-carbonitrile (11.3 g) as a light brown solid, which was collected by filtration (rinse well with 5% ethyl acetate/hexane). From the mother liquor a second crop of material (3.76 g) was also obtained. LC/MS calc'd for $C_4H_2IN_3$ (m/e) 218.98, obs'd 218 (M−H, ES−).

Step 2: 3-Iodo-1H-pyrazole-4-carbonitrile (3.62 g, 16.5 mmol) was taken up in dry tetrahydrofuran (67 ml) under nitrogen atmosphere. Sodium hydride (992 mg, 24.8 mmol, 60% in oil) was added in one portion and the mixture was placed in a heated (50° C.) sonication bath for 50 minutes. To this mixture was added 2-fluoro-6-iodobenzaldehyde (5.37 g, 21.5 mmol) and the mixture was placed in an oil bath heated to 60-65° C. After 2 hours stirring additional 2-fluoro-6-iodobenzaldehyde (350 mg, 1.4 mmol) was added and the material was stirred for 1 more hour. The flask was cooled to ambient and close to 90% of the solvent was stripped (rotary evaporator). Diethyl ether (30 ml) and water (50 ml) were added and the mixture was vigorously stirred for 30 minutes. The precipitated product was collected by filtration, rinsing well with diethyl ether and water, and drying in a vacuum oven to provide a light tan powder (4.78 g). This solid product was taken up in a solution of 2% methanol in dichloromethane (about 60 ml, heat to dissolve) and transferred to a reparatory funnel. Water (60 ml) was added and the material was shaken and the organic phase collected. This was dried with magnesium sulfate, filtered and stripped to provide the desired 1-(2-formyl-3-iodo-phenyl)-3-iodo-1H-pyrazole-4-carbonitrile as a light yellow powder (3.973 g). LC/MS calc'd for $C_{11}H_5I_2N_3O$ (m/e) 448.99, obs'd 450 (M+H, ES+).

Step 3: A oven dried flask was charged with 1-(2-formyl-3-iodo-phenyl)-3-iodo-1H-pyrazole-4-carbonitrile (1.703 g, 3.79 mmol), 6-tert-butyl-8-fluorophthalazin-1(2H)-one [prepared according to US2010/0222325] (919 mg, 4.17 mmol) and sodium bicarbonate (637 mg, 7.59 mmol) and taken up in dry dimethyl sulfoxide (30 ml). The mixture was degassed with argon in a sonication bath. Copper iodide (722 mg, 3.79 mmol) was added and the material was again degassed thoroughly. With sonication the mixture was heated to 60° C. for 2.5 hours and left at ambient overnight. Additional copper iodide (360 mg) was added and the material was heated for 4 hours at 60° C. under sonication. The flask was cooled to ambient and methylene chloride (40 ml) and water (40 ml) were added, with vigorous stirring. After 5 minutes the material was filtered through a plug of celite, rinsing well with a solution of 1% methanol in methylene chloride. The filtrate was transferred to a separatory funnel and the organic phase was collected. This was shaken with a 50% diluted brine solution (60 ml, some ragging). The methylene chloride phase was collected and the aqueous phases were back extracted with methylene chloride (note: some ragging observed. It helps to use larger volumes of organic and aqueous solutions on back extraction). The combined organic phase was dried with magnesium sulfate, filtered and stripped. The remainder was taken up in methylene chloride and purified through Analogix flash column chromatography eluting first with 100% dichloromethane (hold for 5 minutes) and then switch to a gradient of 1% to 3% methanol in dichloromethane (25 g silica gel) providing the desired 1-[3-(6-tert-butyl-8-fluoro-1-oxo-1H-phthalazin-2-yl)-2-formyl-phenyl]-3-iodo-1H-pyrazole-4-carbonitrile as a light brown powder (1.2 g). LC/MS calc'd for $C_{23}H_{17}FIN_5O_2$ (m/e) 541.32, obs'd 542 (M+H, ES+).

Step 4: 1-[3-(6-tert-Butyl-8-fluoro-1-oxo-1H-phthalazin-2-yl)-2-formyl-phenyl]-3-iodo-1H-pyrazole-4-carbonitrile (1.2 g, 2.22 mmol) was dissolved in a solution of dichloromethane (40 ml) and methanol (80 ml). To this was added a solution of sodium borohydride (21 mg, 0.53 mmol) dissolved in water (0.35 ml) via drop-wise addition. After 10 minutes stirring the volatiles were stripped (rotary evaporator) and the remainder was taken up in dichloromethane (60 ml) and water (50 ml) and shaken in separatory funnel. The organic phase was collected and the aqueous phase was back extracted with dichloromethane (2×50 ml). The organic extracts were combined, dried from magnesium sulfate, filtered and stripped. The crude was purified by Analogix flash column chromatography (40 g column, elute first with 100% dichloromethane [hold for 10 minutes] and then switch to 1% methanol in dichloromethane) which provided the desired product 1-[3-(6-tert-butyl-8-fluoro-1-oxo-1H-phthalazin-2-yl)-2-hydroxymethyl-phenyl]-3-iodo-1H-pyrazole-4-carbonitrile as a light orange colored oil which solidifies on standing (1.029 g). LC/MS calc'd for $C_{23}H_{19}FIN_5O_2$ (m/e) 543.33, obs'd 544 (M+H, ES+).

Step 5: A small round bottom flask was charged with 1-[3-(6-tert-butyl-8-fluoro-1-oxo-1H-phthalazin-2-yl)-2-hydroxymethyl-phenyl]-3-iodo-1H-pyrazole-4-carbonitrile (212 mg, 0.39 mmol), 5-chloropyridin-2-amine (65 mg, 0.51 mmol), XANTPHOS (56 mg, 0.098 mmol), and cesium carbonate (381 mg, 1.17 mmol). Dry dioxane (5.7 ml) was added and the mixture was thoroughly degassed with argon. $Pd_2(dba)_3$ (46 mg, 0.051 mmol) was added and the material was again degassed with argon. The flask was placed in an oil bath heated to 95° C. for 2.5 hours. The flask was cooled to ambient and ethyl acetate (30 ml) and water (30 ml) were added. The contents were shaken in a separatory funnel and the organic phase was collected. The aqueous phase was back extracted with ethyl acetate (2×30 ml), and the organic phase was combined, dried with magnesium sulfate, filtered and stripped. The crude material was purified by preparative thin layer chromatography (2 plates, eluting with 4% methanol in methylene chloride). The product band was collected, providing the desired 1-[3-(6-tert-butyl-8-fluoro-1-oxo-1H-phthalazin-2-yl)-2-hydroxymethyl-phenyl]-3-(5-chloro-pyridin-2-ylamino)-1H-pyrazole-4-carbonitrile as a light yellow powder (111 mg). LC/MS calc'd for $C_{28}H_{23}ClFN_7O_2$ (m/e) 543.98, obs'd 544 (M+H, ES+).

Step 6: 1-[3-(6-tert-Butyl-8-fluoro-1-oxo-1H-phthalazin-2-yl)-2-hydroxymethyl-phenyl]-3-(5-chloro-pyridin-2-ylamino)-1H-pyrazole-4-carbonitrile (111 mg, 0.204 mmol) and dihydrogen tris(dimethylphosphinito)hydroplatinate (10.5 mg, 0.025 mmol) were taken up in tetrahydrofuran (3.8 ml) and water (0.38 ml). The material was stirred and heated to reflux (oil bath) for 1 hour. The mixture was cooled to ambient and the volatiles were stripped (rotary evaporator). The crude remainder was purified by preparative thin layer chromatography (2 plates, eluting first with 7% methanol in methylene chloride and then re-developing again with 7% methanol in methylene chloride). The product band was collected, providing the desired 1-[3-(6-tert-butyl-8-fluoro-1-oxo-1H-phthalazin-2-yl)-2-hydroxymethyl-phenyl]-3-(5-chloro-pyridin-2-ylamino)-1H-pyrazole-4-carboxylic acid amide as an off-white powder (70 mg). LC/MS calc'd for $C_{28}H_{25}ClFN_7O_3$ (m/e) 561.99, obs'd 562 (M+H, ES+).

Example 24

3-[5-(2-Azetidin-3-yl-1,1-dimethyl-ethoxy)-pyridin-2-ylamino]-1-[3-(6-tert-butyl-8-fluoro-1-oxo-1H-phthalazin-2-yl)-2-hydroxymethyl-phenyl]-1H-pyrazole-4-carboxylic acid amide

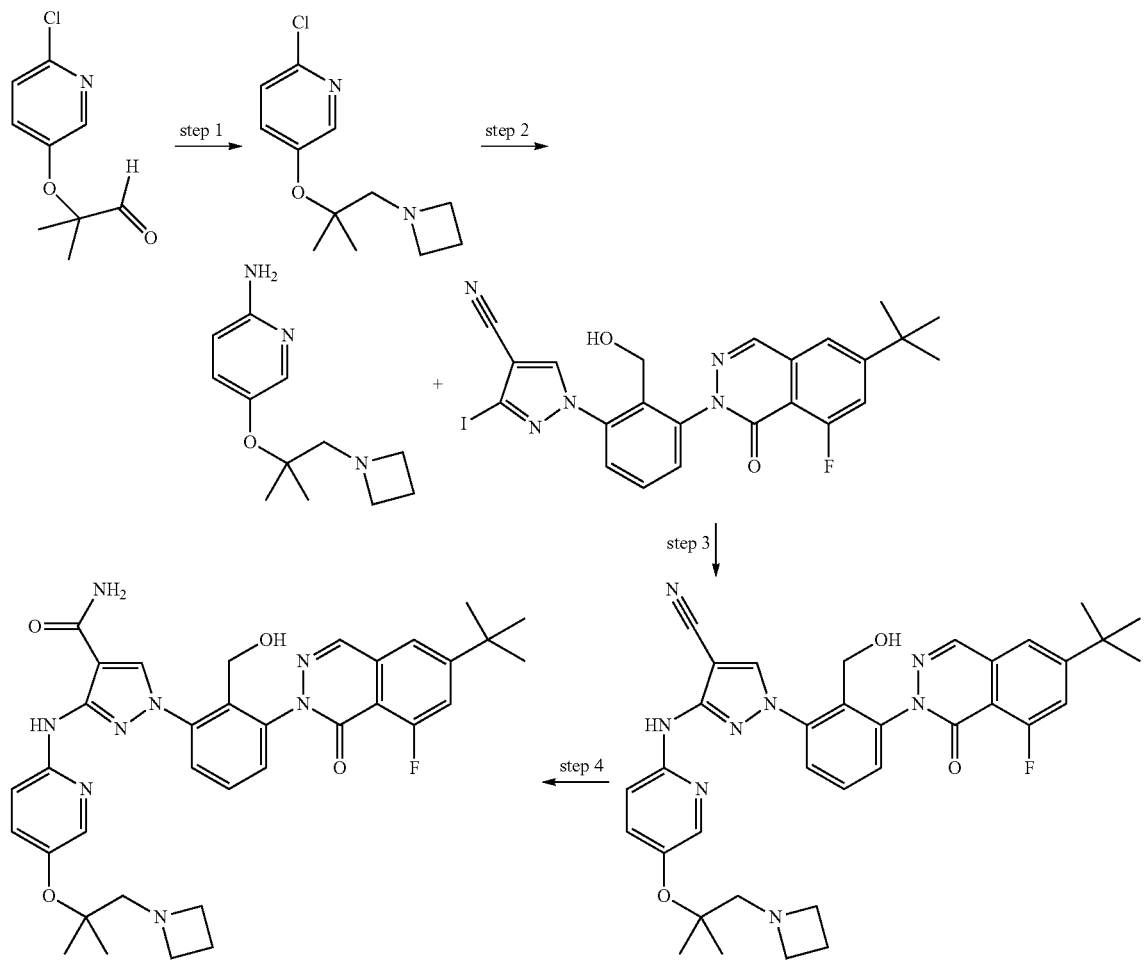

Step 1: 2-(6-Chloropyridin-3-yloxy)-2-methylpropanal [prepared according to US2012/40949 A1] (28 g, 140 mmol, Eq: 1.00) was taken up in dry dichloromethane (252 ml) and cooled to −10° C. (dry ice/acetonitrile cooling bath) under nitrogen atmosphere. Acetic acid (10.4 ml, 182 mmol) and sodium triacetoxyborohydride (41.6 g, 196 mmol) were added. Azetidine (17 ml, 252 mmol) was next added via drop-wise addition over 6 minutes, with efficient stirring. After complete addition the mixture was stirred for 5 minutes and then the cooling bath was removed and the material warmed to ambient. After 1 hour a saturated solution of aqueous sodium bicarbonate (200 ml) was added as well as dichloromethane (80 ml). The biphasic material was transferred to a separatory funnel, agitated and the organic phase was collected. This was shaken with a 5% solution of sodium bicarbonate (200 ml) and then a 50% diluted solution of brine (200 ml). The organic phase was collected and the aqueous phases were back extracted with methylene chloride (2 100 ml). The organic phase was combined, dried with magnesium sulfate, filtered and stripped. The crude remainder was purified via column chromatography (silica gel, 40 g) eluting with a 4% solution of methanol in dichloromethane to provide the desired 5-(2-azetidin-1-yl-1,1-dimethyl-ethoxy)-2-chloro-pyridin (29.66 g) as a golden brown mobile oil. LC/MS calc'd for $C_{12}H_{17}ClN_2O$ (m/e) 240.73, obs'd 241 (M+H, ES+).

Step 2: To a degassed solution of 5-(2-azetidin-1-yl-1,1-dimethyl-ethoxy)-2-chloro-pyridin (21.2 g, 88.1 mmol) in anhydrous tetrahydrofuran (314 ml) was added 2-(dicyclohexylphosphino)biphenyl (6.17 g, 17.6 mmol) and tris(dibenzylideneacetone)dipalladium(0) (8.06 g, 8.81 mmol). Then a solution of 1 M lithium bis(trimethylsilyl)amide in THF (264 ml, 264 mmol) was added via addition funnel over 5 minutes. The reaction mixture was stirred under argon atmosphere at 75° C. over-night. The reaction mixture was poured into a saturated solution of aqueous ammonium chloride (400 ml) and extracted with ethyl acetate (350 ml). The organic phase was collected and washed with 50% diluted brine (350 ml). The organic phase was collected and the aqueous phases were back extracted with ethyl acetate (2×200 ml). The combined organics were dried from magnesium sulfate, filtered and stripped. The remainder was purified by Analogix flash column chromatography (80 g column), eluting with 0% to 12% methanol in dichloromethane to provide the desired 5-(2-azetidin-1-yl-1,1-dimethyl-ethoxy)-pyridin-2-ylamine (10.59 g) as a dark brown semi-viscous oil (as well as a less-pure fraction which could be re-purified under similar conditions to provide another 4.01 g of product). LC/MS calc'd for $C_{12}H_{19}N_3O$ (m/e) 221.3, obs'd 222 (M+H, ES+).

Steps 3 and 4: The 5-(2-azetidin-1-yl-1,1-dimethyl-ethoxy)-pyridin-2-ylamine, prepared in step 2, above, was converted to desired product using a similar protocol to that described in Example 16-C, steps 5 and 6 to provide a crude product. This material was purified by preparative thin layer chromatography (2 plates, eluting first with 14% methanol in methylene chloride and then re-developing twice more with 12% methanol in methylene chloride) to provide the desired 3-[5-(2-azetidin-1-yl-1,1-dimethyl-ethoxy)-pyridin-2-ylamino]-1-[3-(6-tert-butyl-8-fluoro-1-oxo-1H-phthalazin-2-yl)-2-hydroxymethyl-phenyl]-1H-pyrazole-4-carboxylic acid amide as a light brown powder (27 mg). LC/MS calcd for $C_{35}H_{39}FN_8O_4$ (m/e) 654.73, obsd 655 (M+H, ES+).

Table I* depicts additional analogs prepared using procedures similar to those described in the above examples.

TABLE I*

| Example # | Compound Name | Characterization [M + H]+ or [M − H]− |
|---|---|---|
| I-25 | 1-[3-(6-tert-butyl-8-fluoro-1-oxo-1H-phthalazin-2-yl)-2-hydroxymethyl-phenyl]-3-(5-methyl-4,5,6,7-tetrahydro-pyrazolo[1,5a]pyrazin-2-ylamino)-1H-pyrazole-4-carboxylic acid amide | Calc'd 586, Obs'd 586 |
| I-26 | 1-[3-(6-tert-butyl-8-fluoro-1-oxo-1H-phthalazin-2-yl)-2-hydroxymethyl-phenyl]-3-(pyridin-2-ylamino)-1H-pyrazole-4-carboxylic acid amide | Calc'd 528, Obs'd 528 |
| I-27 | 1-[3-(6-tert-Butyl-8-fluoro-1-oxo-1H-phthalazin-2-yl)-2-hydroxymethyl-phenyl]-3-(4-methanesulfonyl-phenylamino)-1H-pyrazole-4-carboxylic acid amide | Calc'd 606, Obs'd 606 |
| I-28 | 1-[3-(6-tert-butyl-8-fluoro-1-oxo-1H-phthalazin-2-yl)-2-hydroxymethyl-phenyl]-3-(1-methyl-1H-pyrazol-3-ylamino)-1H-pyrazole-4-carboxylic acid amide | Calc'd 531, Obs'd 531 |
| I-29 | 1-[3-(6-tert-butyl-8-fluoro-1-oxo-1H-phthalazin-2-yl)-2-hydroxymethyl-phenyl]-3-(pyrazin-2-ylamino)-1H-pyrazole-4-carboxylic acid amide | Calc'd 529, Obs'd 529 |
| I-30 | 1-[3-(6-tert-butyl-8-fluoro-1-oxo-1H-phthalazin-2-yl)-2-hydroxymethyl-phenyl]-3-(5-fluoro-pyridin-2-ylamino)-1H-pyrazole-4-carboxylic acid amide | Calc'd 546, Obs'd 546 |
| I-31 | 1-[3-(6-tert-butyl-8-fluoro-1-oxo-1H-phthalazin-2-yl)-2-hydroxymethyl-phenyl]-3-(1,5-dimethyl-1H-pyrazol-3-ylamino)-1H-pyrazole-4-carboxylic acid amide | Calc'd 545, Obs'd 545 |
| I-32 | 1-[3-(6-tert-butyl-8-fluoro-1-oxo-1H-phthalazin-2-yl)-2-hydroxymethyl-phenyl]-3-(5-trifluoromethyl-pyridin-2-ylamino)-1H-pyrazole-4-carboxylic acid amide | Calc'd 596, Obs'd 596 |
| I-33 | 1-[3-(6-tert-butyl-8-fluoro-1-oxo-1H-phthalazin-2-yl)-2-hydroxymethyl-phenyl]-3-(5-methyl-pyridin-2-ylamino)-1H-pyrazole-4-carboxylic acid amide | Calc'd 542, Obs'd 542 |
| I-34 | 1-[3-(6-tert-butyl-1-oxo-1H-phthalazin-2-yl)-2-hydroxy-methyl-phenyl]-3-(1,5-dimethyl-1H-pyrazol-3-ylamino)-1H-pyrazole-4-carboxylic acid amide | Calc'd 527, Obs'd 527 |
| I-35 | 1-[3-(6-tert-butyl-1-oxo-1H-phthalazin-2-yl)-2-hydroxy-methyl-phenyl]-3-(5-fluoro-pyridin-2-ylamino)-1H-pyrazole-4-carboxylic acid amide | Calc'd 528, Obs'd 528 |
| I-36 | 1-[3-(6-tert-butyl-1-oxo-1H-phthalazin-2-yl)-2-hydroxy-methyl-phenyl]-3-(pyrazin-2-ylamino)-1H-pyrazole-4-carboxylic acid amide | Calc'd 511, Obs'd 511 |
| I-37 | 1-[3-(6-tert-butyl-1-oxo-1H-phthalazin-2-yl)-2-hydroxy-methyl-phenyl]-3-(5-methyl-pyridin-2-ylamino)-1H-pyrazole-4-carboxylic acid amide | Calc'd 524, Obs'd 524 |
| I-38 | 1-[3-(6-tert-Butyl-8-fluoro-1-oxo-1H-phthalazin-2-yl)-2-hydroxymethyl-phenyl]-3-(5-methanesulfonyl-pyridin-2-ylamino)-1H-pyrazole-4-carboxylic acid amide | 606 |

Example 39

1-[3-(6-tert-Butyl-8-fluoro-1-oxo-1H-phthalazin-2-yl)-2-hydroxymethyl-phenyl]-3-(5-cyano-pyridin-2-ylamino)-1H-pyrazole-4-carboxylic acid amide

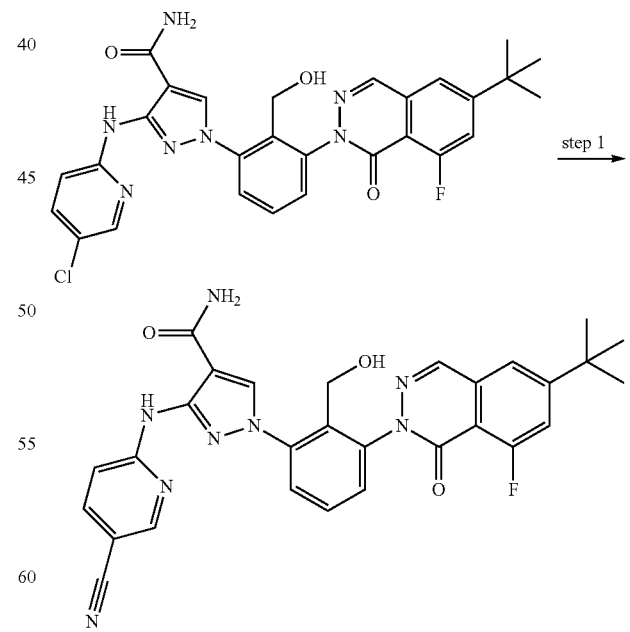

Step 1. Take up 1-[3-(6-tert-butyl-8-fluoro-1-oxo-1H-phthalazin-2-yl)-2-hydroxymethyl-phenyl]-3-(5-chloro-pyridin-2-ylamino)-1H-pyrazole-4-carboxylic acid amide (prepared in example 23, above) (31 mg, 55.2 μmol), zinc cyanide (51.8 mg, 441 µmol) and 2-dicyclohexylphosphino-2',6'-dimethoxybiphenyl (6 mg, 14.6 µmol) in 1.5 ml of dry dimethylformamide in a small capacity microwave tube and thoroughly degas with argon. Add tris(dibenzylideneacetone)dipalladium(0) (7 mg, 7.6 µmol) and degas again. The mixture was heated in a microwave reactor at 150° C. for 60 minutes. The solvent was stripped (rotary evaporator/pump) and the remainder was taken up in ethyl acetate (25 ml) and water (25 mL) and shaken in a reparatory funnel. The organic phase was collected and the aqueous phase was back extracted with ethyl acetate (2×20 ml). The organic phase was combined, dried from magnesium sulfate, filtered and stripped. The crude was purified by preparative thin layer chromatography (1 plate, eluting with 9.5% methanol in dichloromethane). The product band was collected, providing semi-pure desired product (21 mg, 91% pure). For greater purity the material was again loaded onto 1 preparative thin layer chromatography plate and eluted with 7% methanol in dichloromethane. Re-develop the plate with 7% and then 8.5% and finally 9% methanol in dichloromethane, at which point a more polar impurity was separated. The less polar product band was collected, providing the desired 1-[3-(6-tert-butyl-8-fluoro-1-oxo-1H-phthalazin-2-yl)-2-hydroxymethyl-phenyl]-3-(5-cyano-pyridin-2-ylamino)-1H-pyrazole-4-carboxylic acid amide as an off-white solid (17 mg, 56%). LC/MS calc'd for $C_{29}H_{25}FN_8O_3$ (m/e) 552.57, obs'd 553 (M+H, ES+).

Example 40

1-[3-(6-tert-butyl-8-fluoro-1-oxo-1H-phthalazin-2-yl)-2-hydroxymethyl-phenyl]-1H-pyrazole-3-carboxylic acid amide Step 1. 1H-pyrazole-3-carbonitrile (850 mg, 9.13 mmol) was dissolved in 15 mL of dry DMSO and potassium tert-butoxide (1.08 g, 9.13 mmol, Eq: 1.00) was added. The mixture was stirred at room temperature for 20 minutes and 2-bromo-6-fluorobenzaldehyde (3.71 g, 18.3 mmol, Eq: 2) was added. The mixture was stirred at room temperature overnight and then extracted with ethyl acetate and water. The organic layer was dried and concentrated. The crude material was purified by flash chromatography (silica gel, 40 g, 20% to 40% EtOAc in hexanes) to give 1-(3-bromo-2-formylphenyl)-1H-pyrazole-3-carbonitrile (1.83 g, 73%).

Step 2. In a 25 mL container, 1-(3-bromo-2-formylphenyl)-1H-pyrazole-3-carbonitrile (50 mg, 181 µmol, Eq: 1.00), 6-tert-butyl-8-fluorophthalazin-1(2H)-one (79.8 mg, 362 µmol, Eq: 2) and copper (I) iodide (69.0 mg, 362 µmol, Eq: 2.00) were combined with DMSO (2.00 ml) to give a yellow suspension. Sodium bicarbonate (38.0 mg, 453 µmol, Eq: 2.5) was added to it. The mixture was heated in a microwave at 120° C. for 1 hr. The reaction mixture was poured into 25 mL sat NH4Cl and extracted with EtOAc (3×25 mL). The organic layers were dried over $MgSO_4$ and concentrated in vacuo. The organic layer was concentrated and purified through ISCO flash column chromatography using ethyl acetate (containing 5% methanol) in hexanes (5% to 80% linear gradient in 15 minutes, 12 g silica gel) to give the pure desired product which was triturated with ether in hexanes and filtered to obtain 1-(3-(6-tert-butyl-8-fluoro-1-oxophthalazin-2(1H)-yl)-2-formylphenyl)-1H-pyrazole-3-carbonitrile (19 mg, 25%).

Step 3. In a 25 mL container, 1-(3-(6-tert-butyl-8-fluoro-1-oxophthalazin-2(1H)-yl)-2-formylphenyl)-1H-pyrazole-3-carbonitrile (18 mg, 43.3 µmol, Eq: 1.00), sodium borohydride (6.56 mg, 173 µmol, Eq: 4) were combined with $CH_2Cl_2$

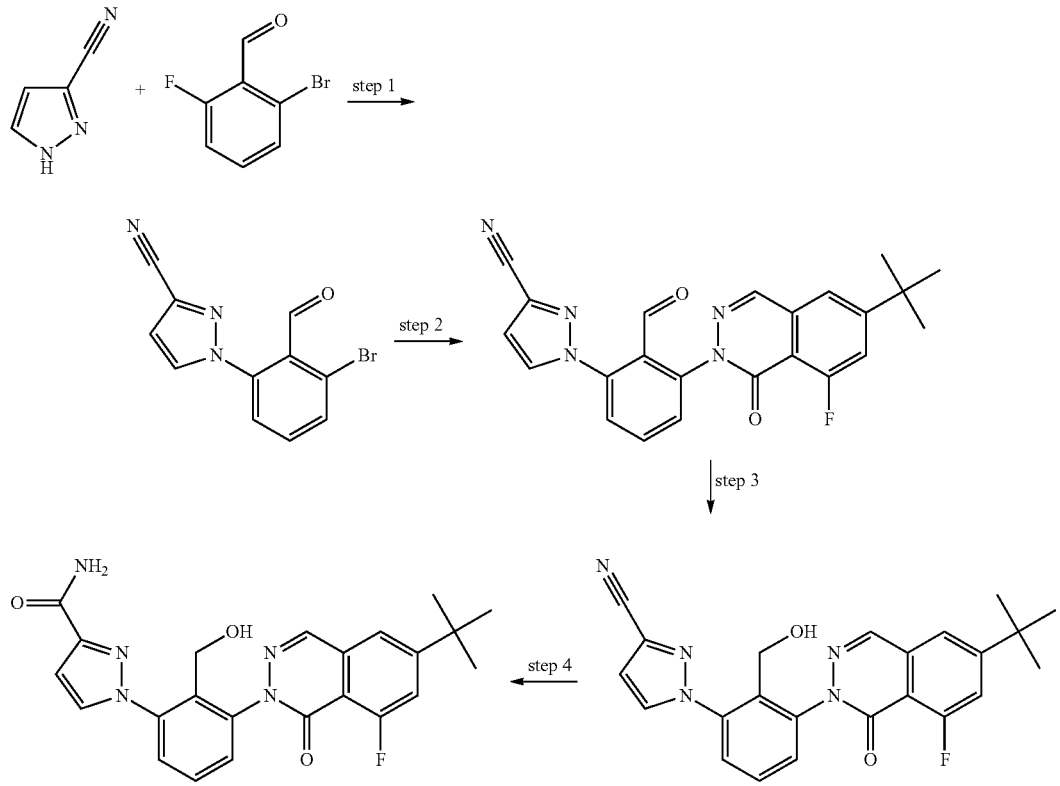 [SMILES: N#Cc1cc[nH]n1 ; O=Cc1c(F)cccc1Br ; N#Cc1ccn(-c2cccc(Br)c2C=O)n1 ; CC(C)(C)c1cc(F)c2c(=O)n(-c3cccc(-n4ccc(C#N)n4)c3C=O)ncc2c1 ; CC(C)(C)c1cc(F)c2c(=O)n(-c3cccc(-n4ccc(C(N)=O)n4)c3CO)ncc2c1 ; CC(C)(C)c1cc(F)c2c(=O)n(-c3cccc(-n4ccc(C#N)n4)c3CO)ncc2c1]

(2 mL) and MeOH (1 mL) to give a white suspension. The mixture was stirred for 1 hr. The reaction mixture was poured into 25 mL sat NH4Cl and extracted with EtOAc (3×25 mL). The organic layers were dried over MgSO4 and concentrated in vacuo. The organic layer was concentrated to give 1-(3-(6-tert-butyl-8-fluoro-1-oxophthalazin-2(1H)-yl)-2-(hydroxymethyl)phenyl)-1H-pyrazole-3-carbonitrile (16 mg, 99%) of white product.

Step 4. In a 10 mL round-bottomed flask, 1-(3-(6-tert-butyl-8-fluoro-1-oxophthalazin-2(1H)-yl)-2-(hydroxymethyl)phenyl)-1H-pyrazole-3-carbonitrile (16 mg, 38.3 µmol, Eq: 1.00) and [hydrogen bis(dimethylphosphinito-kP)]platinum (II) (1 mg, 2.33 µmol, Eq: 0.0608) were combined with ethanol (821 µl) and water (410 µl) to give a colorless solution. The reaction mixture was heated to 80° C. and stirred for 2 h. The reaction mixture was diluted with DCM. The reaction mixture was filtered through glass fiber paper. The crude material was purified by preparative HPLC to give 1-[3-(6-tert-butyl-8-fluoro-1-oxo-1H-phthalazin-2-yl)-2-hydroxymethyl-phenyl]-1H-pyrazole-3-carboxylic acid amide (11 mg, 66%, [M+H]+ 436) of lyophilized white solid.

Example 41

1-[3-(6-tert-butyl-8-fluoro-1-oxo-1H-phthalazin-2-yl)-2-hydroxymethyl-phenyl]-1H-pyrazole-4-carboxylic acid amide 40% EtOAc in hexanes) to give 1-(3-bromo-2-formylphenyl)-1H-pyrazole-4-carbonitrile (1.53 g, 55%).

Step 2. In a 25 mL container, 1-(3-bromo-2-formylphenyl)-1H-pyrazole-4-carbonitrile (100 mg, 362 µmol, Eq: 1.00), 6-tert-butyl-8-fluorophthalazin-1(2H)-one (160 mg, 724 µmol, Eq: 2) and copper (I) iodide (138 mg, 724 µmol, Eq: 2.00) were combined with DMSO (2.00 ml) to give a yellow suspension. Sodium bicarbonate (76.1 mg, 906 µmol, Eq: 2.5) was added to it. The mixture was heated in a microwave at 120° C. for 1 hr. The reaction mixture was poured into 25 mL sat NH4Cl and extracted with EtOAc (3×25 mL). The organic layers were dried over MgSO4 and concentrated in vacuo. The organic layer was concentrated and purified through ISCO flash column chromatography using ethyl acetate (containing 5% methanol) in hexanes (5% to 80% linear gradient in 15 minutes, 24 g silica gel) to give the pure desired product which was triturated with ether in hexanes and filtered to obtain 1-[3-(6-tert-Butyl-8-fluoro-1-oxo-1H-phthalazin-2-yl)-2-formyl-phenyl]-1H-pyrazole-4-carbonitrile (110 mg, 73%). Step 3. The aldehyde is reduced to the alcohol as in Example 22. Step 4. In a 25 mL round-bottomed flask, 1-(3-(6-tert-butyl-8-fluoro-1-oxophthalazin-2(1H)-yl)-2-(hydroxymethyl)phenyl)-1H-pyrazole-4-carbonitrile (89 mg, 213 µmol, Eq: 1.00) and hydrido(dimethylphosphi-

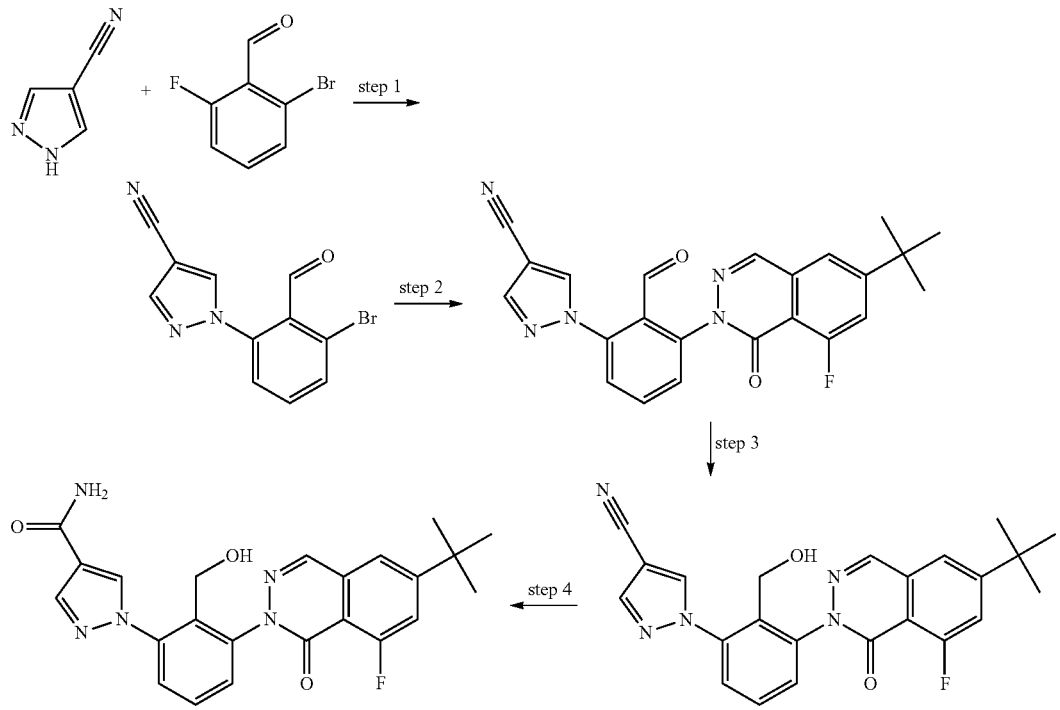

Step 1. 1H-pyrazole-4-carbonitrile (935 mg, 10.0 mmol, Eq: 1.00) was dissolved in 15 mL of dry DMSO and potassium tert-butoxide (1.19 g, 10.0 mmol, Eq: 1.00) was added. The mixture was stirred at room temperature for 20 minutes and 2-bromo-6-fluorobenzaldehyde (4.08 g, 20.1 mmol, Eq: 2) was added. The mixture was stirred at room temperature overnight and then extracted with ethyl acetate and water. The organic layer was dried and concentrated. The crude material was purified by flash chromatography (silica gel, 40 g, 20% to nous acid-kP) (4.58 mg, 10.7 µmol, Eq: 0.05) were combined with Ethanol (1 ml) and Water (1.00 ml) to give a colorless solution. The reaction mixture was heated to 85° C. and stirred for 45 min. Mixture was allowed to come to room temperature and the solvent was removed under vacuum. Purification by reverse phase HPLC gave 1-[3-(6-tert-butyl-8-fluoro-1-oxo-1H-phthalazin-2-yl)-2-hydroxymethyl-phenyl]-1H-pyrazole-4-carboxylic acid amide (51 mg, 56%, [M+H]+ 436)

Example 42

7-[3-(6-tert-Butyl-8-fluoro-1-oxo-1H-phthalazin-2-yl)-2-hydroxymethyl-phenyl]-7H-pyrrolo[2,3-d]pyrimidine-5-carboxylic acid amide

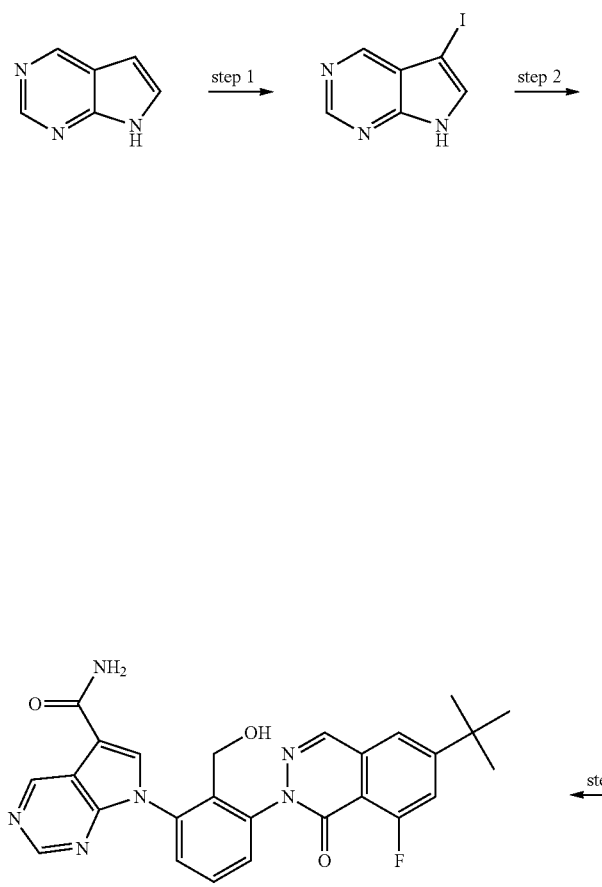
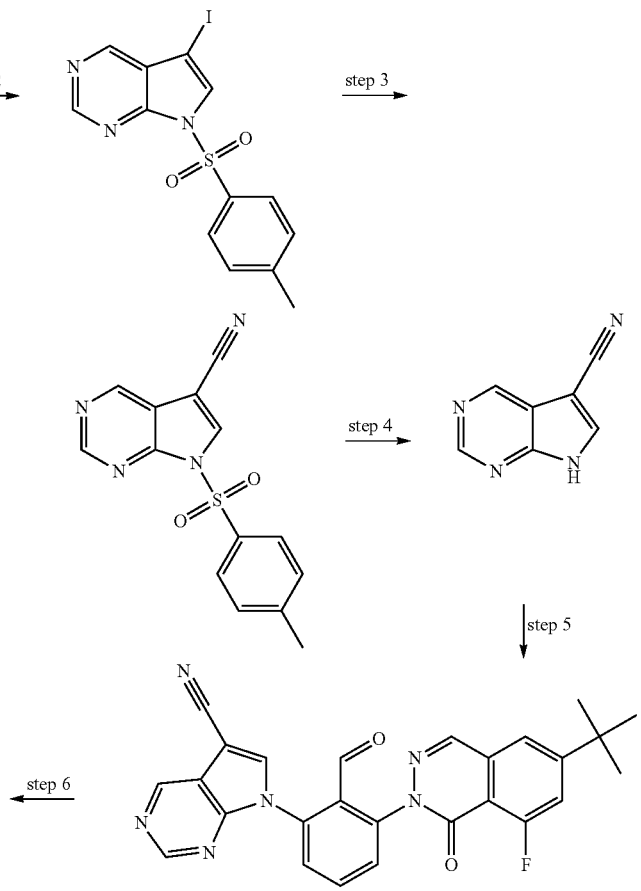

Step 1. In a 250 mL round-bottomed flask, 7H-pyrrolo[2,3-d]pyrimidine (4.34 g, 36.4 mmol, Eq: 1.00) and N-iodosuccinimide (8.61 g, 38.3 mmol, Eq: 1.05) were combined with acetonitrile (60 ml) to give a light brown suspension. The reaction mixture was stirred for 3 h. The reaction mixture was poured into 100 mL H2O and extracted with EtOAc (3×50 mL). The organic layers were dried over MgSO4 and concentrated in vacuo. The crude material was triturated with diethyl ether (2×25 mL) to give 5-iodo-7H-pyrrolo[2,3-d]pyrimidine (7.58 g, 85%) as orange solid.

Step 2. In a 200 mL round-bottomed flask, 5-iodo-7H-pyrrolo[2,3-d]pyrimidine (2.5 g, 10.2 mmol, Eq: 1.00), triethylamine (1.14 g, 1.56 ml, 11.2 mmol, Eq: 1.1) and DMAP (74.8 mg, 612 µmol, Eq: 0.06) were combined with $CH_2Cl_2$ (50.0 ml) to give an orange suspension. Tosyl-Cl (2.00 g, 10.5 mmol, Eq: 1.03) is added in portion into the reaction mixture and reaction mixture is stirred for additional 3 hrs. The reaction mixture was poured into 25 mL $H_2O$ and extracted with DCM (3×25 mL). The organic layers were dried over MgSO4 and concentrated in vacuo to give 2 gm of red oil. The crude material was purified by flash chromatography (silica gel, 80 g, 25% to 70% EtOAc in hexanes) to give 5-iodo-7-tosyl-7H-pyrrolo[2,3-d]pyrimidine (1 g, 24.6%) as yellow solid.

Step 3. In a 20 mL round-bottomed flask, 5-iodo-7-tosyl-7H-pyrrolo[2,3-d]pyrimidine (3.32 g, 8.32 mmol, Eq: 1.00), copper (I) cyanide (2.98 g, 33.3 mmol, Eq: 4), Pd2(dba)3 (305 mg, 333 µmol, Eq: 0.04) and DPPF (738 mg, 1.33 mmol, Eq: 0.16) were combined with Dioxane (48.1 ml) to give a yellow suspension. The reaction was purged with argon and mixture was heated to 80° C. and stirred for h. LCMS at 4 h shows reaction complete. The crude reaction mixture was concentrated in vacuo. The crude material was triturated with ethanol (2×15 mL) to give 1 g of off yellow solid.

Step 4. In a 15 mL round-bottomed flask, 7-tosyl-7H-pyrrolo[2,3-d]pyrimidine-5-carbonitrile (1 g, 3.35 mmol, Eq: 1.00) and TBAF (13.4 ml, 13.4 mmol, Eq: 4.00) were combined with Tetrahydrofuran to give an off-white solution. The reaction mixture was stirred for 3 h. The reaction mixture was poured into 20 mL sat $NH_4Cl$ and extracted with EtOAc (3×25 mL). The organic layers were dried over $MgSO_4$ and concentrated in vacuo. The crude material was triturated with diethyl ether (1×20 mL) to obtain 7H-pyrrolo[2,3-d]pyrimidine-5-carbonitrile (312 mg, 65%).

Step 5. In a 25 mL round-bottomed flask, 7H-pyrrolo[2,3-d]pyrimidine-5-carbonitrile (40.9 mg, 284 µmol, Eq: 1.00), 6-tert-butyl-8-fluoro-2-(1-hydroxy-1,3-dihydrobenzo[c][1,2]oxaborol-4-yl)phthalazin-1(2H)-one (100 mg, 284 µmol, Eq: 1.00), copper acetate (34.8 mg) and pyridine (44.9 mg, 45.9 µl, 568 µmol, Eq: 2) were combined with dichloroethane to give a dark blue suspension. The reaction mixture was flushed with nitrogen. The reaction mixture was heated to 80° C. and stirred for 16 hr. The reaction was diluted with sat NH₄Cl (50 mL) and extracted with EtOAc (3×50 mL). The mixture was separated by flash column using 30-50% EtOAc in hexanes to give the 7-[3-(6-tert-Butyl-8-fluoro-1-oxo-1H-phthalazin-2-yl)-2-hydroxymethyl-phenyl]-7H-pyrrolo[2,3-d]pyrimidine-5-carbonitrile (42 mg, 31%) as a lyophilized white powder.

Step 6. In a 10 mL round-bottomed flask, 7-(3-(6-tert-butyl-8-fluoro-1-oxophthalazin-2(1H)-yl)-2-(hydroxymethyl)phenyl)-7H-pyrrolo[2,3-d]pyrimidine-5-carbonitrile (39 mg, 83.2 μmol, Eq: 1.00) and [hydrogen bis(dimethylphosphinito-kP)]platinum (II) (1 mg, 2.33 μmol, Eq: 0.0280) were combined with Ethanol (2 ml) and Water (1 ml) to give a colorless solution. The reaction mixture was heated to 80° C. and stirred for 2 h. The reaction mixture was diluted with DCM. The reaction mixture was filtered through glass fiber paper. HPLC purification done to obtain 7-[3-(6-tert-Butyl-8-fluoro-1-oxo-1H-phthalazin-2-yl)-2-hydroxymethyl-phenyl]-7H-pyrrolo[2,3-d]pyrimidine-5-carboxylic acid amide (33 mg, 66%, [M+H]+ 487).

Example 43

1-[3-(6-tert-Butyl-8-fluoro-1-oxo-1H-phthalazin-2-yl)-2-hydroxymethyl-phenyl]-6-(4-methyl-piperazin-1-yl)-1H-pyrrolo[2,3-b]pyridine-3-carboxylic acid amide Step 1. In a 25 mL round-bottomed flask, 6-bromo-1H-pyrrolo[2,3-b]pyridine (250 mg, 1.27 mmol, Eq: 1.00), TIPS-OTf (972 mg, 860 μl, 3.17 mmol, Eq: 2.5) and DIEA (492 mg, 665 μl, 3.81 mmol, Eq: 3) were combined with dioxane (6.25 ml) to give a light brown solution. The reaction mixture was heated to 55° C. and stirred for 16 h. The reaction mixture was poured into 20 mL EtOAc and extracted with sat NaHCO₃ (3×10 mL). The organic layers were dried over MgSO₄ and concentrated in vacuo. The crude material was purified by flash chromatography (silica gel, 12 g, 5% to 10% EtOAc in hexanes) to give 6-bromo-1-(triisopropylsilyl)-1H-pyrrolo[2,3-b]pyridine (380 mg, 85%) of colorless oil.

Step 2. In a 25 mL round-bottomed flask, 6-bromo-1-(triisopropylsilyl)-1H-pyrrolo[2,3-b]pyridine (520 mg, 1.47 mmol, Eq: 1.00), palladium (II) acetate (165 mg, 736 μmol, Eq: 0.5) and tri-tert-butylphosphine (149 mg, 182 μl, 736 μmol, Eq: 0.5) were combined with toluene to give a yellow solution. 1-methylpiperazine (442 mg, 491 μl, 4.41 mmol, Eq: 3) and sodium tert-butoxide (424 mg, 4.41 mmol, Eq: 3) were added. The reaction mixture was heated to 80° C. and stirred for 1 h. The reaction mixture was poured into 20 mL EtOAc and extracted with sat NaCl (3×20 mL). The organic layers were dried over MgSO₄ and concentrated in vacuo. The crude material was purified by flash chromatography (silica gel, 12 g, 2% to 5% MeOH in DCM) to give 6-(4-methylpiperazin-1-yl)-1-(triisopropylsilyl)-1H-pyrrolo[2,3-b]pyridine (326 mg, 60%) as yellow oil that solidified upon standing.

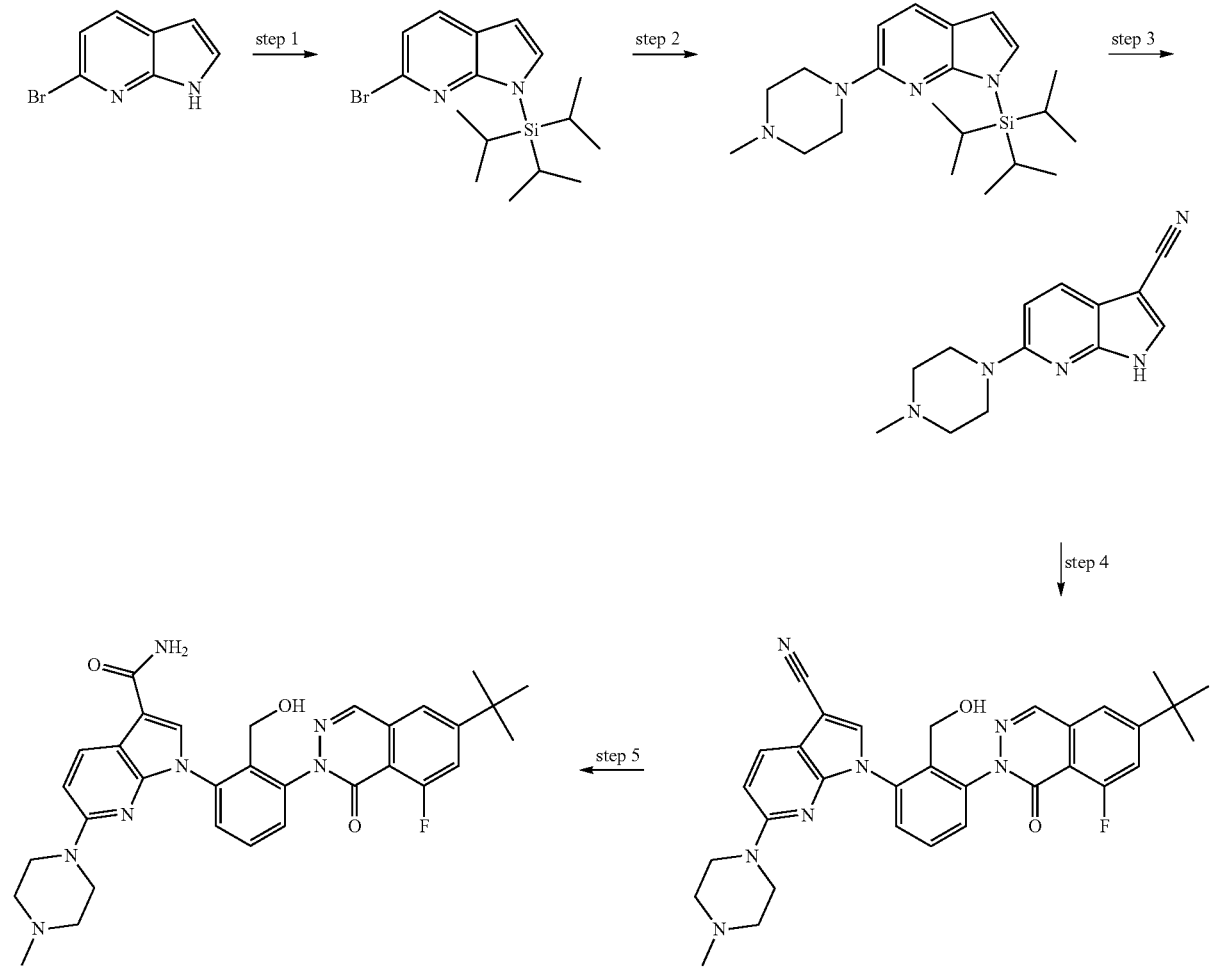

Step 3. In a 25 mL round-bottomed flask, 6-(4-methylpiperazin-1-yl)-1-(triisopropylsilyl)-1H-pyrrolo[2,3-b]pyridine (320 mg, 859 μmol, Eq: 1.00) was combined with DMF (11.8 ml) to give a colorless solution. The reaction mixture was cooled to −20° C. and stirred for 5 min. Chlorosulfonyl isocyanate (365 mg, 224 μl, 2.58 mmol, Eq: 3) in acetonitrile (11.8 ml) was added dropwise and the resultant cooled reaction was stirred at −20° C. and stirred for 3 hrs The reaction mixture was poured into 25 mL EtOAc and extracted with sat NaCl (3×20 mL). The crude material was purified by flash chromatography (silica gel, 12 g, 5% to 10% MeOH in DCM) to give 6-(4-methylpiperazin-1-yl)-1H-pyrrolo[2,3-b]pyridine-3-carbonitrile (113 mg, 55%).

Step 4. In a 25 mL round-bottomed flask, 6-(4-methylpiperazin-1-yl)-1H-pyrrolo[2,3-b]pyridine-3-carbonitrile (110 mg, 456 μmol), 6-tert-butyl-8-fluoro-2-(1-hydroxy-1,3-dihydrobenzo[c][1,2]oxaborol-4-yl)phthalazin-1(2H)-one (177 mg, 501 μmol, Eq: 1.10) and copper acetate (112 mg) were combined with 1,2-dichloroethane (3.03 ml) to give a blue suspension. Pyridine (72.1 mg, 73.7 μl, 912 μmol, Eq: 2) was added. The reaction mixture was heated to 45° C. and stirred for 2 d. The reaction mixture was poured into 20 mL EtOAc and extracted with sat NH₄Cl (3×20 mL). The organic layers were dried over MgSO₄ and concentrated in vacuo. The crude material was purified by flash chromatography (silica gel, 40 g, 5% to 10% MeOH in DCM) to give 1-(3-(6-tert-butyl-8-fluoro-1-oxophthalazin-2(1H)-yl)-2-(hydroxymethyl)phenyl)-6-(4-methylpiperazin-1-yl)-1H-pyrrolo[2,3-b]pyridine-3-carbonitrile (43 mg, 17%) of off white solid.

Step 5. In a 25 mL round-bottomed flask, 1-(3-(6-tert-butyl-8-fluoro-1-oxophthalazin-2(1H)-yl)-2-(hydroxymethyl)phenyl)-6-(4-methylpiperazin-1-yl)-1H-pyrrolo[2,3-b]pyridine-3-carbonitrile (43 mg, 76.0 μmol) and [hydrogen bis(dimethylphosphinito-kP)]platinum (II) (2.00 mg, 4.66 μmol, Eq: 0.0613) were combined with ethanol (1.00 ml) and water (1.00 ml) to give a colorless solution. The reaction mixture was heated to 45° C. and stirred for 1 h. The crude reaction mixture was concentrated in vacuo. Mixture was diluted with acetonitrile and water and filtered. The resultant filtrate was lyophilized to give 1-[3-(6-tert-Butyl-8-fluoro-1-oxo-1H-phthalazin-2-yl)-2-hydroxymethyl-phenyl]-6-(4-methyl-piperazin-1-yl)-1H-pyrrolo[2,3-b]pyridine-3-carboxylic acid amide (35 mg, 97%, [M+H]+ 584).

Example 44

1-[3-(6-tert-Butyl-8-fluoro-1-oxo-1H-phthalazin-2-yl)-2-hydroxymethyl-phenyl]-6-morpholin-4-yl-1H-pyrrolo[2,3-b]pyridine-3-carboxylic acid amide

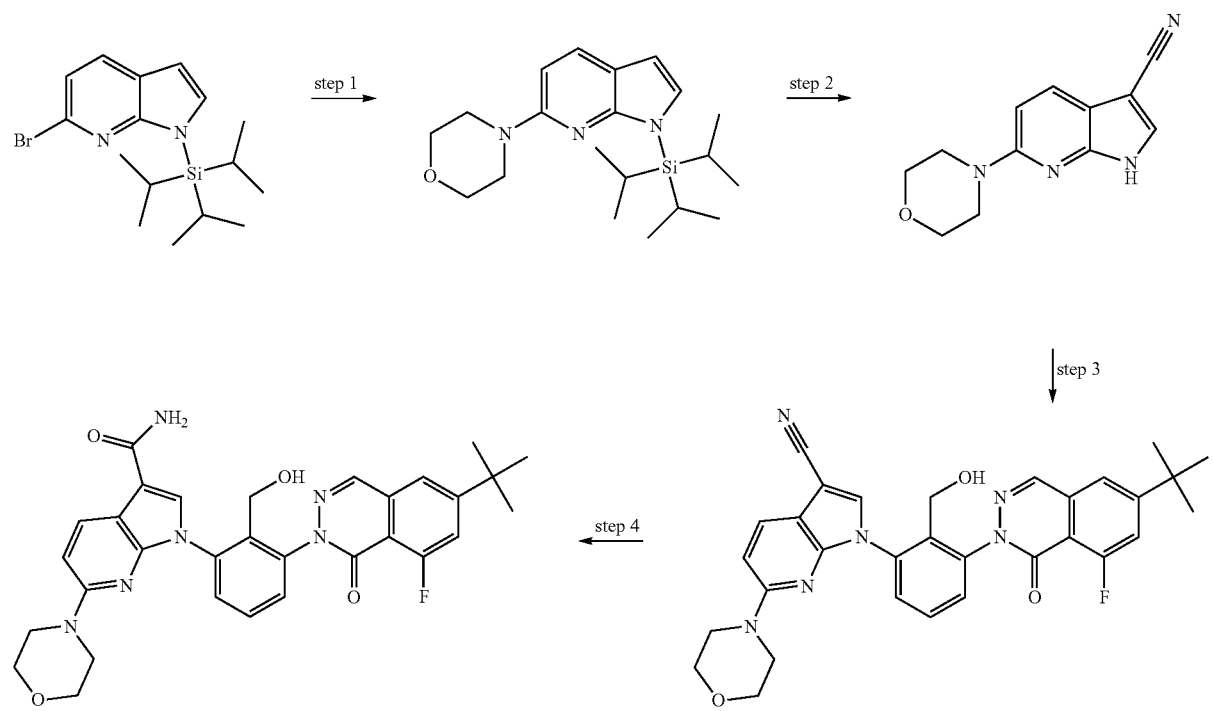

Step 1. In a 25 mL round-bottomed flask, 6-bromo-1-(triisopropylsilyl)-1H-pyrrolo[2,3-b]pyridine (800 mg, 2.26 mmol, Eq: 1.00), palladium (II) acetate (254 mg, 1.13 mmol, Eq: 0.5) and tri-tert-butylphosphine (229 mg, 279 μl, 1.13 mmol, Eq: 0.5) were combined with toluene to give a yellow solution. Morpholine (789 mg, 789 μl, 9.06 mmol, Eq: 4) and sodium tert-butoxide (653 mg, 6.79 mmol, Eq: 3) were added. The reaction mixture was heated to 80° C. and stirred for 1 h. The reaction mixture was poured into 20 mL sat NaCl and extracted with EtOAc (3×20 mL). The organic layers were dried over MgSO₄ and concentrated in vacuo. The crude material was purified by flash chromatography (silica gel, 80 g, 10% to 15% EtOAc in hexanes) to give 4-(1-(triisopropylsilyl)-1H-pyrrolo[2,3-b]pyridin-6-yl)morpholine (703 mg, 86%) as a light brown oil.

Step 2. In a 25 mL round-bottomed flask, 4-(1-(triisopropylsilyl)-1H-pyrrolo[2,3-b]pyridin-6-yl)morpholine (803 mg, 2.23 mmol) was combined with DMF (1.00 ml) to give a colorless solution. The reaction mixture was cooled to −20° C. and stirred for 5 min. Chlorosulfonyl isocyanate (474 mg, 291 μl, 3.35 mmol, Eq: 1.5) in Acetonitrile (1 ml) was added dropwise and the resultant cooled reaction was stirred at −20° C. and stirred for 3 h. The reaction mixture was poured into sat NaCl (25 mL) and extracted with EtOAc (3×20 mL). The organic layers were dried over MgSO₄ and concentrated in vacuo to give 390 mg of oil. In a 25 mL round-bottomed flask, crude cyano compound and TBAF (1.02 ml, 1.02 mmol, Eq: 1) were combined with THF (2.00 ml) to give a white suspension. The reaction mixture was stirred for 1 h. LC-MS at t=1 h showed the reaction was complete. The reaction mixture was poured into 20 mL DCM and extracted with sat NaHCO₃ (2×25 mL). The organic layers were dried over MgSO₄ and concentrated in vacuo. The crude material was purified by flash chromatography (silica gel, 24 g, 50% EtOAc in hexanes) to give 6-morpholino-1H-pyrrolo[2,3-b]pyridine-3-carbonitrile (180 mg, 35%) as white solid.

Step 3. In a 25 mL round-bottomed flask, 6-morpholino-1H-pyrrolo[2,3-b]pyridine-3-carbonitrile (65 mg, 285 μmol, Eq: 1.00), 6-tert-butyl-8-fluoro-2-(1-hydroxy-1,3-dihydrobenzo[c][1,2]oxaborol-4-yl)phthalazin-1(2H)-one (150 mg, 427 μmol, Eq: 1.5) and copper acetate (69.8 mg) were combined with 1,2-dichloroethane (3 ml) to give a blue suspension. Pyridine (45.1 mg, 46.1 μl, 570 μmol, Eq: 2) was added. The reaction mixture was heated to 45° C. and stirred for 2 d. The reaction mixture was poured into 20 mL sat NH₄Cl and extracted with EtOAc (3×20 mL). The organic layers were dried over MgSO₄ and concentrated in vacuo. The crude material was purified by flash chromatography (silica gel, 40 g, 5% to 10% MeOH in DCM, then silica gel, 12 g, 30% to 45% EtOAc in hexanes) gave 1-(3-(6-tert-butyl-8-fluoro-1-oxophthalazin-2(1H)-yl)-2-(hydroxymethyl)phenyl)-6-morpholino-1H-pyrrolo[2,3-b]pyridine-3-carbonitrile (157 mg, 50%) as colorless oil which foams upon being dried.

Step 4. In a 25 mL round-bottomed flask, 1-(3-(6-tert-butyl-8-fluoro-1-oxophthalazin-2(1H)-yl)-2-(hydroxymethyl)phenyl)-6-morpholino-1H-pyrrolo[2,3-b]pyridine-3-carbonitrile (75 mg, 136 μmol, Eq: 1.00) and [hydrogen bis(dimethylphosphinito-kP)]platinum (II) (2 mg, 4.66 μmol, Eq: 0.0343) were combined with ethanol (1 ml) and water (1.00 ml) to give a colorless solution. The reaction mixture was heated to 45° C. and stirred for 1 h, then concentrated in vacuo. Mixture was diluted with acetonitrile and water and filtered. The resultant filtrate was lyophilized to give 1-[3-(6-tert-Butyl-8-fluoro-1-oxo-1H-phthalazin-2-yl)-2-hydroxymethyl-phenyl]-6-morpholin-4-yl-1H-pyrrolo[2,3-b]pyridine-3-carboxylic acid amide (70 mg, 90%, [M+H]+ 571).

Example 45

1-[3-(6-tert-Butyl-8-fluoro-1-oxo-1H-phthalazin-2-yl)-2-hydroxymethyl-phenyl]-6-(6-ethoxy-pyridin-3-yl)-1H-pyrrolo[2,3-b]pyridine-3-carboxylic acid amide

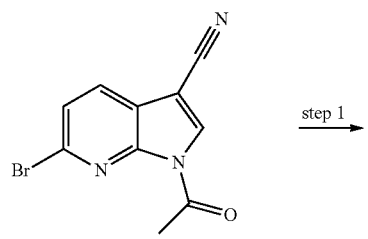

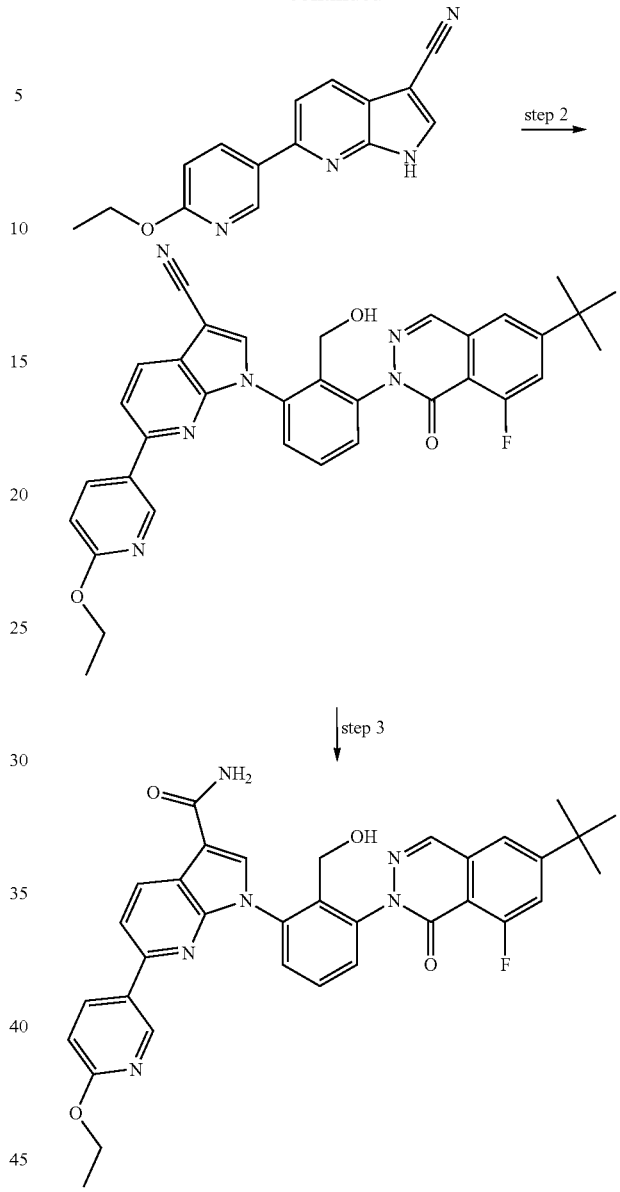

Step 1. In a 100 mL round-bottomed flask, 1-acetyl-6-bromo-1H-pyrrolo[2,3-b]pyridine-3-carbonitrile (250 mg, 947 μmol, Eq: 1.00), triethylamine (575 mg, 792 μl, 5.68 mmol, Eq: 6) and X-PHOS (181 mg, 379 μmol, Eq: 0.40) were combined with dioxane (25 ml) to give a colorless solution. [1,1'-bis(diphenylphosphino)ferrocene]dichloropaladium(II) (173 mg, 237 μmol, Eq: 0.25) and 2-ethoxy-5-pyridineboronic acid (205 mg, 1.23 mmol, Eq: 1.3) were added and the resultant mixture was degassed for 5 minutes under Nitrogen. The reaction mixture was heated to 100° C. and stirred for O/N h. The reaction mixture was poured into 50 mL H₂O and extracted with EtOAc (3×50 mL). The organic layers were dried over MgSO₄ and concentrated in vacuo. The crude material was purified by flash chromatography (silica gel, 40 g, 20% to 30% EtOAc in hexanes) to give 6-(6-ethoxypyridin-3-yl)-1H-pyrrolo[2,3-b]pyridine-3-carbonitrile (167 mg, 67%).

Step 2. In a 25 mL round-bottomed flask, 6-(6-ethoxypyridin-3-yl)-1H-pyrrolo[2,3-b]pyridine-3-carbonitrile (110 mg, 416 μmol, Eq: 1.00), 6-tert-butyl-8-fluoro-2-(1-hydroxy-1,3-dihydrobenzo[c][1,2]oxaborol-4-yl)phthalazin-1(2H)-one (161 mg, 458 μmol, Eq: 1.10) and copper acetate (102 mg) were combined with 1,2-Dichloroethane (3 ml) to give a blue suspension. Pyridine (65.8 mg, 67.3 μl, 832 μmol, Eq: 2) was added. The reaction mixture was heated to 45° C. and stirred for 2 d. The reaction mixture was poured into 20 mL sat NH$_4$Cl and extracted with EtOAc (3×20 mL). The organic layers were dried over MgSO$_4$ and concentrated in vacuo. The crude material was purified by flash chromatography (silica gel, 40 g, 5% to 10% MeOH in DCM) then by SFC to give 1-(3-(6-tert-butyl-8-fluoro-1-oxophthalazin-2(1H)-yl)-2-(hydroxymethyl)phenyl)-6-(6-ethoxypyridin-3-yl)-1H-pyrrolo[2,3-b]pyridine-3-carbonitrile (36 mg, 15%).

Step 3. In a 25 mL round-bottomed flask, 1-(3-(6-tert-butyl-8-fluoro-1-oxophthalazin-2(1H)-yl)-2-(hydroxymethyl)phenyl)-6-(6-ethoxypyridin-3-yl)-1H-pyrrolo[2,3-b]pyridine-3-carbonitrile (36 mg, 61.2 μmol) and [hydrogen bis(dimethylphosphinito-kP)]platinum (II) (263 μg, 0.612 μmol, Eq: 0.01) were combined with ethanol (480 μl) and water (480 μl) to give a colorless solution. The reaction mixture was heated to 45° C. and stirred for 1 h. The crude reaction mixture was concentrated in vacuo. Mixture was diluted with acetonitrile and water and filtered. The resultant filtrate was lyophilized to give 1-[3-(6-tert-butyl-8-fluoro-1-oxo-1H-phthalazin-2-yl)-2-hydroxymethyl-phenyl]-6-(6-ethoxy-pyridin-3-yl)-1H-pyrrolo[2,3-b]pyridine-3-carboxylic acid amide (31 mg, 84%, [M+H]+ 607).

Example 46

1-[3-(6-tert-Butyl-8-fluoro-1-oxo-1H-phthalazin-2-yl)-2-hydroxymethyl-phenyl]-6-(2-fluoro-phenyl)-1H-pyrrolo[2,3-b]pyridine-3-carboxylic acid amide

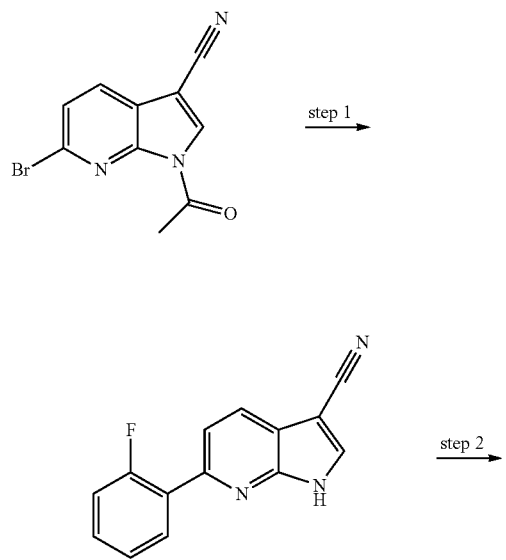

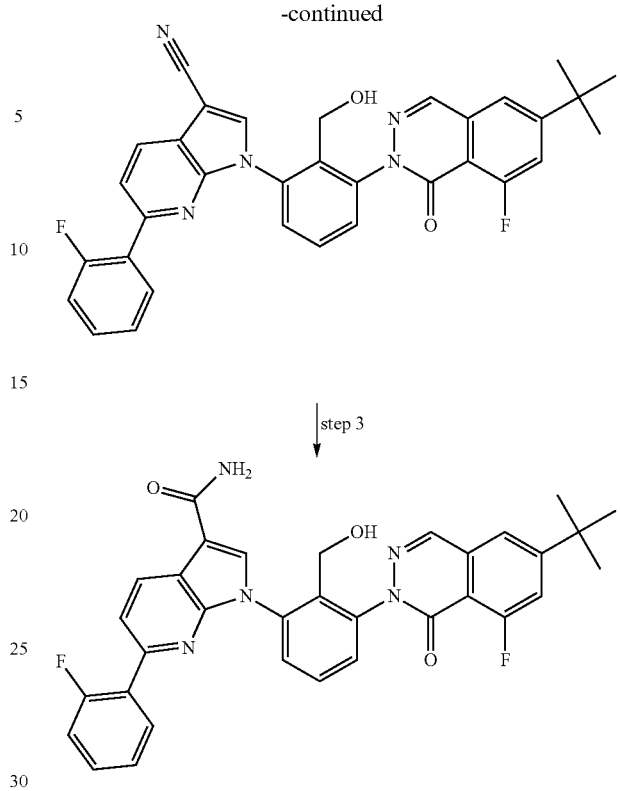

Step 1. In a 100 mL round-bottomed flask, 1-acetyl-6-bromo-1H-pyrrolo[2,3-b]pyridine-3-carbonitrile (250 mg, 947 μmol, Eq: 1.00), triethylamine (575 mg, 792 μl, 5.68 mmol, Eq: 6) and X-PHOS (181 mg, 379 μmol, Eq: 0.40) were combined with dioxane (25.0 ml) to give a colorless solution. [1,1'-bis(diphenylphosphino)ferrocene]dichloropaladium(II) (173 mg, 237 μmol, Eq: 0.25) and 2-fluorophenylboronic acid (265 mg, 1.89 mmol) were added and the resultant mixture was degassed for 5 minutes under Nitrogen. The reaction mixture was heated to 100° C. and microwaved for 1 hr. The reaction mixture was poured into 50 mL EtOAc and washed with H$_2$O. The organic layers were dried over MgSO$_4$ and concentrated in vacuo. The crude material was purified by flash chromatography (silica gel, 40 g, 20% to 30% EtOAc in hexanes) to give 6-(2-fluorophenyl)-1H-pyrrolo[2,3-b]pyridine-3-carbonitrile (220 mg, 98%).

Step 2. In a 25 mL round-bottomed flask, 6-(2-fluorophenyl)-1H-pyrrolo[2,3-b]pyridine-3-carbonitrile (200 mg, 843 μmol), 6-tert-butyl-8-fluoro-2-(1-hydroxy-1,3-dihydrobenzo[c][1,2]oxaborol-4-yl)phthalazin-1(2H)-one (297 mg, 843 μmol, Eq: 1.00) and copper acetate (207 mg,) were combined with 1,2-dichloroethane (10 ml) to give a blue suspension. Pyridine (133 mg, 136 μl, 1.69 mmol, Eq: 2) was added. The reaction mixture was heated to 45° C. and stirred for 2 d. The reaction mixture was poured into 20 mL sat NH$_4$Cl and extracted with EtOAc (3×20 mL). The organic layers were dried over MgSO$_4$ and concentrated in vacuo. The crude material was purified by flash chromatography (silica gel, 40 g, 50% to 60% EtOAc in hexanes), then by SFC gave 1-(3-(6-tert-butyl-8-fluoro-1-oxophthalazin-2(1H)-yl)-2-(hydroxymethyl)phenyl)-6-(2-fluorophenyl)-1H-pyrrolo[2,3-b]pyridine-3-carbonitrile (163 mg, 13%).

Step 3. In a 25 mL round-bottomed flask, 1-(3-(6-tert-butyl-8-fluoro-1-oxophthalazin-2(1H)-yl)-2-(hydroxymethyl)phenyl)-6-(2-fluorophenyl)-1H-pyrrolo[2,3-b]pyridine-3-carbonitrile (65 mg, 116 μmol) and [hydrogen bis (dimethylphosphinito-kP)]platinum (II) (497 μg, 1.16 μmol, Eq: 0.01) were combined with Ethanol (853 μl) and Water (853 μl) to give a colorless solution. The reaction mixture was heated to 45° C. and stirred for 1 h. Mixture was concentrated in vacuo, then diluted with acetonitrile and water and filtered. The resultant filtrate was lyophilized to give 1-[3-(6-tert-Butyl-8-fluoro-1-oxo-1H-phthalazin-2-yl)-2-hydroxymethyl-phenyl]-6-(2-fluoro-phenyl)-1H-pyrrolo[2,3-b]pyridine-3-carboxylic acid amide (61 mg, 91%, [M+H]+ 580).

Example 47

1-[3-(6-tert-Butyl-8-fluoro-1-oxo-1H-phthalazin-2-yl)-2-hydroxymethyl-phenyl]-6-(2-chloro-phenyl)-1H-pyrrolo[2,3-b]pyridine-3-carboxylic acid amide

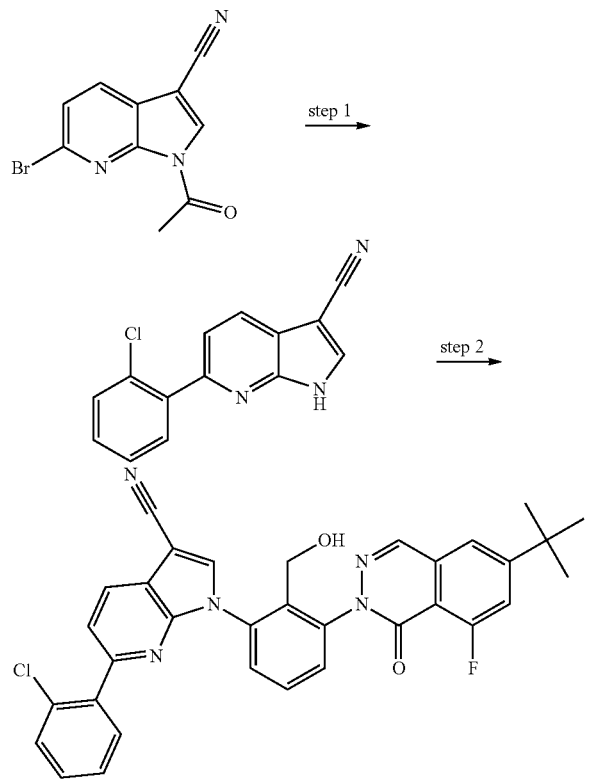

Step 1. In a 100 mL round-bottomed flask, 1-acetyl-6-bromo-1H-pyrrolo[2,3-b]pyridine-3-carbonitrile (250 mg, 947 μmol, Eq: 1.00), triethylamine (575 mg, 792 μl, 5.68 mmol, Eq: 6) and X-PHOS (181 mg, 379 μmol, Eq: 0.40) were combined with dioxane (25.0 ml) to give a colorless solution. [1,1'-bis(diphenylphosphino)ferrocene]dichloropaladium(II) (173 mg, 237 μmol, Eq: 0.25) and 2-chlorophenylboronic acid (296 mg, 1.89 mmol) were added and the resultant mixture was degassed for 5 minutes under Nitrogen. The reaction mixture was heated to 100° C. and stirred overnight. The reaction mixture was poured into 50 mL H₂O and extracted with EtOAc (3×50 mL). The organic layers were dried over MgSO₄ and concentrated in vacuo. The crude material was purified by flash chromatography (silica gel, 40 g, 20% to 30% EtOAc in hexanes) to give 6-(2-chlorophenyl)-1H-pyrrolo[2,3-b]pyridine-3-carbonitrile (142 mg, 59%).

Step 2. In a 25 mL round-bottomed flask 6-(2-chlorophenyl)-1H-pyrrolo[2,3-b]pyridine-3-carbonitrile (125 mg, 493 μmol), 6-tert-butyl-8-fluoro-2-(1-hydroxy-1,3-dihydrobenzo[c][1,2]oxaborol-4-yl)phthalazin-1(2H)-one (174 mg, 493 μmol, Eq: 1.00) and copper acetate (121 mg) were combined with 1,2-dichloroethane (6.25 ml) to give a blue suspension. Pyridine (78.0 mg, 79.7 μl, 985 μmol, Eq: 2) was added. The reaction mixture was heated to 45° C. and stirred for 2 d. The reaction mixture was poured into sat NH₄Cl (20 mL) and extracted with EtOAc (3×20 mL). The organic layers were dried over MgSO₄ and concentrated in vacuo. The crude material was purified by flash chromatography (silica gel, 40 g, 5% to 10% MeOH in DCM), then by SFC to 1-(3-(6-tert-butyl-8-fluoro-1-oxophthalazin-2(1H)-yl)-2-(hydroxymethyl)phenyl)-6-(2-chlorophenyl)-1H-pyrrolo[2,3-b]pyridine-3-carbonitrile (4.5 mg, 2%).

Step 3. In a 25 mL round-bottomed flask, 1-(3-(6-tert-butyl-8-fluoro-1-oxophthalazin-2(1H)-yl)-2-(hydroxymethyl)phenyl)-6-(2-chlorophenyl)-1H-pyrrolo[2,3-b]pyridine-3-carbonitrile (4 mg, 6.92 μmol) and [hydrogen bis(dimethylphosphinito-kP)]platinum (II) (29.7 μg, 0.0692 μmol, Eq: 0.01) were combined with Ethanol (853 μl) and Water (853 μl) to give a colorless solution. The reaction mixture was heated to 45° C. and stirred for 1 h, then concentrated in vacuo. Mixture was diluted with acetonitrile and water and filtered. The resultant filtrate is lyophalized to give 1-[3-(6-tert-Butyl-8-fluoro-1-oxo-1H-phthalazin-2-yl)-2-hydroxymethyl-phenyl]-6-(2-chloro-phenyl)-1H-pyrrolo[2,3-b]pyridine-3-carboxylic acid amide (3.9 mg, 95%, [M+H]+ 596).

Example 48

6-bromo-1-[3-(6-tert-butyl-8-fluoro-1-oxo-1H-phthalazin-2-yl)-2-hydroxymethyl-phenyl]-1H-pyrrolo[2,3-b]pyridine-3-carboxylic acid amide

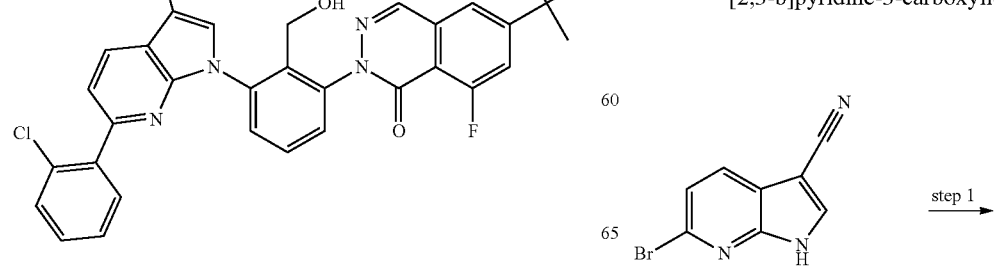

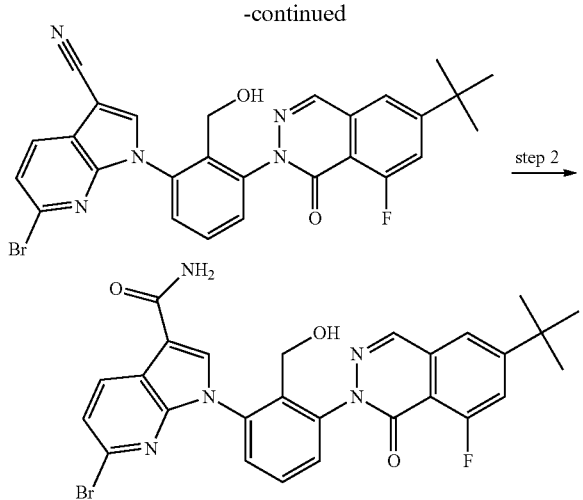

Step 1. In a 25 mL round-bottomed flask, 6-bromo-1H-pyrrolo[2,3-b]pyridine-3-carbonitrile (75.0 mg, 338 µmol, Eq: 1.19), 6-tert-butyl-8-fluoro-2-(1-hydroxy-1,3-dihydrobenzo[c][1,2]oxaborol-4-yl)phthalazin-1(2H)-one (100 mg, 284 µmol, Eq: 1.00) and copper acetate (52.2 mg) were combined with 1,2-dichloroethane (3.00 ml) to give a blue suspension. Pyridine (44.9 mg, 45.9 µl, 568 µmol, Eq: 2) was added. The reaction mixture was heated to 45° C. and stirred for 2 d. Mixture was poured into 20 mL sat NH₄Cl and extracted with EtOAc (3×20 mL). The organic layers were dried over MgSO₄ and concentrated in vacuo. The crude material was purified by flash chromatography (silica gel, 40 g, 25% to 45% EtOAc in hexanes) to give 6-bromo-1-(3-(6-tert-butyl-8-fluoro-1-oxophthalazin-2(1H)-yl)-2-(hydroxymethyl)phenyl)-1H-pyrrolo[2,3-b]pyridine-3-carbonitrile (16 mg, 10.3%).

Step 2. In a 25 mL round-bottomed flask, 6-bromo-1-(3-(6-tert-butyl-8-fluoro-1-oxophthalazin-2(1H)-yl)-2-(hydroxymethyl)phenyl)-1H-pyrrolo[2,3-b]pyridine-3-carbonitrile (14 mg, 25.6 µmol) and [hydrogen bis(dimethylphosphinito-kP)]platinum (II) (110 µg, 0.256 µmol, Eq: 0.01) were combined with Ethanol (2.99 ml) and Water (2.99 ml) to give a colorless solution. The reaction mixture was heated to 45° C. and stirred for 1 h. The crude reaction mixture was concentrated in vacuo. Purification by HPLC gave 6-bromo-1-[3-(6-tert-butyl-8-fluoro-1-oxo-1H-phthalazin-2-yl)-2-hydroxymethyl-phenyl]-1H-pyrrolo[2,3-b]pyridine-3-carboxylic acid amide (11 mg, 77%, [M+H]+ 565).

Example 49

1-[3-(6-tert-Butyl-8-fluoro-1-oxo-1H-phthalazin-2-yl)-2-hydroxymethyl-phenyl]-6-(1,2-dihydroxy-ethyl)-1H-pyrrolo[2,3-b]pyridine-3-carboxylic acid amide

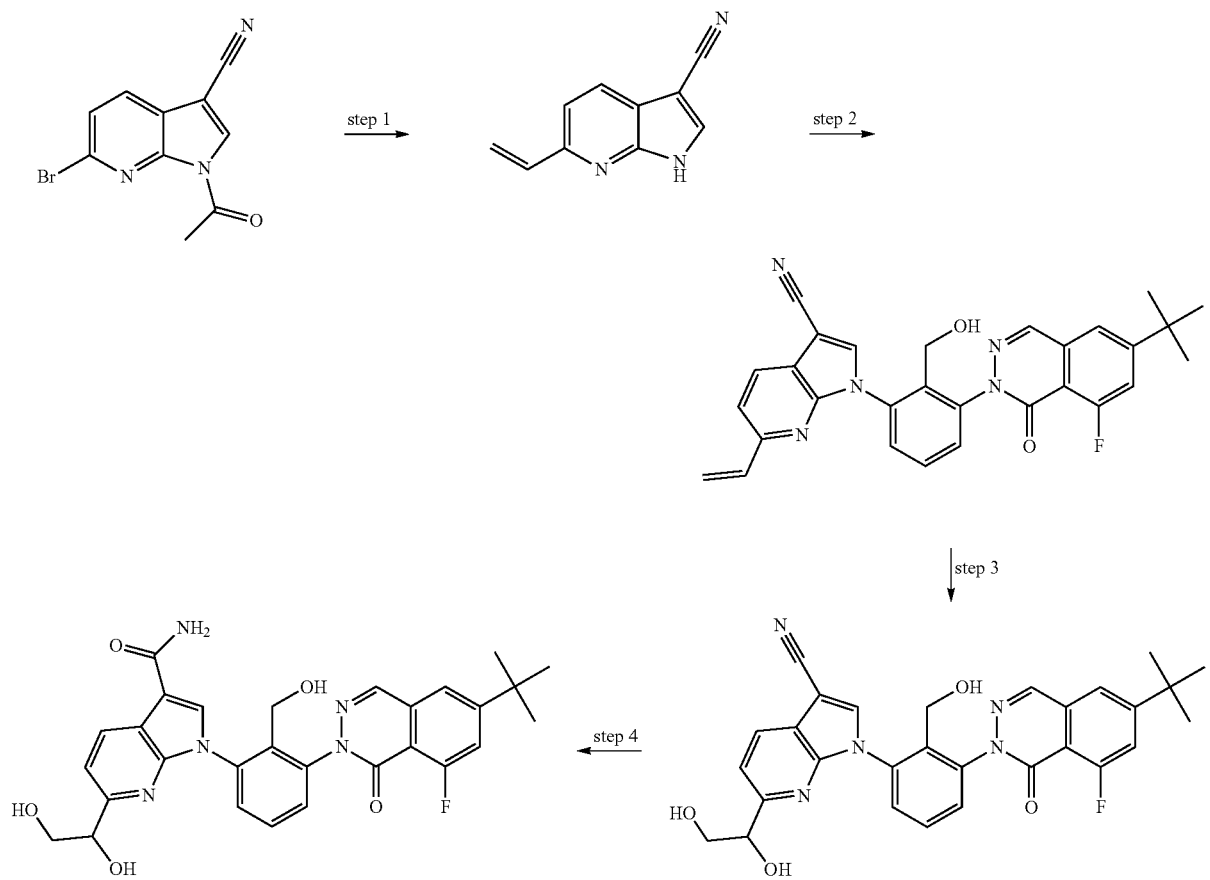

Step 1. In a 25 mL round-bottomed flask, 1-acetyl-6-bromo-1H-pyrrolo[2,3-b]pyridine-3-carbonitrile (372 mg, 1.41 mmol, Eq: 1.00), 2,6-ditert-butyl-4-methylphenol (5 mg, 22.7 µmol, Eq: 0.0161) and tributyl(vinyl)tin (536 mg, 494 µl, 1.69 mmol, Eq: 1.20) were combined with toluene (8 ml) to give a light yellow solution. Mixture is degassed with nitrogen bubbling through it for 5 minutes and tetrakis(triphenylphosphine)palladium (0) (130 mg, 113 µmol, Eq: 0.08) was added The reaction is again degassed with nitrogen and the reaction mixture was heated to 80° C. and stirred for over night. Mixture was poured onto 15 mL sat NaHCO₃ and extracted with EtOAc (3×25 mL). The organic layers were dried over MgSO₄ and concentrated in vacuo. The crude material was purified by flash chromatography (silica gel, 40 g, 10% to 20% EtOAc in hexanes) to give two products: 1-acetyl-6-vinyl-1H-pyrrolo[2,3-b]pyridine-3-carbonitrile (160 mg), and 6-vinyl-1H-pyrrolo[2,3-b]pyridine-3-carbonitrile (138 mg).

Step 2. In a 25 mL round-bottomed flask, 6-vinyl-1H-pyrrolo[2,3-b]pyridine-3-carbonitrile (138 mg, 816 µmol, Eq: 1.00), 6-tert-butyl-8-fluoro-2-(1-hydroxy-1,3-dihydrobenzo[c][1,2]oxaborol-4-yl)phthalazin-1(2H)-one (287 mg, 816 µmol, Eq: 1.00) and copper acetate (200 mg) were combined with 1,2-Dichloroethane (3.58 ml) to give a blue suspension. Pyridine (129 mg, 132 µl, 1.63 mmol, Eq: 2) was added. The reaction mixture was heated to 45° C. and stirred for 2 d. The reaction mixture was poured into 20 mL sat NH₄Cl and extracted with sat EtOAc (3×20 mL). The organic layers were dried over MgSO₄ and concentrated in vacuo. The crude material was purified by flash chromatography (silica gel, 40 g, 5% to 10% MeOH in DCM), then by HPLC to give 1-(3-(6-tert-butyl-8-fluoro-1-oxophthalazin-2(1H)-yl)-2-(hydroxymethyl)phenyl)-6-vinyl-1H-pyrrolo[2,3-b]pyridine-3-carbonitrile (51 mg, 13%).

Step 3. In a 10 mL pear-shaped flask, 1-(3-(6-tert-butyl-8-fluoro-1-oxophthalazin-2(1H)-yl)-2-(hydroxymethyl)phenyl)-6-vinyl-1H-pyrrolo[2,3-b]pyridine-3-carbonitrile (50 mg, 101 µmol, Eq: 1.00), 4-methylmorpholine N-oxide (17.8 mg, 152 µmol, Eq: 1.50) and osmium tetroxide (41.2 mg, 50.9 µl, 4.05 µmol, Eq: 0.04) were combined with acetone (2 ml) to give a colorless solution. The reaction mixture was stirred for 2 d. Reaction was quenched with sodium sulphite, extracted with ethyl acetate and evaporated. Additional 4-methylmorpholine N-oxide (17.8 mg, 152 µmol, Eq: 1.50), osmium tetroxide (41.2 mg, 50.9 µl, 4.05 µmol, Eq: 0.04) and acetone (3 ml) were added to give a brown solution and reaction was continued for a day. Reaction was quenched with sodium sulphite, extracted with ethyl acetate and evaporated. Crude 1-(3-(6-tert-butyl-8-fluoro-1-oxophthalazin-2(1H)-yl)-2-(hydroxymethyl)phenyl)-6-(1,2-dihydroxyethyl)-1H-pyrrolo[2,3-b]pyridine-3-carbonitrile (15 mg) was taken to next step.

Step 4. In a 25 mL round-bottomed flask, 1-(3-(6-tert-butyl-8-fluoro-1-oxophthalazin-2(1H)-yl)-2-(hydroxymethyl)phenyl)-6-(1,2-dihydroxyethyl)-1H-pyrrolo[2,3-b]pyridine-3-carbonitrile (14 mg, 26.5 µmol, Eq: 1.00) and [hydrogen bis(dimethylphosphinito-kP)]platinum (II) (373 µg, 0.870 µmol, Eq: 0.0328) were combined with Ethanol (200 µl) and Water (200 µl) to give a colorless solution. The reaction mixture was heated to 45° C. and stirred for 1 h. The crude reaction mixture was concentrated in vacuo. Mixture was diluted with acetonitrile and water and filtered. The resultant filtrate is lyophilized to give 1-[3-(6-tert-butyl-8-fluoro-1-oxo-1H-phthalazin-2-yl)-2-hydroxymethyl-phenyl]-6-(1,2-dihydroxy-ethyl)-1H-pyrrolo[2,3-b]pyridine-3-carboxylic acid amide (11.2 mg, 77%, [M+H]+ 546).

Example 50

1-[3-(6-tert-Butyl-8-fluoro-1-oxo-1H-phthalazin-2-yl)-2-hydroxymethyl-phenyl]-6-(1,1-dioxo-1lambda*6*-thiomorpholin-4-yl)-1H-pyrrolo[2,3-b]pyridine-3-carboxylic acid amide

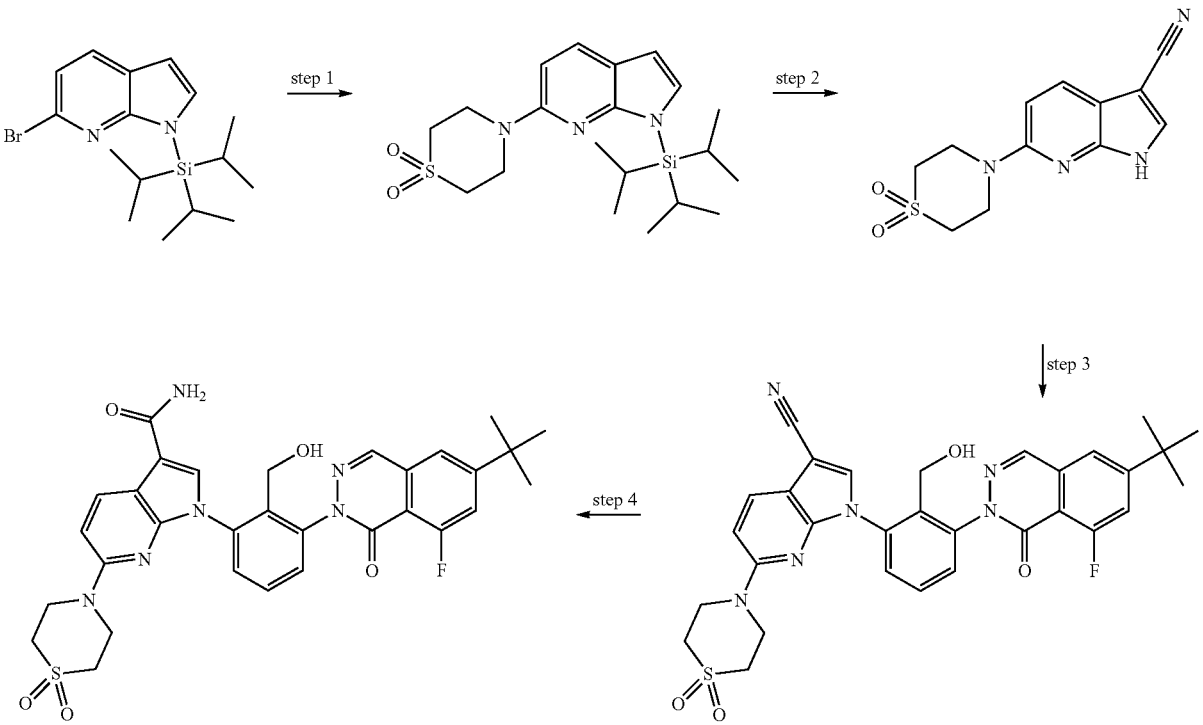

Step 1. In a 25 mL round-bottomed flask, 6-bromo-1-(triisopropylsilyl)-1H-pyrrolo[2,3-b]pyridine (420 mg, 1.19 mmol, Eq: 1.00) and thiomorpholine 1,1-dioxide (482 mg, 3.57 mmol) were combined with toluene (3 ml) to give a yellow solution. Bis(tri-tert-butylphosphine)palladium(0) (60.7 mg, 119 µmol) and sodium tert-butoxide (400 mg, 4.16 mmol, Eq: 3.5) were added. The reaction mixture was heated to 80° C. and stirred for 1 h. The reaction mixture was poured into 20 mL sat NaCl and extracted with EtOAc (3×20 mL). The organic layers were dried over MgSO$_4$ and concentrated in vacuo. The crude material was purified by flash chromatography (silica gel, 40 g, 20% to 40% EtOAc in hexanes) to give 6-(1,1-Dioxo-1lambda*6*-thiomorpholin-4-yl)-1-triisopropylsilanyl-1H-pyrrolo[2,3-b]pyridine (327 mg, 68%) as a yellow oil that solidified as off white solid upon standing.

Step 2. In a 25 mL round-bottomed flask 6-(1,1-Dioxo-1lambda*6*-thiomorpholin-4-yl)-1-triisopropylsilanyl-1H-pyrrolo[2,3-b]pyridine (322 mg, 790 µmol, Eq: 1.00) was combined with DMF (11.9 ml) to give a colorless solution. The reaction mixture was cooled to −20° C. and stirred for 5 min. Chlorosulfonyl isocyanate (335 mg, 206 µl, 2.37 mmol, Eq: 3) in acetonitrile (11.9 ml) was added dropwise and the resultant cooled reaction was stirred at −20° C. and stirred for 3 hrs The reaction mixture was poured into 25 mL EtOAc and washed with sat NaCl (3×20 mL). After evaporation, crude material was purified by flash chromatography (silica gel, 12 g, 5% to 10% MeOH in DCM) to obtain 6-(1,1-dioxo-1lambda*6*-thiomorpholin-4-yl)-1H-pyrrolo[2,3-b]pyridine-3-carbonitrile (122 mg, 56%).

Step 3. In a 25 mL round-bottomed flask, 6-(1,1-dioxo-1lambda*6*-thiomorpholin-4-yl)-1H-pyrrolo[2,3-b]pyridine-3-carbonitrile (122 mg, 442 µmol), 6-tert-butyl-8-fluoro-2-(1-hydroxy-1,3-dihydrobenzo[c][1,2]oxaborol-4-yl)phthalazin-1(2H)-one (155 mg, 442 µmol, Eq: 1.00) and copper acetate (108 mg) were combined with 1,2-dichloroethane (3.89 ml) to give a blue suspension. Pyridine (69.8 mg, 71.4 µl, 883 µmol, Eq: 2) was added. The reaction mixture was heated to 45° C. and stirred for 2 d. The reaction mixture was poured into 20 mL sat NH$_4$Cl and extracted with EtOAc (3×20 mL). The organic layers were dried over MgSO$_4$ and concentrated in vacuo. The crude material was purified by flash chromatography (silica gel, 40 g, 5% to 10% MeOH in DCM), then by HPLC to give 1-[3-(6-tert-butyl-8-fluoro-1-oxo-1H-phthalazin-2-yl)-2-hydroxymethyl-phenyl]-6-(1,1-dioxo-1lambda*6*-thiomorpholin-4-yl)-1H-pyrrolo[2,3-b]pyridine-3-carbonitrile (22 mg, 8%)

Step 4. In a 25 mL round-bottomed flask, 1-[3-(6-tert-butyl-8-fluoro-1-oxo-1H-phthalazin-2-yl)-2-hydroxymethyl-phenyl]-6-(1,1-dioxo-1lambda*6*-thiomorpholin-4-yl)-1H-pyrrolo[2,3-b]pyridine-3-carbonitrile (22 mg, 36.6 µmol) and [hydrogen bis(dimethylphosphinito-kP)]platinum (II) (1.1 mg, 2.56 µmol, Eq: 0.07) were combined with Ethanol (200 µl) and Water (200 µl) to give a colorless solution. The reaction mixture was heated to 45° C. and stirred for 1 h. The crude reaction mixture was concentrated in vacuo, then diluted with acetonitrile and water and filtered and purified by HPLC to obtain 1-[3-(6-tert-Butyl-8-fluoro-1-oxo-1H-phthalazin-2-yl)-2-hydroxymethyl-phenyl]-6-(1,1-dioxo-1lambda*6*-thiomorpholin-4-yl)-1H-pyrrolo[2,3-b]pyridine-3-carboxylic acid amide (15.5 mg, 68%, [M+H]+ 619).

Example 51

1-[3-(6-tert-Butyl-8-fluoro-1-oxo-1H-phthalazin-2-yl)-2-hydroxymethyl-phenyl]-6-(2-dimethylaminoethylamino)-1H-pyrrolo[2,3-b]pyridine-3-carboxylic acid amide

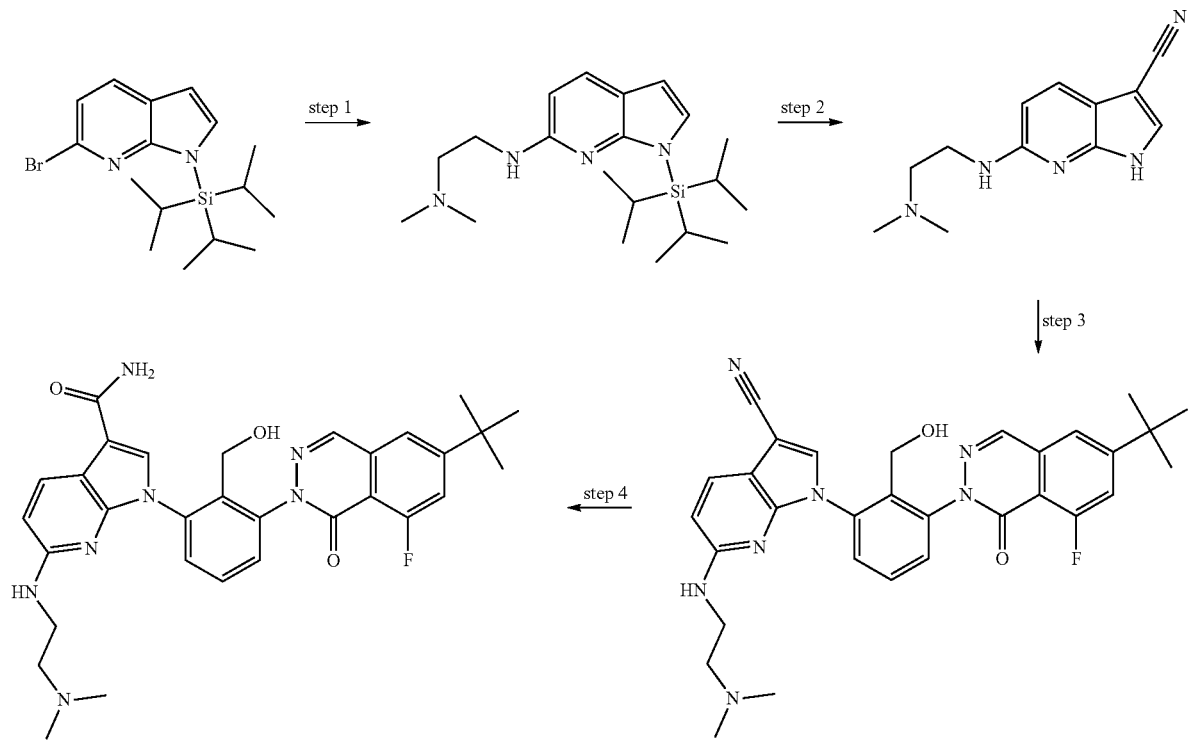

Step 1. In a 25 mL round-bottomed flask, 6-bromo-1-(triisopropylsilyl)-1H-pyrrolo[2,3-b]pyridine (713 mg, 2.02 mmol, Eq: 1.00), N,N-dimethylethylenediamine (1.07 g, 1.32 ml, 12.1 mmol, Eq: 6) and bis(tri-tert-butylphosphine)palladium(0) (206 mg, 404 μmol, Eq: 0.2) were combined with toluene (2 ml) to give a yellow solution. Sodium tert-butoxide (582 mg, 6.05 mmol, Eq: 3) was added. The reaction mixture was heated to 80° C. and stirred for 1 h, then poured into 20 mL sat NaCl and extracted with EtOAc (3×20 mL). The organic layers were dried over MgSO$_4$ and concentrated in vacuo. The crude material was purified by flash chromatography (silica gel, 12 g, 2% to 5% MeOH in DCM) to give N1,N1-dimethyl-N2-(1-(triisopropylsilyl)-1H-pyrrolo[2,3-b]pyridin-6-yl)ethane-1,2-diamine (405 mg, 56%) as yellow oil that solidified upon standing.

Step 2. In a 25 mL round-bottomed flask, N1,N1-dimethyl-N2-(1-(triisopropylsilyl)-1H-pyrrolo[2,3-b]pyridin-6-yl)ethane-1,2-diamine (405 mg, 1.12 mmol) was combined with DMF (14.9 ml) to give a colorless solution. The reaction mixture was cooled to −20° C. and stirred for 5 min. Chlorosulfonyl isocyanate (477 mg, 293 μl, 3.37 mmol, Eq: 3) in acetonitrile (14.9 ml) was added dropwise and the resultant cooled reaction was stirred at −20° C. and stirred for 3 hrs The reaction mixture was poured into 25 mL sat NaCl and extracted with EtOAc (3×20 ml). After evaporation, crude g, 5% to 10% MeOH in DCM), then by HPLC to give 1-(3-(6-tert-butyl-8-fluoro-1-oxophthalazin-2(1H)-yl)-2-(hydroxymethyl)phenyl)-6-(2-(dimethylamino)ethylamino)-1H-pyrrolo[2,3-b]pyridine-3-carbonitrile (18 mg, 3.5%)

Step 4. In a 25 mL round-bottomed flask, 1-(3-(6-tert-butyl-8-fluoro-1-oxophthalazin-2(1H)-yl)-2-(hydroxymethyl)phenyl)-6-(2-(dimethylamino)ethylamino)-1H-pyrrolo[2,3-b]pyridine-3-carbonitrile (19 mg, 34.3 μmol, Eq: 1.00) and [hydrogen bis(dimethylphosphinito-kP)]platinum (II) (1.47 mg, 3.43 μmol, Eq: 0.1) were combined with Ethanol (271 μl) and Water (271 μl) to give a colorless solution. The reaction mixture was heated to 45° C. and stirred for 1 h. The crude reaction mixture was concentrated in vacuo, then diluted with acetonitrile and water and filtered. The resultant filtrate was lyophilized to give 1-[3-(6-tert-Butyl-8-fluoro-1-oxo-1H-phthalazin-2-yl)-2-hydroxymethyl-phenyl]-6-(2-dimethylamino-ethylamino)-1H-pyrrolo[2,3-b]pyridine-3-carboxylic acid amide (14.2 mg, 71%, [M+H]+ 572).

Example 52

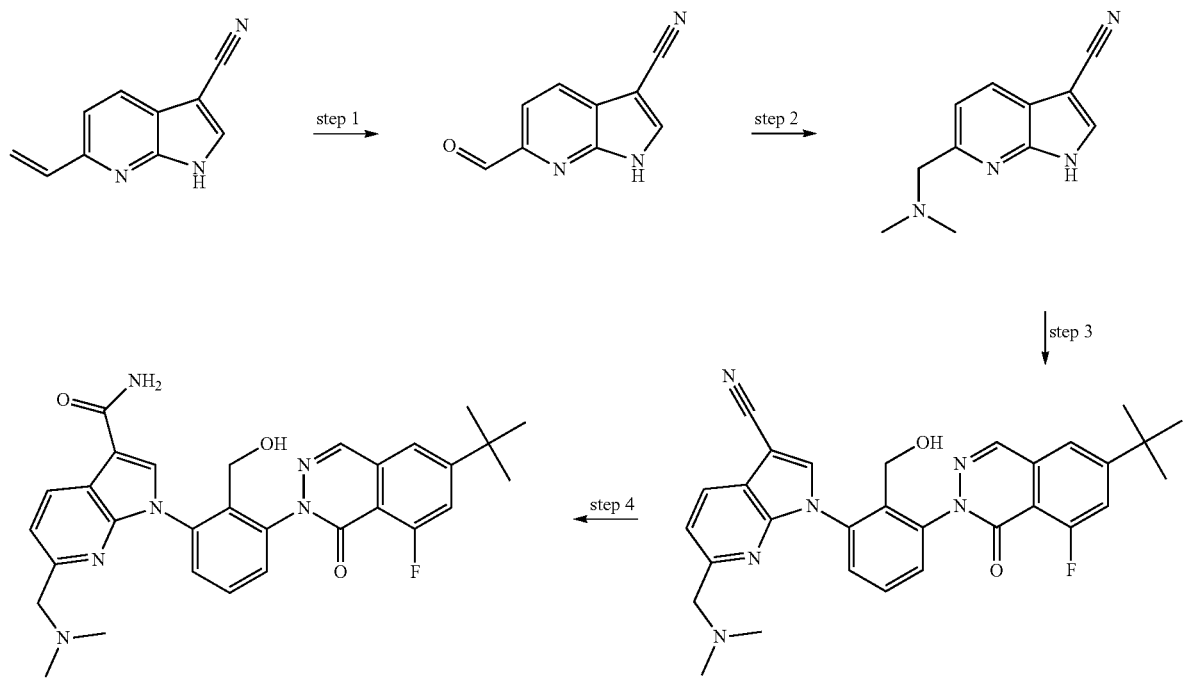

material was purified by flash chromatography (silica gel, 12 g, 5% to 10% MeOH in DCM) to obtain 6-(2-(dimethylamino)ethylamino)-1H-pyrrolo[2,3-b]pyridine-3-carbonitrile (211 mg, 82%).

Step 3. In a 25 mL round-bottomed flask, 6-(2-(dimethylamino)ethylamino)-1H-pyrrolo[2,3-b]pyridine-3-carbonitrile (211 mg, 920 μmol), 6-tert-butyl-8-fluoro-2-(1-hydroxy-1,3-dihydrobenzo[c][1,2]oxaborol-4-yl)phthalazin-1(2H)-one (324 mg, 920 μmol, Eq: 1.00) and copper acetate (226 mg) were combined with 1,2-Dichloroethane (6.73 ml) to give a blue suspension. Pyridine (146 mg, 149 μl, 1.84 mmol, Eq: 2) was added. The reaction mixture was heated to 45° C. and stirred for 2 d. Mixture was poured into 20 mL sat NH$_4$Cl and extracted with EtOAc (3×20 mL). The organic layers were dried over MgSO$_4$ and concentrated in vacuo. The crude material was purified by flash chromatography (silica gel, 40

Step 1. In a 10 mL pear-shaped flask, 6-vinyl-1H-pyrrolo[2,3-b]pyridine-3-carbonitrile (274 mg, 1.62 mmol), 4-methylmorpholine N-oxide (17.8 mg, 152 μmol, Eq: 1.50) and osmium tetroxide (3.29 g, 4.07 ml, 324 μmol, Eq: 0.2) were combined with acetone (3 ml) to give a colorless solution. The reaction mixture was maintained at room temperature and stirred for 2 d. The reaction was quenched with sodium sulphite, extracted with ethyl acetate and evaporated. Additional 4-methylmorpholine N-oxide (17.8 mg, 152 μmol, Eq: 1.50) and osmium tetroxide (41.2 mg, 50.9 μl, 4.05 μmol, Eq: 0.04) and acetone (3 ml) were added to give a brown solution and reaction was continued for a day. The reaction was quenched with sodium sulphite, extracted with ethyl acetate and evaporated. Crude 6-formyl-1H-pyrrolo[2,3-b]pyridine-3-carbonitrile was taken to next step.

Steps 2 and 3. After following standard reductive amination conditions, 6-((dimethylamino)methyl)-1H-pyrrolo[2,3-b]pyridine-3-carbonitrile (18 mg, 89.9 µmol), 6-tert-butyl-8-fluoro-2-(1-hydroxy-1,3-dihydrobenzo[c][1,2]oxaborol-4-yl)phthalazin-1(2H)-one (38.0 mg, 108 µmol, Eq: 1.20) and copper acetate (22.0 mg) were combined with 1,2-Dichloroethane (574 µl) to give a blue suspension. Pyridine (14.2 mg, 14.5 µl, 180 µmol, Eq: 2) was added. The reaction mixture was heated to 45° C. and stirred for 2 d. The reaction mixture was poured into 20 mL EtOAc and extracted with sat NH4Cl (3×20 mL). The organic layers were dried over MgSO4 and concentrated in vacuo. Crude 1-(3-(6-tert-butyl-8-fluoro-1-oxophthalazin-2(1H)-yl)-2-(hydroxymethyl)phenyl)-6-((dimethylamino)methyl)-1H-pyrrolo[2,3-b]pyridine-3-carbonitrile (8 mg) was not purified but taken to next step.

Step 4. In a 25 mL round-bottomed flask, 1-(3-(6-tert-butyl-8-fluoro-1-oxophthalazin-2(1H)-yl)-2-(hydroxymethyl)phenyl)-6-((dimethylamino)methyl)-1H-pyrrolo[2,3-b]pyridine-3-carbonitrile (8 mg, 15.3 µmol, Eq: 1.00) and [hydrogen bis(dimethylphosphinito-kP)]platinum (II) (655 µg, 1.53 µmol, Eq: 0.1) were combined with Ethanol (1 mL) and Water (1 mL) to give a colorless solution. The reaction mixture was heated to 45° C. and stirred for 1 h. The crude reaction mixture was concentrated in vacuo. The LCMS of crude shows the desired product. The reaction mixture was diluted with acetonitrile and water and filtered and passed through HPLC purification followed by lyophalization to give 1-[3-(6-tert-Butyl-8-fluoro-1-oxo-1H-phthalazin-2-yl)-2-hydroxymethyl-phenyl]-6-dimethylaminomethyl-1H-pyrrolo[2,3-b]pyridine-3-carboxylic acid amide (2.5 mg, 30%, [M+H]+ 543)

Example 53

3-(4-Acetyl-phenylamino)-1-[3-(6-tert-butyl-1-oxo-1H-phthalazin-2-yl)-2-hydroxymethyl-phenyl]-1H-pyrazole-4-carbonitrile

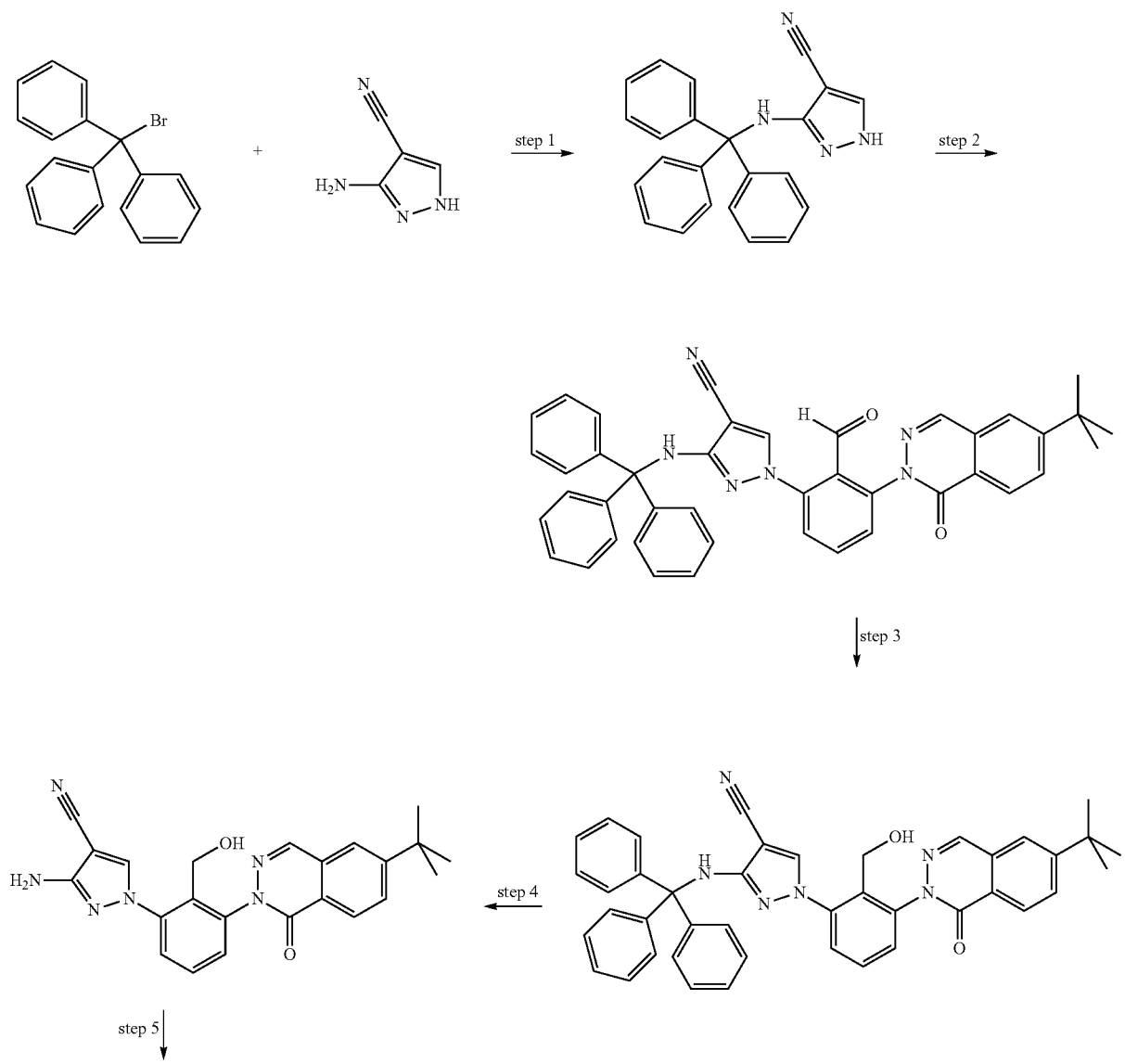

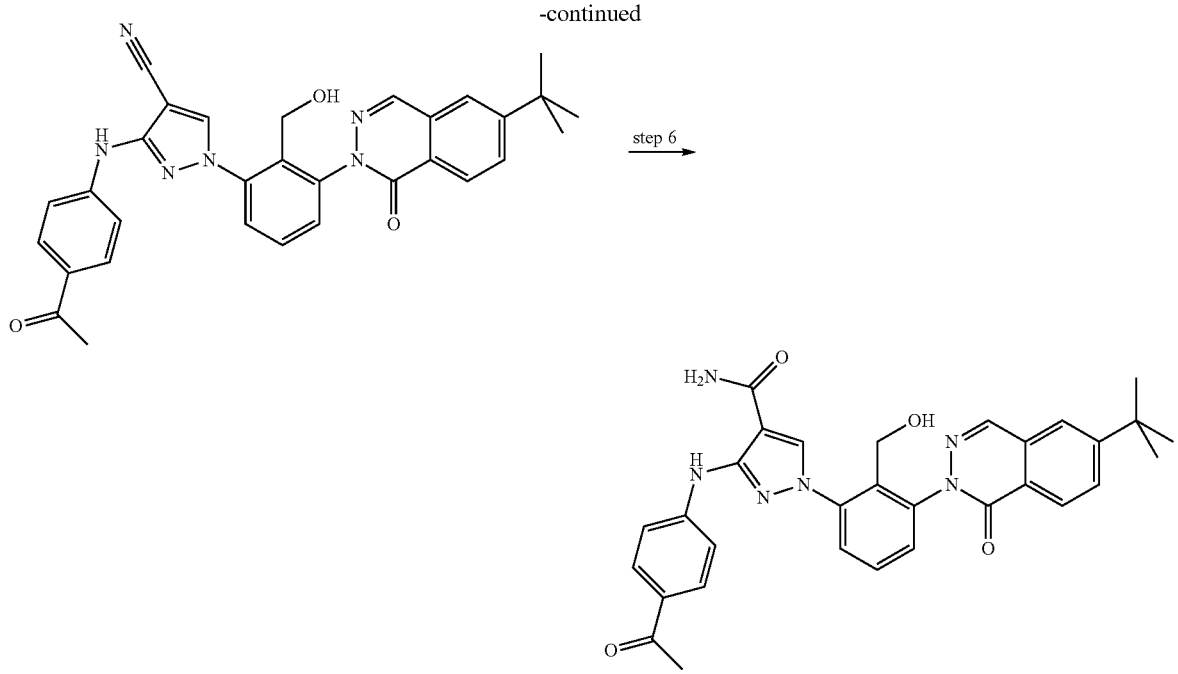

Step 1. To a solution of dry acetonitrile (10 mL) and dry tetrahydrofuran (30 mL) was added 5-amino-1H-pyrazole-4-carbonitrile (1.0 g, 9.25 mmol) followed by triethylamine (1.08 mL, 1.74 mmol). The resulting suspension was allowed to stir at room temperature for five minutes and then cooled to 0° C. A solution of (bromomethanetriyl)tribenzene (1.89 g, 5.84 mmol) in dry tetrahydrofuran (10 mL) was added dropwise via an addition funnel equipped with a nitrogen inlet, at such a rate that the temperature did not rise above 5° C. The addition funnel was then rinsed with dry tetrahydrofuran (5 mL) and the reaction mixture was stirred at 0° C. for 10 minutes, then allowed to warm to room temperature and stirred for 2 hours. The volatiles were removed in vacuo and residue was dissolved in EtOAc (150 mL) and washed once water (100 mL), once with saturated aqueous sodium chloride, dried over $Na_2SO_4$, filtered and concentrated in vacuo. The crude product was applied to an 80 g silica gel cartridge using methylene chloride, and the column was eluted with a 10-30% EtOAc/hexanes gradient. The product containing fractions were combined to give 3-(Trityl-amino)-1H-pyrazole-4-carbonitrile (1.3 g, 41%) as an off-white semi-crystalline solid.

Step 2. To degassed DMF (1.5 mL) were added 5-(tritylamino)-1H-pyrazole-4-carbonitrile (1.36 g, 3.89 mmol), 2-bromo-6-(6-tert-butyl-1-oxophthalazin-2(1H)-yl)benzaldehyde (1.0 g, 2.6 mmol), copper (I) iodide (494 mg, 2.6 mmol) and potassium carbonate (717 mg, 5.19 mmol). The reaction was inerted five times by alternating vacuum and a nitrogen purge and then heat to 100° C. (external); for 8 hr. TLC the following morning showed trace amounts of starting materials. The reaction was diluted with EtOAc (50 mL) and through a pad of diatomaceous earth. The pad was rinsed with additional EtOAc (50 mL) and concentrated in vacuo. The crude material was bound to silica column and purified over a 40 g silica gel cartridge, eluting the column with a 20-40% EtOAc/hexanes, isocratic hold for 5 minutes, then 40-100% EtOAc/hexanes gradient over 20 minutes. The product containing fractions were combined and concentrated to give 1-[3-(6-tert-Butyl-1-oxo-1H-phthalazin-2-yl)-2-formyl-phenyl]-3-(trityl-amino)-1H-pyrazole-4-carbonitril (632 mg, 37%).

Step 3. To a solution of 1-[3-(6-tert-Butyl-1-oxo-1H-phthalazin-2-yl)-2-formyl-phenyl]-3-(trityl-amino)-1H-pyrazole-4-carbonitril (632 mg, 0.965 mmol) in methylene chloride (20 mL) and methanol (10 mL), at 0° C. was added sodium borohydride (37 mg, 0.965 mmol). The resulting turbid reaction mixture was stirred at 0° C. for 5 minutes and then allowed to stir at room temperature for 10 minutes. The reaction was then judged to be complete by TLC. The volatiles removed in vacuo and the crude product was bound to silica gel and purified over a 40 g silica gel cartridge eluting the column with a 20-50% EtOAc/hexanes gradient to give 1-[3-(6-tert-Butyl-1-oxo-1H-phthalazin-2-yl)-2-hydroxymethyl-phenyl]-3-(trityl-amino)-1H-pyrazole-4-carbonitrile (482 mg, 76%).

Step 4. 1-(3-(6-tert-butyl-1-oxophthalazin-2(1H)-yl)-2-(hydroxymethyl)phenyl)-3-(tritylamino)-1H-pyrazole-4-carbonitrile (382 mg 0.582 mmol) was dissolved in $Et_2O$ (30 mL) and cooled to 0° C. in. MeOH (2 mL) was added followed by saturated ethereal HCl (2 mL, prepared by bubbling HCl gas into 100 mL of ether). The reaction mixture was allowed to stir at 0° C. for 30 minutes, after which, it was judged to be complete by TLC. The volatiles were removed in vacuo and residue was partitioned between saturated aqueous $NaHCO_3$ (100 mL) and EtOAc (100 mL) and stirred vigorously. The aqueous layer was separated and extracted with EtOAc (50 mL). The combined organic layers were dried over Na2SO4, filtered and concentrated in vacuo. The oily residue was bound to silica gel and the crude product was purified over a 25 g silica gel cartridge eluting the column with a 20-70% EtOAc/hexanes gradient to give 3-Amino-1-[3-(6-tert-butyl-1-oxo-1H-phthalazin-2-yl)-2-hydroxymethyl-phenyl]-1H-pyrazole-4-carbonitril (178 mg, 74%) as a white-powdery solid.

Step 5. To a 5 mL microwave reaction vial were introduced 3-amino-1-(3-(6-tert-butyl-1-oxophthalazin-2(1H)-yl)-2-(hydroxymethyl)phenyl)-1H-pyrazole-4-carbonitrile (50 mg, 0.121 mmol), 1-(4-bromophenyl)ethanone (29 mg, 0.145 mmol), Pd₂(dba)₃ (7.7 mg, 0.008 mmol), 2-(DICYCLOHEXYLPHOSPHINO)-3,6-DIMETHOXY-2'-4'-6'-TRI-I-PROPYL-1,1'-BIPHENYL (Brett-Phos) (9.1 mg, 0.017 mmol), cesium carbonate (59 mg, 0.181 mmol) and suspended in t-butanol (1.5 mL). The reaction vessel was inerted three times by alternating vacuum and an Ar purge, then stirred at room temperature for 5 minutes to give a heterogeneous mixture that turned color from purplish-red to reddish-orange. The reaction was heat to 100° C. (external), during which the color of the reaction mixture changed to orange after ~2 minutes of heating. After 1.5 hr, the reaction was judged complete by TLC. The mixture was diluted with EtOAc, filtered through a pad of diatomaceous earth and bound to silica gel. The crude product was purified over silica gel using a 12 g silica gel cartridge eluting the column with a 30%-100% EtOAc/hexanes gradient to give 3-(4-Acetyl-phenylamino)-1-[3-(6-tert-butyl-1-oxo-1H-phthalazin-2-yl)-2-hydroxymethyl-phenyl]-1H-pyrazole-4-carbonitrile (40 mg, 62%) as a white powder.

Step 6. Followed the same procedure as Example 22 step 4. Thus 3-(4-Acetyl-phenylamino)-1-[3-(6-tert-butyl-1-oxo-1H-phthalazin-2-yl)-2-hydroxymethyl-phenyl]-1H-pyrazole-4-carbonitrile (114 mg, 0.214 mmol) gave crude carboxamide, which was purified over silica gel using a 12 g RediSep silica gel cartridge eluting the column with a 30%-100% (20% MeOH/EtOAc)/hexanes gradient to give 3-(4-Acetyl-phenylamino)-1-[3-(6-tert-butyl-1-oxo-1H-phthalazin-2-yl)-2-hydroxymethyl-phenyl]-1H-pyrazole-4-carboxylic acid amide (99 mg, 84%, [M+H]+ 551) as an off-white powder.

Example 54

1-[3-(6-tert-Butyl-1-oxo-1H-phthalazin-2-yl)-2-hydroxymethyl-phenyl]-3-(pyridin-2-ylamino)-1H-pyrazole-4-carboxylic acid amide

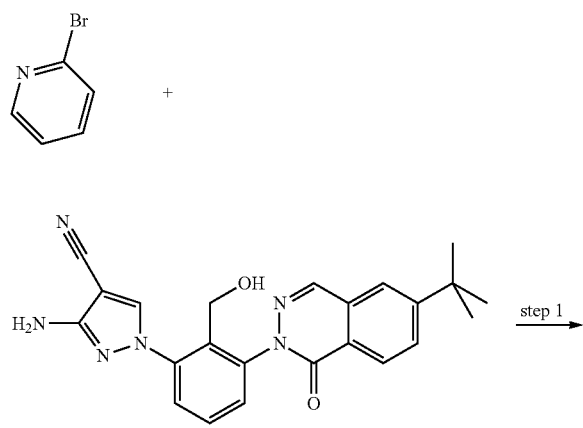

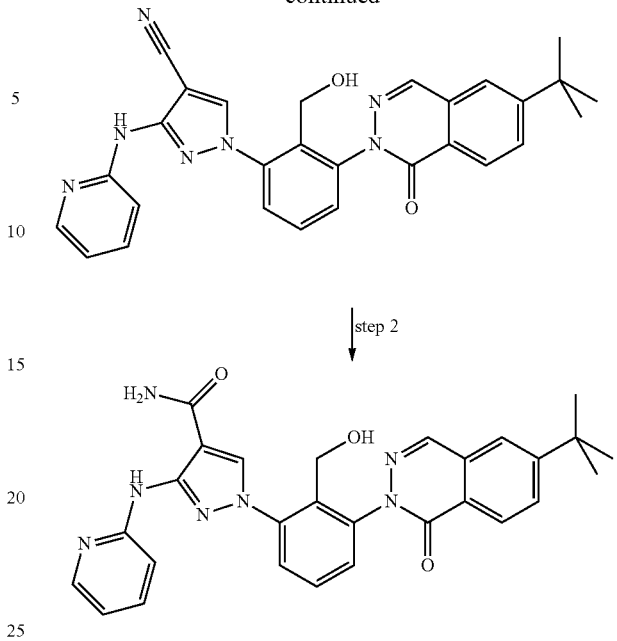

Step 1. To a 5 mL microwave reaction vial were introduced 3-amino-1-(3-(6-tert-butyl-1-oxophthalazin-2(1H)-yl)-2-(hydroxymethyl)phenyl)-1H-pyrazole-4-carbonitrile (25 mg, 0.060 mmol), 2-bromopyridine (11 mg, 0.072 mmol), Pd₂(dba)₃ (3.9 mg, 0.004 mmol), 2-(DICYCLOHEXYLPHOSPHINO)-3,6-DIMETHOXY-2'-4'-6'-TRI-I-PROPYL-1,1'-BIPHENYL (Brett-Phos) (4.5 mg, 0.008 mmol), cesium carbonate (29.5 mg, 0.091 mmol) and suspended in t-butanol (0.609 mL). The reaction vessel was inerted three times by alternating vacuum and an Ar purge, then stirred at room temperature for 5 minutes to give a heterogeneous mixture that turned color from purplish-red to reddish-orange. The reaction was heat to 100° C. (external), during which the color of the reaction mixture changed to orange after ~2 minutes of heating. After 2 hr, the reaction was judged complete by TLC. The mixture was diluted with EtOAc, filtered through a pad of diatomaceous earth and bound to silica gel. The crude product was purified over silica gel using a 12 g RediSep silica gel cartridge eluting the column with a 30%-100% EtOAc/hexanes gradient to give 1-[3-(6-tert-Butyl-1-oxo-1H-phthalazin-2-yl)-2-hydroxymethyl-phenyl]-3-(pyridin-2-ylamino)-1H-pyrazole-4-carbonitrile (15 mg, 51%) as a white powder.

Step 2. Followed the same procedure as Example 22 step 4. Thus 1-[3-(6-tert-butyl-1-oxo-1H-phthalazin-2-yl)-2-hydroxymethyl-phenyl]-3-(pyridin-2-ylamino)-1H-pyrazole-4-carbonitrile (15 mg, 0.0305 mmol) gave crude carboxamide, which was purified over silica gel using a 12 g RediSep silica gel cartridge eluting the column with a 30%-100% (20% MeOH/EtOAc)/hexanes gradient to obtain 1-[3-(6-tert-Butyl-1-oxo-1H-phthalazin-2-yl)-2-hydroxymethyl-phenyl]-3-(pyridin-2-ylamino)-1H-pyrazole-4-carboxylic acid amide (10 mg, 67%, [M+H]+ 510) as an off-white powder, which contained 5-10% of pyridine hydrolyzed amide by-product.

Example 55

1-[3-(6-tert-Butyl-1-oxo-1H-phthalazin-2-yl)-2-hydroxymethyl-phenyl]-3-(5-dimethylaminomethyl-pyridin-2-ylamino)-1H-pyrazole-4-carboxylic acid amide

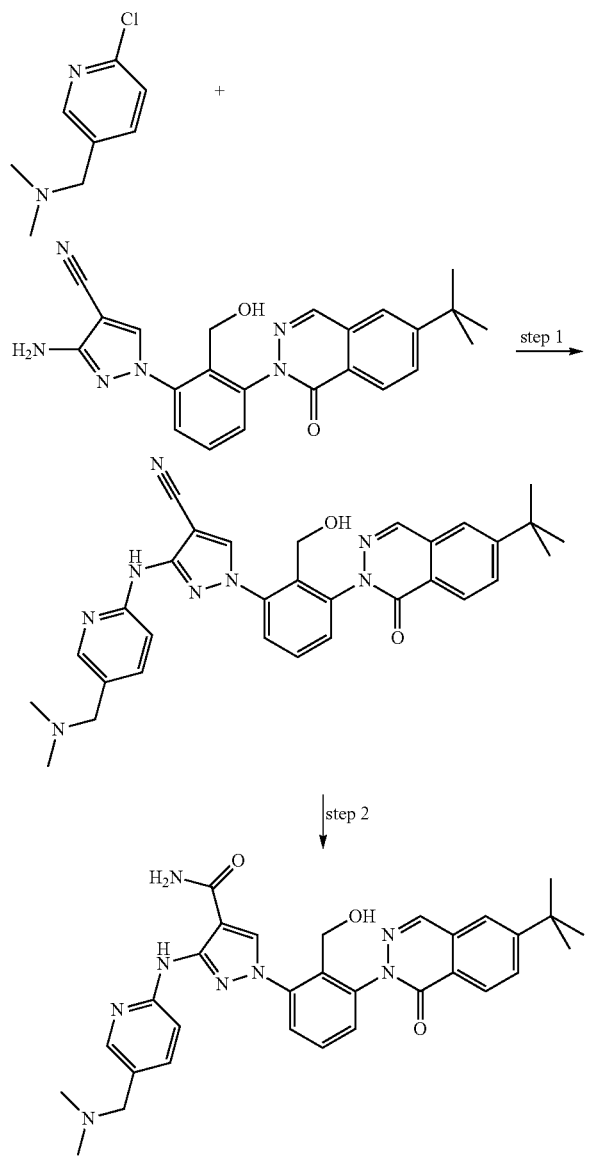

Step 1. To a 5 mL microwave reaction vial were introduced 3-amino-1-(3-(6-tert-butyl-1-oxophthalazin-2(1H)-yl)-2-(hydroxymethyl)phenyl)-1H-pyrazole-4-carbonitrile (25 mg, 0.06 mmol), 1-(6-chloropyridin-3-yl)-N,N-dimethylmethanamine (13 mg, 0.075 mmol), Pd$_2$(dba)$_3$ (4 mg, 0.004 mmol), 2-(DICYCLOHEXYLPHOSPHINO)-3,6-DIMETHOXY-2'-4'-6'-TRI-I-PROPYL-1,1'-BIPHENYL (Brett-Phos) (4.5 mg, 0.008 mmol), cesium carbonate (30 mg, 0.091 mmol) and suspended in t-butanol (0.609 mL). The reaction vessel was inerted three times by alternating vacuum and an Ar purge, then stirred at room temperature for 5 minutes to give a heterogeneous mixture that turned color from purplish-red to reddish-orange. The reaction was heat to 100° C. (external), during which the color of the reaction mixture changed to orange after ~2 minutes of heating. After 4 hr, the reaction was judged complete by TLC. The mixture was diluted with EtOAc, filtered through a pad of diatomaceous earth and bound to silica gel. The crude product was purified over silica gel using a 12 g RediSep silica gel cartridge eluting the column with a 30%-100% EtOAc/hexanes gradient to give a 30-100% EtOAc/hexanes gradient to give 1-[3-(6-tert-Butyl-1-oxo-1H-phthalazin-2-yl)-2-hydroxymethyl-phenyl]-3-(5-dimethylaminomethyl-pyridin-2-ylamino)-1H-pyrazole-4-carbonitrile (18 mg, 54%) as a white powder.

Step 2. Followed the same procedure as Example 22 step 4. Thus 1-[3-(6-tert-Butyl-1-oxo-1H-phthalazin-2-yl)-2-hydroxymethyl-phenyl]-3-(5-dimethylaminomethyl-pyridin-2-ylamino)-1H-pyrazole-4-carbonitril (18 mg, 0.0328 mmol) gave crude carboxamide, which was purified over silica gel using a 12 g RediSep silica gel cartridge eluting the column with a 30%-100% (20% MeOH/EtOAc)/hexanes gradient to give 1-[3-(6-tert-Butyl-1-oxo-1H-phthalazin-2-yl)-2-hydroxymethyl-phenyl]-3-(5-dimethylaminomethyl-pyridin-2-ylamino)-1H-pyrazole-4-carboxylic acid amide (10 mg, 54%, [M+H]+ 567) as an off-white powder.

Example 56

1-[3-(6-tert-Butyl-8-fluoro-1-oxo-1H-phthalazin-2-yl)-phenyl]-1H-pyrazole-4-carboxylic acid amine

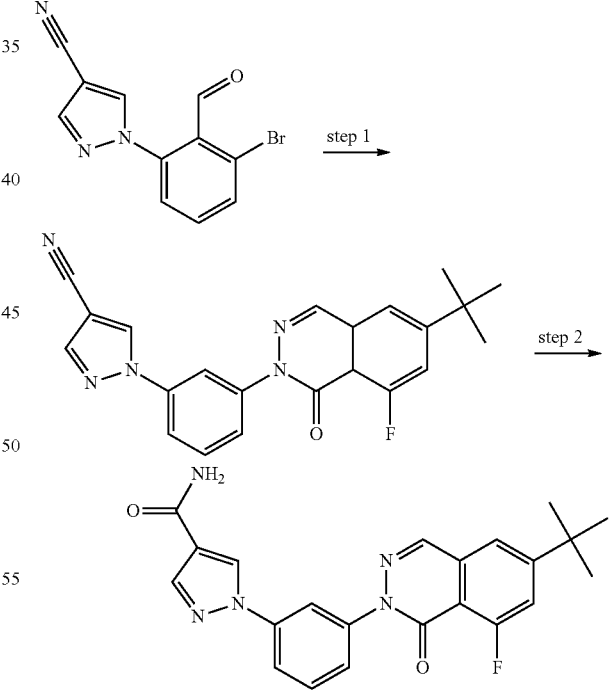

Step 1. In a similar fashion as the step 2 in example for Example 21, 1-(3-bromo-2-formylphenyl)-1H-pyrazole-4-carbonitrile (100 mg, 362 μmol, obtained above in Example 41 was transformed to 1-(3-(6-tert-butyl-8-fluoro-1-oxophthalazin-2(1H)-yl)phenyl)-1H-pyrazole-4-carbonitrile (88 mg, 63%).

Step 2. In a 25 mL round-bottomed flask, 1-(3-(6-tert-butyl-8-fluoro-1-oxophthalazin-2(1H)-yl)phenyl)-1H-pyrazole-4-carbonitrile (87 mg, 225 µmol, Eq: 1.00) and hydrido (dimethylphosphinous acid-kP) (4.82 mg, 11.2 µmol, Eq: 0.05) were combined with Ethanol (1 ml) and Water (1.00 ml) to give a colorless solution. The reaction mixture was heated to 85° C. and stirred for 45 min. After the required reaction time (conversion checked my LCMS and TLC), the reaction was allowed to come to room temperature and the solvent was removed under vacuum. The mixture was then filtered through the HPLC teflon filter and passed through reverphase HPLC and lyophilized overnight to give 1-[3-(6-tert-butyl-8-fluoro-1-oxo-1H-phthalazin-2-yl)-phenyl]-1H-pyrazole-4-carboxylic acid amide (49 mg, 54%, [M+H]+ 406)

Biological Examples

Bruton's Tyrosine Kinase (Btk) Inhibition Assay

The assay is a capture of radioactive $^{33}P$ phosphorylated product through filtration. The interactions of Btk, biotinylated $SH_2$ peptide substrate (Src homology), and ATP lead to phosphorylation of the peptide substrate. Biotinylated product is bound streptavidin sepharose beads. All bound, radio-labeled products are detected by scintillation counter.

Plates assayed are 96-well polypropylene (Greiner) and 96-well 1.2 µm hydrophilic PVDF filter plates (Millipore). Concentrations reported here are final assay concentrations: 10-100 µM compounds in DMSO (Burdick and Jackson), 5-10 nM Btk enzyme (His-tagged, full-length), 30 µM peptide substrate (Biotin-Aca-AAAEEIYGEI-$NH_2$), 100 µM ATP (Sigma), 8 mM imidazole (Sigma, pH 7.2), 8 mM glycerol-2-phosphate (Sigma), 200 µM EGTA (Roche Diagnostics), 1 mM $MnCl_2$ (Sigma), 20 mM $MgCl_2$ (Sigma), 0.1 mg/ml BSA (Sigma), 2 mM DTT (Sigma), 1 µCi $^{33}P$ ATP (Amersham), 20% streptavidin sepharose beads (Amersham), 50 mM EDTA (Gibco), 2 M NaCl (Gibco), 2 M NaCl w/1% phosphoric acid (Gibco), microscint-20 (Perkin Elmer).

$IC_{50}$ determinations are calculated from 10 data points per compound utilizing data produced from a standard 96-well plate assay template. One control compound and seven unknown inhibitors were tested on each plate and each plate was run twice. Typically, compounds were diluted in half-log starting at 100 µM and ending at 3 nM. The control compound was staurosporine. Background was counted in the absence of peptide substrate. Total activity was determined in the presence of peptide substrate. The following protocol was used to determine Btk inhibition.

1) Sample preparation: The test compounds were diluted at half-log increments in assay buffer (imidazole, glycerol-2-phosphate, EGTA, $MnCl_2$, $MgCl_2$, BSA).
2) Bead preparation
  a.) rinse beads by centrifuging at 500 g
  b.) reconstitute the beads with PBS and EDTA to produce a 20% bead slurry
3) Pre-incubate reaction mix without substrate (assay buffer, DTT, ATP, $^{33}P$ ATP) and mix with substrate (assay buffer, DTT, ATP, $^{33}P$ ATP, peptide substrate) 30° C. for 15 min.
4) To start assay, pre-incubate 10 µL Btk in enzyme buffer (imidazole, glycerol-2-phosphate, BSA) and 10 µL of test compounds for 10 min at RT.
5) Add 30 µL reaction mixture without or with substrate to Btk and compounds.
6) Incubate 50 µL total assay mix for 30 min at 30° C.
7) Transfer 40 µL of assay to 150 µL bead slurry in filter plate to stop reaction.
8) Wash filter plate after 30 min, with following steps
  a. 3×250 µL NaCl
  b. 3×250 µL NaCl containing 1% phosphoric acid
  c. 1×250 µL $H_2O$
9) Dry plate for 1 h at 65° C. or overnight at RT
10) Add 50 µL microscint-20 and count $^{33}P$ cpm on scintillation counter.

Calculate percent activity from raw data in cpm percent activity=(sample−bkg)/(total activity−bkg)× 100

Calculate $IC_{50}$ from percent activity, using one-site dose response sigmoidal model $$y=A+((B-A)/(1+((x/C)^D))))$$

x=cmpd conc, y=% activity, A=min, B=max, C=$IC_{50}$, D=1 (hill slope)

Inhibition of B Cell Activation in Whole Blood Measured by CD69 Expression

A procedure to test the ability of Btk inhibitors to suppress B cell receptor-mediated activation of B cells in human blood is as follows:

Human whole blood (HWB) is obtained from healthy volunteers, with the following restrictions: 24 hr drug-free, non-smokers. Blood is collected by venipuncture into Vacutainer tubes anticoagulated with sodium heparin. Test compounds are diluted to ten times the desired starting drug concentration in PBS (20×), followed by three-fold serial dilutions in 10% DMSO in PBS to produce a nine point dose-response curve. 5.5 µl of each compound dilution is added in duplicate to a 2 ml 96-well V bottom plate (Analytical Sales and Services, #59623-23); 5.5 µl of 10% DMSO in PBS is added to control and no-stimulus wells. HWB (100 µl) is added to each well, and after mixing the plates are incubated at 37 C, 5% $CO_2$, 100% humidity for 30 minutes. Goat F(ab')2 anti-human IgM (Southern Biotech, #2022-14) (10 µl of a 500 µg/ml solution, 50 µg/ml final concentration) is added to each well (except the no-stimulus wells) with mixing and the plates are incubated for an additional 20 hours.

At the end of the 20 hour incubation, samples are incubated with florescent-probe-labeled anti-bodies (15 µl PE Mouse anti-Human CD20, BD Pharmingen, #555623, and/or 20 ul APC Mouse anti-Human CD69, BD Pharmingen #555533) for 30 minutes, at 37 C, 5% $CO_2$, 100% humidity. Included are induced control, unstained and single stains for compensation adjustments and initial voltage settings. Samples are then lysed with 1 ml of 1× Pharmingen Lyse Buffer (BD Pharmingen #555899), and plates are centrifuged at 1800 rpm for 5 minutes. Supernatants are removed via suction and the remaining pellets are lysed again with another 1 ml of 1× Pharmingen Lyse Buffer, and plates are spun down as before. Supernatants are aspirated and remaining pellets are washed in FACs buffer (PBS+1% FBS). After a final spin, the supernatants are removed and pellets are resuspended in 180 µl of FACs buffer. Samples are transferred to a 96 well plate suitable to be run on the HTS 96 well system on the BD LSR II flow cytometer.

Using appropriate excitation and emission wavelengths for the fluorophores used, data are acquired and percent positive cell values are obtained using Cell Quest Software. Results are initially analyzed by FACS analysis software (Flow Jo). The IC50 for test compounds is defined as the concentration which decreases by 50% the percentage of CD69-positive cells that are also CD20-positive after stimulation by anti-IgM (average of 8 control wells, after subtraction of the average of 8 wells for the no-stimulus background). The IC50 values are calculated using XLfit software version 3, equation 201.

Representative compound data for this assay are listed below in Table II.

TABLE II

| Compound | FRET BTK IC50 (μM) | Ramos IC50 (μM) | Human Whole Blood CD69 IC50 (μM) |
|---|---|---|---|
| I-1 | 0.05 | 11.15 | |
| I-2 | 0.28083 | 1.595 | |
| I-3 | 0.02702 | | >5 |
| I-4 | 0.01157 | | 3.603 |
| I-5 | | | 4.373 |
| I-6 | 1.255 | | >5 |
| I-7 | 0.1299 | | >5 |
| I-8 | 0.01823 | | 1.913 |
| I-9 | 0.00251 | | 1.261 |
| I-10 | 0.8325 | | >5 |
| I-11 | 0.05135 | | >0.5 |
| I-12 | 0.6955 | | >0.5 |
| I-13 | 0.03935 | | |
| I-14 | 0.02673 | | 4.737 |
| I-15 | 0.0032 | 0.04 | 0.759 |
| I-16 | 0.02 | 0.27 | 1.43 |
| I-17 | 0.0041 | | 2.66 |
| I-18 | | | 10.68 |
| I-19 | | | 0.048 |
| I-20 | | | 0.01 |
| I-21 | | | 0.26 |
| I-22 | 0.09154 | | |
| I-23 | 0.00029 | | |
| I-24 | 0.00018 | | |
| I-25 | 0.00009 | | |
| I-26 | 0.00036 | | |
| I-27 | 0.00009 | | |
| I-28 | 0.00022 | | |
| I-29 | 0.00043 | | |
| I-30 | 0.00024 | | |
| I-31 | 0.00029 | | |
| I-32 | 0.00057 | | |
| I-33 | 0.00024 | | |
| I-34 | 0.00051 | | |
| I-35 | 0.00056 | | |
| I-36 | 0.00083 | | |
| I-37 | 0.00113 | | |
| I-38 | 0.00017 | | |
| I-39 | 0.00018 | | |
| I-40 | 0.33306 | | |
| I-41 | 0.26774 | | |
| I-42 | 0.00732 | | |
| I-43 | 0.00283 | | |
| I-44 | 0.01028 | | |
| I-45 | 0.01104 | | |
| I-46 | 0.01428 | | |
| I-47 | 0.02835 | | |
| I-48 | 0.00774 | | |
| I-49 | 0.01391 | | |
| I-50 | 0.01274 | | |
| I-51 | 3.56218 | | |
| I-52 | | | 1.07 |
| I-53 | 0.00012 | | |
| I-54 | 0.00095 | | |
| I-55 | 0.00039 | | |
| I-56 | 3.7 | | |

Inhibition of B-Cell Activation—B Cell FLIPR Assay in Ramos Cells

Inhibition of B-cell activation by compounds of the present invention is demonstrated by determining the effect of the test compounds on anti-IgM stimulated B cell responses.

The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of $0.5 \times 10^6$/mL in tissue culture flasks. On day of assay, cells are counted and set at a concentration of $1 \times 10^6$/mL1 in growth media supplemented with 1 μM FLUO-3AM (TefLabs Cat-No. 0116, prepared in anhydrous DMSO and 10% Pluronic acid) in a tissue culture flask, and incubated at 37° C. (4% $CO_2$) for one h. To remove extracellular dye, cells were collected by centrifugation (5 min, 1000 rpm), resuspended in FLIPR buffer (described below) at $1 \times 10^6$ cells/mL and then dispensed into 96-well poly-D-lysine coated black/clear plates (BD Cat-No. 356692) at $1 \times 10^5$ cells per well. Test compounds were added at various concentrations ranging from 100 μM to 0.03 μM (7 concentrations, details below), and allowed to incubate with cells for 30 min at RT. Ramos cell $Ca^{2+}$ signaling was stimulated by the addition of 10 μg/mL anti-IgM (Southern Biotech, Cat-No. 2020-01) and measured on a FLIPR (Molecular Devices, captures images of 96 well plates using a CCD camera with an argon laser at 480 nM excitation).

Media/Buffers:

Growth Medium: RPMI 1640 medium with L-glutamine (Invitrogen, Cat-No. 61870-010), 10% Fetal Bovine Serum (FBS, Summit Biotechnology Cat-No. FP-100-05); 1 mM Sodium Pyruvate (Invitrogen Cat. No. 11360-070).

FLIPR buffer: HBSS (Invitrogen, Cat-No. 141175-079), 2 mM $CaCl_2$ (Sigma Cat-No. C-4901), HEPES (Invitrogen, Cat-No. 15630-080), 2.5 mM Probenecid (Sigma, Cat-No. P-8761), 0.1% BSA (Sigma, Cat-No. A-7906), 11 mM Glucose (Sigma, Cat-No. G-7528)

Compound Dilution Details:

In order to achieve the highest final assay concentration of 100 μM, 24 μL of 10 mM compound stock solution (made in DMSO) is added directly to 576 μL of FLIPR buffer. The test compounds are diluted in FLIPR Buffer (using Biomek 2000 robotic pipettor) resulting in the following dilution scheme: vehicle, $1.00 \times 10^{-4}$ M, $1.00 \times 10^{-5}$, $3.16 \times 10^{-6}$, $1.00 \times 10^{-6}$, $3.16 \times 10^{-7}$, $1.00 \times 10^{-7}$, $3.16 \times 10^{-8}$.

Assay and Analysis:

Intracellular increases in calcium were reported using a max-min statistic (subtracting the resting baseline from the peak caused by addition of the stimulatory antibody using a Molecular Devices FLIPR control and statistic exporting software. The $IC_{50}$ was determined using a non-linear curve fit (GraphPad Prism software).

Mouse Collagen-Induced Arthritis (mCIA)

On day 0 mice are injected at the base of the tail or several spots on the back with an emulsion of Type II Collagen (i.d.) in Complete Freund's adjuvant (CFA). Following collagen immunization, animals will develop arthritis at around 21 to 35 days. The onset of arthritis is synchronized (boosted) by systemic administration of collagen in Incomplete Freund's adjuvant (IFA; i.d.) at day 21. Animals are examined daily after day 20 for any onset of mild arthritis (score of 1 or 2; see score description below) which is the signal to boost. Following boost, mice are scored and dosed with candidate therapeutic agents for the prescribed time (typically 2-3 weeks) and dosing frequency, daily (QD) or twice-daily (BID).

Rat Collagen-Induced Arthritis (rCIA)

On day 0, rats are injected with an emulsion of Bovine Type II Collagen in Incomplete Freund's adjuvant (IFA) is injected intradermally (i.d.) on several locations on the back. A booster injection of collagen emulsion is given around day 7, (i.d.) at the base of the tail or alternative sites on the back. Arthritis is generally observed 12-14 days after the initial collagen injection. Animals may be evaluated for the development of arthritis as described below (Evaluation of arthritis) from day 14 onwards. Animals are dosed with candidate therapeutic agents in a preventive fashion starting at the time of secondary challenge and for the prescribed time (typically 2-3 weeks) and dosing frequency, daily (QD) or twice-daily (BID).

Evaluation of Arthritis:

In both models, developing inflammation of the paws and limb joints is quantified using a scoring system that involves the assessment of the 4 paws following the criteria described below:

Scoring:

1=swelling and/or redness of paw or one digit.

2=swelling in two or more joints.

3=gross swelling of the paw with more than two joints involved.

4=severe arthritis of the entire paw and digits.

Evaluations are made on day 0 for baseline measurement and starting again at the first signs or swelling for up to three times per week until the end of the experiment. The arthritic index for each mouse is obtained by adding the four scores of the individual paws, giving a maximum score of 16 per animal.

Rat In Vivo Asthma Model

Male Brown-Norway rats are sensitized i.p. with 100 µg of OA (ovalbumin) in 0.2 ml alum once every week for three weeks (day 0, 7, and 14). On day 21 (one week following last sensitization), the rats are dosed q.d. with either vehicle or compound formulation subcutaneously 0.5 hour before OA aerosol challenge (1% OA for 45 minutes) and terminated 4 or 24 hours after challenge. At time of sacrifice, serum and plasma are collected from all animals for serology and PK, respectively. A tracheal cannula is inserted and the lungs are lavaged 3× with PBS. The BAL fluid is analyzed for total leukocyte number and differential leukocyte counts. Total leukocyte number in an aliquot of the cells (20-100 µl) is determined by Coulter Counter. For differential leukocyte counts, 50-200 µl of the sample is centrifuged in a Cytospin and the slide stained with Diff-Quik. The proportions of monocytes, eosinophils, neutrophils and lymphocytes are counted under light microscopy using standard morphological criteria and expressed as a percentage. Representative inhibitors of Btk show decreased total leucocyte count in the BAL of OA sensitized and challenged rats as compared to control levels.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula I,

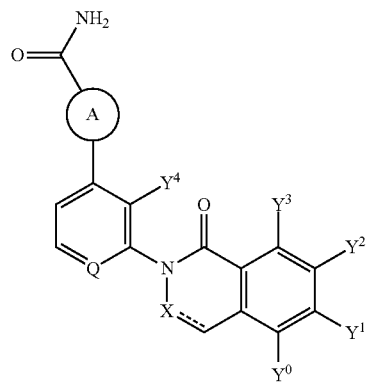

wherein:

--- is either a single or double bond;

A is 5-membered heteroaryl or a 5,6-membered bicyclic heteroaryl, wherein the $CONH_2$ is attached to the 5-membered heteroaryl, each optionally substituted with one or more A';

A' is —NHR or $R^4$;

R is H, —$R^1$, —$R^1$—$R^2$—$R^3$, or —$R^1$—$R^3$; or —$R^2$—$R^3$;

$R^1$ is aryl, heteroaryl, cycloalkyl, heterocycloalkyl, or heteroaryl fused with a heterocycloalkyl, each of which is optionally substituted with one or more $R^{1'}$ or $R^{1'''}$;

each $R^{1'}$ is independently halo, nitro, cyano, lower alkyl sulfonamido, —$S(O)_2$, or oxo;

each $R^{1''}$ is independently lower alkyl, cycloalkyl, heterocycloalkyl, lower alkoxy, amino, or amido, each optionally substituted with one or more $R^{1'''}$;

each $R^{1'''}$ is independently hydroxy, halo, amino, alkyl amino, dialkyl amino, or heterocycloalkyl;

$R^2$ is —C(=O), —C(=O)O, —C(=O)$NR^{2'}$, —NHC(=O)O, —C($R^{2'}$)$_2$, —O, —C(=NH)$NR^{2'}$, or —S(=O)$_2$;

each $R^{2'}$ is independently H or lower alkyl;

$R^3$ is H or $R^4$;

$R^4$ is lower alkyl, lower haloalkyl, lower alkoxy, amino, lower alkyl amino, lower dialkyl amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, heterocycloalkyl alkyl, bicyclic cycloalkyl, bicyclic heterocycloalkyl, spirocycloalkyl, or spiroheterocycloalkyl, each of which is optionally substituted with one or more lower alkyl, halo, lower alkyl amino, lower dialkyl amino, hydroxy, hydroxy lower alkyl, lower alkoxy, halo, nitro, amino, amido, acyl, cyano, oxo, guanidino, hydroxylamino, carboxy, carbamoyl, carbamate, halo lower alkoxy, or halo lower alkyl, wherein two lower alkyl groups may together form a ring;

Q is CH or N;

X is CH, N, or N(X');

X' is lower alkyl;

$Y^0$ is H, halogen or lower alkyl;

$Y^1$ is $Y^{1a}$, $Y^{1b}$, $Y^{1c}$, or $Y^{1d}$;

$Y^{1a}$ is H or halogen;

$Y^{1b}$ is lower alkyl, optionally substituted with one or more substituents selected from the group consisting of lower haloalkyl, halogen, hydroxy, amino, cyano, and lower alkoxy;

$Y^{1c}$ is lower cycloalkyl, optionally substituted with one or more substituents selected from the group consisting of lower alkyl, lower haloalkyl, halogen, hydroxy, amino, cyano, and lower alkoxy;

$Y^{1d}$ is amino, optionally substituted with one or more lower alkyl, alkoxy lower alkyl, or hydroxy lower alkyl;

$Y^2$ is H, halogen or lower alkyl;

$Y^3$ is H, halogen, lower alkyl, lower haloalkyl, lower alkoxy, or lower hydroxy alkyl; and $Y^4$ is H, lower alkyl, or lower hydroxyalkyl;

or a pharmaceutically acceptable salt thereof.

2. The compound of claim 1, wherein $Y^0$ is H, $Y^2$ is H, $Y^3$ is F or H, and $Y^4$ is hydroxymethyl.

3. The compound of claim 2, wherein Q is CH, X is N, and ---- is a double bond.

4. The compound of claim 3, wherein A is furanyl, imidazolyl, thiazolyl, pyrrolyl, pyrazolyl, phenyl, indolyl, pyrrolo[2,3-b]pyridinyl, or oxazolyl.

5. The compound of claim 4, wherein $Y^1$ is tert-butyl or cyclopropyl.

6. The compound of claim 5, wherein $Y^3$ is F.

7. The compound of claim 6, wherein A is furanyl optionally substituted with one or more A'.

8. The compound of claim 6, wherein A is imidazolyl optionally substituted with one or more A'.

9. The compound of claim 6, wherein A is thiazolyl optionally substituted with one or more A'.

10. The compound of claim 6, wherein A pyrrolyl optionally substituted with one or more A'.

11. The compound of claim 6, wherein A is pyrazolyl optionally substituted with one or more A'.

12. The compound of claim 6, wherein A phenyl optionally substituted with one or more A'.

13. The compound of claim 6, wherein A is indolyl optionally substituted with one or more A'.

14. The compound of claim 6, wherein A is pyrrolo[2,3-b]pyridinyl optionally substituted with one or more A'.

15. The compound of claim 6, wherein A oxazolyl optionally substituted with one or more A'.

16. A compound selected from the group consisting of:

4-[3-(6-tert-Butyl-1-oxo-1H-phthalazin-2-yl)-2-hydroxymethyl-phenyl]-1-methyl-1H-imidazole-2-carboxylic acid amide;

2-[3-(6-tert-Butyl-1-oxo-1H-phthalazin-2-yl)-2-hydroxymethyl-phenyl]-thiazole-4-carboxylic acid amide;

4-[3-(6-tert-Butyl-1-oxo-1H-phthalazin-2-yl)-2-hydroxymethyl-phenyl]-1H-pyrrole-2-carboxylic acid amide;

4-[3-(6-tert-Butyl-1-oxo-1H-phthalazin-2-yl)-2-hydroxymethyl-phenyl]-1-methyl-1H-pyrrole-2-carboxylic acid amide;

5-[3-(6-tert-Butyl-1-oxo-1H-phthalazin-2-yl)-2-hydroxymethyl-phenyl]-1-methyl-1H-pyrrole-2-carboxylic acid amide;

2-[3-(6-tert-Butyl-1-oxo-1H-phthalazin-2-yl)-2-hydroxymethyl-phenyl]-4-methyl-oxazole-5-carboxylic acid amide;

2-[3-(6-tert-Butyl-8-fluoro-1-oxo-1H-phthalazin-2-yl)-2-hydroxymethyl-phenyl]-thiazole-4-carboxylic acid amide;

4-[3-(6-tert-Butyl-8-fluoro-1-oxo-1H-phthalazin-2-yl)-2-hydroxymethyl-phenyl]-1-methyl-1H-imidazole-2-carboxylic acid amide;

4-[3-(6-tert-Butyl-8-fluoro-1-oxo-1H-phthalazin-2-yl)-2-hydroxymethyl-phenyl]-1-methyl-1H-pyrrole-2-carboxylic acid amide;

5-[3-(6-tert-Butyl-8-fluoro-1-oxo-1H-phthalazin-2-yl)-2-hydroxymethyl-phenyl]-furan-2-carboxylic acid amide;

4-[3-(6-tert-Butyl-8-fluoro-1-oxo-1H-phthalazin-2-yl)-2-hydroxymethyl-phenyl]-furan-2-carboxylic acid amide;

4-[3-(6-tent-Butyl-8-hydroxymethyl-1-oxo-1H-phthalazin-2-yl)-2-hydroxymethyl-phenyl]-1-methyl-1H-pyrrole-2-carboxylic acid amide;

4-[3-(6-Cyclopropyl-8-fluoro-1-oxo-1H-isoquinolin-2-yl)-2-hydroxymethyl-phenyl]-1-methyl-1H-pyrrole-2-carboxylic acid amide;

4-[3-(6-tert-Butyl-3-methyl-1-oxo-3,4-dihydro-1H-phthalazin-2-yl)-2-hydroxymethyl-phenyl]-1-methyl-1H-pyrrole-2-carboxylic acid amide;

1-[3-(6-tert-Butyl-8-fluoro-1-oxo-1H-phthalazin-2-yl)-2-hydroxymethyl-phenyl]-1H-pyrrolo[2,3-b]pyridine-3-carboxylic acid amide;

4-[2-(6-tert-Butyl-8-fluoro-1-oxo-1H-phthalazin-2-yl)-3-hydroxymethyl-pyridin-4-yl]-1-methyl-1H-pyrrole-2-carboxylic acid amide;

1-[3-(6-tert-Butyl-8-fluoro-1-oxo-1H-phthalazin-2-yl)-2-hydroxymethyl-phenyl]-1H-indole-3-carboxylic acid amide;

1-[3-(6-tert-Butyl-1-oxo-1H-phthalazin-2-yl)-2-hydroxymethyl-phenyl]-1H-indole-3-carboxylic acid amide;

1-[3-(6-tert-Butyl-1-oxo-1H-phthalazin-2-yl)-2-hydroxymethyl-phenyl]-3-[4-(morpholine-4-carbonyl)-phenylamino]-1H-pyrazole-4-carboxylic acid amide;

1-[3-(6-tert-Butyl-8-fluoro-1-oxo-1H-phthalazin-2-yl)-2-hydroxymethyl-phenyl]-3-[4-(morpholine-4-carbonyl)-phenylamino]-1H-pyrazole-4-carboxylic acid amide;

1-[3-(6-tert-Butyl-8-fluoro-1-oxo-1H-phthalazin-2-yl)-phenyl]-3-[4-(morpholine-4-carbonyl)-phenylamino]-1H-pyrazole-4-carboxylic acid amide;

1-[3-(6-tert-Butyl-8-fluoro-1-oxo-1H-phthalazin-2-yl)-2-hydroxymethyl-phenyl]-3-[4-(1-hydroxy-1-methyl-ethyl)-phenylamino]-1H-pyrazole-4-carboxylic acid amide;

1-[3-(6-tert-Butyl-8-fluoro-1-oxo-1H-phthalazin-2-yl)-2-hydroxymethyl-phenyl]-3-(5-chloro-pyridin-2-ylamino)-1H-pyrazole-4-carboxylic acid amide;

3-[5-(2-Azetidin-1-yl-1,1-dimethyl-ethoxy)-pyridin-2-ylamino]-1-[3-(6-tert-butyl-8-fluoro-1-oxo-1H-phthalazin-2-yl)-2-hydroxymethyl-phenyl]-1H-pyrazole-4-carboxylic acid amide;

1-[3-(6-tert-Butyl-8-fluoro-1-oxo-1H-phthalazin-2-yl)-2-hydroxymethyl-phenyl]-3-(5-methyl-4,5,6,7-tetrahydro-pyrazolo[1,5-c]pyrazin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(pyridin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(4-methanesulfonyl-phenylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(1-methyl-1H-pyrazol-3-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(pyrazin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(5-fluoro-pyridin-2-ylamino)-1H-pyrazole-4-carboxylic acid amide;

1-[3-(6-tent-Butyl-8-fluoro-1-oxo-1H-phthalazin-2-yl)-2-hydroxymethyl-phenyl]-3-(1,5-dimethyl-1H-pyrazol-3-ylamino)-1H-pyrazole-4-carboxylic acid amide;

1-[3-(6-tent-Butyl-8-fluoro-1-oxo-1H-phthalazin-2-yl)-2-hydroxymethyl-phenyl]-3-(5-trifluoromethyl-pyridin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(5-methyl-pyridin-2-ylamino)-1H-pyrazole-4-carboxylic acid amide;

1-[3-(6-tert-Butyl-1-oxo-1H-phthalazin-2-yl)-2-hydroxymethyl-phenyl]-3-(1,5-dimethyl-1H-pyrazol-3-ylamino)-1H-pyrazole-4-carboxylic acid amide;

1-[3-(6-tert-Butyl-1-oxo-1H-phthalazin-2-yl)-2-hydroxymethyl-phenyl]-3-(5-fluoro-pyridin-2-ylamino)-1H-pyrazole-4-carboxylic acid amide;

1-[3-(6-tert-Butyl-1-oxo-1H-phthalazin-2-yl)-2-hydroxymethyl-phenyl]-3-(pyrazin-2-ylamino)-1H-pyrazole-4-carboxylic acid amide;

1-[3-(6-tert-Butyl-1-oxo-1H-phthalazin-2-yl)-2-hydroxymethyl-phenyl]-3-(5-methyl-pyridin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(5-methanesulfonyl-pyridin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-3-(5-cyano-pyridin-2-ylamino)-1H-pyrazole-4-carboxylic acid amide;

1-[3-(6-tert-Butyl-8-fluoro-1-oxo-1H-phthalazin-2-yl)-2-hydroxymethyl-phenyl]-1H-pyrazole-3-carboxylic acid amide;

1-[3-(6-tert-Butyl-8-fluoro-1-oxo-1H-phthalazin-2-yl)-2-hydroxymethyl-phenyl]-1H-pyrazole-4-carboxylic acid amide;

7-[3-(6-tert-Butyl-8-fluoro-1-oxo-1H-phthalazin-2-yl)-2-hydroxymethyl-phenyl]-7H-pyrrolo[2,3-d]pyrimidine-5-carboxylic acid amide;

1-[3-(6-tert-Butyl-8-fluoro-1-oxo-1H-phthalazin-2-yl)-2-hydroxymethyl-phenyl]-6-(4-methyl-piperazin-1-yl)-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-morpholin-4-yl-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-(6-ethoxy-pyridin-3-yl)-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-(2-fluoro-phenyl)-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-(2-chloro-phenyl)-1H-pyrrolo[2,3-b]pyridine-3-carboxylic acid amide;

6-Bromo-1-[3-(6-tert-butyl-8-fluoro-1-oxo-1H-phthalazin-2-yl)-2-hydroxymethyl-phenyl]-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-(1,2-dihydroxy-ethyl)-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-(1,1-dioxo-1$\lambda^6$-thiomorpholin-4-yl)-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-(2-dimethylamino-ethylamino)-1H-pyrrolo[2,3-b]pyridine-3-carboxylic acid amide;

1-[3-(6-tert-Butyl-8-fluoro-1-oxo-1H-phthalazin-2-yl)-2-hydroxymethyl-phenyl]-6-dimethylaminomethyl-1H-pyrrolo[2,3-b]pyridine-3-carboxylic acid amide;

3-(4-Acetyl-phenylamino)-1-[3-(6-tert-butyl-1-oxo-1H-phthalazin-2-yl)-2-hydroxymethyl-phenyl]-1H-pyrazole-4-carboxylic acid amide;

1-[3-(6-tert-Butyl-1-oxo-1H-phthalazin-2-yl)-2-hydroxymethyl-phenyl]-3-(pyridin-2-ylamino)-1H-pyrazole-4-carboxylic acid amide;

1-[3-(6-tert-Butyl-1-oxo-1H-phthalazin-2-yl)-2-hydroxymethyl-phenyl]-3-(5-dimethylaminomethyl-pyridin-2-ylamino)-1H-pyrazole-4-carboxylic acid amide; and 1-[3-(6-tert-Butyl-8-fluoro-1-oxo-1H-phthalazin-2-yl)-phenyl]-1H-pyrazole-4-carboxylic acid amide.

17. A method for treating rheumatoid arthritis comprising administering to a patient in need thereof a therapeutically effective amount of the compound of claim 1.

18. A pharmaceutical composition comprising the compound of claim 1, admixed with at least one pharmaceutically acceptable carrier, excipient or diluent.

* * * * *